United States Patent [19]

Winn et al.

[11] Patent Number: 5,250,548

[45] Date of Patent: Oct. 5, 1993

[54] ANGIOTENSIN II RECEPTOR ANTAGONISTS

[75] Inventors: Martin Winn, Deerfield; Biswanath De, Buffalo Grove; Thomas M. Zydowsky, Waukegan; Daniel J. Kerkman, Lake Villa; John F. DeBernardis, Lindenhurst; Saul H. Rosenberg; Kazumi Shiosaki, both of Libertyville; Fatima Z. Basha, Lake Forest; Andrew S. Tasker, Lindenhurst; Thomas W. von Geldern, Richmond; Jeffrey A. Kester, Deerfield; Steven Boyd, Mundelein; Diane M. Yamamoto; Anthony K. L. Fung, Gurnee, all of Ill.

[73] Assignee: Abbott Laboratories, Abbott Park, Ill.

[21] Appl. No.: 844,351

[22] Filed: Mar. 2, 1992

Related U.S. Application Data

[63] Continuation-in-part of Ser. No. 744,241, Aug. 15, 1991, which is a continuation-in-part of Ser. No. 580,400, Sep. 10, 1990, abandoned.

[51] Int. Cl.$^5$ ............... A61K 31/44; C07D 401/12
[52] U.S. Cl. ................... 514/340; 546/276
[58] Field of Search ............... 514/227.8, 235.5, 255, 514/318, 336, 340; 544/60, 232, 243, 333, 335, 337, 360; 546/22, 24, 256, 255, 257, 261, 262, 263, 264, 265, 266, 275, 276, 278, 279, 280, 281, 283, 284, 286, 287, 288, 289, 290, 292, 293, 294, 295, 296, 297, 298, 299, 300, 301, 302, 303, 304, 305, 314, 316, 315

[56] References Cited

U.S. PATENT DOCUMENTS 4,880,804  11/1989  Carini et al. ............... 514/234.5

FOREIGN PATENT DOCUMENTS

| 2051705 | 12/1991 | Canada . |
|---|---|---|
| 442473 | 8/1981 | European Pat. Off. . |
| 0323841 | 7/1989 | European Pat. Off. . |
| 407342 | 1/1991 | European Pat. Off. . |
| 419048 | 3/1991 | European Pat. Off. . |
| 424317 | 4/1991 | European Pat. Off. . |
| 435827 | 7/1991 | European Pat. Off. . |
| 453210 | 10/1991 | European Pat. Off. . |
| 465323 | 1/1992 | European Pat. Off. . |
| WO91/15209 | 10/1991 | PCT Int'l Appl. . |
| WO91/19697 | 12/1991 | PCT Int'l Appl. . |

Primary Examiner—John M. Ford
Assistant Examiner—Y. N. Gupta
Attorney, Agent, or Firm—Steven R. Crowley

[57] ABSTRACT

Compounds are disclosed having the formula:

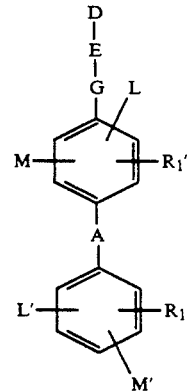

The compounds of the invention are angiotensin II receptor antagonists.

16 Claims, No Drawings

ANGIOTENSIN II RECEPTOR ANTAGONISTS

This is a continuation-in-part of U.S. patent application Ser. No. 744,241, filed Aug. 15, 1991, which is a continuation-in-part of U.S. patent application Ser. No. 580,400, filed Sep. 10, 1990, abandoned.

TECHNICAL FIELD

This invention relates to compounds and compositions which block angiotensin II receptors, processes for making such compounds, synthetic intermediates employed in these processes and a method of treating hypertension, edema, renal failure, benign prostatic hypertrophy, diabetic nephropathy, diabetic retinopathy, Alzheimer's disease or congestive heart failure with such compounds. The present invention also relates to compositions and a method for treating glaucoma, preventing or treating atherosclerosis, preventing or treating stroke and treatment of a variety of obesity-related disorders with such compounds. The present invention also relates to compositions and a method for treating CNS disorders.

BACKGROUND OF THE INVENTION

Blood pressure is regulated by a multitude of interrelated factors involving neural, vascular and volume-related effects. The renin-angiotensin system (RAS) is one of the important blood pressure regulating systems.

The RAS functions as shown in the scheme below. Low renal perfusion pressure stimulates the juxtaglomerular cells of the kidney to produce the proteolytic enzyme renin. This enzyme acts on a circulating protein, angiotensinogen, cleaving off a decapeptide angiotensin I. Angiotensin I is then cleaved to the octapeptide angiotensin II by angiotensin converting enzyme (ACE). Angiotensin II is the most powerful pressor substance in the RAS. Angiotenin II binds to vascular smooth muscle receptors and induces vasoconstriction, but has little or no stimulating action on the heart.

Peptidyl and non-peptidyl angiotensin II receptor antagonists are known. The peptidyl compound saralasin or [Sar[1],Ala[8]] angiotensin II has been found to be a potent antagonist of the actions of angiotensin II. Saralasin, however, has several disadvantages. Because it is a peptide, saralasin has very poor oral bioavailability. The use of saralasin, therefore, is limited to administration to hospitalized patients by continuous intravenous infusion. Saralasin is also known to cause an initial increase in blood pressure after intravenous administration due to its activity as an angiotensin receptor agonist. Therefore, non-peptidyl angiotensin II receptor antagonists are preferred.

DISCLOSURE OF THE INVENTION

In accordance with the present invention, there are compounds of the formula (I):

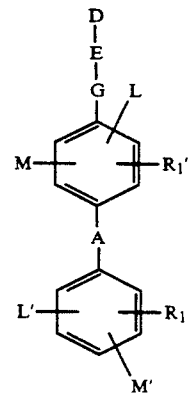

wherein
A is
(i) a covalent bond,
(ii) —O—,
(iii) —C(O)—,
(iv) —CH$_2$—,

Renin-Angiotensin System

Human
Angiotensinogen: H$_2$N—Asp—Arg—Val—Tyr—Ile—His—Pro—Phe—His—<u>Leu—Val</u>—Ile—His—
Protein ↓ Renin Angiotensin I: H$_2$N—Asp—Arg—Val—Tyr—Ile—His—Pro—<u>Phe—His</u>—Leu—OH

↓ ACE

Angiotensin II: H$_2$N—<u>Asp—Arg</u>—Val—Tyr—Ile—His—Pro—Phe—OH

↓ Aminopeptidase

Angiotensin III: H$_2$N—Arg—Val—Tyr—Ile—His—Pro—Phe—OH

↓ Angiotensinases

Inactive Fragments

Inhibitors of renin (for example enalkiren) and inhibitors of ACE (for example, captopril and enalapril) have clinical efficacy in treating hypertension and congestive heart failure. ACE inhibitors, however, have reported side effects including cough and skin rash.

(v) —S—, —S(O)— or —S(O)$_2$—;
E-G is
(i) —N(R$_5$)—,
(ii) —O—,
(iii) —S—, (iv) —N(R₅)—CH(R₅)—,
(v) —O—CH(R₅)—,
(vi) —S—CH(R₅)—,
(vii) —C(R₅')(R₅)—CH(R₅)—,
(viii) —CH(R₅)—C(R₅')(R₅)—,
(ix) —CH(R₅)—N(R₅)—,
(x) —CH(R₅)—O—,
(xi) —CH(R₅)—S—,
(xii) —N(R₅)—N(R₅)—,
(xiii) —C(R₅)=C(R₅)— or
(xiv) —CH(R₅)—C(R₅')(R₅)—N(R₅)— wherein at each occurrence R₅ is independently selected from hydrogen, loweralkyl, alkoxy-substituted loweralkyl, halo-substituted loweralkyl, carboxy-substituted loweralkyl, heterocyclic-substituted loweralkyl, alkenyl, alkynyl, cycloalkyl or cycloalkylalkyl and R₅' is hydrogen, halo, hydroxy, carboxy, alkoxy or thioalkoxy;

L, L', M and M' are independently selected from
(i) hydrogen,
(ii) loweralkyl,
(iii) halo-substituted loweralkyl,
(iv) halo,
(v) —CN,
(vi) —NO₂,
(vii) —OH,
(viii) hydroxy-substituted loweralkyl,
(ix) alkoxy-substituted loweralkyl,
(x) —NH₂,
(xi) alkylamino,
(xii) dialkylamino,
(xiii) —SH,
(xiv) alkoxy and
(xv) thioalkoxy;

R₁ and R₁' are independently selected from
(i) tetrazolyl,
(ii)

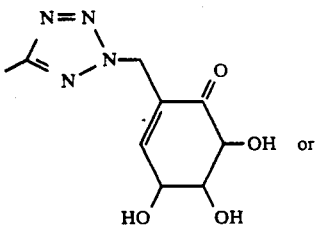

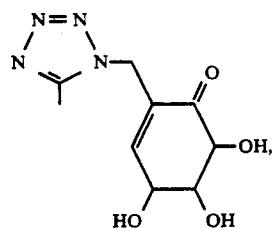

(iii)

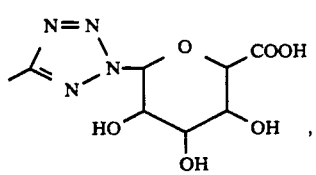

(iv) —NH—C(=N(R₅₀ₐ))(R₅₁ₐ) wherein R₅₀ₐ is hydrogen, —CN or —NO₂ and R₅₁ₐ is hydrogen, loweralkyl, alkylamino, dialkyamino, alkoxy or thioalkoxy, (v) —NH(R₅₁ᵦ) wherein R₅₁ᵦ is a 5-membered aromatic heterocyclic ring wherein the heterocyclic ring contains 1, 2, 3 or 4 nitrogen atoms or 1 nitrogen atom and 1 oxygen atom or 2 nitrogen atoms and 1 oxygen atom or 1 oxygen atom and 1 sulfur atom and wherein the 5-membered heterocyclic ring is unsubstituted or susbstituted with a substitutent selected from amino, alkylamino, dialkylamino, hydroxy, alkoxy, thioalkoxy, halo, loweralkyl and halo-substituted loweralkyl, (vi) —COOR₆ or —CH₂COOR₆ wherein R₆ is hydrogen or a carboxy-protecting group or (vii) —NHS(O)₂R₇ or —CH2NHS(O)₂R₇ or —NHC(O)R₇ₐ or —CH2NHC(O)R₇ₐ wherein R₇ is loweralkyl, halo-substituted loweralkyl or —NR₇ᵦR₇c wherein R₇ᵦ and R₇c are independently selected from hydrogen and loweralkyl and R₇ₐ is loweralkyl, halo-substituted loweralkyl, amino, alkylamino, dialkylamino or —COOH;

(viii) —C(O)NR₅₀R₅₁ or —CH₂C(O)NR₅₀R₅₁ or —NHC(O)NR₅₀R₅₁ or —CH₂NHC(O)NR₅₀R₅₁ or —NHC(S)NR₅₀R₅₁ or —CH₂NHC(S)NR₅₀R₅₁ wherein R₅₀ and R₅₁ are independently selected from hydrogen, loweralkyl, hydroxy, alkoxy, hydroxy-substituted loweralkyl, alkoxy-substituted loweralkyl, alkoxy-substituted alkoxy and —S(O)₂R₅₀ₐ wherein R₅₀ₐ is loweralkyl or aryl, or R₅₀ and R₅₁ taken together with the nitrogen atom to which they are attached form a 5- to 7-membered aliphatic heterocycle;

(ix) —CH₂OR₅₂ wherein R₅₂ is selected from hydrogen, loweralkyl and —C(O)R₅ wherein R₅₃ is hydrogen, loweralkyl or aryl;

(x) —CH(OH)R₅₂ₐ or —C(O)R₅₂ₐ wherein R₅₂ₐ is loweralkyl, halo-substituted loweralkyl, —CF₂COOR₅₃ₐ or —CH₂COOR₅₃ₐ wherein R₅₃ₐ is hydrogen or a carboxy-protecting group, (xii) —CH₂NR₅₄R₅₅ wherein R₅₄ is selected from hydrogen, loweralkyl, —C(O)R₅₆, —C(O)NR₅₆R₅₇ and —S(O)₂R₅₈ wherein R₅₆ is selected from hydrogen, loweralkyl and aryl and R₅₈ is selected from lower alkyl and halo-substituted loweralkyl and wherein R₅₅ and R₅₇ are independently selected from hydrogen, loweralkyl, hydroxy and alkoxy;

(xiii) —SO₃H, —OSO₃H or —CH₂SO₃H,
(xiv) —OPO₃H₂, —PO₃H₂ or —CH₂PO₃H₂,
(xv) —SO₂NR₅₀R₅₁ or —CH₂SO₂NR₅₀R₅₁ wherein R₅₀ and R₅₁ are defined as above and
(xvi) —C(O)NHSO₂R₆₀, —C(O)NHC(O)R₆₀ or —C(O)NHNHSO₂R₆₀ wherein R₆₀ is loweralkyl, halo-substituted loweralkyl or aryl;

with the proviso that one of R₁ and R₁' is hydrogen, but R₁ and R₁' are not both hydrogen; and D is

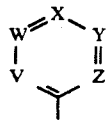

wherein V, W, X, Y and Z are independently selected from N, —N(O)—, CH, C(R$_3$) and C(R$_4$), wherein
(1) 0, 1 or 2 of V, W, X, Y and Z are C(R$_3$),
(2) one of V, W, X, Y and Z is C(R$_4$), and
(3) 0, 1, 2 or 3 of V, W, X, Y and Z are N, and wherein R$_3$ is
(i) hydrogen,
(ii) loweralkyl,
(iii) halo,
(iv) halo-substituted loweralkyl,
(v) thioalkoxy,
(vi) alkoxy-substituted loweralkyl,
(vii) thioalkoxy-substituted loweralkyl,
(viii) aryl,
(ix) arylalkyl,
(x) —NO$_2$,
(xi) —COOR$_8$ wherein R$_8$ is hydrogen or a carboxy-protecting group,
(xii) —OR$_9$ wherein R$_9$ is hydrogen, loweralkyl, halo-substituted loweralkyl, aryl, arylalkyl, heterocyclic-substituted loweralkyl or —C(O)R$_{10}$ wherein R$_{10}$ is loweralkyl, halo-substituted loweralkyl, —PO$_3$H$_2$ or —NR$_{11}$R$_{12}$ wherein R$_{11}$ and R$_{12}$ are independently selected from hydrogen and loweralkyl and
(xiii) —NR$_{13}$R$_{14}$ or —CH$_2$NR$_{13}$R$_{14}$ wherein R$_{13}$ and R$_{14}$ are independently selected from (1) hydrogen, (2) lower alkyl, (3) arylalkyl, (4) —C(O)R$_{15}$, (5) —S(O)$_2$R$_{15}$ wherein R$_{15}$ is loweralkyl or halo-substituted loweralkyl and (6) —R$_{1\text{-}6}$—R$_{17}$ wherein R$_{16}$ is alkylene and R$_{17}$ is
(a) —NR$_{18}$R$_{19}$ wherein R$_{18}$ and R$_{19}$ are independently selected from hydrogen and loweralkyl or
(b) unsubstituted or loweralkyl substituted aziridinyl, azetidinyl, pyrrolidinyl, piperidinyl, piperazinyl, morpholinyl, thiomorpholinyl, pyridinyl or pyrimidinyl, or R$_{13}$ and R$_{14}$ taken together with the nitrogen atom to which they are attached form a 5- to 7-membered aliphatic heterocycle and R$_4$ is
(i) hydrogen,
(ii) loweralkyl,
(iii) halo-substituted loweralkyl,
(iv) —CN,
(v) —NO$_2$,
(vi) —NH$_2$,
(vii) —NH—C(=N(R$_{25a}$))(R$_{26a}$) wherein R$_{25a}$ is hydrogen, —CN or —NO$_2$ and R$_{26a}$ is hydrogen, loweralkyl, alkylamino, dialkylamino, alkoxy or thioalkoxy,
(viii) —NH(R$_{26b}$) wherein R$_{26b}$ is a 5-membered aromatic heterocyclic ring wherein the heterocyclic ring contains 1, 2, 3 or 4 nitrogen atoms or 1 nitrogen atom and 1 oxygen atom or 2 nitrogen atoms and 1 oxygen atom or 1 oxygen atom and 1 sulfur atom and wherein the 5-membered heterocyclic ring is unsubstituted or substituted with a substitutent selected from amino, alkylamino, dialkylamino, hydroxy, alkoxy, thioalkoxy, halo, loweralkyl and halo-substituted loweralkyl,
(ix) —CHO or —CH(=N—OH),
(x) tetrazolyl,
(xi) —NHS(O)$_2$R$_{20}$ or —CH$_2$NHS(O)$_2$R$_{20}$ or —NHC(O)R$_{21}$ or —N(OH)C(O)R$_{21}$ or —CH$_2$NHC(O)R$_{21}$ or —CH$_2$N(OH)C(O)R$_{21}$ wherein R$_{20}$ is loweralkyl, halo-substituted loweralkyl or —NR$_{27a}$R$_{27b}$ wherein R$_{27a}$ and R$_{27b}$ are independently selected from hydrogen, —OH and loweralkyl and R$_{21}$ is loweralkyl, halo-substituted loweralkyl, amino, alkylamino, dialkylamino or —COOH,
(xii) —CH(OH)R$_{22}$ or —C(O)R$_{22}$ wherein R$_{22}$ is loweralkyl, halo-substituted loweralkyl, —CF$_2$COOR$_{23}$ or —CH$_2$COOR$_{23}$ wherein R$_{23}$ is hydrogen or a carboxy-protecting group,
(xiii) —COOR$_{24}$ or —CH$_2$COOR$_{24}$ wherein R$_{24}$ is hydrogen or a carboxy-protecting group,
(xiv) —C(O)NR$_{25}$R$_{26}$ or —CH$_2$C(O)NR$_{25}$R$_{26}$ or —NHC(O)NR$_{25}$R$_{26}$ or —CH$_2$NHC(O)NR$_{25}$R$_{26}$ or —NHC(S)NR$_{25}$R$_{26}$ or —CH$_2$NHC(S)NR$_{25}$R$_{26}$ wherein R$_{25}$ and R$_{26}$ are independently selected from hydrogen, loweralkyl, hydroxy, alkoxy, hydroxy-substituted loweralkyl, alkoxy-substituted loweralkyl, alkoxy-substituted alkoxy and —S(O)$_2$R$_{28a}$ wherein R$_{28a}$ is loweralkyl or aryl, or R$_{25}$ and R$_{26}$ taken together with the nitrogen atom to which they are attached form a 5- to 7-membered aliphatic heterocycle;
(xv) —CH$_2$OR$_{27}$ wherein R$_{27}$ is selected from hydrogen, loweralkyl and —C(O)R$_{28}$ wherein R$_{28}$ is hydrogen, loweralkyl or aryl;
(xvi) —CH$_2$NR$_{29}$R$_{30}$ wherein R$_{29}$ is selected from hydrogen, loweralkyl, —C(O)R$_{31}$, —C(O)NR$_{31}$R$_{32}$ and —S(O)$_2$R$_{33}$ wherein R$_{31}$ is selected from hydrogen, loweralkyl and aryl and R$_{33}$ is selected from loweralkyl and halo-substituted loweralkyl and wherein R$_{30}$ and R$_{32}$ are independently selected from hydrogen, loweralkyl, hydroxy and alkoxy;
(xvii) —SO$_3$H, —OSO$_3$H or —CH$_2$SO$_3$H,
(xviii) —OPO$_3$H, —PO$_3$H$_2$ or —CH$_2$PO$_3$H$_2$,
(xix) —SO$_2$NR$_{25}$R$_{26}$ or —CH$_2$SO$_2$NR$_{25}$R$_{26}$ wherein R$_{25}$ and R$_{26}$ are defined as above and
(xx) —C(O)NHSO$_2$R$_{59}$, —C(O)NHC(O)R$_{59}$ or —C(O)NHNHSO$_2$R$_{59}$ wherein R$_{59}$ is loweralkyl, halo-substituted loweralkyl or aryl;
or a pharmaceutically acceptable salt or prodrug thereof.

In one preferred embodiment of the present invention represented by formula (IA), V and X are N, W is C(R$_3$) and Z is C(R$_4$).

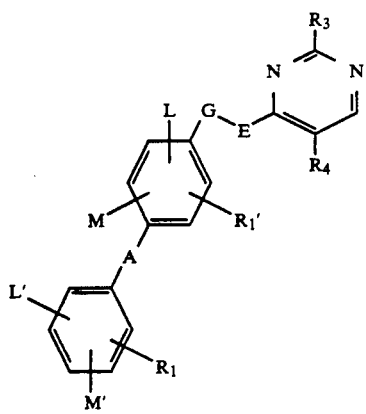

(I A)

In another preferred embodiment of the present invention represented by formula (I M), V and Z are N, W is C(R$_3$) and Y is C(R$_4$).

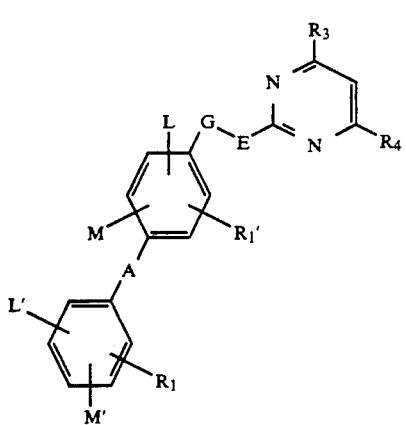

(I M)

In another preferred embodiment of the present invention represented by formula (IR), X is N, V is C(R$_3$) and Z is C(R$_4$).

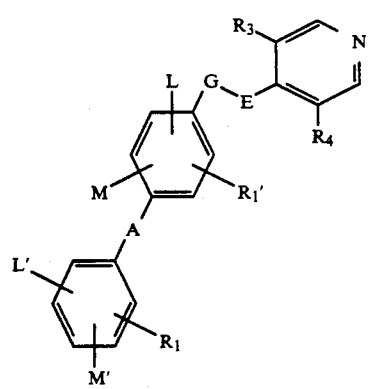

(I R)

In another preferred embodiment of the present invention represented by formula (I S), W and Z are N, X is C(R$_3$) and V is C(R$_4$)

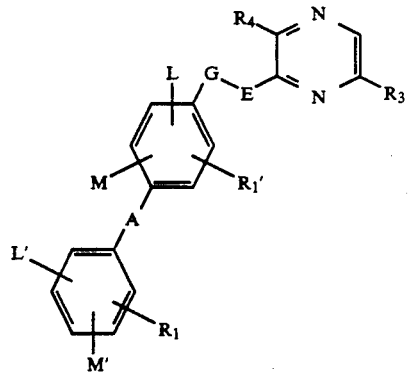

(I S)

In another preferred embodiment of the present invention represented by formula (I T), V and W are N, and Z is C(R$_4$).

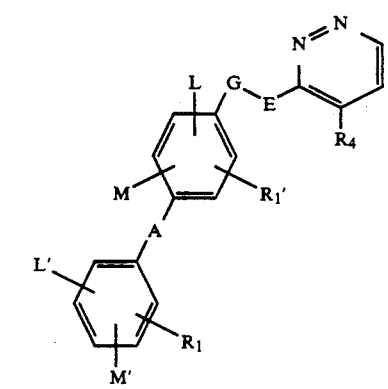

(I T)

In another preferred embodiment of the present invention represented by formula (I V), Z is N and V is C(R$_4$).

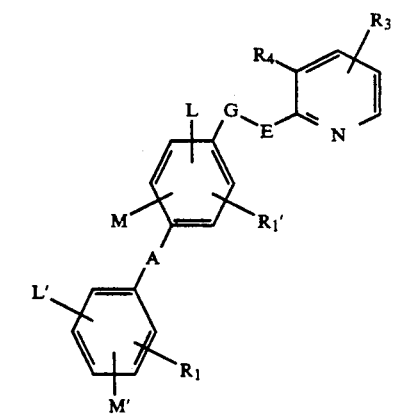

(I V)

In yet another preferred embodiment of the present invention represented by formula (I W), V is C(R$_4$), W, X and Z are N and Y is C(R$_3$).

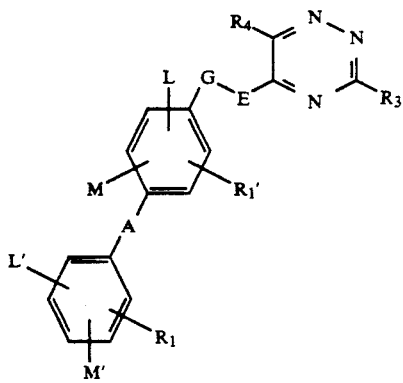

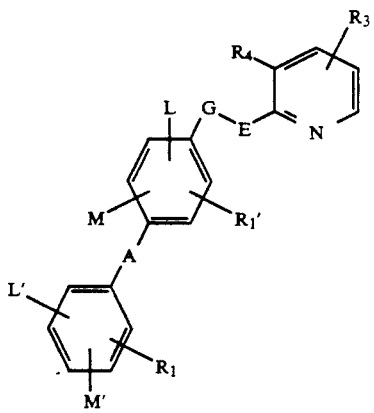

More preferred compounds of the invention are compounds of the formula:

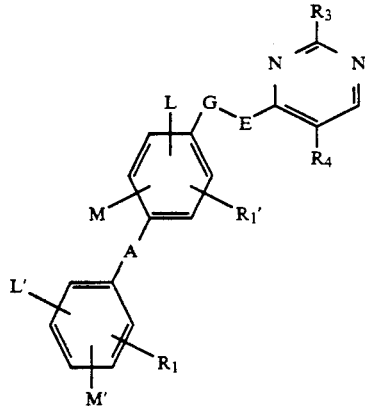

wherein

A is a covalent bond;

E is —N($R_5$)—wherein $R_5$ is defined as above;

G is $CH_2$;

L, L', M and M' are defined as above;

$R_1'$ is hydrogen;

$R_1$ is tetrazolyl;

$R_3$ is defined as above; and $R_4$ is —$COOR_{24}$ wherein $R_{24}$ is hydrogen or a carboxy-protecting group or —$C(O)NR_{25}R_{26}$ wherein $R_{25}$ and $R_{26}$ are independently selected from hydrogen, loweralkyl, hydroxy, alkoxy, hydroxy-substituted loweralkyl, alkoxy-substituted loweralkyl and alkoxy-substituted alkoxy, or $R_{25}$ and $R_{26}$ taken together with the nitrogen atom to which they are attached form a 5- to 7-membered aliphatic heterocycle;

or a pharmaceutically acceptable salt or prodrug thereof.

More preferred compounds of the invention also are compounds of the formula:

wherein

A is a covalent bond;

E is —N($R_5$)—wherein $R_5$ is defined as above;

G is $CH_2$;

L, L', M and M' are defined as above;

$R_1'$ is hydrogen;

$R_1$ is tetrazolyl;

$R_3$ is loweralkyl, halo-substituted loweralkyl, halo, alkoxy or thioalkoxy; and $R_4$ is —$COOR_{24}$ wherein $R_{24}$ is hydrogen or a carboxy-protecting group or —$C(O)NR_{25}R_{26}$ wherein $R_{25}$ and $R_{26}$ are independently selected from hydrogen, loweralkyl, hydroxy, alkoxy, hydroxy-substituted loweralkyl, alkoxy-substituted loweralkyl and alkoxy-substituted alkoxy, or $R_{25}$ and $R_{26}$ taken together with the nitrogen atom to which they are attached form a 5- to 7-membered aliphatic heterocycle;

or a pharmaceutically acceptable salt or prodrug thereof.

The term "loweralkyl" as used herein refers to branched or straight chain alkyl groups comprising one to ten carbon atoms, including methyl, ethyl, propyl, isopropyl, n-butyl, t-butyl, neopentyl and the like.

The term "alkenyl" as used herein refers to a branched or straight chain comprising two to ten carbon atoms which has one or more carbon-carbon double bonds, including vinyl, propenyl, butenyl and the like.

The term "alkenyl" as used herein refers to a branched or straight chain comprising two to ten carbon atoms which has one or more carbon-carbon triple bonds, including ethynyl, propynyl, butynyl and the like.

The term "cycloalkyl" as used herein refers to an alicyclic group comprising from 3 to 7 carbon atoms, including cyclopropyl, cyclobutyl, cyclopentyl, cyclohexyl and the like.

The term "cycloalkylalkyl" as used herein refers to a loweralkyl radical to which is appended a cycloalkyl group, including cyclopentylmethyl, cyclohexylmethyl and the like.

The term "alkylene" as used herein refers to a 1 to 10 carbon straight or branched chain di-radical, including —$CH_2$—, —$CH(CH_3)$—, —$CH_2CH_2CH_2$—, —$CH(CH_3)CH_2CH_2$— and the like.

The term "halo-substituted loweralkyl" refers to a loweralkyl radical in which one or more of the hydrogen atoms are replaced by halogen, including chloromethyl, fluoroethyl, trifluoromethyl, pentafluoroethyl and the like.

The term "hydroxy-substituted loweralkyl" refers to a loweralkyl radical to which is appended one or two hydroxy (—OH) groups.

The term "halogen" or "halo" as used herein refers to I, Br, Cl or F.

The term "alkoxy" refers to $R_{34}O$— wherein $R_{34}$ is a loweralkyl or benzyl group. Representative examples of alkoxy groups include methoxy, ethoxy, t-butoxy, benzyloxy and the like.

The term "thioalkoxy" as used herein refers to $R_{35}S$— wherein $R_{35}$ is a loweralkyl or benzyl group.

The term "alkoxy-substituted loweralkyl" as used herein refers to a loweralkyl radical to which is appended an alkoxy group.

The term "thioalkoxy-substituted loweralkyl" as used herein refers to a a loweralkyl radical to which is appended a thioalkoxy group. Representative thioalkoxy-substituted loweralkyl groups include methylthiomethyl, methylthioethyl, ethylthioethyl, propylthiomethyl and the like.

The term "hydroxy-substituted loweralkyl" as used herein refers to a loweralkyl radical to which is appended one or two hydroxy (—OH) groups.

The term "carboxy-substituted loweralkyl" as used herein refers to a loweralkyl radical to which is appended a carboxy group (—COOH), including carboxymethyl, carboxyethyl and the like.

The term "alkoxycarbonyl" as used herein refers to —$C(O)OR_{36}$ wherein $R_{36}$ is a carboxy-protecting group.

The term "alkoxycarbonyl-substituted loweralkyl" as used herein refers to a loweralkyl radical to which is appended an alkoxycarbonyl group.

The term "alkoxy-substituted alkoxy" as used here refers to an alkoxy radical to which is appended another alkoxy radical, including methoxymethoxy, methoxy ethoxy, ethoxyethoxy and the like.

The term "alkylamino" as used herein refers to —$NHR_{37}$ wherein $R_{37}$ is a loweralkyl group.

The term "dialkylamino" as used herein refers to —$NR_{38}R_{39}$ wherein $R_{38}$ and $R_{39}$ are independently selected from loweralkyl.

The term "alkanoyloxyalkyl" as used herein refers to a loweralkyl radical to which is appended —$OC(O)R_{40}$ wherein $R_{40}$ is loweralkyl.

The term "aroyloxyalkyl" as used herein refers to a loweralkyl radical to which is appended —$OC(O)R_{41}$ wherein $R_{41}$ is aryl.

The term "alkoxycarbonylalkyl" as used herein refers to a loweralkyl radical to which is appended an alkoxycarbonyl group.

The term "alkoxycarbonyloxyalkyl" as used herein refers to a loweralkyl radical to which is appended —$OC(O)OR_{42}$ wherein $R_{42}$ is loweralkyl or cycloalkyl.

The term "alkoxycarbonylaminoalkyl" as used herein refers to a loweralkyl radical to which is appended —$NHC(O)OR_{43}$ wherein $R_{43}$ is loweralkyl.

The term "alkylaminocarbonylaminoalkyl" as used herein refers to a loweralkyl radical to which is appended —$NHC(O)NHR_{44}$ wherein $R_{44}$ is loweralkyl.

The term "alkanoylaminoalkyl" as used herein refers to a loweralkyl radical to which is appended —$NHC(O)R_{45}$ wherein $R_{45}$ is loweralkyl.

The term "heterocycliccarbonyloxyalkyl" as used herein refers to a loweralkyl radical to which is appended —$OC(O)R_{46}$ wherein $R_{46}$ is a heterocyclic group.

The term "aryl" as used herein refers to a phenyl or a $C_9$ or $C_{10}$ bicyclic carbocyclic ring system having one or more aromatic rings, including naphthyl, tetrahydronaphthyl, indanyl, indenyl and the like. Aryl groups can be unsubstituted or substituted with one, two or three substituents independently selected from loweralkyl, halo-substituted loweralkyl, alkoxy, thioalkoxy, alkoxycarbonyl, hydroxy, halo, mercapto, nitro, amino, alkylamino, dialkylamino, carboxaldehyde, carboxy and carboxamide.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "aliphatic heterocycle" as used herein refers to a saturated cyclic group containing 5 to 7 ring atoms and, in particular, at least 1 nitrogen atom in the ring and optionally 1 additional heteroatom selected from S, $S(O)_2$, O and N, with the remaining ring atoms being carbon atoms. The ring can be substituted on a carbon atom or a heteroatom, for example, with loweralkyl, alkoxy or alkoxy-substituted alkoxy. Representative aliphatic heterocycles include, pyrrolidine, piperidine, piperazine, morpholine, thiomorpholine, S,S-dioxothiomorpholine, 4-methoxymethoxypiperidine and the like.

The term "heterocyclic group" or "heterocyclic" as used herein refers to any 3- or 4-membered ring containing a heteroatom selected from oxygen, nitrogen and sulfur, or a 5-, 6- or 7-membered ring containing one, two or three nitrogen atoms; one nitrogen and one sulfur atom; or one nitrogen and one oxygen atom; wherein the 5-membered ring has 0-2 double bonds and the 6- or 7-membered ring has 0-3 double bonds; wherein the nitrogen and sulfur heteroatoms can optionally be oxidized; wherein the nitrogen heteroatom can optionally be quaternized; and including any bicyclic group in which any of the above heterocyclic rings is fused to a benzene ring or another 5-, 6- or 7-membered heterocyclic ring independently as defined above. Heterocyclics include indolyl, quinolyl, isoquinolyl, tetrahydroquinolyl, benzofuryl, benzothienyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, benzothienyl, homopiperazinyl, homopiperidinyl, homomorpholinyl and the like.

Heterocyclics can be unsubstituted or monosubstituted or disubstituted with substitutents independently selected from hydroxy, halo, oxo (=O), amino, alkylamino, dialkylamino, alkoxy, thioalkoxy, carboxy, alkoxycarbonyl, loweralkyl, cycloalkyl, —$OSO_3H$ and halo-substituted loweralkyl.

The term "heterocyclic-substituted loweralkyl" as used herein refers to a loweralkyl radical to which is appended a heterocyclic group.

The term "N-protecting group" or "N-protected" as used herein refers to those groups intended to protect an amino group against undersirable reactions during synthetic procedures. Commonly used N-protecting groups are disclosed in Greene, "Protective Groups in Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, t-butyloxycarbonyl (Boc), benzyloxycarbonyl (Cbz) and the like.

As used herein, the term "carboxy-protecting group" refers to a carboxy group which has been esterified with one of the commonly used carboxylic acid protecting ester groups employed to block or protect the carboxylic acid functionality while the reactions involving other functional sites of the compound are carried out. Carboxy-protecting groups are disclosed in Greene, "Protective Groups in Organic Synthesis" pp. 152–186 (1981), which is incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975). Such carboxy-protecting groups are well known to those skilled in the art, having been extensively used in the protection of carboxyl groups in the penicillin and cephalosporin fields, as described in U.S. Pat. No. 3,840,556 and 3,719,667, the disclosures of which are incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press: New York (1987). Representative carboxy-protecting groups are $C_1$ to $C_8$ alkyl (e.g., methyl, ethyl or tertiary butyl and the like), benzyl and substituted derivatives thereof such as alkoxybenzyl or nitrobenzyl groups and the like, dialkylaminoalkyl (e.g., dimethylaminoethyl and the like), alkanoyloxyalkyl groups such as pivaloyloxymethyl or propionyloxymethyl and the like, aroyloxyalkyl, such as benzoyloxyethyl and the like, alkoxycarbonylalkyl, such as methoxycarbonylmethyl, cyclohexyloxycarbonylmethyl and the like, alkoxycarbonyloxyalkyl, such as t-buyloxycarbonyloxymethyl and the like, alkoxycarbonylaminoalkyl, such as t-butyloxycarbonylaminomethyl and the like, alkylaminocarbonylaminoalkyl, such as methylaminocarbonylaminomethyl and the like, alkanoylaminoalkyl, such as acetylaminomethyl and the like, heterocycliccarbonyloxyalkyl, such as 4-methylpiperazinylcarbonyloxymethyl and the like, dialkylaminocarbonylalkyl, such as dimethylaminocarbonylmethyl and the like, (5-(loweralkyl)-2-oxo-1,3-dioxolen-4-yl)alkyl, such as (5-t-butyl-2-oxo-1,3-dioxolen-4-yl)methyl and the like and (5-phenyl-2-oxo-1,3-dioxolen-4-yl)alkyl, such as (5-phenyl-2-oxo-1,3-dioxolen-4-yl)methyl and the like.

When the compounds of formula I contain one asymmetric carbon atom, they can exist as pure enantiomers or mixtures of enantiomers. When the compounds of formula I contain more than one asymmetric carbon atom, they can exist as diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13–30.

In addition, in the compounds of the invention, combinations of substituents and/or variables (i.e., A, D, E, G, $R_1$, $R_2$, $R_3$, $R_4$, etc.) are permissible only if such combinations result in stable compounds.

In general, the compounds of this invention can be prepared by the processes illustrated in Schemes I through XXXII. It should be understood that substituents A, D, E, G, $R_1$, $R_2$, $R_3$, $R_4$, etc. as used herein correspond to the groups identified by formula (I). P is a protecting group. In the course of synthesis, certain groups present in the molecule, particulary carboxylic acid and tetrazole groups, are protected and deprotected as necessary. The term "protecting group" is well known in the art and refers to substituents on functional groups of compounds undergoing chemical transformation which prevent undesired reactions and degradations during a synthesis; see, for example, T. H. Greene, "Protective Groups in Organic Synthesis", John Wiley & Sons, New York (1981) for methods of introducing and removing appropriate protecting groups. Suitable carboxy-protecting groups include t-butyl and benzyl groups. Suitable tetrazole nitrogen-protecting groups include triphenylmethyl (Tr), benzyl, t-butyl, methoxymethyl, benzyloxymethyl, p-nitrobenzyl, 1-ethoxyethyl and the like.

The compounds of formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgment as to the order of synthetic steps, protecting groups required and deprotection conditions. Throughout the following section, not all compounds of formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

SCHEME I A

According to reaction Scheme I A, an intermediate of Formula 1 (prepared as shown in reaction Schemes II, III, IV, V, VI VII and VIII) (E is O, S or $NR_5$), is condensed with an intermediate of Formula 2 (prepared as shown in reaction Schemes IX and X) to afford a compound of Formula 3. In the case wherein $R_1P$ is $COOR_{24}$ or a protected tetrazole ring, the $R_{24}$ carboxy-protecting group or the tetrazole N-protecting group can then be removed to afford a compound of Formula (I A). One suitable method for removing triphenylmethyl N-protecting groups is mild acid treatment, for example using ethanolic hydrogen chloride followed by aqueous work-up.

Alternatively, in the case wherein $R_4$ is an ester group of Formula $COOR_{24}$, the ester may be hydrolyzed to give a compound of Formula 3a and the $R_1$ protecting group, if present, is removed to afford a compound of Formula (I B).

Alternatively, the compound of Formula 3 (in which $R_4$ is an ester group of Formula $COOR_{24}$) may be treated with a suitable reagent for reducing the ester group to a hydroxyl group, for example lithium aluminum hydride. The $R_1$ protecting group, if present, is removed to afford a compound of Formula (I C). The compounds of Formula 3b may also be oxidized with a suitable oxidizing agent such as manganese dioxide or pyridinium chlorochhromate (and the $R_1$ protecting group, if present, removed) to afford the compounds of Formula (I D). The compounds of Formula (I C) also may be further converted by activation (with for example methanesulfonyl chloride) or replacement (with, for example bromine) of the hydroxy group, followed by nucleophilic displacement with an alkoxide anion (e.g. sodium methoxide in methanol) and removal of the $R_1$ protecting groups, if present, to afford an ether of Formula (I E).

SCHEME I B

According to reaction Scheme I B, a compound of Formula 3a is treated with an amine in the presence of a coupling reagent such as 3-(dimethylaminopropyl)-3-ethyl-carbodiimide hydrochloride and a suitable base, preferably N-methylmorpholine, followed by removal of the $R_1$ protecting groups, if present, to afford an amide of Formula (I F). Suitable amines include pyrrolidine, morpholine, 4-methoxymethoxypiperidine, dimethylamine, methylamine, 2-(hydroxyethyl)amine, 2-(methoxymethyl)amine, and 2-(2-methoxyethoxy)amine.

SCHEME I C

According to reaction Scheme I C, a compound of Formula 3b is treated with an acid chloride, for example benzoyl chloride or acetyl chloride, followed by removal of the $R_1$ protecting groups, if present, to afford an ester of Formula (I G).

SCHEME ID

According to reaction Scheme ID, a compound of Formula 3 (in which $R_4$ is a cyano group) is hydrolyzed by standard methods, for example using aqueous potassium hydroxide, followed by removal of the $R_1$ protecting groups, if present, to afford an amide of Formula (I H).

Alternatively, a compound of Formula 3 is treated with a suitable reducing agent, for example lithium aluminum hydride, to afford the aminomethyl compound of Formula 3c. In the case wherein $R_1$ is $COOR_{24}$ or a protected tetrazole ring, the $R_1$ carboxy-protecting group or the tetrazole N-protecting group can then removed to afford a compound of Formula (I J). Alternatively, a compound of Formula 3c is converted to the corresponding amide, carbamate or sulfonylamine by standard methods. Treatment of a compound of Formula 3c with a suitable isocyanate such as methyl isocyanate affords a compound of Formula 3d in which $R_{29}$ is $C(O)NHR_{31}$ (a urea derivative). Treatment of a compound of Formula 3c with a suitable acid chloride such as acetyl chloride or benzoyl chloride, in the presence of a base, affords a compound of Formula 3d in which $R_{29}$ is $C(O)R_{31}$. Treatment of a compound of Formula 3c with a sulfonic acid chloride, for example methanesulfonyl chloride, in the presence of a suitable base (e.g. triethylamine) affords a compound of Formula 3d in which $R_{29}$ is $S(O)_2R_{32}$. In the case wherein $R_1$ is $COOR_{24}$ or a protected tetrazole ring, the $R_{24}$ carboxy-protecting group or the tetrazole N-protecting group can then be removed to afford a compound of Formula (I K).

SCHEME I E

According to reaction Scheme I E, an intermediate of Formula 1 (prepared as shown in reaction Schemes II, III, IV, V, VI VII and VIII) (E is O, S or $NR_5$), is condensed with an intermediate of Formula 2 (prepared as shown in reaction Schemes IX and X) to afford a compound of Formula 3. A compound of Formula 3 is, in turn, reduced to an amino compound of Formula 4 using standard methods. A compound of Formula 4 is then treated with a suitable sulfonyl chloride, for example trifluoromethylsulfonyl chloride, to afford a compound of Formula (I L).

SCHEME I F

According to reaction Scheme I F, an intermediate of Formula 1 (prepared as shown in reaction Schemes II, III, IV, V, VI VII and VIII) (E is O, S or $NR_5$), is condensed with an intermediate of Formula 5 (prepared as shown in reaction Scheme XII) to afford a compound of Formula 6. In the case wherein $R_1P$ is $COOR_{24}$ or a protected tetrazole ring, the $R_{24}$ carboxy-protecting group or the tetrazole N-protecting group can then removed to afford a compound of Formula (I M). One suitable method for removing triphenylmethyl N-protecting groups is mild acid treatment, for example using ethanolic hydrogen chloride followed by aqueous work-up.

Alternatively, in the case wherein $R_4$ is an ester group of Formula $COOR_{24}$, the ester may be hydrolyzed to give a compound of Formula 6a and the $R_1$ protecting group, if present, is removed to afford a compound of Formula (I N).

Alternatively, the compound of Formula 6 (in which $R_4$ is an ester group of Formula $COOR_{24}$) may be treated with a suitable reagent for reducing the ester group to a hydroxyl group, for example lithium aluminum hydride to afford the compounds of Formula 6b. The $R_1$ protecting group, if present, is removed to afford a compound of Formula (I O). The compounds of Formula 6b may also be oxidized with a suitable oxidizing agent such as manganese dioxide or pyridinium chlorochhromate (and the $R_1$ protecting group, if present removed) to afford the compounds of Formula (I P). The compounds of Formula (I O) also may be further converted by activation (with for example methanesulfonyl chloride) or replacement (with, for example bromine) of the hydroxy group, followed by nucleophilic displacement with an alkoxide anion (e.g. sodium methoxide in methanol) and removal of the $R_1$ protecting groups, if present, to afford an ether of Formula (I Q).

SCHEME I G

According to reaction Scheme I G, an intermediate of Formula 1 (prepared as shown in reaction Schemes II through VIII) (E is O, S or $NR_5$), is condensed with an intermediate of Formula 7 (prepared as shown in reaction Scheme XIII) and the $R_1$ protecting group, if present, is removed to afford a compound of Formula (I R).

SCHEME I H

According to reaction Scheme I H, an intermediate of Formula 1 (prepared as shown in reaction Schemes II through VIII) (E is O, S or NR$_5$), is condensed with an intermediate of Formula 8 (prepared as shown in reaction Scheme XIV) and the R$_1$ protecting group, if present, is removed to afford a compound of Formula (I S).

SCHEME I J

According to reaction Scheme I J, an intermediate of Formula 1 (prepared as shown in reaction Schemes II through VIII), is condensed with an intermediate of Formula 9 and the R$_1$ protecting group, if present, is removed to afford a compound of Formula (I T).

Alternatively, an intermediate of Formula 1 (prepared as shown in reaction Schemes II through VIII), is condensed with an intermediate of Formula 10 (prepared as shown in reaction Scheme XI) to give a compound of Formula 11 which is treated with a suitable reagent for reducing the nitro group (for example, catalytic hydrogenation) to give the a compound of Formula 12. A compound of Formula 12 is, in turn, reacted with a sulfonyl chloride such as methanesulfonyl chloride or trifluoromethanesulfonyl chloride and the R$_1$ protecting group, if present, is removed to afford a compound of Formula (I U).

Alternatively, an intermediate of Formula 1 (prepared as shown in reaction Schemes II through VIII), is condensed with an intermediate of Formula 13 and the R$_1$ protecting group, if present, is removed to afford a compound of Formula (I V).

SCHEME I K

According to reaction Scheme I J, an intermediate of Formula 1 (prepared as shown in reaction Schemes II through VIII) (E is O, S or NR$_5$), is condensed with an intermediate of Formula 56 and the R$^1$ protecting group, if present, is removed to afford a compound of Formula (I W).

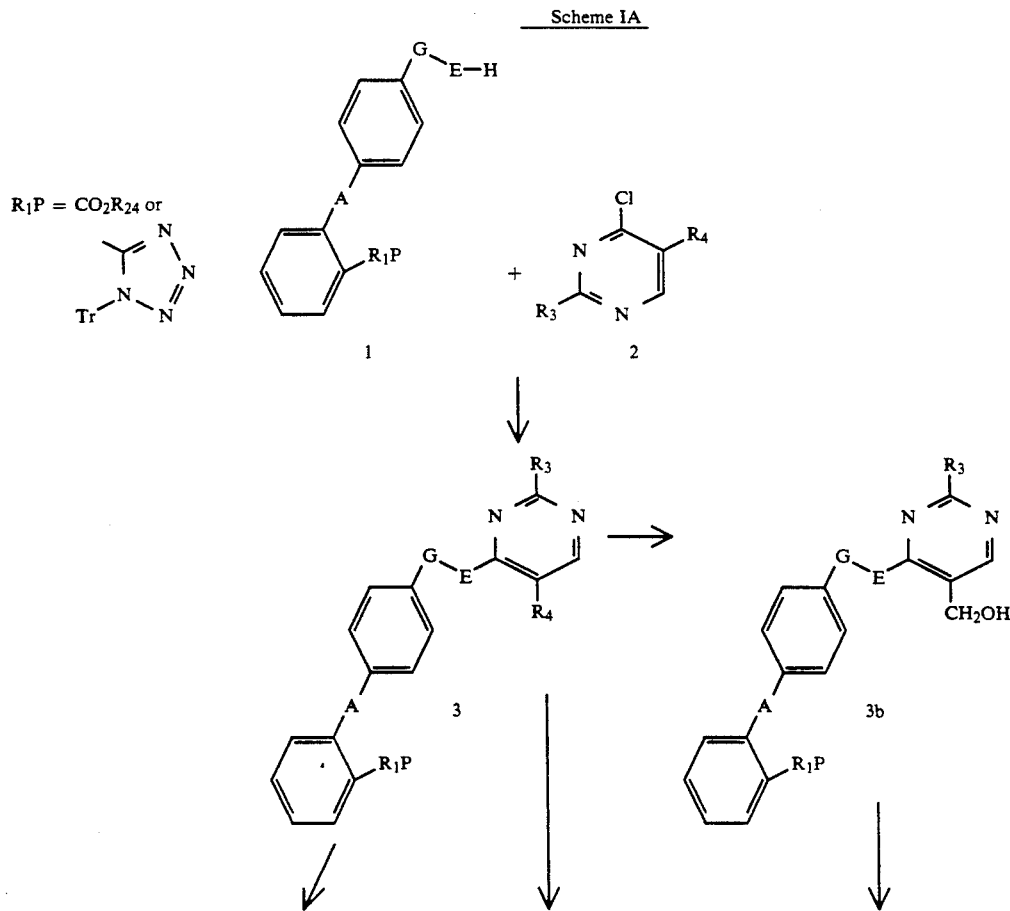

Scheme IA

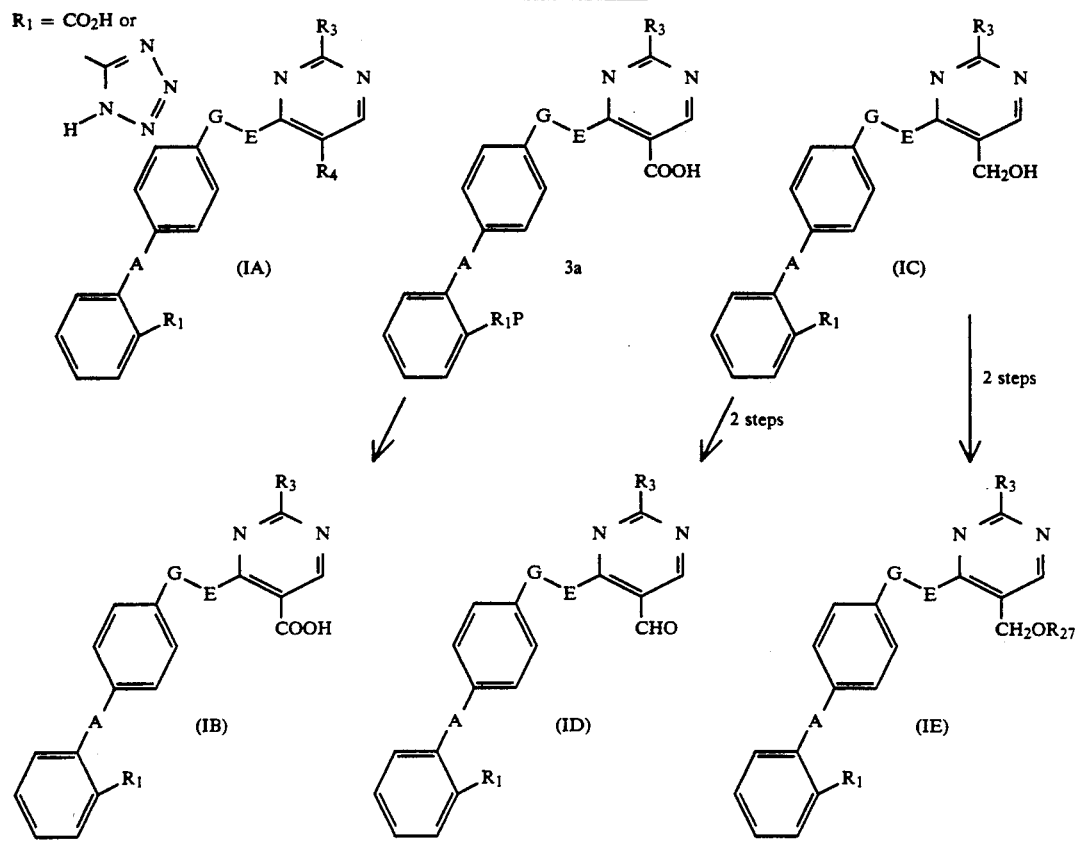
-continued
Scheme 1A
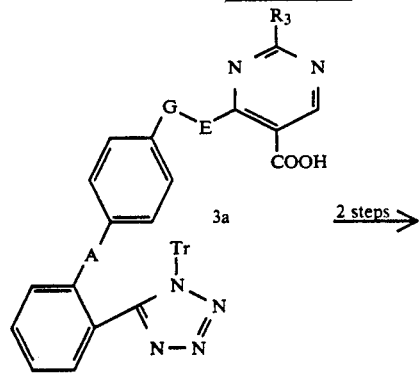
Scheme 1B
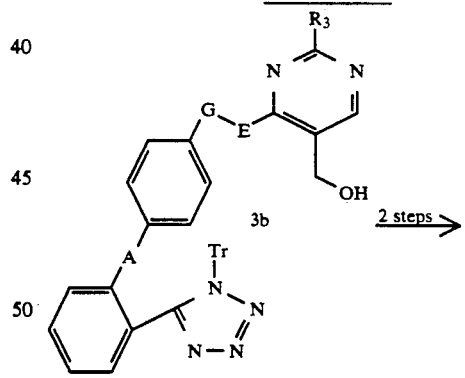
Scheme 1C
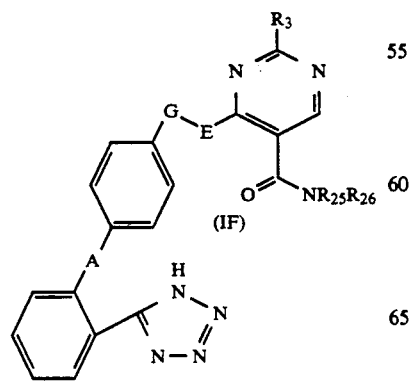
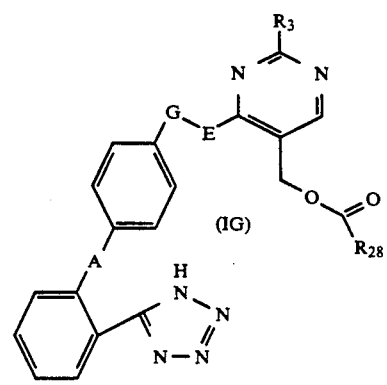

Scheme ID
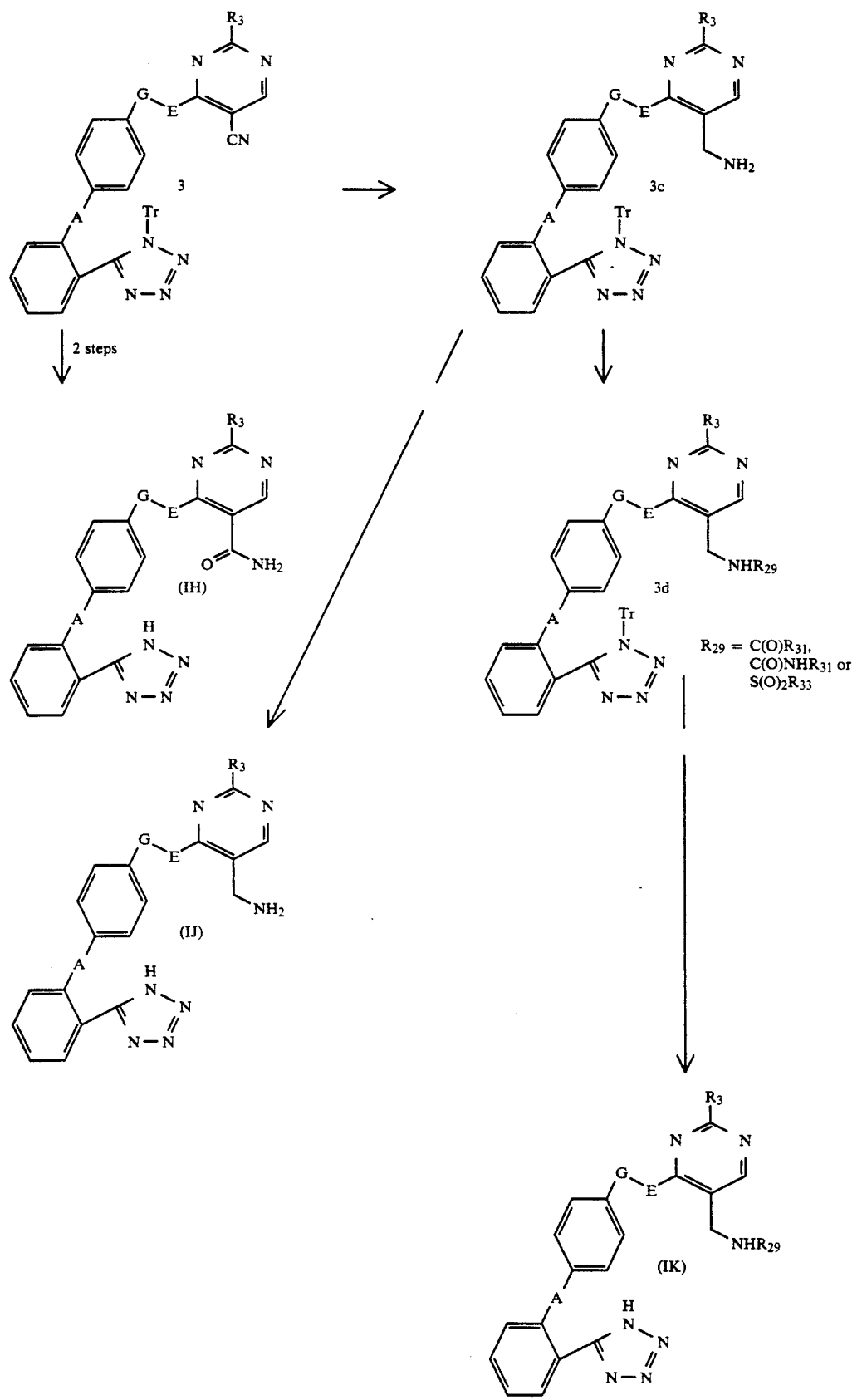

5,250,548
Scheme IE
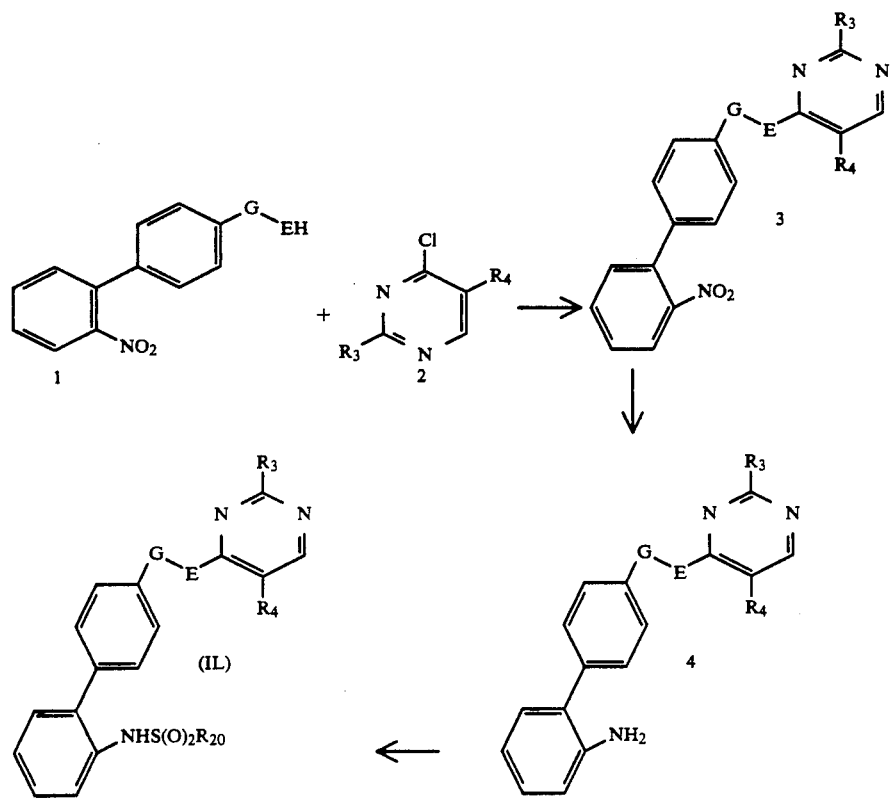
Scheme I F
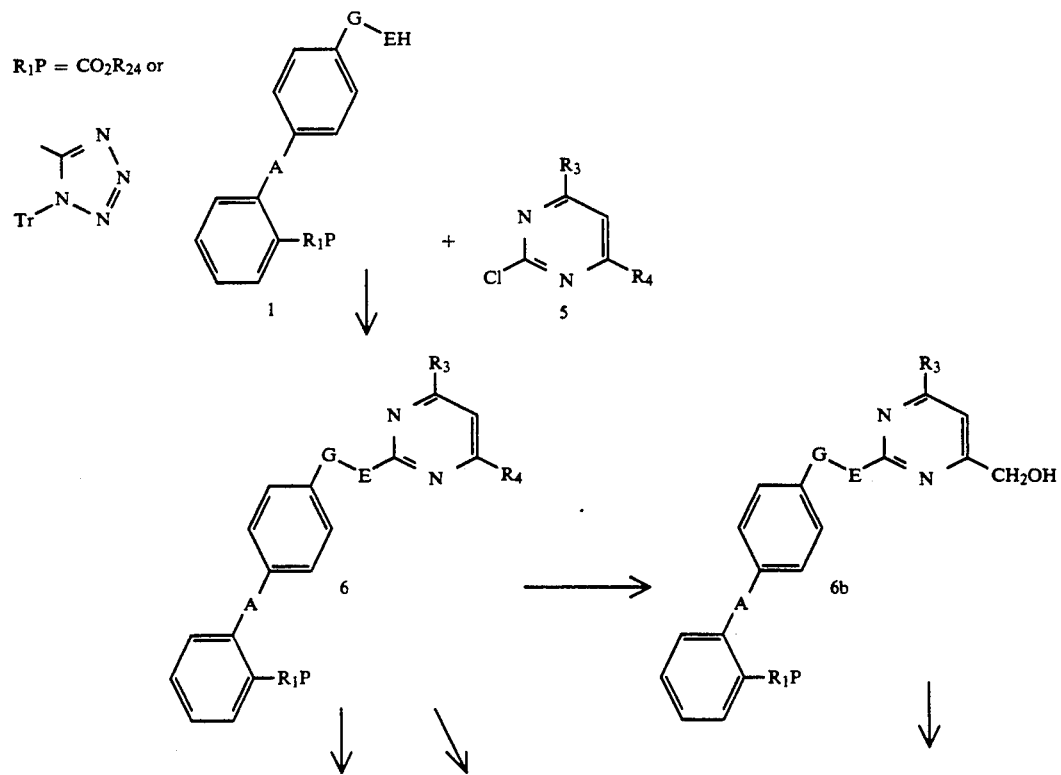

-continued
Scheme I F
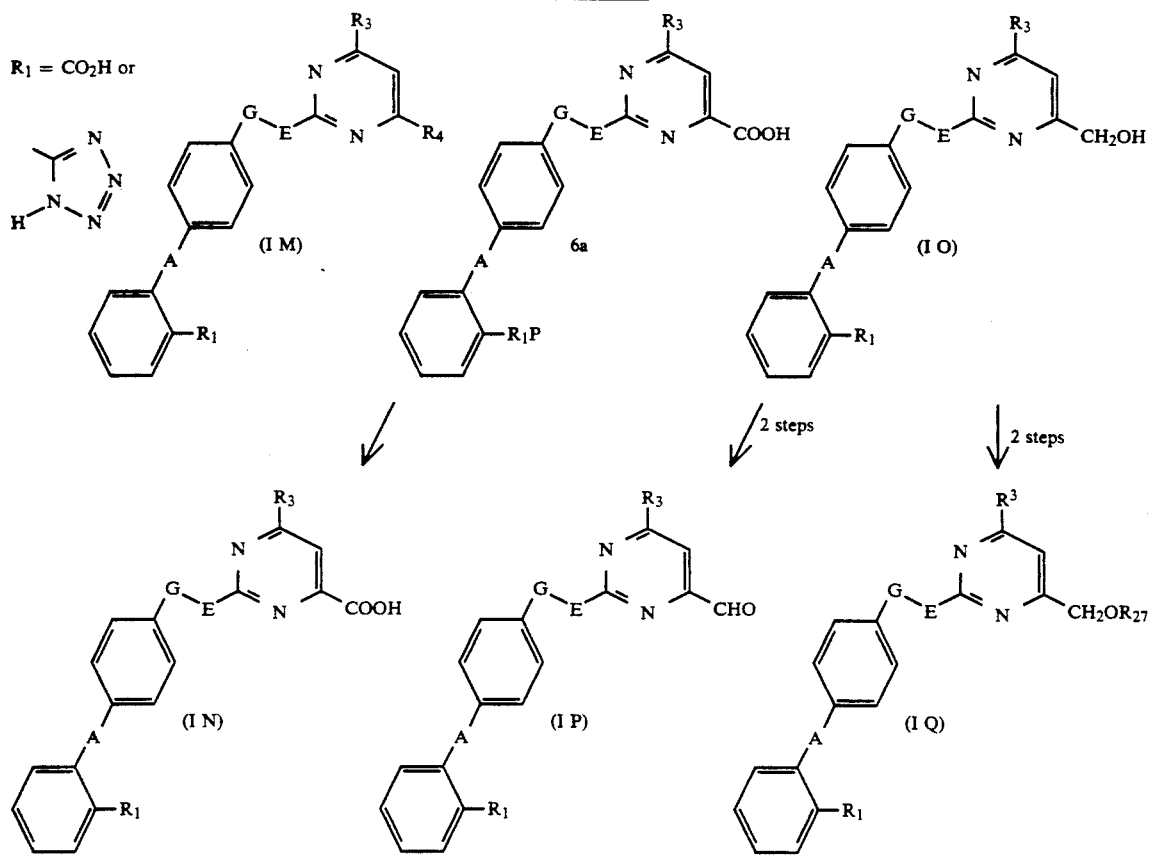
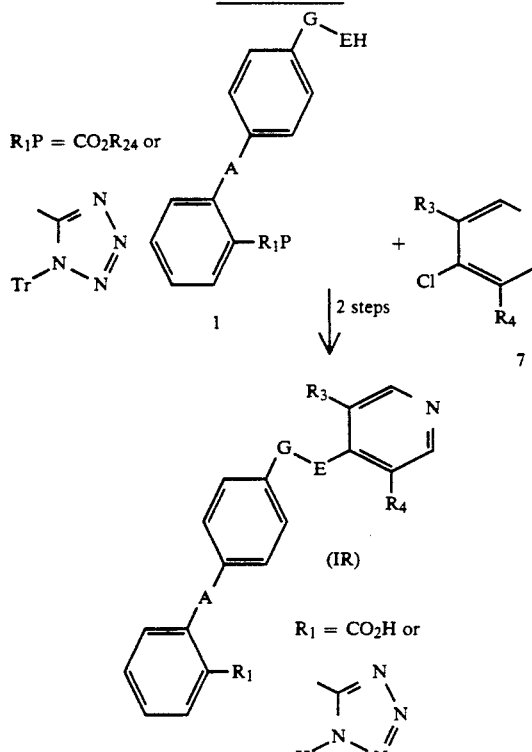
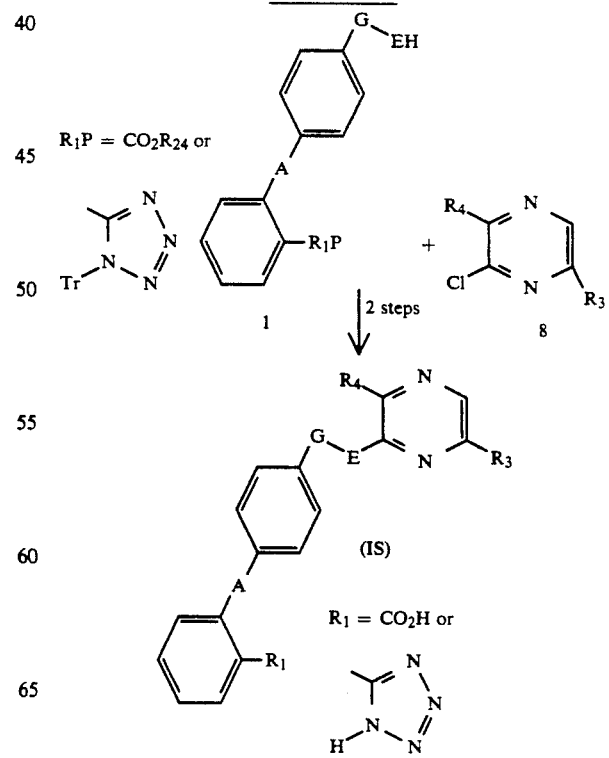

Scheme I J
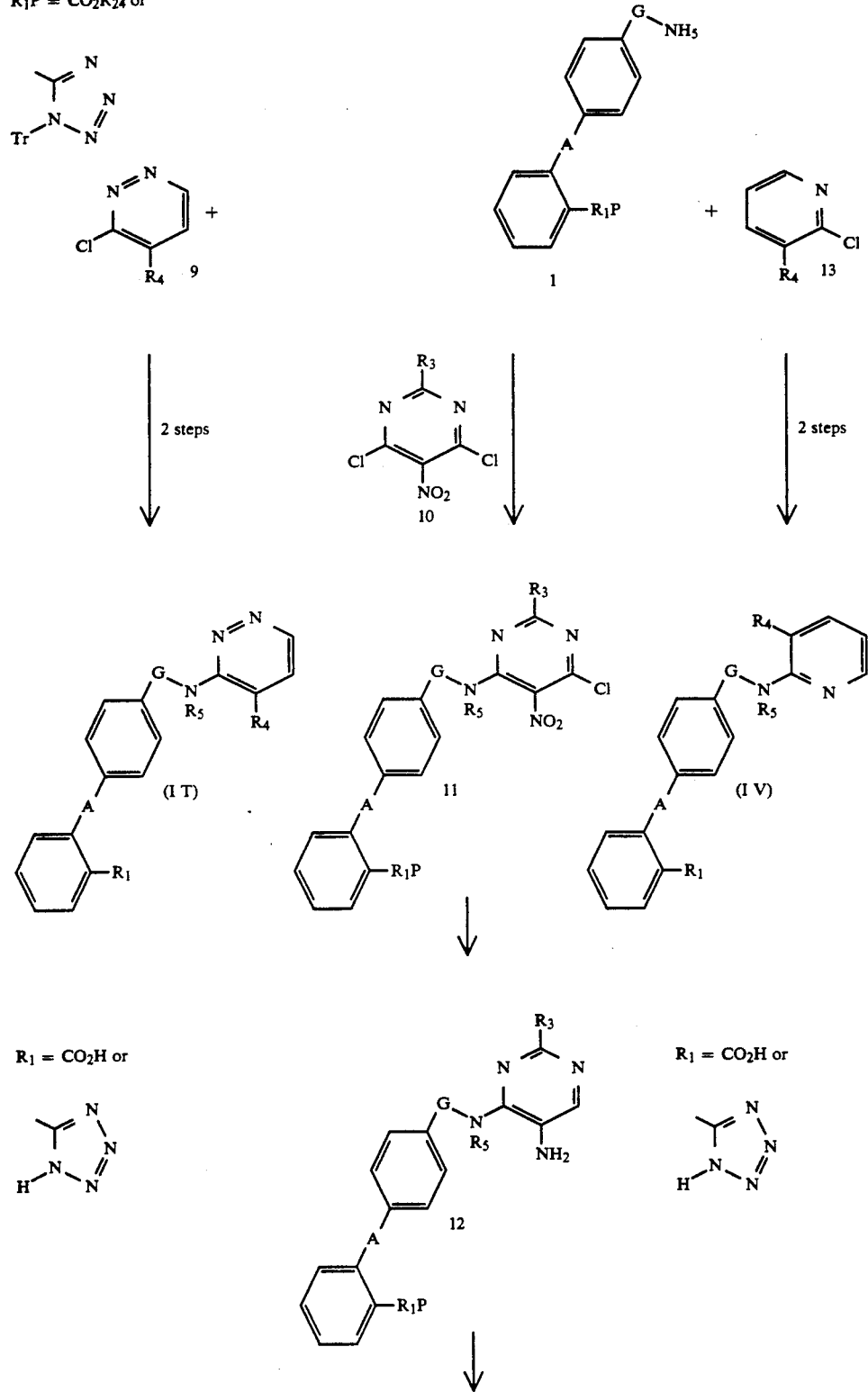

Scheme I J -continued

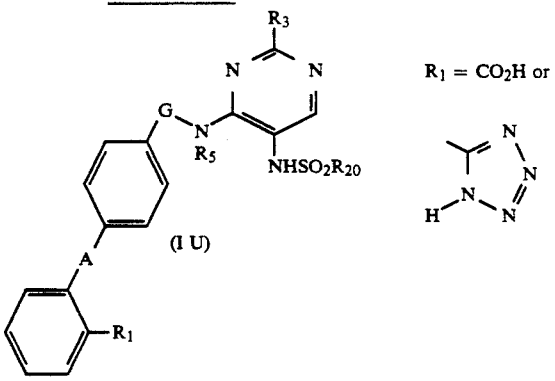

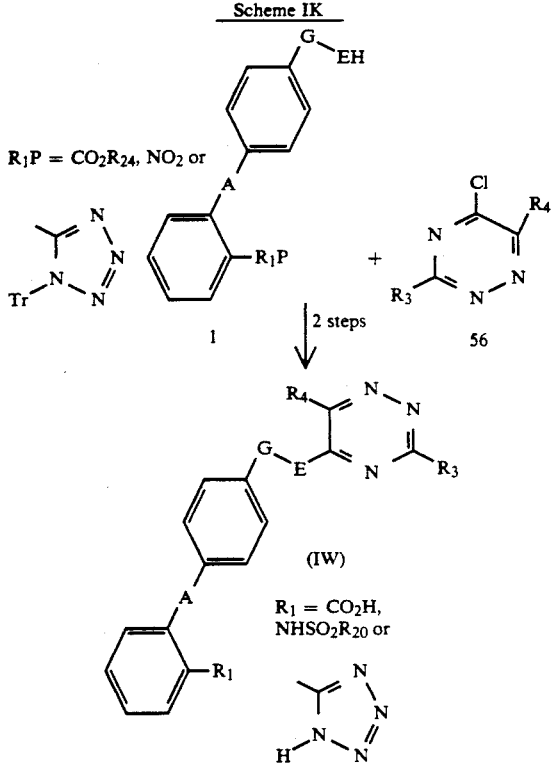

BIPHENYL AND RELATED INTERMEDIATES

Scheme II

According to reaction Scheme II, a compound of Formula 14 is treated with an azide salt such as sodium azide in a polar solvent such as DMF or under phase transfer conditions to afford the corresponding azidomethylbiphenyl compound of Formula 15. The reduction of the azide by standard methods (for example, with LiAlH$_4$) affords an aminomethyl compound of Formula 1 in which E is NH. Alternatively, treatment of a bromomethyl compound of Formula 14 with a suitable primary amine, for example methylamine, affords an intermediate of Formula 1 in which E is NHR$_5$.

Scheme III

According to reaction Scheme III, a cyano compound of Formula 16 is treated with an azide salt such as sodium azide and triethylamine hydrochloride in a polar solvent, preferably at 150° C. in N-methyl-2-pyrrolidinone, to afford the corresponding tetrazole derivative, followed by protection of the tetrazole by treatment with triphenylmethyl chloride to afford a compound of Formula 17. The nitro compound of Formula 17 is then reduced by standard methods (for example catalytic hydrogenation) to afford the aminobiphenyl compound of Formula 1. Acylation of the amino group by standard methods, followed by reduction of the intermediate amide affords a compound of Formula 1 in which E is NHR$_5$.

Scheme IV

According to reaction Scheme IV, 4-bromobenzylidenemalononitrile is reacted with N-(1-butadienyl)-morpholine to afford the compound of Formula 20. The compound of Formula 20 is treated with an azide salt such as sodium azide and triethylamine hydrochloride in a polar solvent, prferably at 150° C. in N-methyl-2-pyrrolidinone, to afford the corresponding terazole derivative, followed by protection of the tetrazole by treatment with triphenylmethyl chloride to afford a compound of Formula 21. The bromo compound of Formula 21 is converted to the corresponding lithio compound which is then treated with tetraisopropylthiuram disulfide to afford the compound of Formula 22. The compound of Formula 22 is converted to the intermediate of Formula 1 by hydrolysis of the thiocarbamate using for example ethanolic potassium hydroxide.

Scheme V

According to reaction Scheme V, 4-acetoxybenzylidenemalononitrile is reacted with N-(1-butadienyl)-morpholine to afford the compound of Formula 24. The compound of Formula 24 is treated with an azide salt such as sodium azide and triethylamine hydrochloride in a polar solvent, preferably at 150° C. in N-methyl-2-pyrrolidinone, to afford the corresponding terazole derivative, followed by protection of the tetrazole by treatment with triphenylmethyl chloride to afford a compound of Formula 25. The acetoxy compound of Formula 25 is converted to the intermediate of Formula 1 by hydrolysis of the acetoxy group using for example methanolic lithium hydroxide.

Scheme VI

According to reaction Scheme VI, a compound of Formula 4 is treated with potassium acetate to afford a compound of Formula 26. The compound of Formula 26 is, in turn, converted to an intermediate of Formula 1 by hydrolysis of the acetyl group using standard methods. Alternatively, the compound of Formula 4 is treated with potassium thioacetate to afford the compound of Formula 27. The compound of Formula 27 is, in turn, converted to an intermediate of Formula 1 by hydrolysis of the acetyl group using standard methods.

Scheme VII

According to reaction Scheme VII, a compound of Formula 28 is treated sequentially with a chlorinating agent (for example phosphorus trichloride, thionyl chloride or oxalyl chloride), ammonia and a dehydrating agent, preferably thionyl chloride, to afford the nitrile of Formula 29. The nitrile is converted to the coresponding tetrazole by treatment with an azide salt such as sodium azide and triethylamine hydrochloride, preferably at 150° C. in N-methyl-2-pyrrolidinone, and the tetrazole is protected by treatment with triphenylmethyl chloride to afford the compound of Formula 30. The compound of Formula 30 is converted to the compound of Formula 31 by bromination under conditions suitable for selective bromination of the benzylic position. The bromine atom is displaced with sodium azide to afford the compound of Formula 32. The azido compound of Formula 32 is then reduced using standard methods (for example catalytic hydrogenation) to afford the intermediate of Formula 1.

Alternatively, a compound of Formula 28 is esterified by standard methods to afford a compound of Formula 33 which is, in turn, converted to the corresponding azidomethyl compound by the procedures outlined above for the conversion of a compound of Formula 30 to a compound of Formula 32. The azidomethyl compound is reduced using standard methods to afford the intermediate of Formula 1 ($R_1$ is $COOR_{24}$).

Scheme VIII

According to reaction Scheme VIII, the nitrile of Formula 34 is converted to the corresponding tetrazole by treatment with an azide salt such as sodium azide and triethylamine hydrochloride, preferably at 150° C. in N-methyl-2-pyrrolidinone, and the tetrazole is protected by treatment with triphenylmethyl chloride to afford the compound of Formula 35. The compound of Formula 35 is converted to the compound of Formula 36 by bromination under conditions suitable for selective bromination of the benzylic position. The bromine atom is displaced with sodium azide to afford the compound of Formula 37. The azido compound of Formula 37 is then reduced using standard methods (for example catalytic hydrogenation) to afford the intermediate of Formula 1.

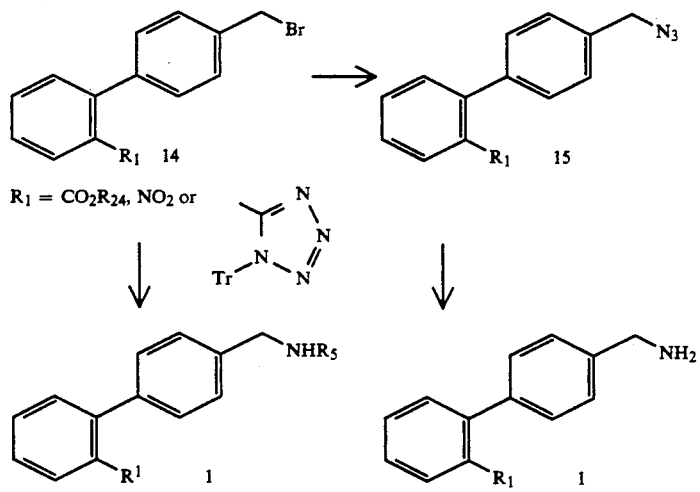

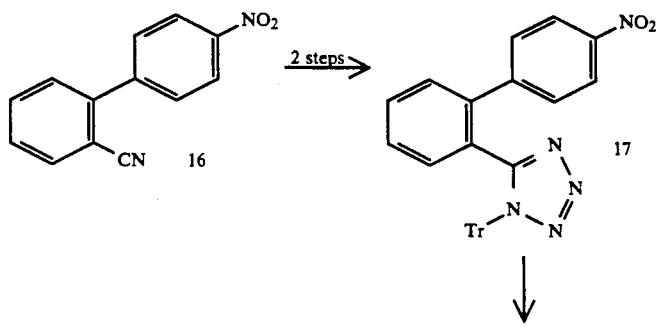

-continued
Scheme III
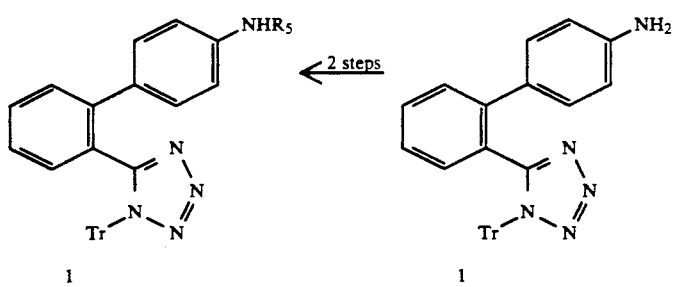
Scheme IV
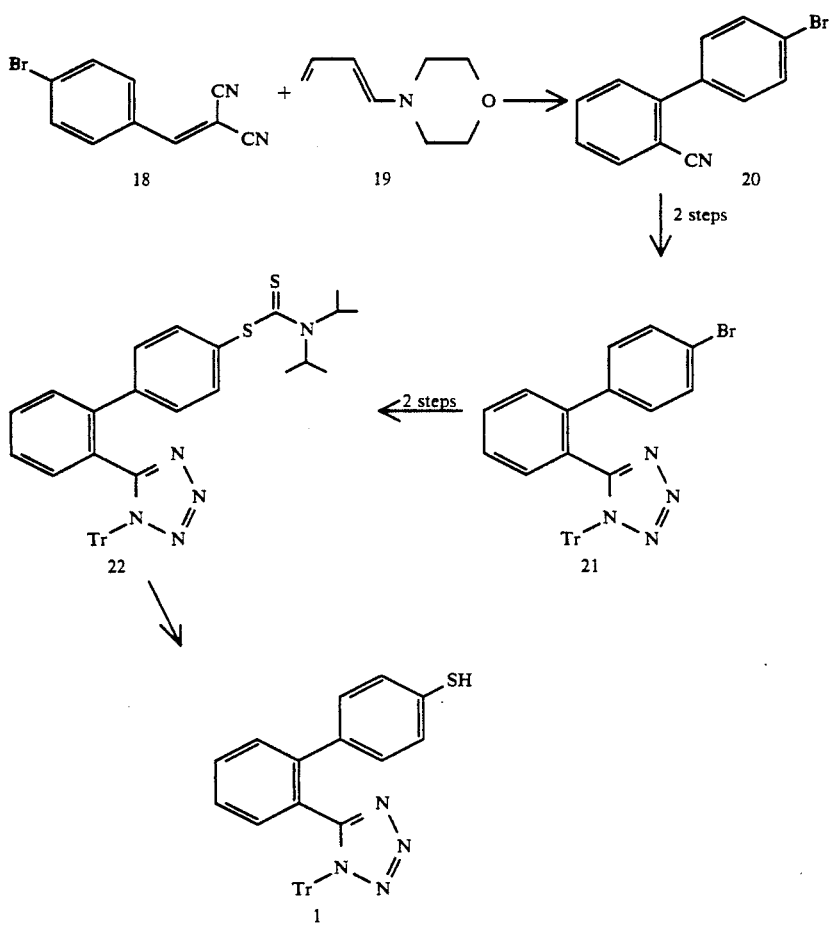
Scheme V
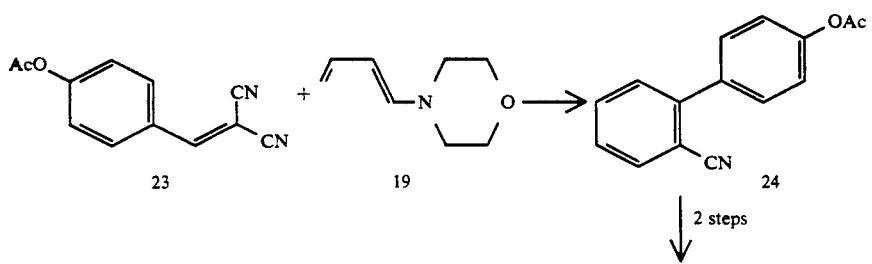

-continued
Scheme V
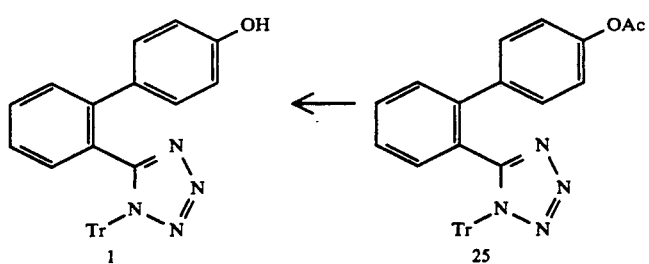
Scheme VI
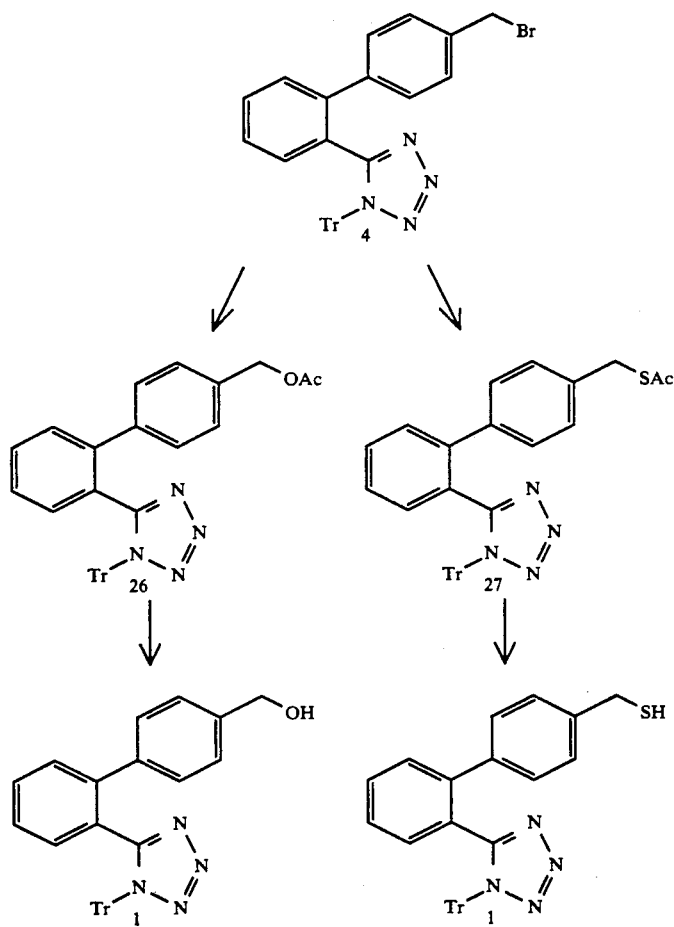
Scheme VII
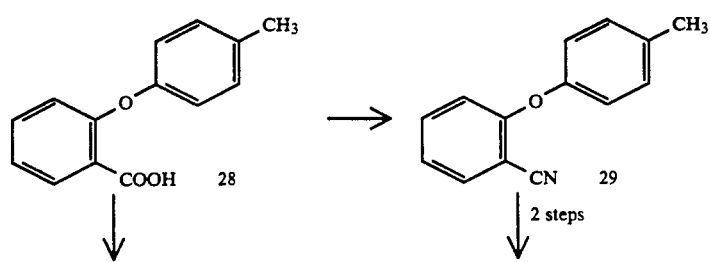

Scheme VII
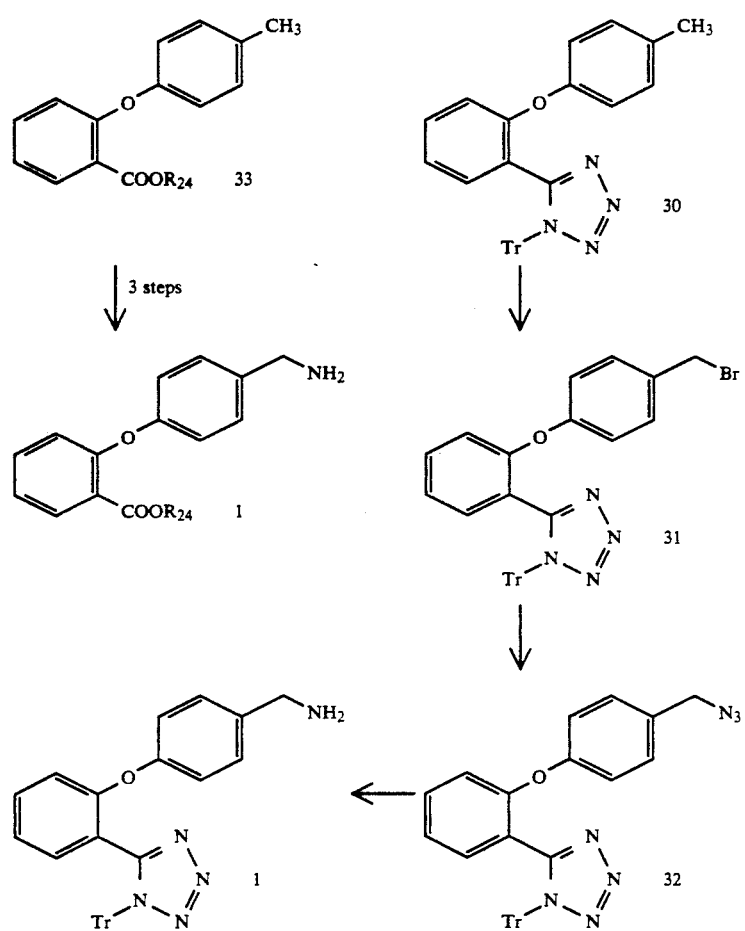
Scheme VIII
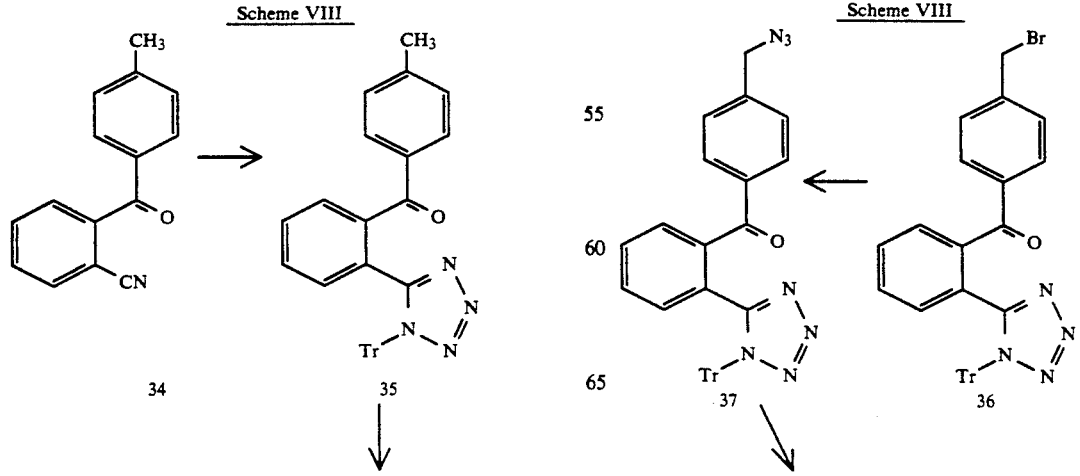

-continued
Scheme VIII

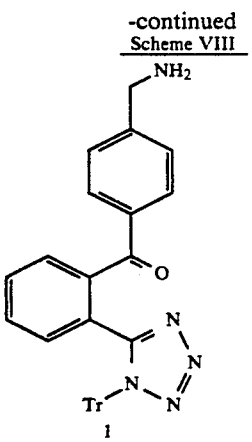

HETEROCYCLIC INTERMEDIATES

Scheme IX

According to reaction Scheme IX, a nitrile of Formula 38 is treated with ethanol and hydrochloric acid to afford a compound of Formula 39 which, in turn, is treated with ammonia to afford the amidine of Formula 40. The amidine of Formula 40 is then condensed with the ethoxymethylene malonate diester of Formula 41 to afford a hydroxy-pyrimidine of Formula 42. The compound of Formula 42 is treated with a chlorinating agent, for example phosphorous oxychloride, to afford the intermediate of Formula 2 in which $R_4$ is a carboxylic ester.

Scheme X

According to reaction Scheme X, the amidine of Formula 40 is condensed with ethoxymethylene malonate derivative of Formula 43 to afford a hydroxy-pyrimidine of Formula 44. The compound of Formula 44 is treated with a chlorinating agent, for example phosphorous oxychloride, to afford the intermediate of Formula 2 in which $R_4$ is a cyano group.

Scheme XI

According to reaction Scheme XI, an amidine of Formula 40 is condensed with a malonate diester in the presence of a suitable base, preferably sodium ethoxide, to afford the pyrimidine compound of Formula 45. A compound of Formula 45 is nitrated by standard methods to afford a compound of Formula 46. The compound of Formula 46 is converted to the intermediate of Formula 10 by treatment with a suitable chlorinating agent, for example phosphorous oxychloride.

Scheme XII

According to reaction Scheme XII, a ketoester of Formula 47 is condensed with urea to afford a pyrimidine compound of Formula 48. The compound of Formula 48 is converted to the intermediate of Formula 5 by treatment with a suitable chlorinating agent, for example phosphorous oxychloride.

Scheme XIII

According to reaction Scheme XIII, a ketoester of Formula 47 is condensed with triazine in the presence of a suitable base such as sodium ethoxide, to afford the pyridine compound of Formula 49. The compound of Formula 49 is converted to the intermediate of Formula 7 by treatment with a suitable chlorinating agent, for example phosphorous oxychloride.

Scheme XIV

According to reaction Scheme XIV, an α-keto aldehyde of Formula 50 is condensed with aminomalonamide to afford a pyrazine compound of Formula 51. The compound of Formula 51 is converted to the intermediate of Formula 8 by hydrolysis to the corresponding acid using standard methods, for example using aqueous sodium hydroxide, followed by esterification of the acid and treatment with a suitable chlorinating agent, for example phosphorous oxychloride.

Scheme XV

According to reaction Scheme XV, a compound of Formula 39 is condensed with formic hydrazide to afford a compound of Formula 52. A compound of Formula 52 is, in turn, treated with a suitable acid such as hydrochloric acid to afford a compound of Formula 53. A compound of Formula 53 is then condensed with a keto malonic ester of Formula 54 to afford an hydroxy triazine of Formula 55. The compound of Formula 55 is converted to the intermediate of Formula 56 by treatment with a suitable chlorinating agent, for example phosphorous oxychloride.

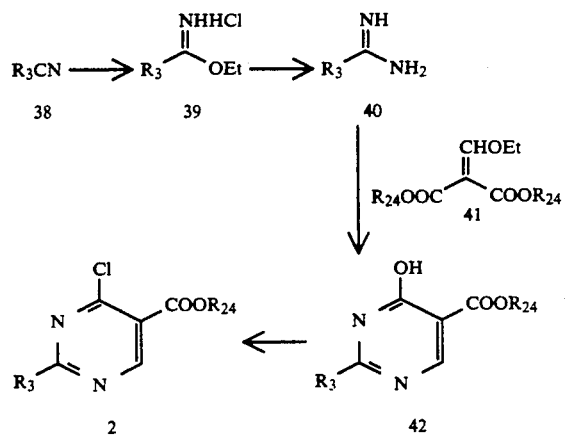

Scheme IX

Scheme X

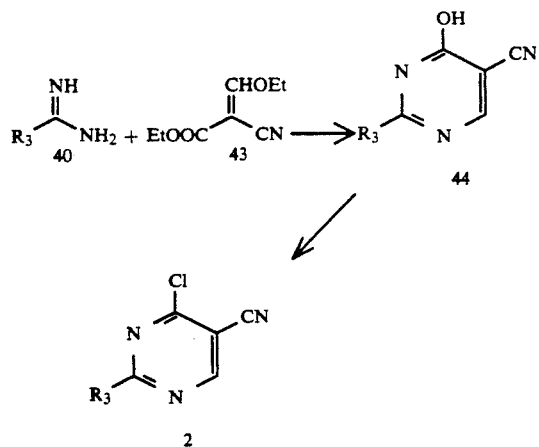
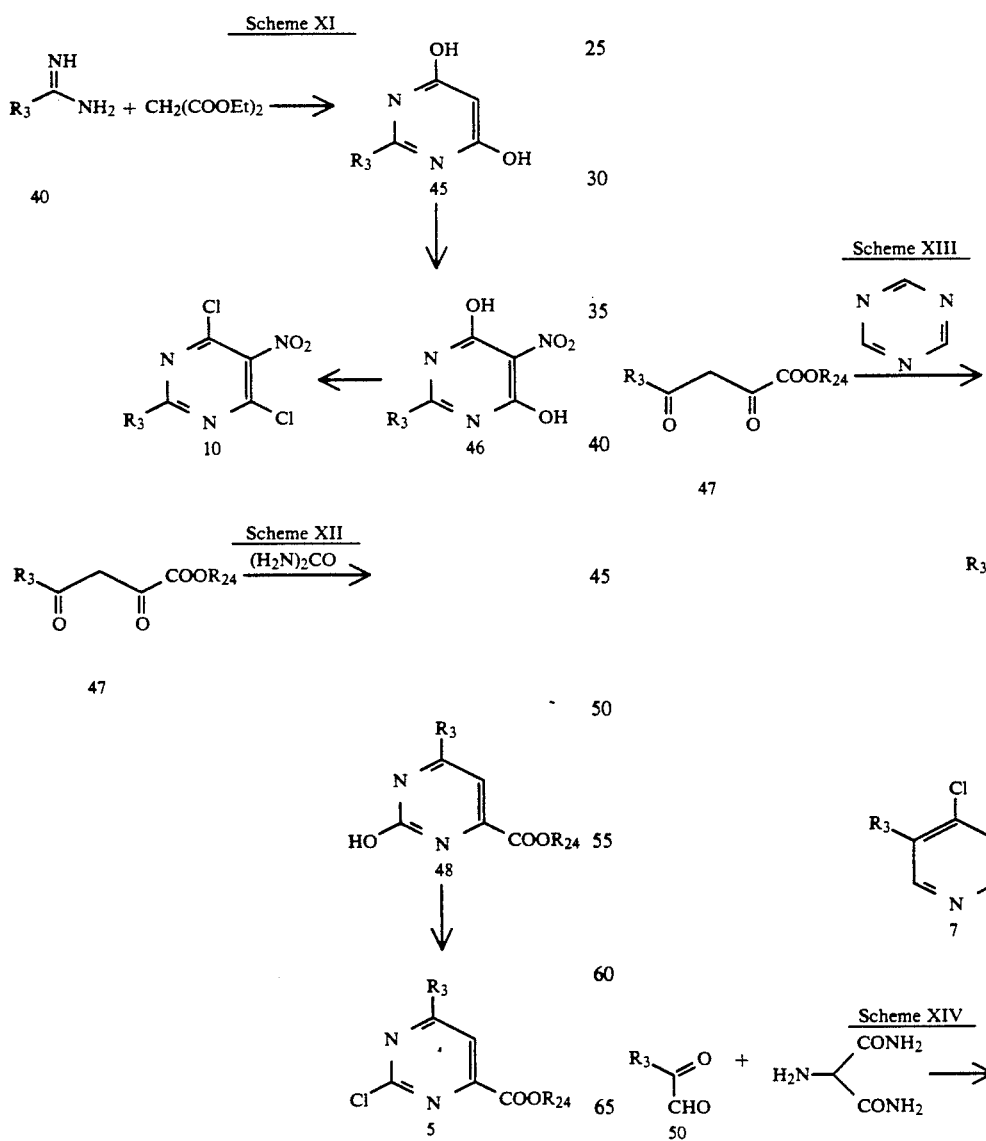

-continued
Scheme XIV

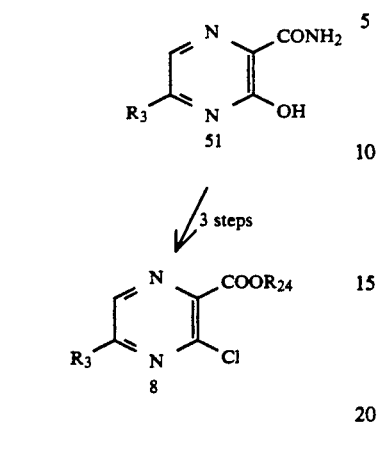

Scheme XV

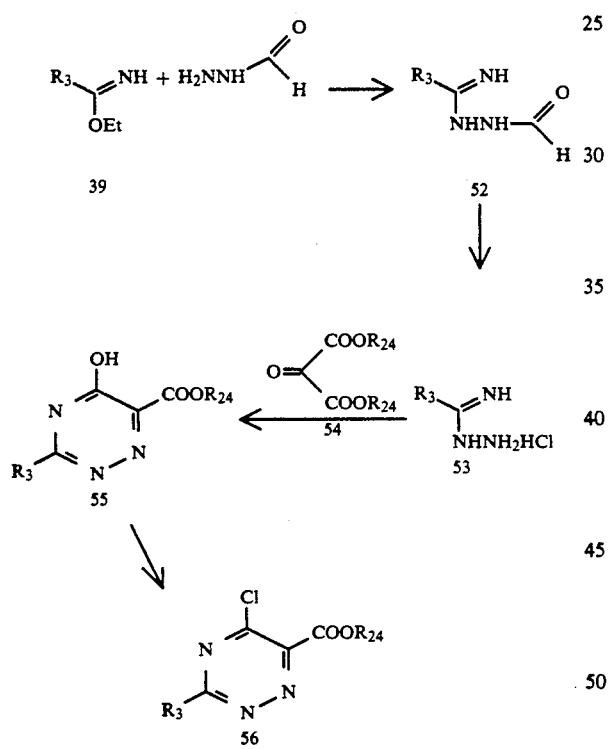

SCHEME XVI

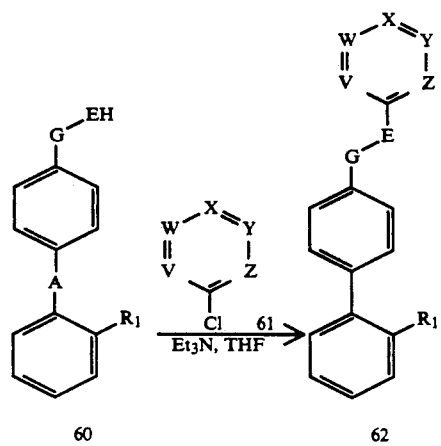

SCHEME XVII

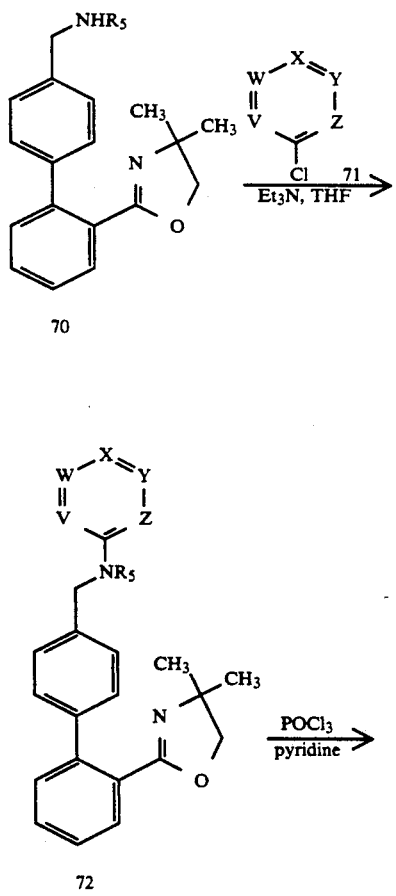

A general process for the preparation of the compounds of the invention is illustrated in Scheme XVI. Reaction of 60 with aryl chloride 61 provides 62.

An alternative process for the preparation of the compounds of the invention wherein R₁ is tetrazolyl is illustrated in Scheme XVII. Amine 70 is reacted with aryl chloride 71 to provide 72. Reaction of 72 with POCl₃ gives nitrile 72, which can be converted to tetrazole 73.

-continued
SCHEME XVII

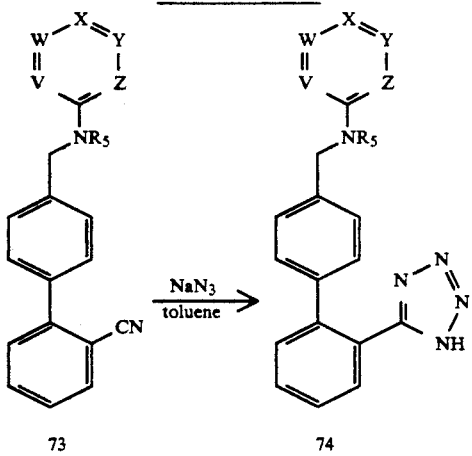

Schemes XVIII–XXXII illustrate methods of preparing compounds of the invention comprising various —G—E— substituents.

Scheme XVIII

Reaction Scheme XVIII illustrates a method of preparing compounds wherein —G—E— is —N($R_5$)—. According Scheme XVIII, a biphenylamine of Formula 82 is alkylated under standard conditions (e.g., $R_5$—X' wherein X' is a leaving group) and then reacted with a chloro-heterocycle to give a compound of Formula 81.

Scheme XIX

According to Scheme XIX, compounds wherein —G—E— is —O— are prepared by coupling a hydroxy-substituted heterocycle with a bromo-biphenyl compound of Formula 80 in the presence of a copper salt to give a compound of Formula 83.

Scheme XX

Reaction Scheme XX illustrates a method of preparing compounds wherein —G—E— is —S—. According to Scheme XX, a biphenyl thiol of Formula 85 is reacted with a chloro-heterocycle to give a compound of Formula 84.

Scheme XXI

Reaction Schemes XXIA and XXIB illustrate alternative methods of preparing compounds wherein —G—E— is —$CH_2$—N($R_5$)—. According to Scheme XXIA, a biphenylmethylamine of the Formula 86 is reacted with a chloroheterocycle in the presence of a base, such as triethylamine or lithium hexamethyldisilazide, to give a compound of Formula 87. Alternatively, according to Scheme XXIB, a chloro-heterocycle is reacted with a primary amine to give a compound of Formula 88. This secondary amine is reacted with a biphenylmethyl bromide 89 to give a compound of Formula 87.

Scheme XXII

According to Scheme XXII, compounds wherein —G—E— is —CH($R_5$)—NH— are prepared by oxidizing a compound of Formula 90, whose preparation is illustrated in Scheme VI, to aldehyde 91. Addition of an organometallic reagent (e.g., $R_5$—M is propyl-Grignard reagent, yields secondary alcohol 92. The alcohol is converted to a leaving group (e.g., X' is a mesylate) which is displaced with a heterocyclic amine to afford a compound of Formula 94.

Scheme XXIII

Reaction Schemes XXIIIA and XXIIIB illustrate alternative methods of preparing compounds wherein —G—E— is —CH($R_5$)—O—. According to Scheme XXIIIA, a compound of Formula 93 having a leaving group X', e.g., mesylate, is reacted with a hydroxy-substituted heterocyclic in the presence of a base to give a compound of Formula 95. Alternatively, according to Scheme XXIIIB, secondary alcohol 92, whose preparation is illustrated in Scheme XXII, is reacted with a chloro-heterocycle in the presence of a base to give a compound of Formula 95.

Scheme XXIV

According to Scheme XXIV, compounds wherein —G—E— is —CH($R_5$)—S— are prepared by reacting a compound of Formula 93, whose preparation is illustrated in Scheme XXII, with a thiol-substituted heterocycle in the presence of a base to give a compound of Formula 96.

Scheme XXV

According to Scheme XXV, compounds wherein —G—E— is —$CH_2$—CH($R_5$)— are prepared by reacting a heterocyclic aldehyde of Formula 97 with a Wittig reagent ($CH_2$=P(Ph)$_3$) to yield vinyl-heterocycle 98. Olefin epoxidation with m-chloroperoxybenzoic acid affords epoxide 99. Epoxide 99 is opened with a Grignard reagent 100 prepared from the corresponding biphenylbromide. The resulting alcohol 101 is oxidized (e.g., Swern oxidation) to afford ketone 102. The ketone is reacted with the desired Wittig reagent (e.g., Pr—P(Ph)$_3$) to give an intermediate olefin which is reduced with hydrogen in the presence of a catalyst (e.g., platinum or palladium) to afford a compound of Formula 103.

Scheme XXVI

According to Scheme XXVI, compounds wherein —G—E— is —CH($R_5$)—$CH_2$— are prepared by converting a biphenyl aldehyde of the Formula 91 to a halo-alkylated compound of the Formula 93A (X' is halogen). Compound 93A is converted into Wittig reagent 110 using triphenylphosphine and a suitable base. This Wittig reagent is reacted with heterocyclic aldehyde 97 to give a compound of the Formula 111. This olefin is reduced with hydrogen in the presence of a catalyst such as platinum or palladium to give a compound of the Formula 112.

Scheme XXVII

According to Scheme XXVII, compounds wherein —G—E— is —N($R_5$)—$CH_2$— are prepared by alkyalting amine 82 with R5Cl in the presence of a base. The resulting amine 82a is reductively aminated with aldehyde 97 to give a compound of the Formula 114.

Scheme XXVIII

According to Scheme XXVIII, compounds wherein —G—E— is —NH—CH($R_5$)— are prepared by reacting a heterocyclic nitrile 115 with an alkyl Grignard reagent (e.g., propylmagnesium bromide) and then hydrolyzing the intermediate imine to give a ketone of the Formula 116. Reductive amination with a biphenylamine 82 yields a compound of the Formula 117.

Scheme XXIX

According to Scheme XXIX, compounds wherein —G—E— is —O—CH($R_5$)— are prepared by reacting a heterocyclic aldehyde with an organometallic reagent (e.g., $R_5$—M is propylmagnesium bromide) to produce a secondary alcohol of the Formula 120. The alcohol is converted to a leaving group (for example, mesylate) and then is coupled with the biphenyl alcohol in the presence of a base to afford a compound of the Formula 121.

Scheme XXX

According to Scheme XXX, compounds wherein —G—E— is —S—CH($R_5$)— are prepared by converting a secondary alcohol to a leaving group (e.g., X' is mesylate) and then displacing it with biphenyl thiol 85 in the presence of a base to afford a compound of the Formula 123.

Scheme XXXI

According to Scheme XXXI, compounds wherein —G—E— is —NH—N($R_5$)— are prepared by converting a biphenylamine 82 into a urea of the Formula 124. The urea is reacted with bromine in the presence of a base to yield hydrazine 125. Alkylation with an alkyl bromide (e.g., $R_5X'$ is propyl bromide), followed by displacement of a chloro heterocycle with the secondary amine 125, affords a compound of the Formula 126.

Scheme XXXII

According to Scheme XXVIII, compounds wherein —G—E— is —N($R_5$)—NH— are prepared by first converting amine 82a to urea 130. Urea 130 is converted to hydrazine 131 by treatment with bromine in base. Hydrazine 131 is reacted with chloro-heterocycle D-Cl to afford a compound of the Formula 132.

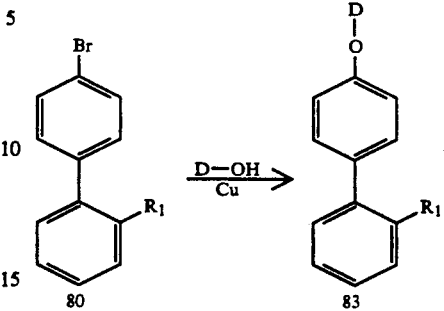

SCHEME XIX

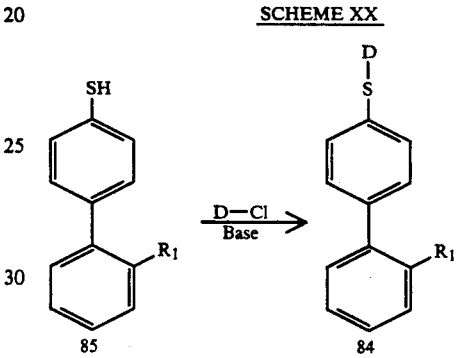

SCHEME XX

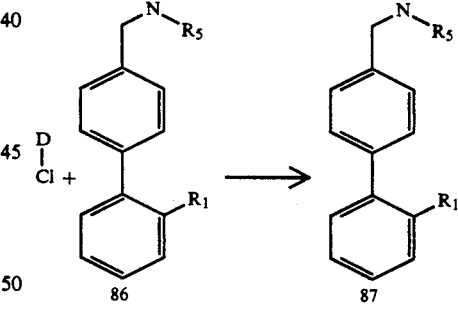

SCHEME XXIA

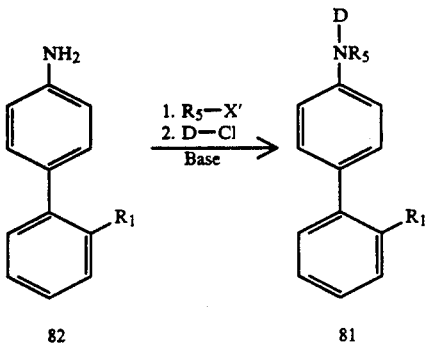

SCHEME XVIII

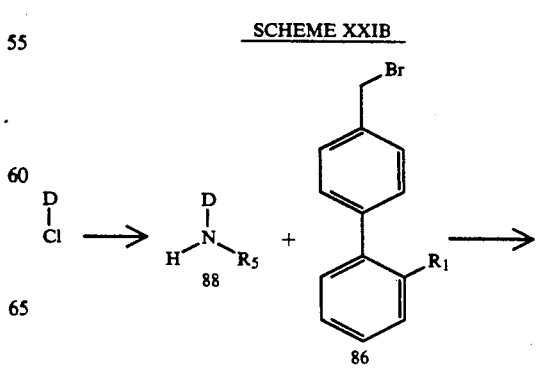

SCHEME XXIB

49
-continued
SCHEME XXIB
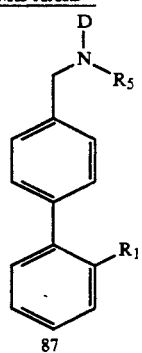
87
SCHEME XXIIIA
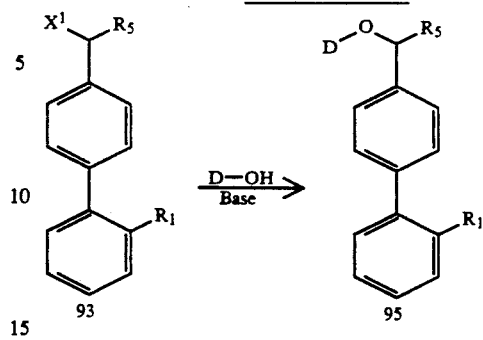
SCHEME XXII
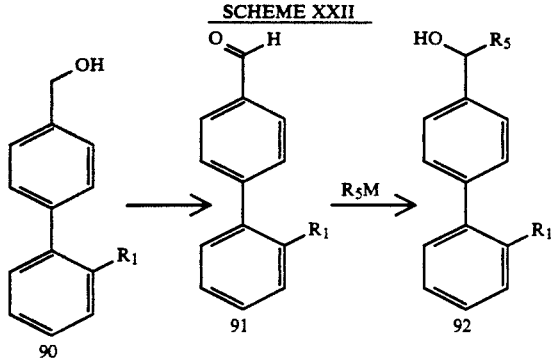
SCHEME XXIIIB
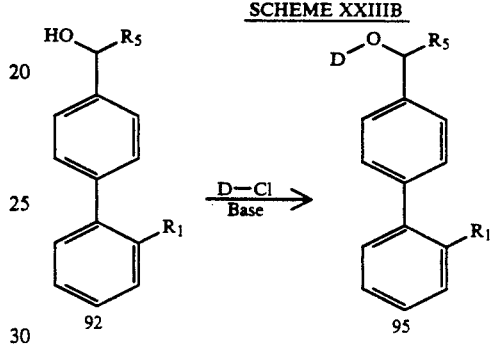
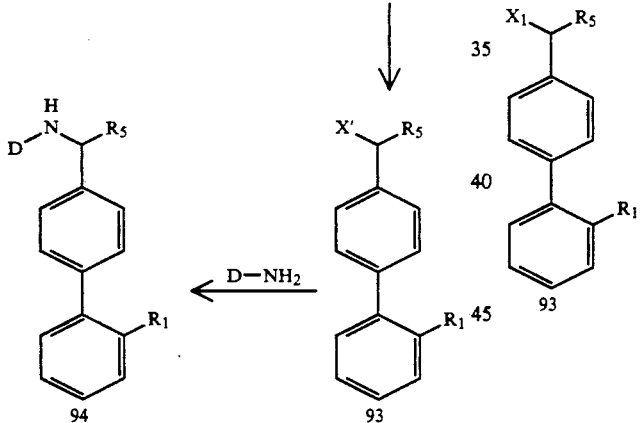
SCHEME XXIV
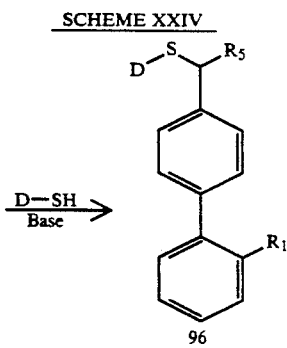
SCHEME XXV
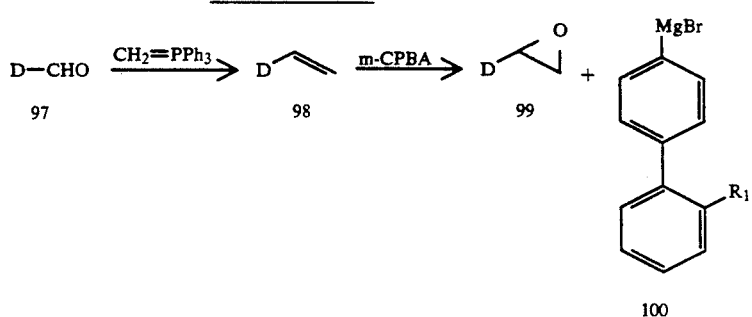

SCHEME XXV
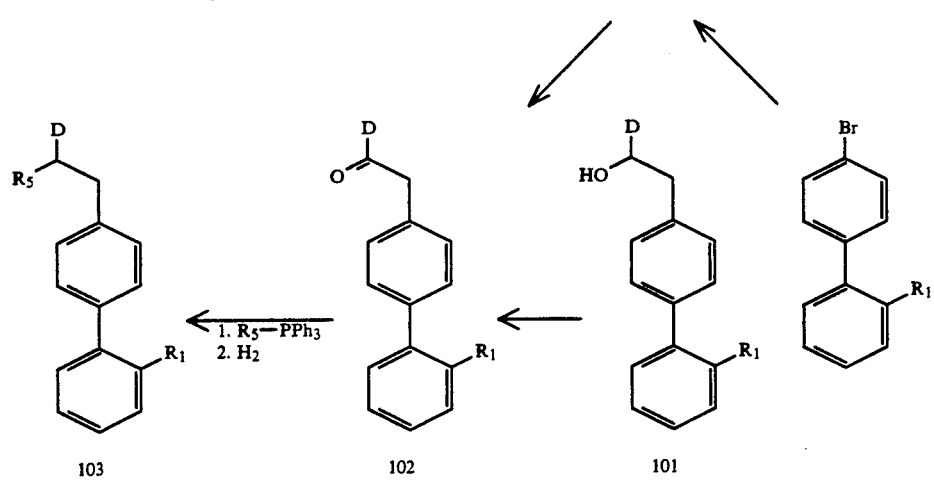
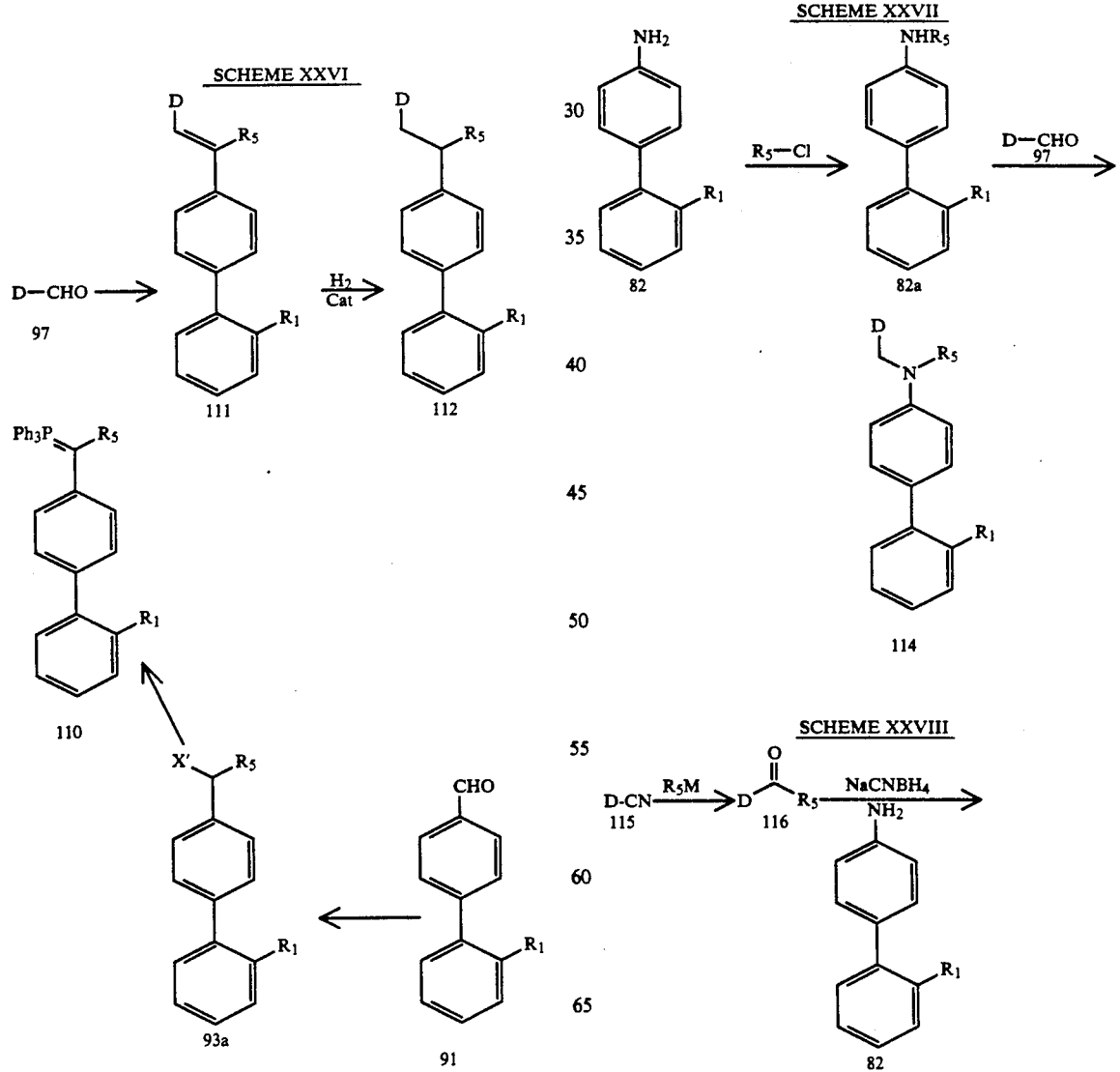

-continued
SCHEME XXVIII
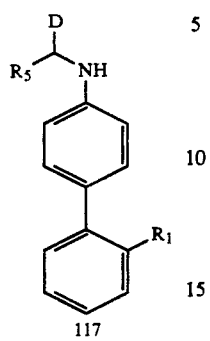
117
SCHEME XXIX
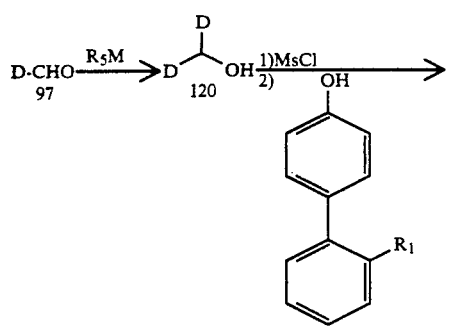
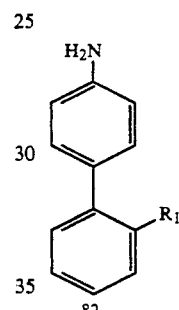
121
SCHEME XXX
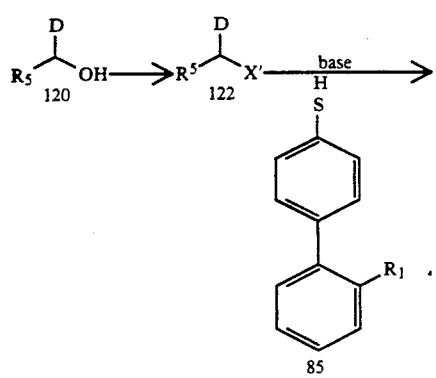
85
-continued
SCHEME XXX
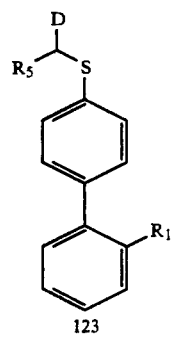
123
SCHEME XXXI
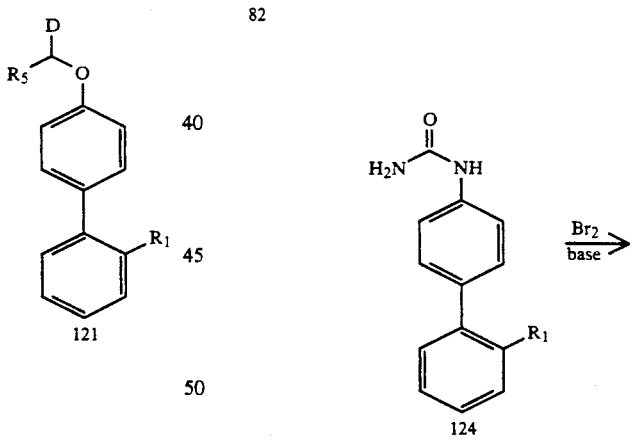
124
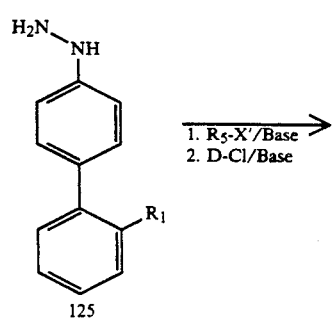
125

-continued
SCHEME XXXI

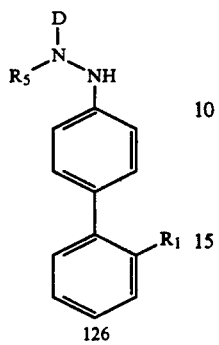

126

SCHEME XXXII

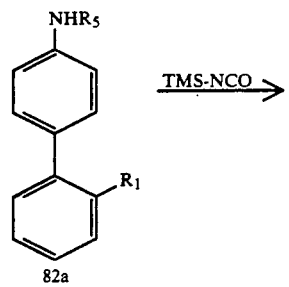

82a

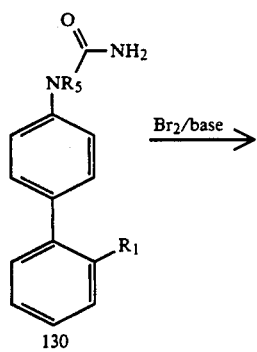

130

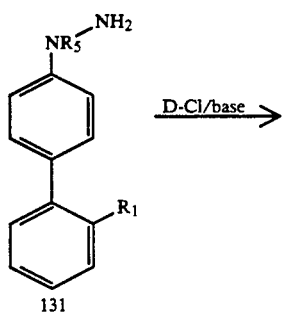

131

-continued
SCHEME XXXII

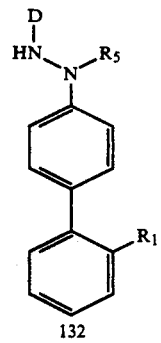

132

Intermediates useful for the preparation of the novel compounds of this invention include a compound of the formula (II):

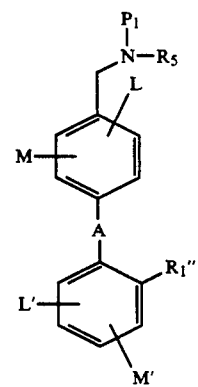

II wherein A, L, L', M, M' and $R_5$ are defined as above; $P_1$ is hydrogen or an N-protecting group; and
$R_1''$ is $R_1$ as defined above, —$NO_2$, —CN, a tetrazolyl group or an N-protected tetrazolyl group wherein the tetrazole is N-protected with a trityl group, a t-butyl group, a benzyl group, a benzyloxymethyl group or a methoxymethyl group.

Preferred intermediates of formula II are those wherein A is a bond; L, L', M and M' are hydrogen; and $R_1''$ is a tetrazolyl group or an N-protected tetrazolyl group.

Other intermediates useful for the preparation of the novel compounds of this invention include a compound of the formula (III):

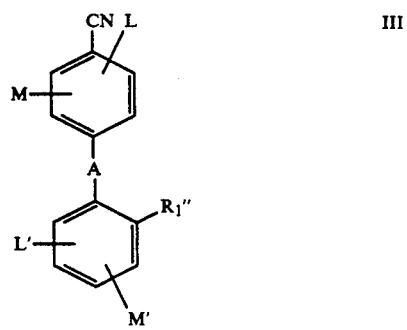

III wherein A, L, L', M and M' are defined as above; and $R_1''$ is $R_1$ as defined above, —$NO_2$, —CN, a tetrazolyl group or an N-protected tetrazolyl group wherein the tetrazole is N-protected with a trityl group, a t-butyl group, a benzyl group, a benzyloxymethyl group or a methoxymethyl group.

Preferred intermediates of formula III are those wherein A is a bond; L, L', M and M' are hydrogen; and $R_1''$ is a tetrazolyl group or an N-protected tetrazolyl group.

The foregoing may be better understood from the following examples, which are presented for the purpose of illustration and not intended to limit the scope of the inventive concept.

EXAMPLE 1

Ethyl 2-n-butyl-4-{N-[(2'-[1H-tetrazol-5-yl]biphenyl-4-yl)methyl]amino}pyrimidine-5-carboxylate

EXAMPLE 1A

N-Triphenylmethyl-5-[2-(4'-azidomethyl-biphenyl)]tetrazole

N-Triphenylmethyl-5-[2-(4'-bromomethyl)biphenyl)-]tetrazole (3.909 g, 7.02 mmol), prepared as described by P. E. Aldrich, et al. in European Patent Application Number 291,969, published Nov. 23, 1988 (Example 6), was dissolved in 11 mL of N,N-dimethylformamide (DMF). Sodium azide (1.16 g, 17.8 mmol) was added and the reaction mixture was stirred for 16 h at ambient temperature. Ice water was added and the resulting precipitate was filtered. The solid was dissolved in chloroform and the chloroform solution was dried over anhydrous sodium sulfate, filtered and concentrated in vacuo. The residue was crystallized from diethyl ether/hexane (2:1) to give 3.24 g (89% yield) of the title compound, m.p. 142°–145° C.

EXAMPLE 1B

N-Triphenylmethyl-5-[2-(4'-aminomethylbiphenyl)]tetrazole

To the compound resulting from Example 1A (1.0 g, 1.93 mmol) dissolved in tetrahydrofuran (14 mL) under nitrogen and cooled in an ice bath was added lithium aluminum hydride (0.173 ). The reaction mixture was stirred for 30 minutes at 0° C. and then quenched with water (0.5 mL) added dropwise followed by 15% sodium hydroxide (0.5 mL). After stirring for 15 minutes, the solids were removed by filtration and washed with tetrahydrofuran. The filtrate was concentrated under reduced pressure to give the title compound as a solid.

EXAMPLE 1C

Ethyl 2-n-butyl-4-{N-[(2'-[N-triphenylmethyl-tetrazol-5-yl]biphenyl-4-yl)methyl]amino}pyrimidine-5-carboxylate The compound resulting from Example 1B was dissolved in 4 mL of THF containing 0.50 g of triethylamine. Ethyl 2-n-butyl-4-chloropyrimidine-5-carboxylate (0.40 g, 1.65 mmol), prepared as described by H. Yamanaka, et al. in *Heterocycles*, 12, 1323–6 (1979), was added and the reaction mixture was stirred at ambient temperature for 1 h. Chloroform was added and the resultant solution was washed with aqueous potassium bicarbonate solution, dried over anhydrous sodium sulfate, filtered and concentrated in vacuo to an oil. The oil was chromatographed on silica gel eluting with 10% ethyl acetate in toluene to give 0.927 g of the title compound after crystallization from diethyl ether, m.p. 116°–118° C.

EXAMPLE 1D

Ethyl 2-n-butyl-4-{N-[(2'-[1H-tetrazol-5-yl]biphenyl-4-yl)methyl]amino}pyrimidine-5-carboxylate The compound resulting from Example 1C (0.25 g, 0.358 mmol) was suspended in 3 mL of ethyl alcohol and three drops of concentrated hydrochloric acid was added. The resultant solution was stirred at ambient temperature for 45 minutes and then concentrated in vacuo. Cold water was added to the residue and the solution was neutralized by the addition of potassium acetate. The aqueous mixture was extracted with chloroform. The chloroform solution was dried over anhydrous sodium sulfate, filtered and concentrated in vacuo. The residue was crystallized from diethyl ether to give 0.123 g (75% yield) of the title compound, m.p. 153°–155° C.; $^1$H NMR (CDCl$_3$) d 0.87 (t, 1H, J=7 Hz), 1.31 (m, 2H), 1.35 (t, 3H, J=7 Hz), 1.62 (m, 2H), 2.51 (t, 2H, J=7 Hz), 3.48 (q, 2H, J=7 Hz), 4.30 (q, 2H, J=7 Hz), 4.81 (d, 1H, J=6 Hz), 7.00 (d, 2H, J=9 Hz), 7.20 (d, 2H, J=9 Hz), 7.40 (dd, 1H), 7.57 (m, 3H), 8.00 (dd, 1H), 8.34 (s, 1H), 8.65 (t, 1H, J=6 Hz).

EXAMPLE 2

2-n-Butyl-5-hydroxymethyl-4-{N-[(2-[1H-tetrazol-5-yl]biphenyl-4-yl)methyl]amino}pyrimidine hydrochloride

EXAMPLE 2A 2-n-Butyl-5-hydroxymethyl-4-{N-[(2-[N-triphenylmethyl-tetrazol-5-yl]biphenyl-4-yl)methyl]amino} pyrimidine The compound resulting from Example 1C (1.0 g, 1.43 mmol) was dissolved in 15 mL of dry THF. The resultant solution was cooled in an ice bath and 0.22 g (5.79 mmol) of lithium aluminum hydride was added to the cooled solution under a nitrogen atmosphere. After 45 minutes 50 mL of THF was added, followed by the dropwise addition of 0.8 mL of water and 0.5 mL of 15% aqueous sodium hydroxide solution. After stirring the mixture for 15 minutes, the solids were filtered and the filtrate was concentrated in vacuo. The residue was taken up in chloroform and the solution was washed with dilute aqueous potassium hydroxide solution, dried over anhydrous sodium sulfate, filtered and concentrated in vacuo. The residue was crystallized from diethyl ether to give 0.686 g (73% yield) of the title compound, m.p. 126°–129° C.

EXAMPLE 2B 2-n-Butyl-5-hydroxymethyl-4{N-[(2-[(1H-tetrazol-5-yl]biphenyl-4-yl)methyl]amino}pyrimidine hydrochloride The compound resulting from Example 2A (0.184 g, 0.28 mmol) was suspended in 2.5 mL of ethyl alcohol and four drops of a concentrated solution of hydrogen chloride in isopropyl alcohol was added. The resultant solution was stirred at ambient temperature for 45 minutes and then concentrated in vacuo. The residue was crystallized from isopropylalcohol/diethyl ether to give 118 mg (93% yield) of the title compound as crystals, m.p. 215°–216° C.; $^1$H NMR (CD$_3$OD)d0.92 (t, 3H, J=7 Hz), 1.37 (m, 2H), 1.74 (m, 2H), 2.80 (t, 2H, J=7

Hz), 4.55 (s, 2H), 4.82 (s, 2H), 7.10 (d, 2H, J=7 Hz), 7.32 (d, 2H, J=7 Hz), 7.50–7.70 (m, 4H), 8.00 (s, 1H).

EXAMPLE 3

Ethyl 2-n-propyl-4-{N-[(2'-(1H-tetrazol-5-yl)biphenyl-4-yl}methyl]amino}pyrimidine-5-carboxylate

EXAMPLE 3A

Ethyl 2-n-propyl-4-{N-[(2'-(N-triphenylmethyl-1H-tetrazol-5-yl)biphenyl-4-yl}methyl]amino}pyrimidine-5-carboxylate The compound resulting from Example 1B (4.70 g, 9.53 mmol) and ethyl 2-n-propyl-4-chloropyrimidine-5-carboxylate, prepared as described by H. Yamanaka et al in *Heterocycles*, 12, 1323 (1979), were reacted by the method described in Example 1C to give the title compound (4.71 g). m.p. 132°–133° C.

EXAMPLE 3B

Ethyl 2-n-propyl-4-{N-[(2'-(1H-tetrazol-5-yl)biphenyl-4-yl}methyl]amino}pyrimidine-5-carboxylate By the procedure described in Example 1D, the compound resulting from Example 3A (400 mg, 0.584 mmol) was treated with hydrochloric acid in ethanol to give the title compound (175 mg). m.p. 146°–147° C. $^1$H NMR (CDCl$_3$, 300 MHz) d 0.90 (t, J=7 Hz, 3H), 1.33 (t, J=7 Hz, 3H), 1.58 (m, 2H), 2.49 (t, J=7 Hz, 2H), 4.30 (q, J=7 Hz, 2H), 4.81 (d, J=6 Hz, 2H), 7.00 (d, J=9 Hz, 2H), 7.20 (d, J=9 Hz, 2H), 7.40 (dd, 1H), 7.57 (m, 3H), 8.00 (dd, 1H), 8.34 (s, 1H), 8.65 (t, J=6 Hz, 1H).

EXAMPLE 4

Ethyl 2-n-pentyl-4-{N-[(2'-(1H-tetrazol-5-yl)biphenyl-4-yl}methyl]amino}pyrimidine-5-carboxylate

EXAMPLE 4A

Ethyl 2-n-Pentyl-4-hydroxy-pyrimidine-5-carboxylate

Hexanecarboxamidine hydrochloride (22.36 g, 0.148 mol) and diethyl ethoxymethylene malonate (31.08 g, 0.143 mol) were dissolved in ethanol (70 mL) in an ice bath. A solution of sodium ethoxide, prepared from dissolving sodium (6.65 g, 0.289 mol) in ethanol (120 mL), was added slowly. The resulting solution was heated at reflux for 2 hours and then concentrated in vacuo. Ether and water (50 mL) were added and the resulting sodium salt was removed by filtration and washed with ether. It was suspended in water and acidified with acetic acid to give the title compound (19.69 g). m.p. 127°–129° C. after crystallization from chloroform/ether.

EXAMPLE 4B

Ethyl 2-n-pentyl-4-chloro-pyrimidine-5-carboxylate

To the compound resulting from Example 4A suspended in phosphorus oxychloride (160 mL) was added triethylamine (8.32 g). The reaction mixture was warmed at 45° C. for 30 minutes. The phosphorus oxychloride was removed under reduced pressure, toluene was added and then also removed under reduced pressure. The residue obtained was dissolved in toluene, washed with water and sodium bicarbonate solution, dried over magnesium sulfate and concentrated under reduced pressure. The crude product was chromatographed on silica gel eluting with methylene chloride to give the title compound (18.27g).

EXAMPLE 4C

Ethyl 2-n-pentyl-4-{N-[(2'-(N-triphenylmethyl-1H-tetrazol-5-yl)biphenyl-4-yl}methyl]amino}pyrimidine-5-carboxylate The compound resulting from Example 1B (2.97 g, 6.02 mmol) and the compound resulting from Example 4B 1.05 g) were reacted by the procedure described in Example 1C to give the title compound (1.38 g). m.p. 107°–108° C.

EXAMPLE 4D

Ethyl 2-n-pentyl-4-{N-[(2'-(1H-tetrazol-5-yl)biphenyl-4-yl}methyl]amino}pyrimidine-5-carboxylate The compound resulting from Example 4C (300 mg, 0.421 mmol) was treated with hydrochloric acid in ethanol by the procedure described in Example 1D to give the title compound (130 mg). m.p. 131–132. $^1$H NMR (CDCl$_3$, 300 MHz) d 0.82 (t, J=7 Hz, 3H), 1.25 (m, 4H), 1.35 (t, J=7 Hz, 3H), 1.65 (m, 2H), 2.50 (t, J=7 Hz, 2H), 4.30 (t, J=7 Hz, 2H), 4.80 (d, J=7 Hz, 2H), 7.00 (d, J=8 Hz, 2H), 7.20 (d, J=8 Hz, 2H), 7.40 (dd, 1H), 7.57 (m, 3H), 8.00 (dd, 1H), 8.34 (s, 1H), 8.65 (t, J=6 Hz, 1H).

EXAMPLES 5–10

Following the procedures described in Example 4, replacing hexanenitrile with the appropriate nitrile, the intermediate 4-chloropyrimidine-5-carboxylate compounds are prepared. These intermediates are then reacted, according to the procedures described in Example 1C, with N-triphenylmethyl-5-[2-(4'-aminomethyl-biphenyl]tetrazole and the triphenylmethyl group is removed as described in Example 1D to give the compounds of Examples 5–10 as disclosed below in Table 1.

TABLE 1

| Example No. | Compound name |
|---|---|
| 5 | Ethyl 2-(1-methylbutyl)-4-{N-[(2'-[1H-tetrazol-5-yl]-biphenyl-4-yl)methyl]amino}pyrimidine-5-carboxylate |
| 6 | Ethyl 2-(1,1-dimethylbutyl)-4-{N-[(2'-[1H-tetrazol-5-yl]biphenyl-4-yl)methyl]amino}-pyrimidine-5-carboxylate |
| 7 | Ethyl 2-(3-methylbutyl)-4-{N-[(2'-[1H-tetrazol-5-yl]-biphenyl-4-yl)methyl]amino}pyrimidine-5-carboxylate |
| 8 | Ethyl 2-[(2-(4'fluorophenyl)ethyl]-4-{N-[(2'-[1H-tetrazol-5-yl]biphenyl-4-yl)methyl]-amino}pyrimidine-5-carboxylate |
| 9 | Ethyl 2-(2-ethoxyethyl)-4-{N-[(2'-[1H-tetrazol-5-yl]-biphenyl-4-yl)methyl]amino}pyrimidine-5-carboxylate |
| 10 | Ethyl 2-(2-ethylthioethyl)-4-{N-[(2'-[1H-tetrazol-5-yl]biphenyl-4-yl)methyl]amino}pyrimidine-5-carboxylate |

EXAMPLE 11

2-n-Butyl-4-{N-[(2'-carboxy-biphenyl-4-yl)methyl]amino}-5-carboethoxypyrimidine

EXAMPLE 11A t-Butyl 4'-aminomethyl-biphenyl-2-carboxylate

Following the procedures described in Example 1A, replacing N-triphenylmethyl-5-[2-(4'-bromomethyl)biphenyl)]tetrazole with t-butyl 4'-bromomethyl-biphenyl-2-carboxylate, prepared as described by D. J. Carini, et al. in European Patent Application Number 324,377, published Jul. 19, 1989, the intermediate t-butyl 4'-azidomethyl-biphenyl-2-carboxylate is prepared. The intermediate azidomethyl compound is then hydrogenated as described in Example 1B, using palladium on carbon catalyst instead of Lindlar catalyst, to give the title compound.

EXAMPLE 11B 2-n-Butyl-4-{N-[(2'-carboxy-biphenyl-4-yl)methyl]amino}-5-carboethoxypyrimidine t-Butyl 4'-aminomethyl-biphenyl-2-carboxylate from Example 11A is reacted, by the method described in Example 1C, with ethyl 2-n-butyl-4-chloropyrimidine-5-carboxylate (0.40 g, 1.65 mmol) to give 2-n-butyl-4-{N-[(2'-t-butoxycarbonyl-biphenyl-4-yl)methyl]amino]-5-carboethoxypyrimidine. The t-butyl protecting group is removed by treatment with trifluoroacetic acid in methylene chloride at ambient temperature to afford the title compound.

EXAMPLE 12

Ethyl 2-n-butyl-4-{N-[(2'-[1H-tetrazol-5-yl]biphenyl-4-yl)]amino}pyrimidine-5-carboxylate

EXAMPLE 12A

N-Triphenylmethyl-5-[2-(4'-amino-biphenyl]tetrazole

4'-Nitrobiphenyl-2-carbonitrile, prepared as described by B. Sain and J. S. Sandhu in *J. Organic Chem.*, 55, 2545-6 (1990), is heated with triethylamine hydrochloride and sodium azide in N-methyl-2-pyrrolidone at 150° C. as described by P. R. Bernstein and E. P. Vacek in *Synthesis*, 1133 (1987), to give the intermediate 5-[2-(4'-nitro)biphenyl]tetrazole. This intermediate is treated with triphenylmethyl chloride in methylene chloride to give N-triphenylmethyl-5-[2-(4'-nitro)biphenyl)]tetrazole which is reduced by hydrogenation to give the title compound.

EXAMPLE 12B

Ethyl 2-n-butyl-4-{N-[(2'-[1H-tetrazol-5-yl]biphenyl-4-yl)]amino}pyrimidine-5-carboxylate By the procedures described in Example 1C and 1D, N-triphenylmethyl-5-[2-(4'-amino)biphenyl]tetrazole from Example 1C is reacted, with ethyl 2-n-butyl-4-chloropyrimidine-5-carboxylate and the condensation product is deprotected to afford the title compound.

EXAMPLE 13

Ethyl 2-Butyl-4-{N-methyl-N-(2'-[1H-tetrazol-5-yl]biphenyl-4-yl)]amino}pyrimidine-5-carboxylate

EXAMPLE 13A

N-Triphenylmethyl-5-[2-(4'-methylamino)biphenyl]]tetrazole

The compound resulting from Example 12A, is refluxed with ethyl formate and toluene to give the intermediate N-triphenyl-5-[2-(4'-formylamino)biphenyl]tetrazole. This intermediate is then reduced with lithium aluminum hydride to afford the title copound.

EXAMPLE 13B

Ethyl 2-butyl-4-{N-[methyl, (2'-[1H-tetrazol-5-yl]biphenyl-4-yl)amino}pyrimidine-5-carboxylate By the procedures described in Example 1C and 1D, N-triphenyl-5-[2-(4'-aminomethyl)biphenyl)]tetrazole from Example 13A is reacted with ethyl 2-n-butyl-4-chloropyrimidine-5-carboxylate and the condensation product is deprotected to afford the title compound.

EXAMPLE 14

2-Butyl-4-{N-[(2'-[1H-tetrazol-5-yl]biphenyl-4-yl)methyl]amino}pyrimidine-5-carbonitrile

EXAMPLE 14A

2-Butyl-4-chloropyrimidine-5-carbonitrile

Pentanecarboxamidine and ethyl (ethoxymethylene)cyanoacetate (commercially available from Aldrich Chemical Co.) are reacted according to the method of S. Nishigaki, et. al. in *Chem Pharm. Bull.*, 18, 1003 (1970), to give 2-butyl-4-hydroxypyridine-5-carbonitrile which is then reacted with phosphorous oxychloride, according to the method of A. R. Todd and F. Bergel in *J. Chem. Soc.*, 364- (1937), to give the title compound.

EXAMPLE 14B

2-Butyl-4-{N-[(2'-[1H-tetrazol-5-yl]biphenyl-4-yl)methyl]amino}pyrimidine-5-carbonitrile By the procedures described in Example 1C and 1D, N-tri-phenylmethyl-5-[2-(4'-aminomethyl)biphenyl)-]tetrazole, the product of Example 1B, is reacted with 2-butyl-4-chloropyrimidine-5-carbonitrile and the condensation product is deprotected to give the title compound.

EXAMPLE 15

2-Butyl-4-{N-[(2'-[1H-tetrazol-5-yl]biphenyl-4-yl)methyl]amino}pyrimidine-5-carboxamide 2-Butyl-4-{N-[(2'-[1H-tetrazol-5-yl]biphenyl-4-yl)methyl]amino}pyrimidine-5-carbonitrile, the product of Example 14, is heated in dilute aqueous potassium hydroxide. Neutralization with acetic acid affords the title compound.

EXAMPLE 16

2-Butyl-5-methoxymethyl-4-{N-[(2'-[1H-tetrazol-5yl]-biphenyl-4-yl)methyl]amino}pyrimidine 2-n-Butyl-5-hydroxymethyl-4-{N-[(2-1H-tetrazol-5-yl]biphenyl-4-yl)methyl]amino}pyrimidine hydrochloride, the product of Example 2B, is converted to 2-butyl-5-bromomethyl-4-{N-[(2'-[1H-tetrazol-5- yl]biphenyl-4-yl)methyl]amino}pyrimidine by treatment with hydrogen bromide in acetic acid according to the method of A. Schellenberger and K. Winter in *Z. Physiol. Chem.*, 322, 164 (1960). The bromomethyl intermediate is then converted to the title compound by treatment with sodium methoxide in methanol.

EXAMPLE 17

2-Butyl-4-{N-[(2'-[1H-tetrazol-5-yl]biphenyl-4-yl)methyl]amino}pyrimidine-5-carboxylic acid hydrochloride To a solution of 0.300 g (0.43 mmol) of ethyl 2-n-butyl-4-{N-[(2'-[N-triphenylmethyl-tetrazol-5-yl]biphenyl-4-yl)methyl]amino}pyrimidine-5-carboxylate (0.25 g, 0.358 mmol), the product of Example 1C, in 3 mL of tetrahydrofuran and 2 mL of methanol, was added a solution of 90 mg of lithium hydroxide hydrate in 0.5 mL of water. After 1 h at ambient temperature, 14 drops of concentrated hydrochloric acid was added. After another hour, the solution was concentrated in vacuo and the residue was treated with cold water and diethyl ether. The resultant solid was filtered and then suspended in acetonitrile containing isopropyl alcohol saturated with hydrogen chloride. The resultant solid was collected by filtration to give 0.19 g (95% yield) of the title compound, m.p. 193°–195° C.; $^1$H NMR (CD$_3$OD) d 0.92 (t, 2H, J=7 Hz), 1.38 (m, 2H), 1.75 (m, 2H), 2.51 (t, 2H, J=7 Hz), 4.86 (s, 1H), 7.09 (d, 2H, J=8 Hz), 7.32 (d, 2H, J=8 Hz), 7.50–7.70 (m, 4H), 8.60 (s, 1H).

EXAMPLE 18

Ethyl 2-n-Butyl-4-{N-methyl-N-[(2'-[1H-tetrazol-5-yl]biphenyl-4-yl)methyl]amino}pyrimidine-5-carboxylate

EXAMPLE 18A

N-Triphenylmethyl-5-[2-(4'-methylaminomethyl-biphenyl)]tetrazole

To N-Triphenylmethyl-5-[2-{4'-bromomethyl-biphenyl)]tetrazole (3.00 g, 5.39 mmol), prepared as described by P. E. Aldrich et al in European Patent Application Number 291965, Nov. 23, 1988, dissolved in tetrahydrofuran (75 mL) was added a solution of 40% methylamine in water (35 mL). The resulting solution was stirred at room temperature for 2 hours and then concentrated in vacuo. The residue obtained was dissolved in chloroform, washed with dilute potassium hydroxide solution, dried over potassium carbonate, and concentrated under reduced pressure to give the title compound.

EXAMPLE 18B

Ethyl 2-n-Butyl-4-{N-methyl-N-[(2'-[N-triphenylmethyl-1H-tetrazol-5-yl]biphenyl-4-yl)methyl]amino}pyrimidine-5-carboxylate The product resulting from Example 18A (5.39 mmol) was dissolved in tetrahydrofuran (15 mL) containing triethylamine (2.75 mL). Ethyl 2-n-butyl-4-chloropyrimidine-5-carboxylate (1.31 g, 5.39 mmol), prepared as described by H. Yamanaka et al in *Heterocycles*, 12, 1323 (1979), was added and the solution was stirred at room temperature for 2 hours. The solution was concentrated under reduced pressure and the residue obtained dissolved in toluene, washed with potassium bicarbonate solution, dried over sodium sulfate and concentrated in vacuo. The crude product was chromatographed on silica gel eluting with 8% ethyl acetate in toluene to give the title compound (2.826 g). m.p. 134°–137° C. dec (crystallized from 1:1 ether/heptane).

EXAMPLE 18C

Ethyl 2-n-Butyl-4-{N-methyl-N-[(2'-[1H-tetrazol-5-yl]biphenyl-4-yl)methyl]amino}pyrimidine-5-carboxylate To the compound resulting from Example 18B (330 mg, 0.463 mmol) dissolved in ethanol (4 mL) was added concentrated hydrochloric acid (0.25 mL). The reaction mixture was stirred 1.5 hours at room temperature and then concentrated under reduced pressure. The residue obtained was dissolved in water and treated with potassium acetate until neutral pH was obtained. The mixture was extracted with chloroform and the combined organic extracts dried over sodium sulfate and concentrated in vacuo. Trituration with ether afforded the title compound m.p. 159°–161° C. $^1$H NMR (CDCl$_3$, 300 MHz) d 0.82 (t, J=7 Hz, 3H), 1.22 (m, 2H), 1.31 (t, J=7 Hz, 3H), 1.57 (m, 2H), 2.38 (t, J=7 Hz, 2H), 2.70 (s, 3H), 4.29 (q, J=7 Hz, 2H), 4.93 (s, 2H), 6.95 (d, J=8 Hz, 2H), 7.05 (d, J=8 Hz, 2H), 7.42 (dd, 1H), 7.50–7.65 (m, 2H), 7.92 (dd, 1H), 8.04 (s, 1H).

EXAMPLE 19

Ethyl 2-methyl-4-{N-butyl-N-[(2'-[1H-tetrazol-5-yl]biphenyl-4-yl)methyl]amino}pyrimidine-5-carboxylate

EXAMPLE 19A

N-Triphenylmethyl-5-[2-(4'-butylaminomethyl-biphenyl)]tetrazole

To N-Triphenylmethyl-5-[2-(4'-bromomethyl-biphenyl)]tetrazole (6.00 g, 10.7 mmol), prepared as described by P. E. Aldrich et al. in European Patent Application Number 291,969, published Nov. 23, 1988, dissolved in tetrahydrofuran (55 mL) was added butylamine (40 mL). The reaction mixture was stirred at room temperature for 2 hours and then concentrated in vacuo. The residue obtained was dissolved in chloroform, washed with dilute potassium hydroxide solution, dried over potassium carbonate and concentrated under reduced pressure to afford the title compound.

EXAMPLE 19B

Ethyl 2-methyl-4-{N-butyl-N-[(2'-[N-triphenylmethyl-1H-tetrazol-5-yl]biphenyl-4-yl)methyl]amino}pyrimidine-5-carboxylate The compound resulting from Example 19A (10.7 mmol) was dissolved in tetrahydrofuran (15 mL) containing triethylamine (4.6 mL). A solution of ethyl 2-methyl-4-chloropyrimidine-5-carboxylate (1.94 g, 9.7 mmol), prepared as described by A. W. Spears and H. Tieckelmann in *J. Org. Chem.*, 25, 2137 (1960), dissolved in tetrahydrofuran (2 mL) was added and the reaction mixture stirred at room temperature for 2 hours. The reaction mixture was concentrated under reduced pressure and the residue dissolved in toluene, washed with postassium bicarbonate, dried over sodium sulfate and concentrated under reduced pressure. The crude material was chromatographed on silica gel eluting with 12% ethyl acetate in toluene to afford the title compound (4.97 g), which was crystallized from 1:1 ether/heptane. m.p. 130°-132° C.

EXAMPLE 19C

Ethyl 2-methyl-4-{N-butyl-N-[(2'-[1H-tetrazol-5-yl]biphenyl-4-yl)methyl]amino}pyrimidine-5-carboxylate The compound resulting from Example 19B (3.50 g, 4.91 mmol) was deprotected by the procedure described in Example 18C to give the title compound (2.08 g). m.p. 164°-166° C. $^1$H NMR (CDCl$_3$, 300 MHz) d 0.85 (t, J=7 Hz, 3H), 1.25 (m, 2H), 1.32 (t, J=7 Hz, 3H), 4.30 (q, J=7 Hz, 2H), 1.50 (m, 2H), 2.24 (s, 3H), 3.38 (t, J=7 Hz, 2H), 4.30 (q, J=7 Hz, 2H), 4.73 (s, 2H), 7.00 (m, 4H), 7.42 (dd, J=8 Hz, 1 Hz, 1H), 7.50-7.62 (m, 2H), 7.75 (dd, J=8 Hz, 1 Hz, 1H)., 8.02 (s, 1H).

EXAMPLES 20-22

Following the procedures described in Example 1C and 1D, the intermediates shown in Table 2 are condensed and the condensation products deprotected to give the compounds of Examples 20, 21 and 22 as disclosed below in Table 2. The intermediates are prepared by literature methods.

TABLE 2

Examples 20-22

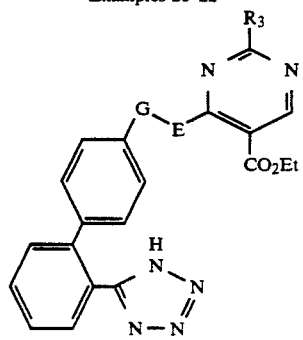

| Example No. | E | R$_3$ | G | Intermediate 1 | Intermediate 2 |
|---|---|---|---|---|---|
| 20 | —S— | -nButyl | — | SH (biphenyl-Tr-tetrazole) | Cl-pyrimidine-CO$_2$Et (nButyl) |
| 21 | —O— | -nButyl | CH$_2$ | —OH (biphenyl-Tr-tetrazole) | Cl-pyrimidine-CO$_2$Et (nButyl) |
| 22 | —O— | -nButyl | — | OH (biphenyl-Tr-tetrazole) | Cl-pyrimidine-CO$_2$Et (nButyl) |

EXAMPLE 23

2-Butyl-5-[N-pyrrolidinylcarbonyl]-4-{N-[(2'-[1H-tetrazol-5-yl]biphenyl-4-yl)methyl]amino}pyrimidine Ethyl 2-butyl-4-{N-[(2'-N-triphenylmethyl-tetrazol-5-yl]biphenyl-4-yl)methyl]amino}pyrimidine-5-carboxylate is hydrolyzed to the corresponding acid as described in Example 17. The lithium hydroxide is neutralized with acetic acid instead of hydrochloric acid to avoid removing the triphenylmethyl protecting group from the tetrazole ring. The carboxylic acid (1 mmol) is dissolved in DMF (10 mL) and the following reagents are sequentially added: N-methylmorpholine (1.1 equivalents), 3-(dimethylaminopropyl)-3-ethyl-carbodiimide hydrochloride (1.1 equivalents), and pyrrolidine (1.1 equivalents). After stirring for 16 h at ambient temperature, the reaction mixture is diluted with ethyl acetate and washed with dilute aqueous sodium bicarbonate solution, dried over anhydrous sodium sulfate, filtered and concentrated in vacuo to give 2-butyl-5-[N-pyrrolidinylcarbonyl]-4-{N-[(2'-[N-triphenylmethyl-tetrazol-5-yl]biphenyl-4-yl)methyl]amino}pyrimidine. The triphenylmethyl group is removed, as described in Step 4 of Example 1, to give the title compound.

EXAMPLES 24–30

Following the procedures of Example 23, replacing pyrrolidine with the appropriate amine (commercially available from Aldrich Chemical Company or readily prepared according to published methods), Examples 24–30 are prepared as disclosed in Table 3.

TABLE 3
Examples 24–30

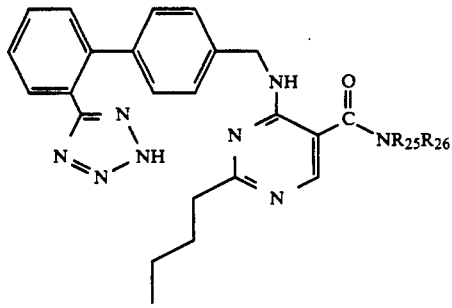

| Example Number | $NR_{25}R_{26}$ |
|---|---|
| 24 | 1-morpholino |
| 25 | 4-methoxymethoxy-1-piperidinyl |
| 26 | —N(CH$_3$)$_2$ |
| 27 | —NHCH$_3$ |
| 28 | —NHCH$_2$CH$_2$OH |
| 29 | —NHCH$_2$CH$_2$OCH$_3$ |
| 30 | —NH(CH$_2$)$_2$O(CH$_2$)$_2$OCH$_3$ |

EXAMPLE 31

2-Butyl-4-{N-[(2'-[1H-tetrazol-5-yl]biphenyl-4-yl)methyl]amino}pyrimidine-5-carboxaldehyde 2-Butyl-5-hydroxymethyl-4-{N-[(2'-[N-triphenylmethyl-tetrazol-5-yl]biphenyl-4-yl)methyl]amino} pyrimidine, the product of Example 2A, is dissolved in methylene chloride. Excess activated manganese dioxide is added and the reaction mixture is stirred at ambient temperature until the reaction is complete according to TLC analysis. The reaction mixture is then filtered and the filtrate is concentrated in vacuo to give the intermediate 2-butyl-4-{N-[(2'-[N-triphenylmethyl-tetrazol-5-yl]biphenyl-4-yl)methyl]amino}pyrimidine-5-carboxaldehyde. The triphenylmethyl group is removed, as described in Example 1D, to give the title compound.

EXAMPLE 32

5-Aminomethyl-2-butyl-4-{N-[(2'-[1H-tetrazol-5-yl]biphenyl-4-yl)methyl]amino}pyrimidine 2-Butyl-4-{N-[(2'-[N-triphenylmethyl-tetrazol-5-yl]biphenyl-4-yl)methyl]amino}pyrimidine-5-carbonitrile, the intermediate in Step 2 of Example 14, is reduced with excess lithium aluminum hydride to afford 5-aminomethyl-2-butyl-4-{N-[(2'-[N-triphenylmethyl-tetrazol-5-yl]biphenyl-4-yl)methyl]amino}pyrimidine. The triphenylmethyl group is removed, as described in Step 4 of Example 1, to give the title compound.

EXAMPLE 33

2-Butyl-5-[methylaminocarbonylaminomethyl]-4-{N-[(2'-H-tetrazol-5-yl]biphenyl-4-yl)methyl]amino} pyrimidine 5-Aminomethyl-2-butyl-4-{N-[(2'-[N-triphenylmethyl-tetrazol-5-yl]biphenyl-4-yl)methyl]amino}pyrimidine, the intermediate from Example 32 is dissolved in THF and treated with one equivalent of methyl isocyanate. Evaporation of the solvent affords 2-butyl-5-[methylaminocarbonylaminomethyl]-4-{N-[(2'-[N-triphenylmethyl-5-yl]biphenyl-4-yl)methyl]amino} pyrimidine. The triphenylmethyl group is removed, as described in Step 4 of Example 1, to give the title compound.

EXAMPLE 34

2-Butyl-5-[acetylaminomethyl]-4-{N-[(2'-[1H-tetrazol-5-yl]biphenyl-4-yl)methyl]amino}pyrimidine 5-Aminomethyl-2-butyl-4-{N-[(2'-[N-triphenylmethyl-tetrazol-5-yl]biphenyl-4-yl)methyl]amino}pyrimidine, the intermediate from Example 32, is dissolved in THF containing 1.1 equivalents of triethyl]amino and was treated with one equivalent of acetyl chloride. After the reaction is complete according to TLC analysis, the reaction mixture is washed with dilute aqueous sodium bicarbonate solution, dried and concentrated in vacuo to give 2-butyl-5-[acetylaminomethyl]-4-{N-[(2'-[N-triphenylmethyl-5-yl]biphenyl-4-yl)methyl]amino} pyrimidine. The triphenylmethyl group is removed, as described in Example 1D, to give the title compound.

EXAMPLE 35

2-Butyl-5-[benzoyloxymethyl]-4-{N-[(2'-[1H-tetrazol-5-yl]biphenyl-4-yl)methyl]amino}pyrimidine 2-n-Butyl-5-hydroxymethyl-4-{N-[(2-[N-triphenylmethyl-tetrazol-5-yl]biphenyl-4-yl)methyl]amino} pyrimidine, the product of Example 2A, is dissolved in chloroform containing triethylamine. One equivalent of benzoyl chloride is added. After the reaction is complete according to TLC analysis, the reaction mixture is washed with dilute aqueous sodium bicarbonate solution, dried and concntrated in vacuo to give 2-butyl-5-[benzoyloxymethyl]-4-{N-[(2'-[N-triphenylmethyl-tetrazol-5-yl]biphenyl-4-yl)methyl]amino}pyrimidine. The triphenylmethyl group is removed, as described in Step 4 of Example 1, to give the title compound.

EXAMPLE 36

2-Butyl-5-[methanesulfonamidomethyl]-4-{N-[(2'-[1H-tetrazol-5-yl]biphenyl-4-yl)methyl]amino}pyrimidine 5-Aminomethyl-2-butyl-4-{N-[(2'-[N-triphenylmethyl-tetrazol-5-yl]biphenyl-4-yl)methyl]amino}pyrimidine, the intermediate from Example 32, is dissolved in THF containing triethylamine and treated with one equivalent of methanesulfonyl chloride. After the reaction is complete according to TLC analysis, the reaction mixture is washed with dilute aqueous sodium bicarbonate solution, dried and concentrated in vacuo to give 2-butyl-5-[methanesulfonamidomethyl]-4-{N-[N-triphenylmethyl-tetrazol-5-yl]biphenyl-4-yl)methyl]amino}pyrimidine. The triphenylmethyl group is removed, as described in Example 1D, to give the title compound.

EXAMPLE 37

2-Butyl-5-[1H-tetrazol-5-yl[-4-{N-[(2'-[1H-tetrazol-5-yl]biphenyl-4-yl)methyl]amino}pyrimidine 2-Butyl-4-{N-[(2'-[1H-tetrazol-5-yl]biphenyl-4-yl)methyl]amino}pyrimidine-5-carbonitrile, the product of Example 14B, is dissolved in N-methylpyrrolidone containing 3 equivalents of triethylamine hydrochloride and 6 equivalents of sodium azide. The reaction mixture is heated at 150° C. for 10 h and then cooled to ambient temperature. It is then neutralized with dilute aqueous hydrochloric acid and filtered to afford the title compound.

EXAMPLE 38

Ethyl 2-butyl-4-{N-[methyl-(2'-trifluoromethylsulfonylamido-biphenyl-4-yl)methyl]amino}pyrimidine-5-carboxylate 4-Bromomethyl-2-nitrobiphenyl, prpepared as described by D. J. Carini, et al. D. J. Carini, et al. on page 105 in European Application Number 324,377 published Jul. 19, 1989, is reacted with excess methylamine in THF in a manner similar to that described in Example 18A, to give 4'-methylaminomethyl-2-nitrobiphenyl. 4'-Methylaminomethyl-2-nitrobiphenyl is reacted, according to the procedures described in Example 1C, with ethyl 2-butyl-4-chloropyrimidine-5-carboxylate to give ethyl 2-butyl-4-{N-[N-methyl-(2'-nitrobiphenyl-4-yl)methyl]amino)pyrimidine-5-carboxylate. Hydrogenation over palladium on carbon in methanol gives the intermediate ethyl 2-butyl-4-{N-[methyl-(2'-aminobiphenyl-4-yl)methyl]amino}pyrimidine-5-carboxylate. The intermediate is dissolved in methylene chloride containing triethylamine and treated at low temperature with trifluoromethanesulfonyl chloride to give the title compound.

EXAMPLE 39

Ethyl 2-butyl-4-{N-[4-(2'-[1H-tetrazol-5-yl]phenoxy)phenylmethyl]amino}pyrimidine-5-carboxylate

EXAMPLE 39A

N-Triphenylmethyl-5-[2-(4-aminomethylphenoxy)phenyl]tetrazole

2-[4-Methylphenoxy]benzoic acid, prepared as described by D. J. Carini in *J. Medicinal Chem.*, 33, 1330- (1990), is converted to the corresponding acid chloride with phosphorous trichloride in benzene. The acid chloride is reacted with ammonia to give 2-(4-methylphenoxy)-benzenecarboxamide. The carboxamide is then dehydrated by treatment with thionyl chloride to give 2-(4'-methylphenoxy)benzonitrile.

The 2-(4'-methylphenoxy)benzonitrile is converted to 2-(4'-methylphenoxy)phenyl-tetrazole by heating at 150° C. with 3 equivalents of triethylamine hydrochloride and 6 equivalents of sodium azide in N-methyl-2-pyrrolidone. The tetrazole intermediate is reacted with triphenylmethyl chloride and triethylamine in refluxing methylene chloride to give N-triphenylmethyl-5-[2-(4'-methylphenoxy)phenyl]tetrazole.

The N-triphenylmethyl-5-[2-(4'-methylphenoxy)phenyl]tetrazole is brominated by treatment with one equivalent of N-bromosuccinimide in refluxing carbon tetrachloride containing a catalytic amount of dibenzoyl peroxide. The resulting bromomethyl compound is reacted with sodium azide in DMF as described in Example 1A to give the corresponding azidomethyl compound. The azidomethyl compound is then reduced, as described in Example 1B, by hydrogenation over Lindlar's catalyst to give the title compound.

EXAMPLE 39B

Ethyl 2-butyl-4-{N-[4-(2'-[1H-tetrazol-5-yl]phenoxy)phenylmethyl]amino}pyrimidine-5-carboxylate Following the procedures described in Example 1C and 1D, the compound resulting from Example 39A is reacted with ethyl 2-butyl-4-chloropyrimidine-5-carboxylate and the condensation product is deprotected to give the title compound.

EXAMPLES 40–44

Following the procedures described in Example 1C and 1D, the intermediates shown in Table 4 are condensed and the condensation products deprotected to give the compounds of Examples 40–44 as disclosed in Table 4. The intermediates are prepared by literature methods.

TABLE 4

Examples 40-44

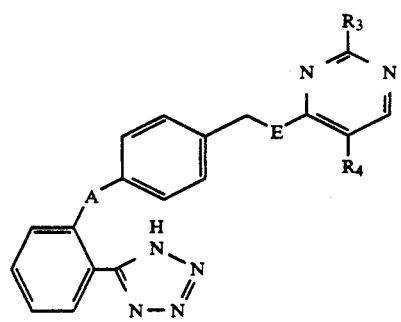

| Ex No | A | E | R₃ | R₄ | Intermediate 1 | Intermediate 2 |
|---|---|---|---|---|---|---|
| 40 | C=O | —NH— | n-butyl | COOEt | (4-aminomethylphenyl)(2-(N-trityl-tetrazol-5-yl)phenyl) ketone | 4-chloro-2-n-butyl-5-ethoxycarbonylpyrimidine |
| 41 | bond | —S— | n-butyl | COOEt | 4'-mercaptomethyl-2-(N-trityl-tetrazol-5-yl)biphenyl | 4-chloro-2-n-butyl-5-ethoxycarbonylpyrimidine |
| 42 | bond | —NH— | —S-propyl | COOEt | 4'-aminomethyl-2-(N-trityl-tetrazol-5-yl)biphenyl | 4-chloro-2-S-propyl-5-ethoxycarbonylpyrimidine |
| 43 | bond | —NH— | pyrrolidinyl | COOEt | 4'-aminomethyl-2-(N-trityl-tetrazol-5-yl)biphenyl | 4-chloro-2-pyrrolidinyl-5-ethoxycarbonylpyrimidine |

TABLE 4-continued

Examples 40-44

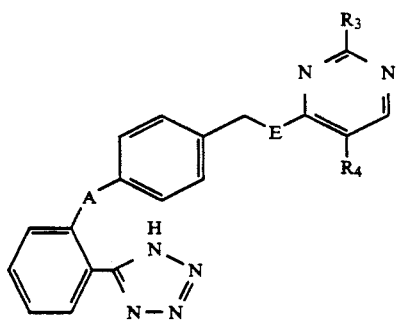

| Ex No | A | E | R3 | R4 | Intermediate 1 | Intermediate 2 |
|---|---|---|---|---|---|---|
| 44 | bond | —N(Me) | n-pentyl | NO2 | (structure: biphenyl-CH2-NHMe with Tr-tetrazole) | (structure: 2-n-butyl-4,6-dichloro-5-nitropyrimidine) *** |

N-Triphenylmethyl-5-[2-(4-aminomethylbenzoyl-phenyl)]tetrazole

2-Cyano-4'-methylbenzophenone, prepared as described by G. W. Ebert and R. D. Rieke in *J. Organic Chem.*, 49, 5280-2 (1984), is converted to 5-[2-(4-methylbenzoyl)phenyl]tetrazole by the procedures described in Step 1 of Example 39. Reaction with triphenylmethyl chloride gives N-triphenylmethyl-5-[2-(4-methylbenzoyl)phenyl]tetrazole.

The N-triphenylmethyl-5-[2-(4'-methylbenzoyl)-phenyl]tetrazole is brominated with N-bromosuccinimide followed by reaction with sodium azide and reduction as described in Step 1 of Example 39 to afford the title compound.

EXAMPLE 45

Methyl 6-n-butyl-2-{N-[(2'-[1H-tetrazol-5-yl]biphenyl-4-yl)methyl]amino}pyrimidine-4-carboxylate

EXAMPLE 45A

Methyl 6-n-butyl-2-chloropyrimidine-4-carboxylate

Methyl 6-n-butyl-2-hydroxypyrimidine-4-carboxylate (prepared as described by Z. Budesinsky and F. Roubinek in *Collection Czechoslovak Chem Commun.*, 26, 2871-2885 (1991)) is refluxed with phosphorous oxychloride, as described by the same authors for the chlorination of methyl 6-methyl-2-hydroxypyrimidine-4-carboxylate, to give the title compound.

EXAMPLE 45B

Methyl 6-n-butyl-2-{N-[(2'-[1H-tetrazol-5-yl]biphenyl-4-yl)methyl]amino}pyrimidine-4-carboxylate By the procedures described in Example 1C and 1D, N-triphenylmethyl-5-[2-(4'-aminomethyl-biphenyl]tetrazole and the compound resulting from Example 45A, are condensed and deprotected to give the title compound.

EXAMPLE 46

2-n-Butyl-5-amino-4-{N-methyl-N-[(2'-(1H-tetrazol-5-yl]biphenyl-4-yl)methyl]amino}pyrimidine 2-n-Butyl-6-chloro-5-nitro-4-{N-[N-methyl-2'-[1H-tetrazol-5-yl]biphenyl-4-yl)methyl]amino}pyrimidine, the product of Example 44 is hydrogenated until 4 equivalents of hydrogen are consumed to yield the title compound.

EXAMPLE 47

2-n-Butyl-5-(methanesulfonylamino)-4-{N-methyl-N-[(2-[1H-tetrazol-5-yl]biphenyl-4-yl)methyl]amino} pyrimidine 2-n-Butyl-5-amino-4-{N-[N-methyl-(2'-(1H-tetrazol-5-yl]biphenyl-4-yl)methyl]amino}pyrimidine, the product of Example 46, is dissolved in chloroform containing triethylamine and treated with one equivalent of methanesulfonyl chloride to give the title compound.

EXAMPLE 48

Ethyl 5-n-butyl-4-{N-[(2'-[1H-tetrazol-5-yl]biphenyl-4-yl)methyl]amino}pyridine-3-carboxylate

EXAMPLE 48A

Ethyl 5-n-butyl-4-chloropyridine-3-carboxylate

Ethyl 5-n-butyl-4-oxo-1,4-dihydropyridine-3-carboxylate (prepared as described by M. Balogh, et al. in *J. Heterocyclic Chem.*, 17, 359-368 (1980)) is refluxed in phosphorous oxychloride to give the title compound.

EXAMPLE 48B

Ethyl 5-n-butyl-4-{N-[(2'-[1H-tetrazol-5-yl]biphenyl-4-yl)methyl]amino}pyridine-3-carboxylate N-triphenylmethyl-5-[2-(4'-aminomethyl-biphenyl)-tetrazole is reacted with the compound resulting from Example 48A, to give an intermediate which is treated with hydrogen chloride as described in Example 1D to give the title compound.

EXAMPLE 49

Methyl 2-{N-butyl-N-[(2'-[1H-tetrazol-5-yl]biphenyl-4-yl)methyl]amino}pyridine-3-carboxylate N-Triphenylmethyl-5-[2-(4'-butylaminomethyl-biphenyl)]tetrazole, the product of Example 19A, is reacted with methyl 2-chloropyridine-3-carboxylate (prepared as described by F. G. Mann and J. A. Reid in *J. Chem. Soc.*, 2057–62 (1952)) in a manner similar to that described in Example 1C, to give an intermediate which is treated with hydrogen chloride, as described in Example 1D, to give the title compound.

EXAMPLE 50

Ethyl 3-{N-butyl-N-[(2'-[1H-tetrazol-5-yl]biphenyl-4-yl)methyl]amino}pyridazine-4-carboxylate By the procedures described in Example 1C and 1D, the compound resulting from Example 19A and ethyl 3-chloropyridazine-4-carboxylate (prepared as described by A. Dornow and W. Abele in *Chem. Berichte*, 97, 3349–3353 (1964)) are condensed and deprotected to give the title compound.

EXAMPLE 51

Methyl 5-n-butyl-3-{N-[(2'-[1H-tetrazol-5-yl]biphenyl-4-yl)methyl]amino}pyrazine-2-carboxylate

EXAMPLE 51A

Methyl 5-n-butyl-3-chloropyrazine-2-carboxylate

2-Oxohexanal (F. Ballistreri, et al., *J. Organic Chem.*, 53, 830 (1988) is reacted (according to the method described by F. L. Muehlmann and A. R. Day in *J. American Chem. Soc.*, 78, 242–4(1956) substituting 2-oxohexanal for the 2-oxopropanal used in the synthesis of 5-methyl-3-hydroxypyrazine-2-carboxamide) with aminomalonamide to give 5-n-butyl-3-hydroxypyrazine-2-carboxamide. The amide is hydrolyzed with sodium hydroxide in water at 95° C. to give 5-n-butyl-3-hydroxypyrazine-2-carboxylic acid. The acid is converted to the corresponding ester with methanol and hydrochloric acid and the ester is chlorinated with phosphorous oxychloride (according to the method described by G. Dick and H. Wood in *J. Chem. Soc.*, 1955, 1379–82) to give the title compound.

EXAMPLE 51B

Methyl 5-n-butyl-3-{N-[(2'-[1H-tetrazol-5-yl]biphenyl-4-yl)methyl]amino}pyrazine-2-carboxylate By the procedures described in Example 1C and 1D, N-triphenylmethyl-5-[2-(4'-aminomethyl-biphenyl]tetrazole and the compound resulting from Example 51A, are condensed and deprotected to give the title compound.

EXAMPLE 52

Ethyl 3-butyl-5-{N-[(2'-[1H-tetrazol-5-yl]biphenyl-4-yl)methyl]amino}-1,2,4-triazine-6-carboxylate

EXAMPLE 52A

Ethyl-3-butyl-5-chloro-1,2,4-triazine-6-carboxylate

Pentanamidrazone hydrochloride (H, Paul, et al., *Chem Berichte*, 101:2033 (1968)) is dissolved in ethyl alcohol containing an equivalent of sodium ethoxide. Diethyl ketomalonate (1 equivalent) is added and the reactionmixture stirred at ambient temperature for 6 h and refluxed for 3 h to give ethyl 3-butyl-5-hydroxy-1,2,4-triazine-6-carboxylate by the method of E. C. Taylor and S. F. Martin, *J. Organic Chem.*, 37:3958 (1972). This intermediate is refluxed for 15 minutes in phosphorous oxychloride to give the title compound.

EXAMPLE 52B

Ethyl 3-butyl-5-{N-[(2'-[1H-tetrazol-5-yl]biphenyl-4-yl)methyl]amino}-1,2,4-triazine-6-carboxylate By the procedures described in Example 1C and 1D, N-triphenylmethyl-5-[2-(4'-aminomethyl-biphenyl)]tetrazole and the compound resulting from Example 52A, are condensed and deprotected to give the title compound.

EXAMPLE 53

4-{N-butyl-N-[(2'-[1H-tetrazol-5-yl]biphenyl-4-yl)methyl]amino}pyrimidine-5-carboxylic acid hydrochloride The compound resulting from Example 83 (7.08 g, 15.5 mmol) was dissolved in water (150 mL) containing potassium hydroxide (8.28 g). The reaction mixture was stirred at room temperature for 24 hours and then acidified with concentrated hydrochloric acid (15 mL). The resulting solid was removed by filtration, dissolved in tetrahydrofuran, dried over sodium sulfate and concentrated under reduced pressure. Trituration of the residue with ether afforded the title compound (7.57 g). $^1$H NMR (DMSO-$d_6$, 300 MHz) d 0.85 (t, J=7 Hz, 3H), 1.18 (m, 2H), 1.52 (m, 2H), 3.45 (t, J=7 Hz, 2H), 4.90 (s, 2H), 7.05 (d, J=8 Hz, 2H), 7.20 (d, J=8 Hz, 2H), 7.50–7.70 (m, 4H), 8.55 (s, 1H), 8.65 (s, 1H).

EXAMPLE 54

2-n-Propyl-4-{N-[(2'-[1H-tetrazol-5-yl]biphenyl-4-yl)methyl]amino}pyrimidine-5-carboxylic acid hydrochloride The compound resulting from Example 3 (500 mg, 0.73 mmol) was hydrolyzed by the procedure described in Example 17 to give the title compound (250 mg). m.p. 223°–225° C. $^1$H NMR (CD$_3$OD, 300 MHz) d 0.99 (t, J=7 Hz, 3H), 1.82 (m, 2H), 2.82 (t, J=7 Hz, 2H), 4.90 (s, 1H), 7.10 (d, J=8 Hz, 2H), 7.32 (d, J=8 Hz, 2H), 7.50–7.70 (m, 4H), 8.70 (s, 1H).

EXAMPLE 55

2-n-Propyl-5-hydroxymethyl-4-{N-[(2'-[1H-tetrazol-5-yl]biphenyl-4-yl)methyl]amino}pyrimidine hydrochloride By the procedure described in Example 2, the compound resulting from Example 3C (1.00 g, 1.46 mmol) was reduced with lithium aluminum hydride (200 mg) to give 2-n-propyl-5-hydroxymethyl-4-{N-[(2'-[N-triphenylmethyl-1H-tetrazol-5-yl]biphenyl-4-yl)methyl]amino}pyrimidine. m.p. 134°-137° C.

The above compound was treated with hydrochloric acid in ethanol by the procedure described in Example 2B to give the title compound (440 mg). m.p. 214°-216° C. $^1$H NMR (CD$_3$OD, 300 MHz) d 0.95 (t, J=7 Hz, 3H), 1.79 (m, 2H), 2.76 (t, J=7 Hz, 2H), 4.55 (s, 2H), 4.83 (s, 2H), 7.10 (d, J=7 Hz, 2H), 7.32 (d, J=7 Hz, 2H), 7.50-7.70 (m, 4H), 8.02 (s, 1H).

EXAMPLE 56

2-n-Pentyl-4-{N-[(2'-[1H-tetrazol-5-yl]biphenyl-4-yl)methyl]amino}pyrimidine-5-carboxylic acid hydrochloride By the procedure described in Example 17, the compound resulting from Example 4C (300 mg, 0.421 mmol) was treated with lithium hydroxide followed by concentrated hydrochloric acid to give the title compound (166 mg). m.p. 166°-168° C. $^1$H NMR (CD$_3$OD, 300 MHz) d 0.90 (t, J=7 Hz, 3H), 1.36 (m, 4H), 1.80 (m, 2H), 2.84 (t, J=7 Hz, 2H), 4.92 (s, 2H), 7.12 (d, J=7 Hz, 2H), 7.32 (d, J=7 Hz, 2H), 7.50-7.70 (m, 4H), 8.72 (s, 1H).

EXAMPLE 57

2-n-Butyl-4-{N-methyl-N-[(2'-[1H-tetrazol-5-yl]biphenyl-4-yl)methyl]amino}pyrimidine-5-carboxylic acid hydrochloride By the procedure described in Example 17, the compound resulting from Example 18B (679 mg, 0.952 mmol) was treated with lithium hydroxide followed by concentrated hydrochloric acid to give the title compound (469 mg). m.p. 165°-169° C. $^1$H NMR (CD$_3$OD, 300 MHz) d 0.92 (t, J=7 Hz, 3H), 1.48 (m, 2H), 1.73 (m, 2H), 2.85 (t, J=7 Hz, 2H), 3.20 (s, 3H), 5.18 (s, 2H), 7.12 (d, J=7 Hz, 2H), 7.27 (d, J=8 Hz, 2H), 7.50-7.70 (m, 4H), 8.58 (s, 1H).

EXAMPLE 58

2-n-Butyl-5-hydroxymethyl-4-{N-methyl-N-[(2'-[1H-tetrazol-5-yl]biphenyl-4-yl)methyl]amino}pyrimidine hydrochloride By the procedure described in Example 2, the compound resulting from Example 18B (700 mg, 0.982 mmol) was reduced with lithium aluminum hydride (140 mg) to give. 2-n-butyl-5-hydroxymethyl-4-{N-methyl-N-[(2'-[N-triphenylmethyl-1H-tetrazol-5-yl]biphenyl-4-yl)methyl]amino}pyrimidine (387 mg). m.p. 133°-137° C.

The above compound was treated with hydrochloric acid in ethanol by the procedure described in Example 2B to give the title compound (185 mg). m.p. 152°-158° C. $^1$H NMR (CD$_3$OD, 300 MHz) d 0.92 (t, J=7 Hz, 3H), 1.38 (m, 2H), 1.73 (m, 2H), 2.80 (t, J=7 Hz, 2H), 3.57 (s, 3H), 4.62 (s, 2H), 5.15 (s, 2H), 7.13 (d, J=8 Hz, 2H), 7.25 (d, J=8 Hz, 2H), 7.50-7.70 (m, 4H), 8.15 (s, 1H).

EXAMPLE 59

Ethyl 2-(2-methoxyethyl)-4-{N-[(2'-[1H-tetrazol-5-yl]biphenyl-4-yl)methyl]amino}pyrimidine-5-carboxylate

EXAMPLE 59A

2-Methoxypropionamidine hydrochloride

Methyl 2-methoxypropionimidate hydrochloride (U.S. Pat. No. 4,007,200) (53 g, 0.345 mol) was dissolved in methanol (400 mL) containing liquid ammonia (70 mL) and kept at room temperature overnight in an autoclave. The reaction mixture was concentrated under reduced pressure, and the residue obtained was dissolved in isopropanol and filtered. The filtrate was concentrated under reduced pressure and the residue crystallized from ether to afford the title compound (47 g).

EXAMPLE 59B

Ethyl 2-(2-methoxyethyl)-4-hydroxy-pyrimidine-5-carboxylate

To the compound resulting from Example 59A (0.345 mol) dissolved in ethanol (200 mL) and cooled in an ice bath was slowly added a solution of 21% sodium ethoxide in ethanol (223 g) followed by the slow addition of diethyl ethoxymethylene malonate (74.6 g, 0.345 mol). The solution was refluxed 2 hours and then concentrated under reduced pressure. Water was added and the solution neutralized with hydrochloric acid and extracted with chloroform (4x). The combined organic extracts were dried over magnesium sulfate and concentrated under reduced pressure. The residue obtained crystallized from ether to afford the title compound in 75% yield. m.p. 115°-118° C.

EXAMPLE 59C

Ethyl 2-(2-methoxyethyl)-4-{N-[(2'-[N-triphenylmethyl-1H-tetrazol-5-yl]biphenyl-4-yl)methyl]amino}pyrimidine-5-carboxylate To the compound resulting from Example 59B (1.84 g, 8.14 mmol) dissolved in methylene chloride (13 mL) containing triethylamine (1.38 mL) and cooled in an ice bath was added methanesulfonyl chloride (1.025 g, 8.96 mmol). After stirring for 5 minutes, a solution of the compound resulting from Example 1B (3.993 g, 8.11 mmol) and triethylamine (1.38 g) in chloroform (5 mL) were added. The mixture was stirred at room temperature for 1.5 hours. Methylene chloride (50 mL) was added and the solution washed with sodium bicarbonate solution, dried over sodium sulfate and concentrated under reduced pressure. The residue obtained was chromatographed on silica gel eluting with 25% ethyl acetate in toluene to give the title compound (4.615 g). m.p. 128°-130° C.

EXAMPLE 59D

Ethyl 2-(2-methoxyethyl)-4-{N-[(2'-[1H-tetrazol-5-yl]biphenyl-4-yl)methyl]amino}pyrimidine-5-carboxylate By the method described in Example 1D, the compound resulting from Example 59C (500 mg, 0.713 mmol) was treated with hydrochloric acid in ethanol to give the title compound (220 mg). m.p. 122°-124° C. $^1$H NMR (CDCl$_3$, 300 MHz) d 1.35 (t, J=7 Hz, 3H), 2.90 (t, J=7 Hz, 2H), 3.25 (s, 3H), 3.78 (t, J=7 Hz, 2H), 4.35 (q, J=7 Hz, 2H), 4.75 (d, J=7 Hz, 2H), 7.07 (d, J=8 Hz, 2H), 7.25 (d, J=8 Hz, 2H), 7.42 (dd, 1H), 7.55 (m, 4H), 7.98 (dd, 1H), 8.57 (s, 1H), 8.70 (t, J=7 Hz, 1H).

EXAMPLE 60

2-(2-Methoxyethyl)-4-{N-[(2'-[1H-tetrazol-5-yl]biphenyl-4-yl)methyl]amino}pyrimidine5-carboxylic acid hydrochloride By the method described in Example 17, the compound resulting from Example 59B (600 mg, 0.856 mmol) was treated with lithium hydroxide followed by concentrated hydrochloric acid to give the title compound (364 mg). m.p. 275° C. $^1$H NMR (CD$_3$OD, 300 MHz) d 3.20 (t, J=7 Hz, 2H), 3.29 (s, 3H), 3.80 (t, J=7 Hz, 2H), 4.90 (s, 2H), 7.12 (d, J=8 Hz, 2H), 7.35 (d, J=8 Hz, 2H), 7.50-7.70 (m, 4H), 8.72 (s, 1H).

EXAMPLE 61

2-(2-Methoxyethyl)-5-hydroxymethyl-4-{N-[(2'-[1H-tetrazol-5-yl]biphenyl-4-yl)methyl]amino}pyrimidine hydrochloride By the method of Example 2, the compound resulting from Example 59C (1.00 g, 1.43 mmol) was reduced with lithium aluminum hydride (210 mg) to give 2-(2-methoxyethyl)-5-hydroxymethyl-4-{N-[(2'-[N-triphenylmethyl-1H-tetrazol-5-yl]biphenyl-4-yl)methyl]amino}pyrimidine (405 mg). m.p. 118°-120° C.

The above compound was treated with hydrochloric acid in ethanol by the procedure described in Example 2B to give the title compound (265 mg). m.p. 218°-220° C. $^1$H NMR (CD$_3$OD, 300 MHz) d 3.01 (t, J=7 Hz, 2H), 3.22 (s, 3H), 3.75 (t, J=7 Hz, 2H), 4.55 (s, 2H), 4.72 (s, 2H), 7.10 (d, J=8 Hz, 2H), 7.32 (d, J=8 Hz, 2H), 7.50-7.70 (m, 4H), 8.00 (s, 1H).

EXAMPLE 62

Ethyl 2-ethyl-4-{N-[(2'-[1H-tetrazol-5-yl]biphenyl-4-yl)methyl]amino}pyrimidine-5-carboxylate

EXAMPLE 62A

Ethyl 2-ethyl-4-{N-[(2'-[N-triphenylmethyl-1H-tetrazol-5-yl]biphenyl-4-yl)methyl]amino}pyrimidine-5-carboxylate By the method described in Example 1C, the compound resulting from Example 1B (3.75 g, 6.85 mmol) was reacted with ethyl 2-ethyl-4-chloropyrimidine-5-carboxylate (1.62 g, 7.54 mmol) to give the title compound (3.709 g). m.p. 134°-136° C.

EXAMPLE 62B

Ethyl 2-ethyl-4-{N-[(2'-[1H-tetrazol-5-yl]biphenyl-4-yl)methyl]amino}pyrimidine-5-carboxylate By the method described in Example 1D, the compound resulting from Example 62A (530 mg, 0.745 mmol) was treated with hydrochloric acid in ethanol to give the title compound (202 mg). m.p. 114°-116° C. $^1$H NMR (CDCl$_3$, 300 MHz) d 1.19 (t, J=7 Hz, 3H), 1.34 (t, J=7 Hz, 3H), 2.55 (q, J=7 Hz, 2H), 4.30 (q, J=7 Hz, 2H), 4.80 (d, J=7 Hz, 2H), 6.99 (d, J=8 Hz, 2H), 7.20 (d, J=8 Hz, 2H), 7.40 (dd, 1H), 7.55 (m, 2H), 7.95 (dd, 1H), 8.32 (s, 1H), 8.65 (t, J=7 Hz, 1H).

EXAMPLE 63

2-Ethyl-4-{N-[(2'-[1H-tetrazol-5-yl]biphenyl-4-yl)methyl]amino}pyrimidine-5-carboxylic acid hydrochloride By the method described in Example 17, the compound resulting from Example 62A (500 mg, 0.745 mmol) was treated with lithium hydroxide followed by concentrated hydrochloric acid to give the title compound (314 mg, 96%). m.p. 200°-202° C. $^1$H NMR (CD$_3$OD, 300 MHz) d 1.32 (t, J=7 Hz, 3H), 2.90 (q, J=7 Hz, 2H), 4.95 (s, 2H), 7.12 (d, J=8 Hz, 2H), 7.35 (d, J=8 Hz, 2H), 7.50-7.70 (m, 4H), 8.72 (s, 1H).

EXAMPLE 64

2-Ethyl-5-hydroxymethyl-4-{N-[(2'-[1H-tetrazol-5-yl]biphenyl-4-yl)methyl]amino}pyrimidine hydrochloride By the method described in Example 2, the compound resulting from Example 62A (1.00 g, 1.49 mmol) was reduced with lithium aluminum hydride (200 mg) to give 2-ethyl-5-hydroxymethyl-4-{N-[(2'-[N-triphenylmethyl-1H-tetrazol-5-yl]biphenyl-4-yl)methyl]amino}pyrimidine (831 mg). m.p. 118°-120° C.

The above compound was reacted with hydrochloric acid in ethanol by the procedure described in Example 2B to give the title compound (488 mg). m.p. 217°-219° C. $^1$H NMR (CD$_3$OD, 300 MHz) d 1.31 (t, J=7 Hz, 3H), 2.83 (q, J=7 Hz, 2H), 4.56 (s, 2H), 4.85 (s, 2H), 7.10 (d, J=8 Hz, 2H), 7.32 (d, J=8 Hz, 2H), 7.50-7.70 (m, 4H), 8.00 (s, 1H).

EXAMPLE 65

Ethyl 2-methyl-4-{N-[(2'-[1H-tetrazol-5-yl]biphenyl-4-yl)methyl]amino}pyrimidine-5-carboxylate

EXAMPLE 65A

Ethyl 2-methyl-4-{N-[(2'-[N-triphenylmethyl-1H-tetrazol-5-yl]biphenyl-4-yl)methyl]amino}pyrimidine-5-carboxylate By the method described in Example 1C, the compound resulting from Example 1B (4.20 g, 8.52 mmol) was reacted with ethyl 2-methyl-4-chloropyrimidine-5-carboxylate (1.75 g, 8.72 mmol), prepared as described by H. Yamanaka in *Heterocycles*, 12, 1323 (1979), to afford the title compound (4.705 g, 84%). m.p. 155°-156° C.

EXAMPLE 65B

Ethyl 2-methyl-4-{N-[(2'-[1H-tetrazol-5-yl]biphenyl-4-yl)methyl]amino}pyrimidine-5-carboxylate By the method described in Example 1D, the compound resulting from Example 65A (1.00 g, 1.52 mmol) was treated with hydrochloric acid in ethanol to give the title compound (439 mg). m.p. 121°-123° C. $^1$H NMR (CDCl$_3$, 300 MHz) d 1.32 (t, J=7 Hz, 3H), 2.28 (s, 3H), 4.71 (q, J=7 Hz, 2H), 4.80 (d, J=7 Hz, 2H), 7.00 (d, J=8 Hz, 2H), 7.15 (d, J=8 Hz, 2H), 7.42 (dd, 1H), 7.55 (m, 2H), 7.98 (dd, 1H), 8.30 (s, 1H), 8.70 (t, J=7 Hz, 1H).

EXAMPLE 66

2-Methyl-4-{N-[(2'-[1H-tetrazol-5-yl]biphenyl-4-yl)methyl]amino}pyrimidine-5-carboxylic acid hydrochloride By the method described in Example 17, the compound resulting from Example 65A (1.00 g, 1.52 mmol) was treated with lithium hydroxide followed by concentrated hydrochloric acid to give the title compound (590 mg, 92%). m.p. 211°-213° C. $^1$H NMR (CD$_3$OD, 300 MHz) d 2.62 (s, 3H), 4.90 (s, 2H), 7.12 (d, J=8 Hz, 2H), 7.35 (d, J=8 Hz, 2H), 7.50-7.70 (m, 4H), 8.72 (s, 1H).

EXAMPLE 67

2-Methyl-5-hydroxymethyl-4-{N-[(2'-[1H-tetrazol-5-yl]biphenyl-4-yl)methyl]amino}pyrimidine hydrochloride By the method of Example 2, the compound resulting from Example 65A (1.00 g, 1.52 mmol) was reduced lithium aluminum hydride (220 mg) to give 2-methyl-5-hydroxymethyl-4-{N-[(2'-(N-triphenylmethyl-1H-tetrazol-5-yl)biphenyl-4-yl)methyl]amino}pyrimidine (849 mg). m.p. 112°-114° C.

The above compound was reacted with hydrochloric acid in ethanol by the procedure described in Example 2B to give the title compound (450 mg). m.p. 185°-187° C. $^1$H NMR (CD$_3$OD, 300 MHz) d 2.56 (s, 3H), 4.55 (s, 2H), 4.85 (s, 2H), 7.10 (d, J=8 Hz, 2H), 7.32 (d, J=8 Hz, 2H), 7.50-7.70 (m, 4H), 8.02 (s, 1H).

EXAMPLE 68

Ethyl 2-methylthio-4-{N-butyl-N-[(2'-[1H-tetrazol-5-yl]biphenyl-4-yl)methyl]amino}pyrimidine-5-carboxylate

EXAMPLE 68A

Ethyl 2-methylthio-4-{N-butyl-N-[(2'-[N-triphenylmethyl-1H-tetrazol-5-yl]biphenyl-4-yl)methyl]amino}pyrimidine-5-carboxylate Using the procedure described in Examples 19A and B, N-triphenylmethyl-5[2-(4'-bromomethyl-biphenyl)-]tetrazole (2.80 g, 5.00 mmol), butylamine and commercially available ethyl 4-chloro-2-methylthio-pyrimidine-5-carboxylate (1.31 g, 5.64 mmol) were reacted to give the title compound (3.02 g). m.p. 122°-124° C.

EXAMPLE 68B

Ethyl 2-methylthio-4-{N-butyl-N-[(2'-[1H-tetrazol-5-yl]biphenyl-4-yl)methyl]amino}pyrimidine-5-carboxylate The compound resulting from Example 68A (500 mg, 0.671 mmol) was dissolved in ethanol and treated with hydrochloric acid by the procedure described in Example 19C to give the title compound (262 mg). m.p. 161°-163° C. following crystallization from ether. $^1$H NMR (DMSO-d$_6$, 300 MHz) d 0.82 (t, J=7 Hz, 3H), 1.21 (t, J=7 Hz, 3H), 1.55 (m, 2H), 2.38 (s, 3H), 3.40 (t, J=7 Hz, 2H), 4.18 (q, J=7 Hz, 2H), 4.79 (s, 2H), 7.05 (d, J=8 Hz, 2H), 7.15 (d, J=8 Hz, 2H), 7.50-7.70 (m, 4H), 8.32 (s, 1H).

EXAMPLE 69

2-Methylthio-4-{N-butyl-N-[(2'-[1H-tetrazol-5-yl]biphenyl-4-yl)methyl]amino}pyrimidine-5-carboxylic acid hydrochloride By the method described in Example 17, the compound resulting from Example 68A (500 mg, 0.671 mmol) was treated with lithium hydroxide followed by concentrated hydrochloric acid to give the title compound (321 mg). $^1$H NMR (DMSO-d$_6$, 300 MHz) d 0.85 (t, J=7 Hz, 3H), 1.20 (m, 2H), 1.55 (m, 2H), 2.38 (s, 3H), 3.46 (t, J=7 Hz, 2H), 4.86 (s, 2H), 7.05 (d, J=8 Hz, 2H), 7.18 (d, J=8 Hz, 2H), 7.50-7.70 (m, 4H), 8.40 (s, 1H).

EXAMPLE 70

Ethyl 4-{N-propyl-N-[(2'-[1H-tetrazol-5-yl]biphenyl-4-yl)methyl]amino}pyrimidine-5-carboxylate

EXAMPLE 70A

Ethyl 4-{N-propyl-N-[(2'-[N-triphenylmethyl-1H-tetrazol-5-yl]biphenyl-4-yl)methyl]amino}pyrimidine-5-carboxylate Using the procedure described in Examples 19A and B, N-triphenylmethyl-5[2-(4'-bromomethyl-biphenyl)-]tetrazole, propylamine, and ethyl 4-chloropyrimidine-5-carboxylate (1.00 g, 5.38 mmol), prepared as described by H. Bredereck, F. Effenberger and E. H. Schweizer in *Chem. Ber.*, 95, 803 (1962), were reacted to give the title compound (2.694 g). m.p. 100°-103° C.

EXAMPLE 70B

Ethyl 4-{N-propyl-N-[(2'-[1H-tetrazol-5-yl]biphenyl-4-yl)methyl]amino}pyrimidine-5-carboxylate The compound resulting from Example 70A (2.60 g, 3.79 mmol) was dissolved in ethanol and treated with hydrochloric acid by the procedure described in Example 19C to give the title compound (1.13 g). m.p. 160°-162° C. $^1$H NMR (DMSO-d$_6$, 300 MHz) d.0.77 (t, J=7 Hz, 3H), 1.23 (t, J=7 Hz, 3H), 1.55 (m, 2H), 3.35 (m, 2H), 4.20 (q, J=7 Hz, 2H), 4.71 (s, 2H), 7.03 (d, J=8 Hz, 2H), 7.15 (d, J=8 Hz, 2H), 7.50-7.70 (m, 4H), 8.45 (s, 1H), 8.58 (s, 1H).

EXAMPLE 71

4-{N-Propyl-N-[(2'-[1H-tetrazol-5yl]biphenyl-4-yl)methyl]amino}pyrimidine-5-carboxylic acid hydrochloride The compound resulting from Example 70 (300 mg, 0.677 mmol) was hydrolyzed with potassium hydroxide in water using the procedure described in Example 53 to give the title compound (280 mg). $^1$H NMR (DMSO-d$_6$, 300 MHz) d 0.79 (t, J=7 Hz, 3H), 1.58 (m, 2H), 3.44 (m, 2H), 4.90 (s, 2H), 7.05 (d, J=8 Hz, 2H), 7.20 (d, J=8 Hz, 2H), 7.50-7.70 (m, 4H), 8.60 (s, 1H), 8.70 (s, 1H).

EXAMPLE 72

Ethyl 3-methyl-5-{N-propyl-N-[(2'-[1H-tetrazol-5-yl]biphenyl-4-yl)methyl]amino}-1.2.4-triazine-6-carboxylate

EXAMPLE 72A

Ethyl 3-methyl-5-chloro-1.2.4-triazine-6-carboxylate

To 3-methyl-5-hydroxy-1,2,4-triazino-6-carboxylate (1.50 g, 8.20 mmol), prepared as described by E. C. Taylor and S. F. Martin in *J. Org. Chem.*, 37, 3958 (1972), suspended in phosphorus oxychloride (12 mL) was added triethylamine (827 mg, 8.20 mmol). The reaction mixture was stirred at room temperature for 1 hour and then the solvent was removed under reduced pressure. To the residue obtained was added toluene, which was then removed under reduced pressure. The residue obtained was dissolved in toluene and washed with water (3 mL) and dilute sodium bicarbonate solution. The organic phase was dried over magnesium sulfate and concentrated under reduced pressure. The residue obtained was dissolved in heptane, filtered and concentrated in vacuo to afford the title compound as an oil.

EXAMPLE 72B

Ethyl 3-methyl-5-{N-propyl-N-[(2'-[N-triphenylmethyl-1H-tetrazol-5-yl]biphenyl-4-yl)methyl]amino}-1.2.4-triazine-6-carboxylate N-Triphenylmethyl-5-[2-(4'-bromomethyl-biphenyl)-]tetrazole (3.28 g, 5.87 mmol) was treated with propylamine by the procedure described in Example 19A to give N-triphenylmethyl-5-[2-(4'-propylaminomethyl-biphenyl)]tetrazole. This was dissolved in tetrahydrofuran (8.5 mL) containing triethylamine (3.1 mL). The compound resulting from Example 72A (1.30 g, 6.47 mmol) was added, and the mixture was stirred at room temperature for 2 hours. The solvents were removed in vacuo and the residue obtained dissolved in toluene and washed with sodium bicarbonate solution. The organic phase was dried over sodium sulfate and concentrated under reduced pressure. The residue obtained was chromatographed on silica gel eluting with 25% ethyl acetate in toluene to afford the title compound (3.91 g). m.p. 178°–179° C.

EXAMPLE 72C

Ethyl 3-methyl-5-{N-propyl-N-[(2'-[1H-tetrazol-5-yl]biphenyl-4-yl)methyl]amino}-1,2,4-triazine-6-carboxylate The compound resulting from Example 72B (600 mg, 0.857 mmol) was suspended in ethanol (8 mL) and treated with hydrochloric acid as described in Example 19C to give the title compound (303 mg). m.p. 120°–122° C. $^1$H NMR (DMSO-d$_6$, 300 MHz) d 0.80 (t, J=7 Hz, 3H), 1.22 (t, J=7 Hz, 3H), 1.55 (m, 2H), 3.40 (m, 2H), 4.28 (q, J=7 Hz, 2H), 4.82 (s, 2H), 7.05 (d, J=8 Hz, 2H), 7.15 (d, J=8 Hz, 2H), 7.50–7.70 (m, 4H).

EXAMPLE 73

3-Methyl-5-{N-propyl-N-[(2'-[1H-tetrazol-5-yl]biphenyl-4-yl)methyl]amino}-1,2,4-triazine-6-carboxylic acid hydrochloride The compound resulting from Example 72 (200 mg, 0.436 mmol) was dissolved in methanol (10 mL) and water (1 mL) containing sodium hydroxide (175 mg). The solution was refluxed 1 hour, cooled in an ice bath and neutralized with concentrated hydrochloric acid. The solvent was removed under reduced pressure and the residue obtained was dissolved in chloroform, dried over sodium sulfate and concentrated in vacuo to give the title compound (173 mg). $^1$H NMR (DMSO-d$_6$, 300 MHz) d 0.89 (t, J=7 Hz, 3H), 1.58 (m, 2H), 2.45 (s, 3H), 3.52 (m, 2H), 4.90 (s, 2H), 7.05 (m, 2H), 7.22 (m, 2H), 7.50–7.70 (m, 4H).

EXAMPLE 74

Ethyl 4-{N-[(2'-[1H-tetrazol-5-yl]biphenyl-4-yl)methyl]amino}pyrimidine-5-carboxylate.

EXAMPLE 74A

Ethyl 4-{N-[(2'-[N-triphenylmethyl-tetrazol-5-yl]biphenyl-4-yl)methyl]amino}pyrimidine-5-carboxylate The product resulting from Example 1A (3.75 g, 7.2 mmol) was treated with lithium aluminum hydride in tetrahydrofuran by the procedure described in Example 1B to afford an amorphous solid. To this solid dissolved in tetrahydrofuran (50 mL) was added N-methylmorpholine (2.2 g, 22 mmol) and ethyl 4-chloropyrimidine-5-carboxylate (1.35 g, 7.2 mmol). The mixture was stirred overnight at room temperature and then concentrated under reduced pressure and the residue obtained partitioned between water and ethyl acetate. The organic layer was washed with water and brine, dried over sodium carbonate/sodium sulfate and concentrated under reduced pressure to afford an amorphous solid. Silica gel chromatography eluting with ethyl acetate in toluene afforded the title compound as a colorless amorphous solid (3.00 g, 81%). $^1$H NMR (CDCl$_3$, 300 MHz) d 1.37 (t, J=7 Hz, 3H), 2.36 (s, 3H), 4.32 (q, J=7 Hz, 2H), 4.68 (d, J=6 Hz, 2H), 7.50–6.90 (m, 22H), 7.95 (m, 1H), 8.52 (br t, 1H), 8.66 (s, 1H), 8.88 (s, 1H). MS (DCl/NH$_3$) m/e 644 (M+H)$^+$.

EXAMPLE 74B

Ethyl 4-{N-[(2'-[5H-tetrazol-5-yl]biphenyl-4-yl)methyl]amino}pyrimidine-5-carboxylate To the product resulting from Example 74 A (1.5 g, 2.3 mmol) dissolved in tetrahydrofuran (15 mL) was added acetic acid (15 mL) and water (2 mL). The solution was refluxed for 1 hour, cooled to room temperature and concentrated under reduced pressure. The residue obtained was triturated with hexane and ether to afford a solid which was recrystallized from ethyl acetate/hexane and then from methylene chloride/hexane. The off-white crystals were dried overnight under vacuum at 60° C. to afford the title compound (670 mg, 62%). $^1$H NMR (DMSO-d$_6$, 300 MHz) d 1.32 (t, J=8 Hz, 3H), 4.32 (q, J=8 Hz, 2H), 4.72 (d, J=6 Hz, 2H), 7.05 (d, J=9 Hz, 2H), 7.25 (d, J=9 Hz, 2H), 7.70–7.50 (m, 4H), 8.60 (s, 1H), 8.70 (br t, 1H), 8.78 (s, 1H). Anal calcd for C$_{21}$H$_{19}$N$_7$O$_2$: C, 62.83; H, 4.77; N, 24.42. Found: C, 62.93; H, 4.82; N, 24.30. MS (DCl/NH$_3$) m/e 402 (M+H)$^+$.

EXAMPLE 75

4-{N-[2'-[5H-tetrazol-5-yl]biphenyl-4-yl)methyl-]amino}pyrimidine-5-carboxylic acid The product resulting from Example 74B (300 mg, 0.75 mmol) was suspended in ethanol (10 mL). A solution of sodium hydroxide (130 mg, 3 mmol) in water (1 mL) was added and the clear solution was stirred for 45 minutes. The reaction was concentrated under reduced pressure and the residue obtained dissolved in water (50 mL). The solution was acidified with acetic acid. The solid was removed by filtration and dissolved in a warm ethanol/methanol mixture and filtered. The filtrate was concentrated under reduced pressure and the colorless powder was dried overnight on hi-vac at 60° C. to afford the title compound (245 mg, 88%). $^1$H NMR (DMSO-$d_6$, 300 MHz) d 4.74 (d, J=6 Hz, 2H), 7.05 (d, J=7 Hz, 2H), 7.25 (d, J=7 Hz, 2H), 7.70-7.50 (m, 4H), 8.59 (s, 1H), 8.72 (s, 1H) 8.91 (br t, 1H). Anal calcd for $C_{19}H_{15}N_7O_2 \cdot 0.65$ EtOH: C, 60.45; H, 4.72; N, 24.39. Found: C, 60.04; H, 4.56; N, 24.60. MS (DCl/NH$_3$) m/e 374 (M+H)$^+$.

EXAMPLE 76

2-Methyl-4-{N-butyl-N-[(2'-[1H-tetrazol-5-yl]biphenyl-4-yl)methyl]amino}pyrimidine-5-carboxylic acid hydrochloride To the compound resulting from Example 19C (0.6 g, 0.842 mmol) dissolved in methanol (4 mL) and tetrahydrofuran (6 mL) was added a solution of lithium hydroxide monohydrate (180 mg) in water (1.5 mL). The mixture was heated at reflux for 5 hours and then concentrated in vacuo. The residue obtained was crystallized from acetonitrile to afford the title compound (289 mg). m.p. 155°-158° C. $^1$H NMR (CD$_3$OD, 300 MHz) d 0.95 (t, J=7 Hz, 3H), 1.30 (m, 2H), 1.69 (m, 2H), 2.60 (s, 3H), 3.70 (m, 2H), 5.08 (m, 2H), 7.10 (d, 2H), 7.20 (s, 2H), 7.55 (d, 2H), 7.50-7.70 (m, 4H), 8.55 (s, 1H).

EXAMPLE 77

2-Methyl-4-{N-butyl-N-[(2'-[1H-tetrazol-5-yl]biphenyl-4-yl)methyl]amino}pyrimidine-5-carboxamide Ethyl 2-methyl-4-{N-[(2'-[N-triphenylmethyl-tetrazol-5-yl]biphenyl-4-yl)methyl]amino}pyrimidine-5-carboxylate was hydrolyzed with sodium hydroxide and neutralized with one equivalent of hyochloric acid to give 2-methyl-4-{N-[(2'-[N-triphenylmethyl-tetrazol-5-yl]biphenyl-4-yl)methyl]amino}pyrimidine-5-carboxylic acid. This compound was treated with thionyl chloride at room temperature for 2 hours. The reaction mixture was concentrated under reduced pressure and the residue obtained dissolved in methylene chloride and cooled to 0° C. Ammonia was added, and the reaction mixture was stirred at 0° C. for several hours. The solvent was removed under reduced pressure and the residue obtained chromatographed on silica gel. The triphenylmethyl protecting group was removed with aqueous hydrochloric acid in dioxane to give the title compound in high yield. $^1$H NMR (DMSO-$d_6$, 300 MHz) d 0.85 (t, J=7 Hz, 3H), 1.22 (m, 2H), 1.55 (m, 2H), 2.55 (s, 3H), 3.58 (m, 2H), 5.00 (s, 2H), 7.08 (d, J=7 Hz, 2H), 7.25 (d, J=7 Hz, 2H), 7.55 (d, J=7 Hz, 1H), 7.59 (d, J=7 Hz, 1H), 7.68 (m, 2H), 8.01 (s, 1H), 8.40 (s, 1H), 8.42 (s, 1H). MS (DCl/NH$_3$) m/e 443 (M+H)$^+$.

EXAMPLE 78

2-Methyl-4-{N-butyl-N-[(2'-[1H-tetrazol-5-yl]biphenyl-4-yl)methyl]amino}pyrimidine-5-(N-morpholinyl)carboxamide The title compound was prepared in analogy to Example 77 using morpholine in place of ammonia. $^1$H NMR (DMSO-$d_6$, 300 MHz) d 0.88 (t, J=7 Hz, 3H), 1.24 (q, J=7 Hz, 2H), 1.56 (m, 2H), 2.52 (s, 3H), 3.30-3.70 (m, 10H), 4.88 (d, J=15 Hz, 1H), 5.00 (d, J=15 Hz, 1H), 7.08 (d, J=7 Hz, 2H), 7.18 (d, J=7 Hz, 2H), 7.52 (d, J=7 Hz, 1H), 7.59 (d, J=7 Hz, 1H), 7.68 (m, 2H), 8.34 (s, 1H). MS (DCl/NH$_3$) m/e 513 (M+H)$^+$.

EXAMPLE 79

2-Methyl-4-{N-butyl-N-[(2'-[1H-tetrazol-5-yl]biphenyl-4-yl)methyl]amino}pyrimidine-5-(N-methoxy)carboxamide The title compound was prepared in analogy to Example 77 using methoxylamine in place of ammonia. $^1$H NMR (DMSO-$d_6$, 300 MHz) d 0.85 (t, J=7 Hz, 3H), 1.20 (q, J=7 Hz, 2H), 1.53 (m, 2H), 2.55 (s, 3H), 3.54 (m, 2H), 3.68 (s, 3H), 5.00 (s, 2H), 7.08 (d, J=7 Hz, 2H), 7.24 (d, J=7 Hz, 2H), 7.53 (d, J=7 Hz, 2H), 7.59 (d, J=7 Hz, 2H), 7.68 (m, 2H), 8.49 (s, 1H), 12.24 (s, 1H). MS (DCl/NH$_3$) m/e 473 (M+H)$^+$.

EXAMPLE 80

Ethyl 2-methyl-4-{N-methoxyethyl-N-[(2'-[1H-tetrazol-5-yl]biphenyl-4-yl)methyl]amino}pyrimidine-5-carboxylate The title compound was prepared in analogy to Example 19 using methoxyethylamine instead of n-butylamine in the first step. $^1$H NMR (DMSO-$d_6$, 300 MHz) d 1.22 (t, J=7 Hz, 3H), 2.56 (s, 3H), 3.19 (s, 3H), 3.55 (t, J=6 Hz, 2H), 3.78 (bt, 2H), 4.20 (q, J=7 Hz, 2H), 4.98 (s, 2H), 7.09 (d, J=7 Hz, 2H), 7.19 (d, J=7 Hz, 2H), 7.54 (d, J=6 Hz, 2H), 7.59 (d, J=6 Hz, 2H), 7.68 (m, 2H), 8.62 (s, 1H). Anal calcd for $C_{25}H_{27}N_7O_3 \cdot HCl$: C, 58.88; H, 5.53; N, 19.22. Found: C, 58.88; H, 5.43; N, 19.03. MS (DCl/NH$_3$) m/e 474 (M+H)$^+$.

EXAMPLE 81

Ethyl 2-methyl-4-{N-methoxyethyl-N-[(2'-[1H-tetrazol-5-yl]biphenyl-4-yl)methyl]amino}pyrimidine-5-carboxylic acid hydrochloride The compound resulting from Example 80 was hydrolyzed by the procedure described in Example 53 to afford the title compound. $^1$H NMR (DMSO-$d_6$, 300 MHz) d 2.55 (s, 3H), 3.18 (s, 3H), 3.55 (t, J=6 Hz, 2H), 3.78 (t, J=6 Hz, 2H), 5.02 (s, 2H), 7.08 (d, J=7 Hz, 2H), 7.23 (d, J=7 Hz, 2H), 7.54 (d, J=7 Hz, 1H), 7.59 (d, J=7 Hz, 1H), 7.68 (t, J=7 Hz, 2H), 8.65 (s, 1H). Anal calcd for $C_{23}H_{23}N_7O_3 \cdot HCl \cdot 0.6 H_2O$: C, 55.98; H, 4.87; N, 19.88. Found: C, 56.25; H, 5.13; N, 19.44. MS (DCl/NH$_3$) m/e 446 (M+H)$^+$.

EXAMPLE 82

Pivaloyloxymethyl 4-{N-butyl-N-[(2'-[1H-tetrazol-5-yl]biphenyl-4-yl)methyl]amino}pyrimidine-5-carboxylate

EXAMPLE 82A

Pivaloyloxymethyl 4-{N-butyl-N-[(2'N-triphenylmethyl-1H-tetrazol-5-yl]biphenyl-4-yl)methyl]amino}pyrimidine-5-carboxylate The compound resulting from Example 119A (300 mg, 0.7 mmol) was dissolved in tetrahydrofuran (6 mL) and treated with 10 drops of triethylamine and triphenylmethyl chloride (300 mg, 1.05 mmol). After stirring for 15 hours at room temperature, the mixture was diluted with ethyl acetate (200 mL) and washed with 0.5N HCl, saturated brine, and dried over sodium sulfate. The filtered solution was concentrated under reduced pressure to afford a colorless solid. The solid was dissolved in ethyl acetate (20 mL) and hexane (200 mL) was added. The solid was removed by filtration and dried to afford 4-{N-butyl-N-[(2'[N-triphenylmethyl-1H-tetrazol-5-yl]biphenyl-4-yl)methyl]amino}pyrimidine-5-carboxylic acid (300 mg. 64%) as an amorphous solid.

The above compound (250 mg, 0.37 mmol) was dissolved in anhydrous dimethylformamide (0.5 mL). Triethylamine (75 mg, 0.75 mmol) and chloromethyl pivalate (112 mg, 0.75 mmol) were added and the reaction was stirred for 16 hours at room temperature. The mixture was poured into ethyl acetate (200 mL) and this solution was washed with water, brine, and dried over sodium carbonate and sodium sulfate. The filtered solution was concentrated under reduced pressure to afford a yellow amorphous solid. Chromatography on silica gel eluting with ethyl acetate-hexane mixtures afforded the title compound as an amorphous solid (200 mg, 68%). $^1$H NMR (CDCl$_3$, 300 MHz) d 0.85 (t, J=7 Hz, 3H), 1.30–1.05 (m, 5H), 1.55 (m, 3H), 3.35 (t, J=7 Hz), 4.68 (s, 2H), 5.90 (s, 2H), 6.80–7.50 (m, 22H), 7.92 (m, 1H), 8.60 (s, 1H), 8.76 (s, 1H). MS (FAB) m/e 786 (M+H)$^+$, 808 (M+Na)$^+$.

EXAMPLE 82B

Pivaloyloxymethyl 4-{N-butyl-N-[(2'-[1H-tetrazol-5-yl]biphenyl-4-yl)methyl]amino}pyrimidine-5-carboxylate The compound resulting from Example 82A (280 mg, 0.36 mmol) was dissolved in tetrahydrofuran (6 mL). Acetic acid (6 mL) and water (1 mL) were added and the solution was refluxed for one hour. The cooled solution was concentrated in vacuo and the residue obtained chromatographed on silica gel eluting with ethanol/methylene chloride mixtures to afford the title compound as an off-white amorphous solid (123 mg, 64%). $^1$H NMR (CDCl$_3$) d 0.89 (t, J=7 Hz, 3H), 1.18 (s, 9H), 1.27 (m, 2H), 1.62 (m, 2H), 3.50 (br t, J=7 Hz, 2H), 4.82 (s, 2H), 5.86 (s, 2H), 7.18 (m, 4H), 7.52 (m, 3H), 8.10 (m, 1H), 8.42 (s, 1H), 8.49 (s, 1H). MS (DCI) m/e 544 (M+H)$^+$.

EXAMPLE 83

Ethyl 4-{N-butyl-N-[(2'-[1H-tetrazol-5-yl]biphenyl-4-yl)methyl]amino}pyrimidine-5-carboxylate

EXAMPLE 83A

Ethyl 4-{N-butyl-N-[(2'-[N-triphenylmethyl-1H-tetrazol-5-yl]biphenyl-4-yl)methyl]amino}pyrimidine-5-carboxylate The compound resulting from Example 19A (5.35 mmol) was reacted with ethyl 4-chloropyrimidine-5-carboxylate (1.00 g, 5.38 mmol), prepared as described by H. Bredereck, F. Effenberger and E. H. Schweizer, Chem. Ber., 95, 803 (1962), by the procedure described in Example 19B to afford the title compound (2.57 g). m.p. 142°–144° C.

EXAMPLE 83B

Ethyl 4-{N-butyl-N-[(2'-[1H-tetrazol-5-yl]biphenyl-4-yl)methyl]amino}pyrimidine-5-carboxylate The compound resulting from Example 83A (2.57 g, 3.75 mmol) was deprotected by the procedure described in Example 19C to afford the title compound (1.286 g) which was crystallized from ether. m.p. 109°–111° C. $^1$H NMR (DMSO-d$_6$, 300 MHz) d 0.82 (t, J=7 Hz, 3H), 1.17 (m, 2H), 1.22 (t, J=7 Hz, 3H), 1.51 (m, 2H), 3.39 (t, J=7 Hz, 2H), 4.21 (q, J=7 Hz, 2H), 4.71 (s, 2H), 7.05 (d, J=8 Hz, 2H), 7.15 (d, J=8 Hz, 2H), 7.50–7.72 (m, 4H), 8.48 (s, 1H), 8.60 (s, 1H).

EXAMPLE 84

3-Nitro-2-[N-propyl-N-[(2'-[1H-tetrazol-5-yl]biphenyl-4-yl)methyl]amino}pyridine

EXAMPLE 84A

3-Nitro-2-[N-propyl-N-[(2'-[N-triphenylmethyl-1H-tetrazol-5-yl]biphenyl-4-yl)methyl]amino}pyridine N-Triphenylmethyl-5-[2-(4'-propylaminomethyl-biphenyl)]tetrazole (4.03 g, 7.53 mmol), prepared as described in Example 72B, was dissolved in 8 mL of tetrahydrofuran containing 2.5 mL of triethylamine. 2-Chloro-3-nitropyridine (1.29 g, 8.14 mmol) was added and the solution was refluxed for 2.5 hours. The solvent was removed in vacuo and the residue obtained dissolved in toluene. This solution was washed with sodium bicarbonate solution, dried over sodium sulfate and concentrated in vacuo to afford crude product. Chromatography on silica gel eluting with 25% ethyl acetate in toluene afforded the title compound in 88% yield (4.35 g, 6.61 mmol).

EXAMPLE 84B

3-Nitro-2-[N-propyl-N-[(2'-[1H-tetrazol-5-yl]biphenyl-4-yl)methyl]amino}pyridine The compound resulting from Example 84A (1.00 g, 1.52 mmol) was dissolved in ethanol (13 mL) containing 1.3 mL of concentrated hydrochloric acid. After 18 hours at ambient temperature, the ethanol was removed in vacuo. Potassium acetate was added to neutralize the remaining hydrochloric acid and the mixture extracted with chloroform. The combined organic extracts were dried over sodium sulfate and the solvent removed under reduced pressure. The residue obtained was crystallized from ether to give 0.53 g of the title compound. ¹H NMR (DMSO-d₆, 300 MHz) d 0.72 (t, J=7 Hz, 3H), 1.50 (m, 2H), 3.18 (t, J=7 Hz, 2H), 4.71 (s, 2H), 6.89 (dd, J=4 Hz, 6 Hz, 1H), 7.03 (d, J=8 Hz, 2H), 7.19 (d, J=8 Hz, 2H), 7.50–7.70 (m, 4H), 8.18 (dd, J=1 Hz, 8 Hz, 1H), 8.40 (dd, J=1 Hz, 6 Hz, 1H).

EXAMPLE 85

Ethyl 6-methyl-2-{N-butyl-N-[(2'-[1H-tetrazol-5-yl]biphenyl-4-yl)methyl]amino}pyridine-3-carboxylate

EXAMPLE 85A

Ethyl 2-chloro-6-methyl pyridine-3-carboxylate

To 2-hydroxy-6-methyl pyridine-3-carboxylic acid (25 g, 0.163 mol) suspended in 50 mL of phosphorous oxychloride and cooled in an ice bath was added phosphorous pentachloride (68 g, 0.313 mol) in portions. The mixture was stirred at 115° C. for 2 hours. The phosphorous oxychloride was removed in vacuo and chased with toluene. Ethanol (80 mL) was added with cooling, and the solution was refluxed for 20 minutes. The ethanol was removed under reduced pressure and the residue obtained dissolved in toluene. The toluene solution was washed with sodium bicarbonate solution, dried over magnesium sulfate and concentrated in vacuo. The residue obtained was dissolved in heptane, stirred with silica gel and filtered. The filtrate was concentrated in vacuo to afford 25.10 g of the title compound.

EXAMPLE 85B

Ethyl 2-butylamino-6-methyl pyridine-3-carboxylate

The compound resulting from Example 85A (15 g, 0.075 mol) was combined with 30 mL of butylamine and 60 mL of ethanol in a bomb and heated at 100° C. for 6 hours. The solution was concentrated in vacuo. The residue obtained was dissolved in toluene, washed with dilute potassium hydroxide solution, dried over sodium sulfate and concentrated in vacuo to give an oil. Purification by column chromatography on silica gel eluting with 5% ethyl acetate in hexane afforded 15.58 g of the title compound.

EXAMPLE 85C

Ethyl 6-methyl-2-{N-butyl-N-[(2'-[N-triphenylmethyl-1H-tetrazol-5-yl]biphenyl-4-yl)methyl]amino}pyridine-3-carboxylate The compound resulting from Example 85B (1.60 g, 6.77 mmol) in 8 mL of tetrahydrofuran and 1,3-dimethyl-3,4,5,6-tetrahydro-2(1H)-pyrimidinone (1.65 g) dissolved in tetrahydrofuran (5 mL) were combined and cooled in an ice bath. Lithium hexamethyldisilazide (6.51 mL of a 1M solution in tetrahydrofuran) was added dropwise and the resulting yellow solution was stirred for 10 minutes at 0° C. N-Triphenylmethyl-5-[2-(4'-bromomethylbiphenyl)]tetrazole (3.55 g, 6.37 mmol) was dissolved in 8 mL of tetrahydrofuran and added slowly to the above solution. The solution was stirred for 1.5 hours at ambient temperature. Concentrated hydrochloric acid (2 drops) was added, and the solution was concentrated in vacuo. Water was added and the mixture extracted with toluene. The combined organic extracts were washed with water (2×), dried over sodium sulfate and concentrated in vacuo. The residue obtained was chromatographed on silica gel eluting with 2% ether in toluene to give 2.41 g of the title compound. m.p. 120°–122° C. (crystallized from heptaneether).

EXAMPLE 85D

Ethyl 6-methyl-2-{N-butyl-N-[(2'-[1H-tetrazol-5-yl]biphenyl-4-yl)methyl]amino}pyridine-3-carboxylate The compound resulting from Example 85C (2.35 g) was treated with hydrogen chloride in ethanol by the procedure described in Example 18C. The product was purified by chromatography on silica gel eluting with 25% ethyl acetate in toluene containing 0.5% formic acid to afford the title compound (1.38 g). ¹H NMR (CDCl₃, 300 MHz) d 0.98 (t, J=7 Hz, 3H), 1.26 (m, 2H), 1.31 (t, J=7 Hz, 3H), 1.62 (m, 2H), 2.41 (s, 3H), 3.40 (t, J=7 Hz, 2H), 4.27 (q, J=7 Hz, 2H), 4.77 (s, 2H), 6.57 (d, J=8 Hz, 1H), 7.12 (d, J=8 Hz, 2H), 7.31 (d, J=8 Hz, 2H), 7.41 (dd, J=8 Hz, 1 Hz, 1H), 7.50–7.60 (m, 2H), 7.81 (d, J=8 Hz, 1H), 8.24 (dd, J=8 Hz, 1 Hz, 1H).

EXAMPLE 86

6-Methyl-2-{N-butyl-N-[(2'-[1H-tetrazol-5-yl]biphenyl-4-yl)methyl]amino}pyridine-3-carboxylic acid To the compound resulting from Example 85D (850 mg) dissolved in ethanol (40 mL) was added a solution of 0.90 g of potassium hydroxide dissolved in 5 mL of water. The reaction mixture was refluxed 90 minutes, acetic acid (4 mL) was added and the solution was concentrated in vacuo. Water was added and the resulting solid filtered. This solid was dissolved in chloroform; the solution was dried over sodium sulfate and concentrated in vacuo. The residue obtained was crystallized from ether to give 530 mg of the title compound. m.p. 175°–177° C. ¹H NMR (CDCl₃, 300 MHz) d 0.91 (t, J=7 Hz, 3H), 1.39 (m, 2H), 1.51 (bm, 2H), 2.65 (s, 2H), 3.50 (bm, 2H), 4.30 (s, 2H), 6.84 (d, J=8 Hz, 2H), 6.95 (d, J=8 Hz, 2H), 7.26 (d, J=8 Hz, 1H), 7.40 (dd, J=8 Hz, 1 Hz, 1H), 7.45–7.55 (m, 2H), 7.92 (dd, J=8 Hz, 1 Hz, 1H), 8.40 (d, J=8 Hz, 1H).

EXAMPLE 87

Ethyl 2-{N-propyl-N-[(2'-[1H-tetrazol-5-yl]biphenyl-4-yl)methyl]amino}pyridine-3-carboxylate

EXAMPLE 87A

Ethyl 2-chloropyridine-3-carboxylate

2-Chloropyridine-3-carboxylic acid (25 g) was refluxed 3 hours in 200 mL of benzene containing 150 mL of thionyl chloride. The reaction mixture was concentrated in vacuo and chased with toluene. The residue obtained was treated with 100 mL of ethanol and refluxed an additional 20 minutes. The ethanol was removed under reduced pressure and the product was dissolved in toluene. The toluene solution was dried over magnesium sulfate and concentrated in vacuo to give the product as a colorless oil which was used without further purification in the next step.

EXAMPLE 87B

Ethyl 2-propylamino-pyridine-3-carboxylate

The compound resulting from Example 87A (10.0 g) was treated with 20 mL of propylamine in 40 mL of ethanol according the procedure described in Example 85B to afford the title compound (9.10 g) as a colorless oil.

EXAMPLE 87C

Ethyl 2-{N-propyl-N-[(2'-[N-triphenylmethyl-1H-tetrazol-5-yl]biphenyl-4-yl)methyl]amino}pyridine-3-carboxylate To the compound resulting from Example 87B (1.41 g, 6.78 mmol) dissolved in 5 mL of tetrahydrofuran was added 1.65 g of 1,3-dimethyl-3,4,5,6-tetrahydro-2(1H)-pyrimidinone. This mixture was treated with 6.78 mL of 1M lithium hexamethyldisilazide followed by 3.55 g (6.35 mmol) of N-triphenylmethyl-5-[2-(4'-bromomethyl-biphenyl)]tetrazole by the procedure described in Example 85C to give 2.25 g of the title compound. m.p. 129°–131° C.

EXAMPLE 87D

Ethyl 2-{N-propyl-N-[(2'-[1H-tetrazol-5-yl]biphenyl-4-yl)methyl]amino}pyridine-3-carboxylate The compound resulting from Example 87C (2.00 g, 2.92 mmol) was treated with hydrogen chloride in ethanol by the procedure described in Example 18C to give the title compound (1.09 g) in 87% yield. $^1$H NMR (CDCl$_3$, 300 MHz) d 0.82 (t, J=7 Hz, 3H), 1.35 (t, J=7 Hz, 3H), 1.60 (m, 2H), 3.23 (t, J=7 Hz, 2H), 4.30 (q, J=7 Hz, 2H), 4.60 (s, 2H), 6.70 (dd, J=8 Hz, 4 Hz, 1H), 7.10 (d, J=8 Hz, 2H), 7.24 (d, J=8 Hz, 2H), 7.42 (dd, J=8 Hz, 1 Hz, 1H), 7.50–7.65 (m, 2H), 7.91 (dd, J=8 Hz, 2 Hz, 1H), 8.04 (dd, J=4 Hz, 2 Hz, 1H), 8.13 (dd, J=8 Hz, 1 Hz, 1H).

EXAMPLE 88

2-{N-Propyl-N-[(2'-[1H-tetrazol-5-yl]biphenyl-4-yl)methyl]amino}pyridine-3-carboxylic acid The compound of Example 87D (400 mg) was converted to the title compound using the procedure described in Example 86 to afford the title compound (278 mg) in 74%. m.p. 202°–204° C. $^1$H NMR (DMSO-d$_6$, 300 MHz) d 0.73 (t, J=7 Hz, 3H), 1.50 (m, 2H), 3.22 (t, J=7 Hz, 2H), 4.67 (s, 2H), 6.80 (dd, J=8 Hz, 4 Hz, 1H), 7.11 (d, J=8 Hz, 2H), 7.21 (d, J=8 Hz, 2H), 7.50–7.70 (m, 4H), 7.76 (dd, J=8 Hz, 2 Hz, 1H), 8.21 (dd, J=4 Hz, 2 Hz, 1H).

EXAMPLE 89

Ethyl 6-methyl-2-{N-propyl-N-[(2'-[1H-tetrazol-5-yl]biphenyl-4-yl)methyl]amino}pyrazine-3-carboxylate

EXAMPLE 89A

Ethyl 2-hydroxy-6-methylpyrazine-3-carboxylate

2-Hydroxy-6-methylpyrazine-3-carboxylic acid (32.5 g), prepared as described in J. Chem. Soc. 1955, 1379, was suspended in 500 mL of ethanol. The solution was cooled in an ice bath and hydrogen chloride gas was bubbled into the solution for 15 minutes. The mixture was stirred overnight at ambient temperature and then refluxed for 2 hours. The ethanol was removed under reduced pressure and the residue obtained crystallized from ethanol/ether to give 21.48 g of the title compound. m.p. 153° C.

EXAMPLE 89B

Ethyl 6-methyl-2-{N-propyl-N-[(2'-[N-triphenylmethyl-1H-tetrazol-5-yl]biphenyl-4-yl)methyl]amino}pyrazine-3-carboxylate To the compound resulting from Example 89A (1.43 g, 7.86 mml) suspended in 8 mL of dimethylformamide was added triethylamine (1.8 g). To the resulting solution was added benzenesulfonyl chloride (1.45 g, 8.21 mmol). The mixture was stirred for 5 minutes at ambient temperature. N-Triphenylmethyl-5-[2-(4'-propylaminomethyl-biphenyl)]tetrazole (3.89 g, 7.17 mmol) dissolved in 3 mL of toluene was then added. The mixture was stirred at 45° C. for 18 hours. Dilute potassium bicarbonate was added and the mixture was extracted with toluene. The combined organic extracts were washed with sodium chloride solution, dried over sodium sulfate and concentrated under reduced pressure. The residue obtained was chromatographed on silica gel eluting with 15% ethyl acetate in toluene to give 3.00 g of the title compound in 60% yield. m.p. 110°–112° C.

EXAMPLE 89C

Ethyl 6-methyl-2-{N-propyl-N-[(2'-[1H-tetrazol-5-yl]biphenyl-4-yl)methyl]amino}pyrazine-3-carboxylate The compound resulting from Example 89B (3.00 g, 1.43 mmol) was treated with hydrogen chloride in ethanol by the procedure described in Example 18C to give the title compound (1.08 g). m.p. 172°–174° C. (crystallized from acetonitrile). $^1$H NMR (CDCl$_3$, 300 MHz) d 0.77 (t, J=7 Hz, 3H), 1.17 (t, J=7 Hz, 3H), 1.52 (m, 2H), 2.50 (s, 3H), 3.21 (t, J=7 Hz, 2H), 4.15 (q, J=7 Hz, 2H), 4.72 (s, 2H), 7.10 (d, J=8 Hz, 2H), 7.20 (d, J=8 Hz, 2H), 7.44 (dd, J=8 Hz, 1 Hz, 1H), 7.50–7.65 (m, 2H), 7.65 (s, 1H), 8.12 (dd, J=8 Hz, 1 Hz, 1H).

EXAMPLE 90

6-Methyl-2-[N-propyl-N-[(2'-[1H-tetrazol-5-yl]biphenyl-4-yl)methyl]amino}pyrazine-3-carboxylic acid The compound resulting from Example 89C (250 mg) was converted to the title compound by the procedure described in Example 86 to give 253 mg of the title compound which crystallized with one equivalent of ether. $^1$H NMR (CDCl$_3$, 300 MHz) d 0.90 (t, J=7 Hz, 3H), 1.20 (t, J=7 Hz, 6H), 1.62 (m, 2H), 2.52 (s, 3H), 3.48 (q, J=7 Hz, 4H), 3.52 (t, J=7 Hz, 2H), 4.66 (s, 2H), 7.05 (d, J=8 Hz, 2H), 7.15 (d, J=8 Hz, 2H), 7.40 (dd, J=8 Hz, 1 Hz, 1H), 7.45–7.60 (m, 4H), 7.91 (s, 1H), 8.01 (dd, J=8 Hz, 1 Hz, 1H).

EXAMPLE 91

2-{N-Butyl-N-[(2'-[1H-tetrazol-5-yl]biphenyl-4-yl)methyl]amino}-4,6-dimethylpyrimidine

EXAMPLE 91A

2-{N-Butyl-N-[(2'-[N-triphenylmethyl-1H-tetrazol-5-yl]biphenyl-4-yl)methyl]amino}-4,6-dimethylpyrimidine 2-Butylamino-4,6-dimethylpyrimidine (968 mg, 5.41 mmol), prepared as described by D. J. Brown and J. M. Lyall, Aust. J. Chem. 1964 17:794, and 1,3-dimethyl-3,4,5,6-tetrahydro-2(1H)-pyrimidinone (1.38 mL) were dissolved in 2 mL of tetrahydrofuran. While cooling in an ice bath, 5.5 mL of a 1M solution of lithium hexamethyldisilazide in tetrahydrofuran was added. After 12 minutes at 0° C., a solution of 2.52 g (4.52 mmol) of N-triphenylmethyl-5-[2-(4'-bromomethyl-biphenyl)]tetrazole in 8 mL of tetrahydrofuran was added. The solution was stirred for 90 minutes at ambient temperature and then quenched by the addition of concentrated hydrochloric acid (2 drops). The reaction mixture was concentrated in vacuo and the residue obtained dissolved in toluene. The toluene solution was washed with dilute sodium hydroxide solution and water, dried over sodium sulfate and concentrated in vacuo. The residue obtained was chromatographed on silica gel eluting with 2% ether in toluene to give 1.65 g of the title compound. m.p. 131°–133° C.

EXAMPLE 91B

2-{N-Butyl-N-[(2'-[1H-tetrazol-5-yl]biphenyl-4-yl)methyl]amino}-4,6-dimethylpyrimidine The compound resulting from Example 91A (1.50 g, 2.29 mmol) was dissolved in 14 mL of methylene chloride and 21 mL of 88% formic acid. After 1 hour at ambient temperature, the solution was concentrated in vacuo. Water was added and the mixture was concentrated again, and the residue obtained was extracted with ether. The combined organic extracts were then extracted with potassium hydroxide solution. The combined aqueous extracts were acidified with formic acid. The oil which separated was extracted with chloroform and the combined organic extracts were dried over sodium sulfate and concentrated in vacuo. The residue obtained was crystallized from ether to afford 708 mg of the title compound. m.p. 148°–150° C. $^1$H NMR (CDCl$_3$, 300 MHz) d 0.92 (t, J=7 Hz, 3H), 1.32 (m, 2H), 1.60 (m, 2H), 2.27 (s, 6H), 3.62 (t, J=7 Hz, 2H), 4.88 (s, 2H), 6.26 (s, 1H), 7.09 (d, J=8 Hz, 2H), 7.20 (d, J=8 Hz, 2H), 7.38 (dd, J=8 Hz, 1 Hz, 1H), 7.45–7.60 (m, 2H), 8.13 (dd, J=8 Hz, 1 Hz, 1H).

EXAMPLE 92

4-{N-Butyl-N-[(2'-[1H-tetrazol-5-yl]biphenyl-4-yl)methyl]amino}-2,6-dimethylpyrimidine

EXAMPLE 92A

4-{N-Butyl-N-[(2'-[N-triphenylmethyl-1H-tetrazol-5-yl]biphenyl-4-yl)methyl]amino}-2,6-dimethylpyrimidine 4-[N-Butylamino-2,6-dimethylpyrimidine (806 mg, 4.50 mmol), prepared as described by D. J. Brown and J. M. Lyall, *Aust. J. Chem.* 1964, 17:794, was reacted by the procedure described in Example 91A. The crude product was purified by chromatography on silica gel eluting with 40% ethyl acetate in toluene to afford the title compound (1.55 g). m.p. 125°–127° C.

EXAMPLE 92B

4-{N-Butyl-N-[(2'-[1H-tetrazol-5-yl]biphenyl-4-yl)methyl]amino}-2,6-dimethylpyrimidine The compound resulting from Example 92A (1.55 g, 2.37 mmol) was dissolved in 14 mL of methylene chloride and 21 mL of 88% formic acid. After 1 hour at ambient temperature, the solution was concentrated in vacuo. The residue obtained was treated with 50 mL of water and the solid obtained removed by filtration. The filtrate was neutralized to pH 8 with sodium bicarbonate and then acidified with 0.5 mL acetic acid. The solid which separated was dissolved in chloroform, and the solution obtained was dried over sodium sulfate and concentrated in vacuo to afford 803 mg of the title compound. $^1$H NMR (DMSO-d$_6$, 300 MHz) d 0.90 (t, J=7 Hz, 3H), 1.29 (m, 2H), 1.50 (m, 2H), 2.21 (s, 3H), 2.34 (s, 3H), 3.42 (bm, 2H), 4.77 (bs, 2H), 6.42 (s, 1H), 7.05 (d, J=8 Hz, 2H), 7.12 (d, J=8 Hz, 2H), 7.45–7.58 (m, 4H).

EXAMPLE 93

3-Amino-2-{N-propyl-N-[(2'-[1H-tetrazol-5-yl]biphenyl-4-yl)methyl]amino}pyridine hydrochloride

EXAMPLE 93A

3-Amino-2-{N-propyl-N-[(2'-[N-triphenylmethyl-1H-tetrazol-5-yl]biphenyl-4-yl)methyl]amino}-pyridine hydrochloride The compound resulting from Example 84A (2.00 g) was dissolved in 250 mL of ethyl acetate and hydrogenated using 200 mg of 10% palladium on carbon as a catalyst. Upon completion of the reaction, the catalyst was removed by filtration and the filtrate concentrated in vacuo. The residue obtained was chromatographed on silica gel eluting with 25% ethyl acetate in hexane to give 1.20 g of the title compound.

EXAMPLE 93B

3-Amino-2-{N-propyl-N-[(2'-[1H-tetrazol-5-yl]biphenyl-4-yl)methyl]amino}pyridine hydrochloride The compound resulting from Example 93A (420 mg) was refluxed in a mixture of 7 mL of tetrahydrofuran, 7 mL of acetic acid, and 0.25 mL of water for 90 minutes. The solvents were removed under reduced pressure and the crude product chromatographed on silica gel eluting with 5% water and 5% formic acid in ethyl acetate. The residue obtained was treated with hydrochloric acid to give the title compound (100 mg). $^1$H NMR (CDCl$_3$, 300 MHz) d 0.98 (t. J=7 Hz, 3H), 1.21 (m, 2H), 3.55 (t, J=7 Hz, 2H), 4.23 (s, 2H), 4.60 (s, 2H), 6.75 (m, 2H), 7.09 (d, J=8 Hz, 2H), 7.25 (d, J=8 Hz, 2H), 7.40–7.60 (m, 3H), 7.85 (dd, 1H), 8.15 (dd, 1H).

EXAMPLE 94

3-Methanesulfonamido-2-{N-propyl-N-[(2'-[1H-tetrazol-5-yl]biphenyl-4-yl)methyl]amino}pyridine To the compound resulting from Example 93A (500 mg, 0.8 mmol) dissolved in 10 mL of methylene chloride containing 0.11 mL of triethylamine was added methanesulfonyl chloride (0.92 mL, 1.04 mmol). After 18 hours, the reaction mixture was washed with water, dried over magnesium sulfate and concentrated in vacuo. The residue obtained was chromatographed on silica gel eluting with 25% ethyl acetate in hexane to give the N-triphenylmethyl intermediate. This compound was refluxed in 12 mL of tetrahydrofuran containing 12 mL of acetic acid and 1 mL of water for 1 hour. The solvents were removed under reduced pressure and the residue obtained chromatographed on silica gel eluting with 10% methanol in methylene chloride to give the title compound. $^1$H NMR (CDCl$_3$, 300 MHz) d 0.95 (t, J=8 Hz, 3H), 1.45 (m, 2H), 3.05 (s, 3H), 3.15 (t, J=7 Hz, 2H), 4.11 (s, 2H), 7.02 (d, J=8 Hz, 2H), 7.08 (d, J=8 Hz, 2H), 7.15 (dd, 1H), 7.42 (dd, J=8 Hz, 1 Hz, 1H), 7.45–7.60 (m, 3H), 7.95 (dd, J=8 Hz, 1 Hz, 1H), 8.19 (dd, 1H).

EXAMPLE 95

Ethyl
4-{N-butyl-N-[(2'-[1H-tetrazol-5-yl]biphenyl-4-yl)methyl]amino}pyrimidine-5-acetate

EXAMPLE 95A

Ethyl
4-{N-butyl-N-[(2'-[N-triphenylmethyl-1H-tetrazol-5-yl]biphenyl-4-yl)methyl]amino}pyrimidine-5-acetate Ethyl 4-chloropyrimidine-5-acetate (300 mg, 1.5 mmol), prepared as described by G. G. Massarol and G. Signorelli, *Boll. Chim. Farm.* 1966, 105(5): 400, N-triphenylmethyl-5-[2-(4''-butylaminomethyl-biphenyl)-]tetrazole (0.84 g, 1.5 mmol) and 1.5 mL of diisopropylethylamine in 3 mL of toluene were refluxed for 4 days. The product was chromatographed on silica gel to give 300 mg of the title compound.

EXAMPLE 95B

Ethyl
4-{N-butyl-N-[(2'-[1H-tetrazol-5-yl]biphenyl-4-yl)methyl]amino}pyrimidine-5-acetate The compound resulting from Example 95A (380 mg) was refluxed in 10 mL of tetrahydrofuran, 10 mL of acetic acid and 1 mL of water for 1 hour. The product was chromatographed on silica gel eluting with 10% ethanol in methylene chloride to give 130 mg of the title compound. $^1$H NMR (CDCl$_3$, 300 MHz) d 0.90 (t, J=7 Hz, 3H), 1.22 (t, J=7 Hz, 3H), 1.26 (m, 2H), 1.55 (m, 2H), 3.36 (t, J=7 Hz, 2H), 3.45 (s, 2H), 4.15 (q, J=7 Hz, 2H), 4.25 (s, 2H), 7.09 (d, J=8 Hz, 2H), 7.14 (d, J=8 Hz, 2H), 7.44 (dd, J=8 Hz, 1 Hz, 1H), 7.50–7.65 (m, 2H), 7.72 (s, 1H), 8.00 (dd, J=8 Hz, 1 Hz, 1H), 8.17 (s, 1H).

EXAMPLE 96

Ethyl
2-methyl-4-{N-propyl-N-[(2'-[1H-tetrazol-5-yl]biphenyl-4-yl)methyl]amino}pyrimidine-5-carboxylate

EXAMPLE 96A

N-Triphenylmethyl-5-[2-(4'-propylaminomethyl-biphenyl)]tetrazole

To N-triphenylmethyl-5-[2-(4'-bromomethyl-biphenyl)]tetrazole (2.8 g, 5 mmol) dissolved in tetrahydrofuran (50 mL) was added propylamine (2.5 mL). The reaction was stirred for 4 hours at ambient temperature and then concentrated in vacuo. The residue obtained was dissolved in ethyl acetate, washed with water and saturated sodium chloride, dried over sodium sulfate and concentrated under reduced pressure to afford the title compound.

EXAMPLE 96B

Ethyl
2-methyl-4-{N-propyl-N-[(2'-[N-triphenylmethyl-1H-tetrazol-5-yl]biphenyl-4-yl)methyl]amino}pyrimidine-5-carboxylate The compound resulting from Example 96A (2.5 mmol) was dissolved in tetrahydrofuran (15 mL) containing N-methylmorpholine (1.1 mL). Ethyl 2-methyl-4-chloropyrimidine-5-carboxylate (502 mg, 2.5 mmol) was added and the reaction mixture stirred at ambient temperature for 16 hours. The reaction mixture was concentrated under reduced pressure and the residue obtained dissolved in ethyl acetate. This solution was washed with water and saturated brine, dried over sodium sulfate and concentrated under reduced pressure. The crude material was chromatographed on silica gel eluting with a gradient of ethyl acetate in toluene to afford the title compound as a light yellow oil which solidified on standing (1.2 g, 68%).

EXAMPLE 96C

Ethyl-2-methyl-4-{N-propyl-N-[(2'-[1H-tetrazol-5-yl]biphenyl-4-yl)methyl]amino}pyrimidine-5-carboxylate The compound resulting from Example 96B (200 mg, 0.286 mmol) was suspended in 5 mL of ethanol and hydrogen chloride saturated ethanol (500 mL) was added. After stirring for 2 hours at ambient temperature, the reaction mixture was concentrated under reduced pressure. The residue obtained was dissolved in ethyl acetate (50 mL), washed with water, dried over sodium sulfate and concentrated under reduced pressure to afford a light yellow oil. This oil was dissolved in ethyl acetate (20 mL) and hexane (200 mL) was added. The resulting solid was collected by filtration and dried under vacuum to afford the title compound as a colorless amorphous solid (75 mg, 57%). $^1$H NMR (CDCl$_3$, 300 MHz) d 0.84 (t, J=7.5 Hz, 3H), 1.33 (t, J=7.5 Hz, 3H), 1.60 (m, 2H), 2.35 (s, 3H), 3.39 (t, J=7.5 Hz, 2H), 4.30 (q, J=7.5 Hz, 2H), 4.78 (s, 2H), 7.04 (s, 4H), 7.45 (dd, J=7.5 Hz, 2 Hz, 1H), 7.50–7.62 (m, 2H), 7.97 (dd, J=7.5 Hz, 2 Hz, 1H), 8.16 (s, 1H).

EXAMPLE 97

Ethyl
2-n-propyl-4-{N-propyl-N-[(2'-[1H-tetrazol-5-yl]biphenyl-4-yl)methyl]amino}pyrimidine-5-carboxylate

EXAMPLE 97A

Ethyl
2-n-propyl-4-{N-propyl-N-[(2'-[N-triphenylmethyl-1H-tetrazol-5-yl]biphenyl-4-yl)methyl]amino}pyrimidine-5-carboxylate The compound resulting from Example 96A (1.2 g, 2.2 mmol) was dissolved in tetrahydrofuran (20 mL) containing N-methylmorpholine (1 mL). Ethyl 2-n-propyl-4-chloropyrimidine-5-carboxylate (563 mg, 2.5 mmol) was added and the reaction mixture stirred at ambient temperature for 60 hours. The reaction was worked up and purified by the procedure described in Example 96B to provide the title compound as a colorless amorphous solid (1.08 g, 60%).

EXAMPLE 97B

Ethyl
2-n-propyl-4-{N-propyl-N-[(2'-[1H-tetrazol-5-yl]biphenyl-4-yl)methyl]amino}pyrimidine-5-carboxylate The compound resulting from Example 97A (300 mg, 0.41 mmol) was deprotected by the procedure described in Example 96C to afford the title compound as a colorless amorphous solid (120 mg, 60%). $^1$H NMR (CDCl$_3$, 300 MHz) d 0.93 (t, J=8 Hz, 3H), 1.30 (t, J=7.5 Hz, 3H), 1.72 (m, 4H), 2.77 (t, J=7.5 Hz, 2H), 3.63 (bt, J=8 Hz, 2H), 4.26 (q, J=7.5 Hz, 2H), 4.86 (s, 2H), 7.00 (d, J=9 Hz, 2H), 7.08 (d, J=9 Hz, 2H), 7.40 (dd, J=7.5 Hz, 2 Hz, 1H), 7.55 (m, 2H), 7.95 (dd, J=7.5 Hz, 2 Hz, 1H), 8.39 (s, 1H).

EXAMPLE 98

2-n-Propyl-4-{N-propyl-N-[(2'-[1H-tetrazol-5-yl]biphenyl-4-yl)methyl]amino}pyrimidine-5-carboxylic acid To the compound resulting from Example 97 (630 mg, 1.3 mmol) dissolved in ethanol (25 mL) was added a solution of sodium hydroxide (520 mg, 13 mmol) in 2.5 mL of water. The mixture was refluxed for 2.5 hours, cooled to ambient temperature and concentrated under reduced pressure. The residue obtained was suspended in water (50 mL) and washed with ether. The aqueous phase was acidified with 12N hydrochloric acid and extracted with methylene chloride. The combined organic extracts were washed with saturated brine, dried over sodium sulfate and concentrated under reduced pressure to afford the title compund as an amorphous solid (440 mg, 74%). $^1$H NMR (DMSO-d$_6$, 300 MHz) d 0.76 (t, J=7.5 Hz, 3H), 0.85 (t, J=7.5 Hz, 3H), 1.55 (m, 2H), 1.65 (m, 2H), 2.65 (t, J=7.5 Hz, 2H), 3.38 (m, 2H), 4.85 (s, 2H), 7.04 (d, J=8 Hz, 2H), 7.18 (d, J=8 Hz, 2H), 7.50–7.70 (m, 4H), 8.50 (s, 1H).

EXAMPLE 99

2-Methyl-4-{N-propyl-N-[(2'-[1H-tetrazol-5-yl]biphenyl-4-yl)methyl]amino}pyrimidine-5-carboxylic acid The compound resulting from Example 96 (250 mg, 0.546 mmol) was hydrolyzed and worked up according to the procedure described in Example 98. The crude product was recrystallized from methylene chloride and hexane to afford the title compound as a colorless amorphous solid (140 mg, 55%). $^1$H NMR (CD$_3$OD, 300 MHz) d 0.90 (t, J=7.5 Hz, 3H), 1.72 (m, 2H), 2.59 (s, 3H), 3.70 (bt, J=7.5 Hz, 2H), 5.07 (s, 2H), 7.10 (d, J=9 Hz, 2H), 7.22 (bd, J=9 Hz, 2H), 7.57 (dt, J=7.5 Hz, 1 Hz, 2H), 7.68 (m, 2H), 8.46 (s, 1H).

EXAMPLE 100

Ethyl 2-methyl-4-{N-pentyl-N-[(2'-[1H-tetrazol-5-yl]biphenyl-4-yl)methyl]amino}pyrimidine-5-carboxylate

EXAMPLE 100A

N-Triphenylmethyl-5-[2-(4'-pentylaminomethyl-biphenyl)]tetrazole

Using the procedure described in Example 96A, N-triphenylmethyl-5-[2-(4'-bromomethyl-biphenyl)]tetrazole (3.00 g, 5.4 mmol) was reacted with n-pentylamine (6 mL) in tetrahydrofuran (50 mL) to afford the title compound as a yellow oil (3.00 g, 98%).

EXAMPLE 100B

Ethyl 2-methyl-4-{N-pentyl-N-[(2'N-triphenylmethyl-1H-tetrazol-5-yl]biphenyl-4-yl)methyl]amino}pyrimidine-5-carboxylate Using the procedure described in Example 96B, the compound resulting from Example 100A (2.00 g, 3.5 mmol), ethyl 2-methyl-4-chloropyrimidine-5-carboxylate (703 mg, 3.5 mmol), and N-methylmorpholine (2 mL) in tetrahydrofuran (30 mL) were stirred for 60 hours at ambient temperature. Work up and chromatography using ethyl acetate and toluene mixtures provided the title compound as a colorless amorphous solid (1.00 g, 47%).

EXAMPLE 100C

Ethyl 2-methyl-4-{N-pentyl-N-[(2'-[1H-tetrazol-5-yl]biphenyl-4-yl)methyl]amino}pyrimidine-5-carboxylate To the compound resulting from Example 100B (1.00 g, 1.3 mmol) dissolved in tetrahydrofuran (25 mL) was added acetic acid (4 mL) and water (1 mL). The reaction mixture was refluxed for 24 hours and then the cooled reaction mixture was concentrated under reduced pressure. The residue obtained was dissolved in ethyl acetate (200 mL) and washed with water and saturated sodium chloride, dried over sodium sulfate and concentrated under reduced pressure. The residue obtained was triturated with ether and the resulting solid collected by filtration to afford the title compund as a colorless amorphous solid (390 mg, 62%). $^1$H NMR (DMSO-d$_6$, 300 MHz) d 0.82 (t, J=7.5 Hz, 3H), 1.10–1.28 (m, 4H), 1.24 (t, J=7.5 Hz, 3H), 1.50 (m, 2H), 2.40 (s, 3H), 3.30 (m, 2H), 4.20 (q, J=7.5 Hz, 2H), 4.80 (s, 2H), 7.05 (d, J=8 Hz, 2H), 7.16 (d, J=8 Hz, 2H), 7.50–7.70 (m, 4H), 8.40 (s, 1H).

EXAMPLE 101

2-Methyl-4-{N-pentyl-N-[(2'-[1H-tetrazol-5-yl]biphenyl-4-yl)methyl]amino}pyrimidine-5-carboxylic acid The compound resulting from Example 99 (250 mg, 0.51 mmol) was hydrolyzed with sodium hydroxide (206 mg) using the procedure described in Example 98. The crude product was dissolved in methylene chloride and hexane was added. The resulting solid was collected by filtration to afford the title compound as an amorphous solid (150 mg, 59%). $^1$H NMR (CD$_3$OD, 300 MHz) d 0.90 (t, J=7.5 Hz, 3H), 1.30 (m, 4H), 1.70 (m, 2H), 2.55 (s, 3H), 3.72 (t, J=7.5 Hz, 2H), 5.07 (s, 2H), 7.10 (d, J=8 Hz, 2H), 7.22 (d, J=8 Hz, 2H), 7.56 (m, 2H), 7.67 (m, 2H), 8.27 (s, 1H).

EXAMPLE 102

Ethyl 2-methyl-4-{N-(2-methylpropyl)-N-[(2'-[1H-tetrazol-5-yl]biphenyl-4-yl)methyl]amino}pyrimidine-5-carboxylate

EXAMPLE 102A

N-Triphenylmethyl-5-{2-[4'-(2-methylpropyl)aminomethyl]}tetrazole

Using the procedure described in Example 96A, N-triphenylmethyl-5-[2-(4'-bromomethyl-biphenyl)]tetrazole (3.00 g, 5.4 mmol) in tetrahydrofuran (50 mL) was treated with isobutylamine (3.9 g) and worked up to afford the title compound as a light yellow amorphous solid (3.00 g).

EXAMPLE 102B

Ethyl 2-methyl-4-{N-(2-methylpropyl)-N-[(2'-[N-triphenylmethyl-1H-tetrazol-5-yl]biphenyl-4-yl)methyl]amino}pyrimidine-5-carboxylate Using the procedure described in Example 100B, the compound resulting from Example 102A (1.5 g), ethyl 2-methyl-4-chloropyrimidine-5-carboxylate (543 mg, 2.7 mmol) and N-methylmorpholine (3 mL) were mixed in tetrahydrofuran (25 mL) and stirred for 18 hours at ambient temperature. Work up and chromatography eluting with ethyl acetate and toluene mixtures afforded the title compound as an amorphous solid (1.18 g, 81%).

EXAMPLE 102C

Ethyl 2-methyl-4-{N-(2-methylpropyl)-N-[(2'-[1H-tetrazol-5-yl]biphenyl-4-yl)methyl]amino}pyrimidine-5-carboxylate The compound resulting from Example 102B (1.15 g, 1.6 mmol) was dissolved in tetrahydrofuran (20 mL). Acetic acid (10 mL) and water (1 mL) were added and the reaction mixture was refluxed for 4 hours. The cooled reaction mixture was concentrated under reduced pressure and the residue obtained dissolved in ethyl acetate. The organic layer was washed with water and brine, dried over sodium sulfate and concentrated under reduced pressure. Trituration of the residue with ether/hexane afforded the title compound as a colorless amorphous solid (670 mg, 88%). $^1$H NMR (CDCl$_3$, 300 MHz) d 0.80 (d, J=7.5 Hz, 6H), 1.38 (t, J=7.5 Hz, 3H), 1.95 (m, 1H), 2.20 (s, 3H), 3.18 (bd, J=7.5 Hz, 2H), 3.38 (q, J=7.5 Hz, 2H), 4.62 (s, 2H), 6.98 (d, J=9 Hz, 2H), 7.01 (d, J=9 Hz, 2H), 7.46 (dd, J=7.5 Hz, 2 Hz, 2H), 7.52–7.63 (m, 4H), 8.00 (s, 1H), 8.13 (dd, J=7.5 Hz, 2 Hz, 1H).

EXAMPLE 103

2-Methyl-4-{N-(2-methylpropyl)-N-[(2'-[1H-tetrazol-5-yl]biphenyl-4-yl)methyl]amino}pyrimidine-5-carboxylic acid The compound resulting from Example 102 (300 mg, 0.64 mmol) was hydrolyzed with sodium hydroxide (254 mg) by the procedure described in Example 98. The crude product was dissolved in tetrahydrofuran (50 mL) and hexane (100 mL) was added. The solid obtained was filtered to afford the title compound as a colorless amorphous solid (240 mg, 86%). $^1$H NMR (DMSO-d$_6$, 300 MHz) d 0.77 (d, J=7 Hz, 6H), 2.00 (m, 1H), 3.30 (d, J=7.5 Hz, 2H), 4.85 (s, 2H), 7.06 (d, J=9 Hz, 2H), 7.18 (d, J=9 Hz, 2H), 7.50–7.60 (m, 2H), 7.60–7.70 (m, 3H), 8.55 (s, 1H).

EXAMPLE 104

Ethyl 2-methyl-4-{N-(3-methylbutyl)-N-[(2'-[1H-tetrazol-5-yl]biphenyl-4-yl)methyl]amino}pyrimidine-5-carboxylate

EXAMPLE 104A

N-Triphenylmethyl-5-{2-[4'-(2-methylbutyl-)aminomethyl-biphenyl]}tetrazole

Using the procedure described in Example 96A, N-triphenylmethyl-5-[2-(4'-bromomethyl-biphenyl)]tetrazole (1.5 g, 2.7 mmol) and isoamylamine (1.7 mL) in tetrahydrofuran (25 mL) were reacted to afford the title compound as a pale yellow amorphous solid.

EXAMPLE 104B

Ethyl 2-methyl-4-{N-(3-methylbutyl)-N-[(2'-[N-triphenylmethyl-1H-tetrazol-5-yl]biphenyl-4-yl)methyl]amino}pyrimidine-5-carboxylate Using the procedure described in Example 96B, the compound resulting from Example 104A was reacted with ethyl 2-methyl-4-chloropyrimidine-5-carboxylate and N-methylmorpholine (2 mL) in tetrahydrofuran (25 mL) for 72 hours. Normal work up and chromatography eluting with ethyl acetate/toluene mixtures afforded the title compound as a colorless oil (1.3 g, 87%).

EXAMPLE 104C

Ethyl 2-methyl-4-{N-(3-methylbutyl)-N-[(2'-[1H-tetrazol-5-yl]biphenyl-4-yl)methyl]amino}pyrimidine-5-carboxylate The compound resulting from Example 104B (1.3 g, 1.8 mmol) was deprotected using acetic acid (20 mL) and water (1 mL) in refluxing tetrahydrofuran (20 mL) by the procedure described in Example 102. The crude product was dissolved in methylene chloride and hexane was added. Filtration of the resulting solid afforded the title compound as an amorphous solid (640 mg, 74%). $^1$H NMR (CDCl$_3$, 300 MHz) d 0.82 (d, J=6 Hz, 6H), 1.32 (t, J=6 Hz, 3H), 1.42 (m, 3H), 2.27 (s, 3H), 3.41 (bt, J=7.5 Hz, 2H), 4.30 (q, J=7.5 Hz, 2H), 4.74 (s, 2H), 7.02 (d, J=8 Hz, 2H), 7.07 (d, J=8 Hz, 2H), 7.44 (dd, J=7 Hz, 2 Hz, 1H), 7.51–7.62 (m, 2H), 8.05 (dd, J=7 Hz, 2 Hz, 1H), 8.07 (s, 1H).

EXAMPLE 105

2-Methyl-4-{N-(3-methylbutyl)-N-[(2'-[1H-tetrazol-5-yl]biphenyl-4-yl)methyl]amino}pyrimidine-5-carboxylic acid Following the procedure described in Example 98, the compound resulting from Example 104C (270 mg, 0.56 mmol) was hydrolyzed using sodium hydroxide (230 mg). The crude product was dissolved in methylene chloride and hexane was added. Filtration of the solid obtained afforded the title compound as an amorphous solid (200 mg, 80%). $^1$H NMR (DMSO-d$_6$, 300 MHz) d 0.82 (d, J=6 Hz, 6H), 1.40 (m, 3H), 2.46 (s, 3H), 3.47 (bt, J=6 Hz, 2H), 4.88 (s, 2H), 7.06 (d, J=8 Hz, 2H), 7.20 (d, J=8 Hz, 2H), 7.50–7.70 (m, 4H), 8.52 (s, 1H).

EXAMPLE 106

Ethyl 2-methyl-4-{N-[1-(2-butenyl)]-N-[(2'-[1H-tetrazol-5-yl]biphenyl-4-yl)methyl]amino}pyrimidine-5-carboxylate The compound resulting from Example 65A (600 mg, 0.91 mmol) was dissolved in anhydrous dimethylformamide (12 mL) under a nitrogen atmosphere. The solution was cooled to 0° C. and crotyl bromide (500 mL, 4.5 mmol) was added followed by 60% oil dispersion sodium hydride (54 mg, 1.4 mmol) in portions. After 1 hour at 0° C., the cooling bath was removed and the reaction was stirred at ambient temperature for 30 minutes. The reaction mixture was cautiously poured into saturated aqueous ammonium chloride solution (100 mL) and extracted with ethyl acetate (3×100 mL). The combined organic ectracts were washed with water and brine, dried over sodium sulfate and sodium carbonate, and concentrated under reduced pressure. Chromatography using ethyl acetate and toluene mixtures provided an orange foam (570 mg, 88%). The foam was deprotected using acetic acid (5 mL) and water (1 mL) in tetrahydrofuran (10 mL) according to the procedure described in Example 100C. Chromatography eluting with ethanol/methylene chloride mixtures afforded an off-white solid. Trituration with ethyl acetate/hexane (1:7) afforded the title compound as an amorphous solid (130 mg, 34%). MS (DCl/NH$_3$) m/e 470 (M+H)$^+$.

EXAMPLE 107

Ethyl 2-methyl-4-{N-[1-(2-propenyl)]-N-[(2'-[1H-tetrazol-5-yl]biphenyl-4-yl)methyl]amino}pyrimidine-5-carboxylate

EXAMPLE 107A

N-Triphenylmethyl-5-[2-(4'-[1-(2-propenyl)-]aminomethyl-biphenyl)]tetrazole

Following the procedure described in Example 96A, N-triphenylmethyl-5-[2-(4'-bromomethyl-biphenyl)]tetrazole (2.00 g, 3.6 mmol) and allylamine (3 mL) were reacted in tetrahydrofuran (10 mL). Normal work up afforded the title compound as an amorphous solid.

EXAMPLE 107B

Ethyl 2-methyl-4-{N-[1-(2-propenyl)]-N-[(2'-[N-triphenylmethyl-1H-tetrazol-5-yl]biphenyl-4-yl)methyl]amino}pyrimidine-5-carboxylate The compound resulting from Example 107A was reacted with ethyl 2-methyl-4-chloropyrimidine-5-carboxylate (720 mg, 3.6 mmol) and N-methylmorpholine (2 mL) in tetrahydrofuran (15 mL). Normal work up and chromatography using ethyl acetate/tolune mixtures afforded the title compound as an amorphous solid (1.5 g, 80%).

EXAMPLE 107C

Ethyl 2-methyl-4-{N-[1-(2-propenyl)]-N-[(2'-[1H-tetrazol-5-yl]biphenyl-4-yl)methyl]amino}pyrimidine-5-carboxylate The compound resulting from Example 107B (1.5 g, 2.1 mmol) was deblocked with acetic acid (30 mL) and water (3 mL) in refluxing tetrahydrofuran (30 mL) for 3 hours according to the procedure described in Example 100C. Normal work up afforded a colorless solid which was triturated with hexane to afford a partially purified product. Recrystallization from methylcyclohexane afforded the title compound as an amorphous solid (260 mg, 27%). $^1$H NMR (CDCl$_3$, 300 MHz) d 1.30 (t, J=7.5 Hz, 3H), 2.27 (s, 3H), 3.97 (d, J=6 Hz, 2H), 4.27 (q, J=7.5 Hz, 2H), 4.82 (s, 2H), 5.08–5.14 (m, 2H), 5.70–5.85 (m, 1H), 7.02 (d, J=9 Hz, 2H), 7.06 (d, J=9 Hz, 2H), 7.46 (dd, J=7.5 Hz, 2 Hz, 1H), 7.52–7.63 (m, 2H), 8.03 (dd, J=7.5 Hz, 2 Hz, 1H), 8.12 (s, 1H).

EXAMPLE 108

2-Methyl-4-{N-[1-(2-propenyl)]-N-[(2'-[1H-tetrazol-5-yl]biphenyl-4-yl)methyl]amino}pyrimidine-5-carboxylic acid The compound resulting from Example 107 (660 mg, 1.45 mmol) was hydrolyzed with sodium hydroxide (580 mg, 14.5 mmol) by the procedure described in Example 98. The crude product was dissolved in ethanol and ether was added. Filtration of the solid afforded the title compound as an amorphous solid (210 mg, 34%). $^1$H NMR (DMSO-d$_6$, 300 MHz) d 2.50 (s, 3H), 4.10 (d, J=6 Hz, 2H), 4.87 (s, 2H), 5.11–5.25 (m, 2H), 5.70–5.85 (m, 1H), 7.05 (d, J=7.5 Hz, 2H), 7.21 (d, J=7.5 Hz, 2H), 7.52–7.70 (m, 4H), 8.60 (s, 1H).

EXAMPLE 109

Ethyl 2-methyl-4-{N-ethyl-N-[(2'-[1H-tetrazol-5-yl]biphenyl-4-yl)methyl]amino}pyrimidine-5-carboxylate

EXAMPLE 109A

N-Triphenylmethyl-5-[2-(4'-ethylaminomethyl-biphenyl)]tetrazole

Following the procedure described in Example 96A, N-triphenylmethyl-5-[2-(4'-bromomethyl-biphenyl)]tetrazole (3.00 g, 5.4 mmol) in tetrahydrofuran (50 mL) was treated with 70% ethylamine in water (5 mL). Normal work up afforded the title compound as an amorphous solid.

EXAMPLE 109B

Ethyl 2-methyl-4-{N-ethyl-N-[(2'[N-triphenylmethyl-1H-tetrazol-5-yl]biphenyl-4-yl)methyl]amino}pyrimidine-5-carboxylate Following the procedure described in Example 96B, the compound resulting from Example 109A was dissolved in tetrahydrofuran (25 mL) and treated with N-methylmorpholine (2 mL) and ethyl 2-methyl-4-chloropyrimidine-5-carboxylate (914 mg). After stirring overnight at ambient temperature, normal work up and chromatography eluting with ethyl acetate and toluene mixtures provided the title compound as a light yellow semi-solid (2.00 g, 67%).

EXAMPLE 109C

Ethyl 2-methyl-4-{N-ethyl-N-[(2'-[1H-tetrazol-5-yl]biphenyl-4-yl)methyl]amino}pyrimidine-5-carboxylate Following the procedure described in Example 100C., the compound resulting from Example 109B (1.25 g, 1.8 mmol) was deblocked using acetic acid (20 mL) and water (2 mL) in refluxing tetrahydrofuran (20 mL) for 3.5 hours. Normal work up afforded a crude product which was triturated with hexane to afford a partially purified product. Recrystallization from methylene chloride/methylcyclohexane afforded the title compound as an amorphous solid (450 mg, 56%). $^1$H NMR (CDCl$_3$, 300 MHz) d 1.14 (t, J=7.5 Hz, 3H), 1.32 (t, J=7.5 Hz, 3H), 2.25 (s, 3H), 3.40 (q, J=7.5 Hz, 2H), 4.28 (q, J=7.5 Hz, 2H), 4.72 (s, 2H), 7.01 (d, J=9 Hz, 2H), 7.06 (d, J=9 Hz, 2H), 7.46 (dd, J=7.5 Hz, 1 Hz, 1H), 7.50–7.62 (m, 2H), 8.02 (dd, J=7.5 Hz, 1 Hz, 1H), 8.06 (s, 1H).

EXAMPLE 110

2-Methyl-4-{N-ethyl-N-[(2'-[1H-tetrazol-5-yl]biphenyl-4-yl)methyl]amino}pyrimidine-5-carboxylic acid Following the procedure described in Example 98, the compound resulting from Example 109 (250 mg, 0.56 mmol) was hydrolyzed with sodium hydroxide (225 mg, 5.6 mmol). Normal work up afforded an off-white solid which was dissolved in ethanol (5 mL) and ether (200 mL) was added. Filtration afforded the title compound as an amorphous solid (36 mg, 15%). $^1$H NMR (DMSO-d$_6$, 300 MHz) d 1.10 (t, J=7.5 Hz, 3H), 2.25 (s, 3H), 3.45 (q, J=7.5 Hz, 2H), 4.87 (s, 2H), 7.05 (d, J=9 Hz, 2H), 7.52–7.70 (m, 4H), 8.50 (s, 1H).

EXAMPLE 111

Ethyl
4-{N-[(2'-[1H-tetrazol-5-yl]biphenyl-4-yl)methyl-
]amino}pyrimidine-5-carboxylate

EXAMPLE 111A

Ethyl
4-{N-[(2'-[N-triphenylmethyl-1H-tetrazol-5-yl]biphe-
nyl-4-yl)methyl]amino}pyrimidine-5-carboxylate The compound resulting from Example 1B (7.2 mmol) and ethyl 2-methyl-4-chloropyrimidine-5-carboxylate (1.35 g, 7.2 mmol) were reacted by the method described in Example 96B to afford crude product. Chromatography eluting with ethyl acetate/toluene mixtures provided the title compund as an amorphous solid (300 g, 81%).

EXAMPLE 111B

Ethyl
4-{N-[(2'-[1H-tetrazol-5-yl]biphenyl-4-yl)methyl-
]amino}pyrimidine-5-carboxylate Following the procedure described in Example 100C, the compound resulting from Example 111A (1.5 g, 2.3 mmol) was treated with acetic acid (15 mL) and water (2 mL) in tetrahydrofuran (15 mL). Normal work up afforded a colorless solid. Recrystallization from ethyl acetate/hexane followed by methylene chloride/hexane provided the title compound as an amorphous solid (670 mg, 62%). $^1$H NMR (DMSO-d$_6$, 300 MHz) d 1.32 (t, J=7 Hz, 3H), 4.33 (q, J=7 Hz, 2H), 4.72 (d, J=6 Hz, 2H), 7.04 (d, J=8 Hz, 2H), 7.25 (d, J=8 Hz, 2H), 7.50-7.70 (m, 4H), 8.60 (s, 1H), 8.70 (bt, J=6 Hz, 1H), 8.77 (s, 1H).

EXAMPLE 112

4-{N-[(2'-[1H-tetrazol-5-yl]biphenyl-4-yl)methyl-
]amino}pyrimidine-5-carboxylic acid Following the procedure described in Example 98, the compound resulting from Example 111 (300 mg, 0.75 mmol) was hydrolyzed using sodium hydroxide. The crude reaction mixture was dissolved and acidified with acetic acid. The product was filtered and redissolved in warm methanol/ethanol and filtered. The filtrate was concentrated under reduced pressure to afford the title compound as an amorphous solid (245 mg, 88%). $^1$H NMR (DMSO-d$_6$, 300 MHz) d 4.73 (d, J=6 Hz, 2H), 7.05 (d, J=9 Hz, 2H), 7.25 (d, J=9 Hz, 2H), 7.52-7.70 (m, 4H), 8.60 (s, 1H), 8.72 (s, 1H), 8.90 (bt, J=6 Hz, 1H).

EXAMPLE 113

Ethyl
2-trifluoromethyl-4-{N-propyl-N-[(2'-[1H-tetrazol-5-
yl]biphenyl-4-yl)methyl]amino}pyrimidine-5-carboxy-
late

EXAMPLE 113A

Ethyl
2-trifluoromethyl4-{N-propyl-N-[(2'-[N-triphenylmeth-
yl-1H-tetrazol-5-yl]biphenyl-4-yl)methyl]amino}
pyrimidine-5-carboxylate Following the procedure described in Example 96B, the compound resulting from Example 96A (5 mmol) was treated with ethyl 2-trifluoromethyl-4-chloropyrimidine-5-carboxylate (1.3 g, 5 mmol), prepared according to Barane et al. *J. Org. Chem.* 1959, 24: 198. Normal work up and chromatography using ethyl acetate/hexane mixtures provided an off-white foam. Recrystallization from ethyl acetate/hexane provided the title compound as colorless needles (2.2 g, 70%).

EXAMPLE 113B

Ethyl
2-trifluoromethyl-4-{N-propyl-N-[(2'-[1H-tetrazol-5-
yl]biphenyl-4-yl)methyl]amino}pyrimidine-5carboxy-
late Following the procedure described in Example 100, the compound resulting from Example 113A was deblocked using acetic acid (20 mL) and water (2 mL) in refluxing tetrahydrofuran for 2 hours. Chromatography eluting with ethanol in methylene chloride provided a partially purified product. Recrystallization from methylcyclohexane provided the title compound as an amorphous solid (590 mg, 68%). $^1$H NMR (CDCl$_3$, 300 MHz) d 0.93 (t, J=7.5 Hz, 3H), 1.44 (t, J=7.5 Hz, 3H), 1.72 (m, 2H), 3.60 (t, J=7.5 Hz, 2H), 4.31 (q, J=7.5 Hz, 2H), 4.90 (s, 2H), 7.17-7.20 (m, 4H), 7.42 (dd, J=7 Hz, 1Hz, 1H), 7.52-7.63 (m, 2H), 8.20 (dd, J=7 Hz, 1 Hz, 1H), 8.60 (s, 1H).

EXAMPLE 114

2-Trifluoromethyl-4-{N-propyl-N-[(2'-[1H-tetrazol-5-
yl]biphenyl-4-yl)methyl]amino}pyrimidine-5-carboxy-
lic acid Following the procedure described in Example 98, the compound resulting from Example 113 (350 mg, 0.69 mmol) was suspended in water (10 mL). Solid sodium hydroxide (2.3 g) was added followed by ethanol (4 mL). After stirring at ambient temperature for 1 hour, the reaction was worked up. Chromatography of the residue using water, acetic acid and ethyl acetate mixtures provided a partially purified product. The residue was dissolved in ethyl acetate and hexane was added. Filtration afforded the title compound as an amorphous solid (230 mg, 67%). $^1$H NMR (DMSO-d$_6$, 300 MHz) d 0.78 (t, J=8 Hz, 3H), 1.50-1.61 (m, 2H), 3.40 (m, 2H), 4.84 (m, 2H), 7.05 (d, J=9 Hz, 2H), 7.23 (d, J=9 Hz, 2H), 7.51-7.70 (m, 4H), 8.62 (s, 1H).

EXAMPLE 115

Ethyl
2-trifluoromethyl-4-{N-butyl-N-[(2'-[1H-tetrazol-5-
yl]biphenyl-4-yl)methyl]amino}pyrimidine-5-carboxy-
late

EXAMPLE 115A

Ethyl
2-trifluoromethyl-4-{N-butyl-N-[(2'-[N-triphenylmeth-
yl-1H-tetrazol-5-yl]biphenyl-4-yl)methyl]amino}
pyrimidine-5-carboxylate Following the procedure described in Example 96B, the compound resulting from Example 19 (5.6 mmol) was reacted with ethyl 2-trifluoromethyl-4-chloropyrimidine-5-carboxylate (1.1 g, 5.9 mmol). Normal work up and chromatography using ethyl acetate/hexane mixtures afforded the title compound as an amorphous solid (3.1 g, 72%).

EXAMPLE 115B

Ethyl 2-trifluoromethyl-4-{N-butyl-N-[(2'-[1H-tetrazol-5-yl]biphenyl-4-yl)methyl]amino}pyrimidine-5-carboxylate Following the procedure described in Example 100, the compound resulting from Example 115A (3.1 g, 4 mmol) was deblocked using acetic acid (50 mL) and water (3 mL) in tetrahydrofuran (50 mL) at reflux for 2 hours. Chromatography using ethanol in methylene chloride containing acetic acid provided a substantially purified product. Chromatography using ethanol in methylene chloride mixtures provided the title compound as an amorphous solid (900 mg, 42%). $^1$H NMR (CDCl$_3$, 300 MHz) d 0.95 (t, J=7 Hz, 3H), 1.33 (m, 2H), 1.34 (t, J=6 Hz, 3H), 1.67 (m, 2H), 3.65 (t, J=8 Hz, 2H), 4.30 (t, J=7 Hz, 3H), 4.88 (s, 2H), 7.20 (m, 4H), 7.40–7.65 (m, 3H), 8.20 (bd, J=8 Hz, 1H), 8.60 (s, 1H).

EXAMPLE 116

2-Trifluoromethyl-4-{N-butyl-N-[(2'-[1H-tetrazol-5-yl]biphenyl-4-yl)methyl]amino}pyrimidine-5-carboxylic acid Following the procedure described in Example 98, the compound resulting from Example 115 (850 mg, 1.6 mmol) was hydrolyzed using sodium hydroxide (850 mg). Normal work up afforded a colorless solid. The crude product was dissolved in ether and hexane was added. The solid was collected by filtration and the process was repeated. Filtration afforded the title compound as an amorphous solid (600 mg, 75%). $^1$H NMR (DMSO-d$_6$, 300 MHz) d 0.83 (t, J=7.5 Hz, 3H), 1.20 (m, 2H), 1.52 (m, 2H), 3.45 (bt, J=7.5 Hz, 2H), 4.82 (s, 2H), 7.05 (d, J=8 Hz, 2H), 7.23 (d, J=8 Hz, 2H), 7.51–7.70 (m, 4H), 8.62 (s, 1H).

EXAMPLE 117

Ethyl 1-{N-butyl-N-[(2'-[1H-tetrazol-5-yl]biphenyl-4-yl)methyl]amino}benzene-2-carboxylate

EXAMPLE 117A

Ethyl 1-(N-butylamino)benzene-2-carboxylate

A mixture of ethyl anthranilate (4.96 g, 30 mmol), potassium carbonate (13.8 g, 100 mmol), and n-butyl iodide (25 mL) was stirred at ambient temperature for 48 hours and refluxed for 8 hours. The cooled reaction mixture was diluted with ethyl acetate and filtered. The filtrate was concentrated under reduced pressure and the residue obtained chromatographed eluting with ethyl acetate/hexane mixtures to afford the title comound as a light yellow liquid (2.2 g, 33%).

EXAMPLE 117B

Ethyl 1-{N-butyl-N-[(2'-[N-triphenylmethyl-1H-tetrazol-5-yl]biphenyl-4-yl)methyl]amino}benzene-2-carboxylate The compound resulting from Example 117A (2.00 g, 9 mmol), potassium carbonate (1.38 g, 10 mmol), and N-triphenylmethyl-5-[2-(4'-bromomethyl-biphenyl)]tetrazole (2.00 g, 3 mmol) in anhydrous dimethylformamide (3 mL) were stirred at 55° C. for 20 hours. The cooled reaction mixture was poured into ethyl acetate and washed with saturated brine, dried over sodium carbonate and sodium sulfate, and concentrated under reduced pressure. Flash chromatography eluting with ethyl acetate/hexane mixtures provided the title compound as an amorphous solid (800 mg, 46%).

EXAMPLE 117C

Ethyl 1-{N-butyl-N-[(2'-[1H-tetrazol-5-yl]biphenyl-4-yl)methyl]amino}benzene-2-carboxylate The compound resulting from Example 117A (790 mg, 1.2 mmol) was deblocked following the procedure described in Example 100C. Chromatography eluting with ethanol in methylene chloride provided the title compound as an amorphous solid (370 mg, 70%). $^1$H NMR (CDCl$_3$, 300 MHz) d 0.91 (t, J=7.5 Hz, 3H), 1.36 (t, J=7 Hz, 3H), 1.40 (m, 2H), 1.58 (m, 2H), 3.15 (t, J=7.5 Hz, 2H), 4.07 (s, 2H), 4.25 (q, J=7.5 Hz, 2H), 6.97–7.17 (m, 5H), 7.32–7.61 (m, 6H), 8.21 (dd, J=7 Hz, 2 Hz, 1H).

EXAMPLE 118

1-{N-Butyl-N-[(2'-[1H-tetrazol-5-yl]biphenyl-4-yl)methyl]amino}benzene-2-carboxylic acid The compound resulting from Example 117 (300 mg, 0.66 mmol) was hydrolyzed following the procedure described in Example 98. The crude product was dissolved in methylene chloride and hexane was added. Filtration afforded the title compound as an amorphous solid (230 mg, 79%). $^1$H NMR (DMSO-d$_6$, 300 MHz) d 0.75 (t, J=7.5 Hz, 3H), 1.10–1.28 (m, 2H), 3.07 (t, J=7 Hz, 2H), 4.27 (s, 2H), 7.05 (d, J=9 Hz, 2H), 7.22 (d, J=9 Hz, 2H), 7.40–7.55 (m, 2H), 7.95 (dd, J=9 Hz, 2 Hz, 1H).

EXAMPLE 119

1-(Ethyloxycarbonyloxy)ethyl 4-{N-butyl-N-[(2'-[1H-tetrazol-5-yl]biphenyl-4-yl)methyl]amino}pyrimidine-5-carboxylate

EXAMPLE 119A

4-{N-butyl-N-[(2'-[N-triphenylmethyl-1H-tetrazol-5-yl]biphenyl-4-yl)methyl]amino}pyrimidine-5-carboxylic acid The compound resulting from Example 83A (3.25 g, 4.6 mmol) was dissolved in a 2:3 mixture of ethanol/tetrahydrofuran (50 mL). To this was added a solution of sodium hydroxide (3.25 g) in water (8 mL). After stirring at ambient temperature for 48 hours, an additional aliquot of sodium hydroxide (1.00 g) was added and stirring was continued for an additional 24 hours. The reaction mixture was concentrated under reduced pressure and the residue obtained suspended in water (100 mL). Concentrated hydrochloric acid was added and the suspension was extracted with ethyl acetate. The combined organic extracts were dried over sodium sulfate and concentrated under reduced pressure to afford the title compound as an amorphous solid (3.00 g, 98%).

EXAMPLE 119B 1-(Ethyloxycarbonyloxy)ethyl 4-{N-butyl-N-[(2'-[N-triphenylmethyl-1H-tetrazol-5-yl]biphenyl-4-yl)methyl]amino}pyrimidine-5-carboxylate The compound resulting from Example 119A (1.00 g, 1.5 mmol) was dissolved in anhydrous dimethylformamide (3 mL) and potassium carbonate (616 mg, 4.5 mmol), 1-chloroethyl ethyl carbonate (460 mg, 3 mmol), sodium iodide (450 mg) and triethylamine (5 drops) were added. After stirring at ambient temperature for 30 hours, the reaction mixture was poured into saturated aqueous ammonium chloride and extracted with ethyl acetate. The combined organic extracts were washed with brine, dried over sodium sulfate and sodium carbonate, and concentrated under reduced pressure. Chromatography eluting with ethyl acetate/hexane mixtures provided the title compound as an amorphous solid (470 mg, 40%).

EXAMPLE 119C 1-(Ethyloxycarbonyloxy)ethyl 4-{N-butyl-N-[(2'-[1H-tetrazol-5-yl]biphenyl-4-yl)methyl]amino}pyrimidine-5-carboxylate Following the procedure described in Example 82B, the compound resulting from Example 119B (430 mg, 0.54 mmol) was deblocked using aqueous acetic acid in refluxing tetrahydrofuran. Chromatography eluting with ethanol in methylene chloride produced on off-white amorphous solid. Recrystallization from ether/hexane afforded the title compound as an amphorphous solid (119 mg, 40%). $^1$H NMR (CDCl$_3$, 300 MHz) d 0.88 (t, J=7.5 Hz, 3H), 1.27 (m, 2H), 1.27 (t, J=6 Hz, 3H), 1.60 (m, 2H), 1.60 (d, J=6 Hz, 3H), 3.48 (m, 2H), 4.18 (m, 2H), 4.85 (s, 2H), 7.00 (q, J=6 Hz, 1H), 7.13 (d, J=9 Hz, 2H), 7.19 (d, J=9 Hz, 2H), 7.46 (dd, J=7.5 Hz, 2 Hz, 1H), 7.58 (m, 2H), 8.12 (dd, J=7.5 Hz, 2 Hz, 1H), 8.33 (s, 1H), 8.47 (s, 1H).

EXAMPLE 120

1-(Cyclohexyloxycarbonyloxy)ethyl 4-{N-butyl-N-[(2'-[1H-tetrazol-5-yl]biphenyl-4-yl)methyl]amino}pyrimidine-5-carboxylate

EXAMPLE 120A 1-(Cyclohexyloxycarbonyloxy)ethyl 4-{N-butyl-N-[(2'-[N-triphenylmethyl-1H-tetrazol-5-yl]biphenyl-4-yl)methyl]amino}pyrimidine-5-carboxylate Following the procedure described in Example 119 B, the compound resulting from Example 119A (1.00 g, 1.5 mmol), triethylamine (450 mg), sodium iodide (100 mg) and 1-chloroethyl cyclohexylcarbonate (775 mg, 3.8 mmol), prepared according to Yoshimura et al., *J. Antitiotics.* 1987, Vol. XL, No. 1, 81–90,were mixed in dimethylformamide (3 mL). After stirring for90 hours at ambient temperature, normal work up and chromatography eluting with ethyl acetate/hexane mixtures provided the title compound as an amorphous solid (510 mg, 41%).

EXAMPLE 120B 1-(Cyclohexyloxycarbonyloxy)ethyl 4-{N-butyl-N-[(2'-[1H-tetrazol-5-yl]biphenyl-4-yl)methyl]amino}pyrimidine-5-carboxylate Following the procedure described in Example 82B, the compound resulting from Example 120A (510 mg, 0.62 mmol) was deblocked. Chromatography eluting with ethanol in methylene chloride provided a light yellow oil. Trituration with ether/hexane provided the title compound as an off-white amorphous solid (100 mg, 28%). $^1$H NMR (CDCl$_3$, 300 MHz) d 0.88 (t, J=7 Hz, 3H), 1.20–1.93 (m, 14H), 1.60 (d, J=6 Hz, 3H), 3.48 (m, 2H), 4.60 (m, 1H), 4.85 (s, 2H), 6.88 (q, J=6 Hz, 1H), 7.13 (d, J=9 Hz, 2H), 7.17 (d, J=9 Hz, 2H), 7.42 (dd, J=7 Hz, 1 Hz, 1H), 7.58 (m, 4H), 8.10 (dd, J=7 Hz, 1 Hz, 1H), 8.35 (s, 1H), 8.48 (s, 1H).

EXAMPLE 121

1-(1-Methylpiperidin-4-ylcarbonyloxy)ethyl 4-{N-butyl-N-[(2'-[1H-tetrazol-5-yl]biphenyl-4-yl)methyl]amino}pyrimidine-5-carboxylate

EXAMPLE 121A 1-(1-Methylpiperidin-4-ylcarbonyloxy)ethyl 4-{N-butyl-N-[(2'-[N-triphenylmethyl-1H-tetrazol-5-yl]biphenyl-4-yl)methyl]amino}pyrimidine-5-carboxylate Following the procedure described in Example 119B, the compound resulting from Example 119A (1.6 g, 2.4 mmol), sodium iodide (200 mg), potassium carbonate (1.38 g) and 1-chloroethyl (1-methylpiperidin-4-yl)carbonate (1.9 g, 8.6 mmol) were reacted in anhydrous dimethylformamide (3 mL). Column chromatography eluting with ethyl acetate/pyridine/acetic acid mixtures afforded the title compound as an amorphous solid (700 mg, 34%).

EXAMPLE 121B 1-(1-Methylpiperidin-4-ylcarbonyloxy)ethyl 4-{N-butyl-N-[(2'-[1H-tetrazol-5-yl]biphenyl-4-yl)methyl]amino}pyrimidine-5-carboxylate Following the procedure described in Example 82B, the compound resulting from Example 121A (650 mg, 0.76 mmol) was deblocked to afford the title compound as an off-white amorphous solid (250 mg, 54%). MS (FAB) m/e 615 (M+H)$^+$.

EXAMPLE 122

(N,N-Diethylaminocarbonyl)methyl 4-{N-butyl-N-[(2'-[1H-tetrazol-5-yl]biphenyl-4-yl)methyl]amino}pyrimidine-5-carboxylate

EXAMPLE 122A (N,N-Diethylaminocarbonyl)methyl 4-{N-butyl-N-[(2'-[N-triphenylmethyl-1H-tetrazol-5-yl]biphenyl-4-yl)methyl]amino}pyrimidine-5-carboxylate Following the procedure described in Example 119B, the compound resulting from Example 119B (1.00 g, 1.5 mmol) was reacted with 2-chloro-N,N-diethylacetamide (335 mg, 2.2 mmol) and triethylamine (3 mmol) in anhydrous dimethylformamide (3 mL). Chromatography eluting with ethyl acetate/hexane mixtures provided the title compound as an off-white amorphous solid (800 mg, 67%).

EXAMPLE 122B (N,N-Diethylaminocarbonyl)methyl 4-{N-butyl-N-[(2'-[1H-tetrazol-5-yl]biphenyl-4-yl)methyl]amino}pyrimidine-5-carboxylate Following the procedure described in Example 82B, the compound resulting from Example 122A (785 mg, 1 mmol) was deblocked. Chromatography eluting with ethanol in methylene chloride provided the title compound as an off-white amorphous solid (490 mg, 90%). $^1$H NMR (CDCl$_3$, 300 MHz) d 0.90–1.00 (m, 6H), 1.22 (t, J=7 Hz, 3H), 1.40 (m, 2H), 1.72 (m, 2H), 3.25 (m, 4H), 3.83 (t, J=7 Hz, 2H), 4.75 (s, 2H), 4.80 (s, 2H), 6.88 (d, J=9 Hz, 2H), 6.95 (d, J=9 Hz, 2H), 7.43 (dd, J=7

Hz, 2 Hz, 1H), 7.48–7.60 (m, 2H), 7.90 (dd, J=7 Hz, 2 Hz, 1H), 8.63 (s, 1H), 8.66 (s, 1H).

EXAMPLE 123

(5-Methyl-2-oxo-1,3-dioxolen-4-yl)methyl 4-{N-butyl-N-[(2'-[1H-tetrazol-5-yl]biphenyl-4-yl)methyl]amino}pyrimidine-5-carboxylate

EXAMPLE 123A (5-Methyl-2-oxo-1,3-dioxolen-4-yl)methyl 4-{N-butyl-N-[(2'-[N-triphenylmethyl-1H-tetrazol-5-yl]biphenyl-4-yl)methyl]amino}pyrimidine-5-carboxylate 4-{N-Butyl-N-[(2'-[N-triphenylmethyl-1H-tetrazol-5-yl]biphenyl-4-yl)methyl]amino}pyrimidine-5-carboxylylic acid (537.8 mg, 0.80 mmol) in dimethylformamide (3 mL) was treated with 4-bromomethyl-5-methyl-2-oxo-1,3-dioxolene (340 mg, 1.8 mmol, Sakamoto, F. et al. *Chem. Pharm. Bull.* 1984, 32: 2241) and diisopropylethylamine (0.31 mL, 1.8 mmol). After 18 hours at ambient temperature, the mixture was diluted with ethyl acetate. The ethyl acetate solution was washed with water and brine, dried over sodium sulfate and evaporated under reduced pressure. Chromatography of the residue on silica gel eluting with 50% ethyl acetate in hexane afforded 414.3 mg (66%) of the desired product as a foam: TLC (50% ethyl acetate/50% hexane) $R_f$=0.18; $^1$H NMR (CDCl$_3$, 300 MHz) d 0.84 (t, 3H), 1.25–1.10 (m, 2H), 1.60–1.45 (m, 2H), 2.13 (s, 3H), 3.38 (t, 2H), 4.66 (s, 2H), 5.40 (s, 2H), 7.55–6.87 (multiplets, total 22H), 7.93–7.87 (m, 1H), 8.62 (s, 2H).

EXAMPLE 123B (5-Methyl-2-oxo-1,3-dioxolen-4-yl)methyl 4-{N-butyl-N-[(2'-[1H-tetrazol-5-yl]biphenyl-4-yl)methyl]amino}pyrimidine-5-carboxylate The resultant compound from Example 123A (404.0 mg, 0.515 mmol) in 15:15:1 acetic acid/tetrahydrofuran/water (10 mL) was heated at reflux for 1 hour. The mixture was evaporated under reduced pressure and chased with several portions of toluene. Chromatography of the residue on silica gel eluting with 3–7% methanol in chloroform afforded 94.7 mg (81%) of the title compound as a foam: TLC (10% methanol/90% chloroform) $R_f$=0.29; $^1$H NMR (CDCl$_3$, 300 MHz) d 0.88 (t, 3H), 1.34–1.18 (m, 2H), 1.66–1.52 (m, 2H), 2.22 (s, 3H), 3.44 (t, 2H), 4.82 (s, 2H), 5.01 (s, 2H), 7.22–7.13 (m, 4H), 7.41–7.47 (m, 1H), 7.66–7.51 (m, 2H), 8.16–8.06 (m, 1H), 8.53 (s, 1H), 8.54 (s, 1H).

EXAMPLE 124

(5-tert-Butyl-2-oxo-1,3-dioxolen-4-yl)methyl 4-{N-butyl-N-[2'-8 1-tetrazol-5-yl]biphenyl-4-yl)methyl]amino}pyrimidine-5-carboxylate

EXAMPLE 124A (5-tert-Butyl-2-oxo-1,3-dioxolen-4-yl)methyl 4-{N-Butyl-N-[(2'-[N-triphenylmethyl-1H-tetrazol-5-yl]biphenyl-4-yl)methyl]amino}pyrimidine-5-carboxylate Using the procedure of Example 123A and replacing 4-bromomethyl-5-methyl-2-oxo-1,3-dioxolene with 4-bromomethyl-5-tert-butyl-2-oxo-1,3-dioxolene (Sakamoto, F. et al. *Chem. Pharm. Bull.* 1984, 32: 2241) gives the title compound.

EXAMPLE 124B (5-tert-Butyl-2-oxo-1,3-dioxolen-4-yl)methyl 4-{N-butyl-N-[(2'-[1H-tetrazol-5-yl]biphenyl-4-yl)methyl]amino}pyrimidine-5-carboxylate The resultant compound from Example 124A is treated in the manner described in Example 123B to give the title compound.

EXAMPLE 125

(5-Phenyl-2-oxo-1,3-dioxolen-4-yl)methyl 4-{N-butyl-N-[(2'-[1H-tetrazol-5-yl]biphenyl-4-yl)methyl]amino}pyrimidine-5-carboxylate

EXAMPLE 125A (5-Phenyl-2-oxo-1,3-dioxolen-4-yl)methyl 4-{N-butyl-N-[(2'-[N-triphenylmethyl-1H-tetrazol-5-yl]biphenyl-4-yl)methyl]amino}pyrimidine-5-carboxylate Using the procedure described in Example 123A and replacing 4-bromomethyl-5-methyl-2-oxo-1,3-dioxolene with 4-bromomethyl-5-phenyl-2-oxo-1,3-dioxolene (Sakamoto, F. et al. *Chem. Pharm. Bull.* 1984, 32, 2241) gives the title compound.

EXAMPLE 125B (5-Phenyl-2-oxo-1,3-dioxolen-4-yl)methyl 4-{N-butyl-N-[(2'-[1H-tetrazol-5-yl]biphenyl-4-yl)methyl]amino}pyrimidine-5-carboxylate The resultant compound from Example 125A is treated in the manner described in Example 123B to give the title compound.

EXAMPLE 126

Acetoxymethyl 4-{N-butyl-N-[(2'-[1H-tetrazol-5-yl]biphenyl-4-yl)methyl]amino}pyrimidine-5-carboxylate

EXAMPLE 126A

4-{N-Butyl-N-[(2'-[1H-tetrazol-5-yl]biphenyl-4-yl)methyl]amino}pyrimidine-5-carboxylic acid To the compound resulting from Example 52A (1.44 g, 2.06 mmol) dissolved in 25 mL of tetrahydrofuran and 25 mL of absolute ethanol was added a solution of 2.7 g of sodium hydroxide dissolved in 5 mL of water. The reaction mixture was stirred at ambient temperature for 24 hours. The solvents were removed under reduced pressure, and 50 mL of water was added. The resulting aqueous solution was acidified to pH ~3 and extracted with ethyl acetate (2×75 mL). The combined organic extracts were dried over magnesium sulfate and concentrated in vacuo to give the title compound (1.28 g, 93%).

EXAMPLE 126B

Acetoxymethyl 4-{N-butyl-N-[(2'-[N-triphenylmethyl-1H-tetrazol-5-yl]biphenyl-4-yl)methyl]amino}pyrimidine-5-carboxylate To the compound resulting from Example 126A (950 mg, 1.41 mmol) dissolved in 3 mL of dimethylformamaide was added chloromethyl acetate (310 mg, 2.83 mmol), prepared as described by L. H. Ulich and R. Adams in *J. Am. Chem. Soc.*, 1921, 43: 660, and triethylamine (400 mL, 2.83 mmol). The reaction was stirred at ambient temperature for 18 hours and then partitioned between ethyl acetate (200 mL) and 2:1 water/brine (100 mL). The organic phase was washed with 2:1 water/brine (100 mL) and brine (50 mL), dried over magnesium sulfate and concentrated in vacuo. Chromatography on silica gel eluting with 2:1 hexane/ethyl acetate afforded 300 mg (29%) of the title compound. $^1$H NMR (CDCl$_3$, 300 MHz) d 0.85 (t, J=7 Hz, 3H), 1.19 (m, 2H), 1.52 (m, 2H), 2.08 (s, 3H), 3.35 (t, J=7 Hz, 2H), 4.67 (s, 2H), 5.88 (s, 2H), 6.91 (m, 6H), 6.95 (d, J=8 Hz, 2H), 7.09 (d, J=8 Hz, 2H), 7.20–7.35 (m, 9H), 7.38 (dd, 1H), 7.44 (dt, 1H), 7.49 (dt, 1H), 7.92 (dd, 1H), 8.60 (s, 1H), 8.69 (s, 1H).

EXAMPLE 126C

Acetoxymethyl 4-{N-butyl-N-[(2'-[1H-tetrazol-5-yl]biphenyl-4-yl)methyl]amino}pyrimidine-5-carboxylate To the compound resulting from Example 126B (300 mg, 0.40 mmol) dissolved in 7 mL of tetrahydrofuran was added a solution of 560 mL of water in 7 mL of acetic acid. The reaction was heated at 95° C. for 1 hour, cooled to ambient temperature, and then concentrated in vacuo and chased with toluene (2×50 mL). The resulting residue was chromatographed on silica gel eluting with a gradient (3%,5%,7%,10%) of ethanol in methylene chloride to provide the title compound (100 mg, 50%) as an amorphous solid, m.p. 65°–69° C. $^1$H NMR (CDCl$_3$, 300 MHz) d 0.90 (t, J=7 Hz, 3H), 1.27 (m, 2H), 1.61 (m, 2H), 2.12 (s, 3H), 3.46 (t, J=7 Hz, 2H), 4.83 (s, 2H), 5.83 (s, 2H), 7.17 (dd, 4H), 7.45 (dd, 1H), 7.52–7.64 (m, 2H), 8.17 (dd, 1H), 8.52 (bs, 2H).

EXAMPLE 127

1-(Benzoyloxy)ethyl 4-{N-butyl-N-[(2'-[1H-tetrazol-5-yl]biphenyl-4-yl)methyl]amino}pyrimidine-5-carboxylate

EXAMPLE 127A 1-(Benzoyloxy)ethyl 4-{N-butyl-N-[(2'-[N-triphenylmethyl-1H-tetrazol-5-yl]biphenyl-4-yl)methyl]amino}pyrimidine-5-carboxylate By the procedure described in Example 126B, the compound resulting from Example 126A (1.00 g, 1.49 mmol) was reacted with 1-chloroethyl benzoate (1.10 g, 5.96 mmol), prepared as described by L. H. Ulich and R. Adams in *J. Am. Chem. Soc.*, 1921, 43:660, to give the title compound (800 mg, 66%). $^1$H NMR (CDCl$_3$, 300 MHz) d 0.80 (t, J=7 Hz, 3H), 1.15 (m, 2H), 1.50 (m, 2H), 1.68 (s, J=6 Hz, 3H), 3.22–3.48 (m, 2H), 4.64 (d, J=16 Hz, 1H), 4.73 (d, J=16 Hz, 1H), 6.89 (m, 6H), 6.92 (d, J=8 Hz, 2H), 7.04 (d, J=8 Hz, 2H), 7.19–7.59 (m, 16H), 7.92 (dd, 1H), 8.02 (m, 2H), 8.58 (s, 1H), 8.67 (s, 1H).

EXAMPLE 127B 1-(Benzoyloxy)ethyl 4-{N-butyl-N-[(2'-[1H-tetrazol-5-yl]biphenyl-4-yl)methyl]amino}pyrimidine-5-carboxylate The compound resulting from Example 127A (800 mg, 0.98 mmol) was treated with 25 mL of tetrahydrofuran, 2 mL of water, and 25 mL of acetic acid by the procedure described in Example 126C to give, after chromatography, the title compound (370 mg, 66%) as an amorphous solid. m.p. 79°–88° C. $^1$H NMR (CDCl$_3$, 300 MHz) d 0.82 (t, J=7 Hz, 3H), 1.20 (m, 2H), 1.53 (m, 2H), 1.70 (d, J=6 Hz, 3H), 3.41 (m, 2H), 4.78 (d, J=2 Hz, 2H), 7.07 (dd, 4H), 7.28 (q, J=6 Hz, 1H), 7.37–7.46 (m, 3H), 7.49–7.62 (m, 3H) 7.99 (dd, 2H), 8.04 (dd, 1H), 8.20 (s, 1H), 8.41 (s, 1H).

EXAMPLE 128

1-(tert-Butylcarbonyloxy)ethyl 4-{N-butyl-N-[(2'-[1H-tetrazol-5-yl]biphenyl-4-yl)methyl]amino}pyrimidine-5-carboxylate

EXAMPLE 128A a-Chloroethyl trimethylacetate

Acetaldehyde (5.6 mL, 0.10 mmol) was added to a flask containing trimethylacetyl chloride (12.3 mL, 0.10 mmol) and a catalytic amount of zinc chloride. After heating at 90° C. for 2 hours, the reaction was cooled to ambient temperature and diluted with 200 mL of ether. This solution was washed with saturated sodium carbonate solution, dried over calcium chloride and distilled (b.p. 53°–57° C. at 24 torr) to provide the title compound as a colorless liquid. $^1$H NMR (CDCl$_3$, 300 MHz) d 1.22 (s, 9H), 1.79 (d, J=6 Hz, 3H), 6.54 (q, J=6 Hz, 1H).

EXAMPLE 128B 1-tert-Butylcarbonyloxy)ethyl 4-{N-butyl-N-[(2'-[N-triphenylmethyl-1H-tetrazol-5-yl]biphenyl-4-yl)methyl]amino}pyrimidine-5-carboxylate The compound resulting from Example 128A (1.00 g, 1.49 mmol) was reacted with a-chloroethyl trimethylacetate (910 mg, 5.95 mmol) by the procedure described in Example 126B to give, after chromatography on silica gel eluting with 2:1 hexane/ethyl acetate, the title compound (760 mg, 64%). $^1$H NMR (CDCl$_3$, 300 MHz) d 0.84 (t, J=7 Hz, 3H), 1.11–1.29 (m, 2H), 1.18 (s, 9H), 1.44–1.57 (m, 2H), 1.52 (d, J=6 Hz, 3H), 3.21–3.49 (m, 2H), 4.65 (d, J=15 Hz, 1H), 4.73 (d,J=15 Hz, 1H), 6.90 (m, 6H), 6.94 (d, J=8 Hz, 2H), 7.00 (q, J=6 Hz, 1H), 7.07 (d, J=8 Hz, 2H), 7.20–7.40 (m, 10H), 7.41–7.53 (m, 2H), 7.92 (dd, 1H), 8.59 (s, 1H), 8.62 (s, 1H).

EXAMPLE 128C 1-(tert-Butylcarbonyloxy)ethyl 4-{N-butyl-N-[(2'-[1H-tetrazol-5-yl]biphenyl-4-yl)methyl]amino}pyrimidine-5-carboxylate The compound resulting from Example 128B (760 mg, 0.95 mmol) was treated with 25 mL of tetrahydrofuran, 2 mL of water, and 25 mL of acetic acid by the procedure described in Example 126C to give, after chromatography, the title compound (380 mg, 72%) as an amorphous solid. m.p. 71°–85° C. $^1$H NMR (CDCl$_3$, 300 MHz) d 0.86 (t, J=7 Hz, 3H), 1.17 (s, 9H), 1.22 (m, 2H), 1.49–1.60 (m, 2H), 1.55 (d, J=6 Hz, 3H), 3.40 (m, 2H), 4.81 (d, J=2 Hz, 2H), 6.97 (q, J=6 Hz, 1H), 7.13 (dd, 4H), 7.45 (dd, 1H), 7.54 (dt, 1H), 7.61 (dt, 1H), 8.03 (dd, 1H), 8.12 (s, 1H), 8.36 (s, 1H).

EXAMPLE 129

Methoxycarbonylmethyl 4-{N-butyl-N-[(2'-[1H-tetrazol-5-yl]biphenyl-4-yl)methyl]amino}pyrimidine-5-carboxylate

EXAMPLE 129A

Methoxycarbonylmethyl 4-{N-butyl-N-[(2'-[N-triphenylmethyl-1H-tetrazol-5-yl]biphenyl-4-yl)methyl]amino}pyrimidine-5-carboxylate The compound resulting from Example 126A (1.28 g, 1.91 mmol) was reacted with methyl bromoacetate (270 mL, 2.85 mmol) by the procedure described in Example 126B to give, after chromatography on silica gel eluting with 2:1 hexane/ethyl acetate, the title compound (800 mg, 56%). $^1$H NMR (CDCl$_3$, 300 MHz) d 0.84 (t, J=7 Hz, 3H), 1.18 (m, 2H), 1.53 (m, 2H), 3.36 (t, J=7 Hz, 2H), 3.74 (s, 3H), 4.69 (s, 2H), 4.72 (s, 2H), 6.91 (m, 6H), 6.96 (d, J=8 Hz, 2H), 7.08 (d, J=8 Hz, 2H), 7.21-7.34 (m, 9H), 7.37 (dd, 1H), 7.44 (dt, 1H), 7.49 (dt, 1H), 7.91 (dd, 1H), 8.60 (s, 1H), 8.76 (s, 1H).

EXAMPLE 129B

Methoxycarbonylmethyl 4-{N-butyl-N-[(2'-[1H-tetrazol-5-yl]biphenyl-4-yl)methyl]amino}pyrimidine-5-carboxylate The compound resulting from Example 129A (780 mg, 1.05 mmol) was treated with 25 mL of tetrahydrofuran, 2 mL of water, and 25 mL of acetic acid by the procedure described in Example 126C to give, after chromatography, the title compound (370 mg, 70%) as an amorphous solid. m.p. 65°-80° C. $^1$H NMR (CDCl$_3$, 300 MHz) d 0.89 (t, J=7 Hz, 3H), 1.28 (m, 2H), 1.62 (m, 2H), 1.53 (t, J=7 Hz, 2H), 3.75 (s, 3H), 4.74 (s, 2H), 4.82 (s, 2H), 7.09 (dt, 1H), 8.02 (dd, 1H), 8.32 (bs, 1H), 8.53 (bs, 1H).

EXAMPLE 130

3-Hydroxymethyl-2-{N-propyl-N-[(2'-[1H-tetrazol-5-yl]biphenyl-4-yl)methyl]amino}pyridine

EXAMPLE 130A

3-Hydroxymethyl-2-{N-propyl-N-[(2'-[N-triphenylmethyl-1H-tetrazol-5-yl]biphenyl-4-yl)methyl]amino}pyridine The compound resulting from Example 87C (2.574 g, 3.758 mmol) in tetrahydrofuran (20 mL) at 0° C. was treated with lithium aluminum hydride (500 mg, 13.2 mmol). After 2 hours, the reaction was quenched sequentially with water (0.5 mL), 15% aqueous sodium hydroxide (0.5 mL), and water (1.5 mL), and the mixture was filtered and the filtrate evaporated under reduced pressure. Chromatography of the residue on silica gel eluting with 20-25% ethyl acetate in hexane afforded 2.290 g (95%) of the desired product as a foam. TLC (20% ethyl acetate/80% hexane) R$_f$=0.08. $^1$H NMR (CDCl$_3$, 300 MHz) δ 0.77 (t, 3H), 1.35-1.49 (m, 2H), 3.02 (t, 2H), 4.00 (br, 1H), 4.17 (s, 2H), 4.60 (s, 2H), 6.87-7.55 (br envelope, 24H), 7.88 (dd, 1H), 8.31 (dd, 1H). MS (DCI/NH$_3$) m/e 643 (M+H)$^+$. Anal calcd for C$_{42}$H$_{38}$N$_6$O.0.35 H$_2$O: C, 77.72; H, 6.01; N, 12.95. Found: C, 78.08; H, 5.94; N, 12.50.

EXAMPLE 130B

3-Hydroxymethyl-2-{N-propyl-N-[(2'-[1H-tetrazol-5-yl]biphenyl-4-yl)methyl]amino}pyridine The compound resulting from Example 130A (403.3 mg, 0.627 mmol) in 15:15:1 (v/v/v) acetic acid/tetrahydrofuran/water (8 mL) was heated at reflux for 90 minutes. The solvent was evaporated under reduced pressure, and toluene was added and evaporated. Chromatography of the residue on silica gel eluting with 3-6% methanol in chloroform afforded 186.6 mg (74%) of the desired product as a solid. TLC (10% methanol/90% chloroform) R$_f$=0.25. $^1$H NMR (CDCl$_3$, 300 MHz) δ 0.96 (t, 3H), 3.16 (br, 2H), 4.40 (s, 2H), 4.64 (s, 2H), 6.99 (d, 2H), 7.06 (d, 2H), 7.11-7.19 (m, 1H), 7.42 (dd, 1H), 7.47-7.62 (m, 2H), 7.71 (dd, 1H), 8.20 (dd, 1H), 8.48 (dd, 1H). MS (DCI/NH$_3$) m/e 401 (M+H)$^+$.

EXAMPLE 131

2-{N-Propyl-N-[(2'-[1H-tetrazol-5-yl]biphenyl-4-yl)methyl]amino}pyridine-3-carboxaldehyde

EXAMPLE 131A

2-{N-Propyl-N-[(2'-[N-triphenylmethyl-1H-tetrazol-5-yl]biphenyl-4-yl)methyl]amino}pyridine-3-carboxaldehyde The compound resulting from Example 130A (1.0123 g, 1.575 mmol) and activated manganese dioxide (3.00 g, 34.5 mmol) in tetrahydrofuran (16 mL) were stirred at ambient temperature for 20 hours. The mixture was filtered and evaporated under reduced pressure and the residue was chromatographed on silica gel eluting with 20% ethyl acetate in hexane to afford 0.964 g (96%) of the desired product as a yellow amorphous solid. TLC (20% ethyl acetate/80% hexane) R$_f$=0.23. $^1$H NMR (CDCl$_3$, 300 MHz) δ 0.76 (t, 3H), 1.52-1.67 (m, 2H), 3.30 (t, 2H), 4.63 (s, 2H), 6.83 (dd, 1H), 6.86-6.95 (m, 6H), 6.99 (d, 2H), 7.07 (d, 2H), 7.18-7.35 (m, 9H), 7.38 (dd, 1H), 7.40-7.53 (m, 2H), 7.92 (dd, 1H), 7.99 (dd, 1H), 8.34 (dd, 1H), 9.97 (s, 1H). MS (DCI/NH$_3$) m/e 641 (M+H)$^+$. Anal calcd for C$_{42}$H$_{36}$N$_6$O.2.75 H$_2$O: C, 73.08; H, 6.06; N, 12.17. Found: C, 73.17; H, 5.77; N, 11.38.

EXAMPLE 131B

2-{N-Propyl-N-[(2'-[1H-tetrazol-5-yl]biphenyl-4-yl)methyl]amino}pyridine-3-carboxaldehyde The compound resulting from Example 131A (351.2 mg, 0.548 mmol) in 15:15:1 (v/v/v) acetic acid/tetrahydrofuran/water (8 mL) was heated at reflux for 90 minutes. The solvent was evaporated under reduced pressure, and toluene was added and evaporated. Chromatography of the residue on silica gel eluting with 2-6% methanol in chloroform afforded 202.1 mg (93%) of the desired product as a yellow amorphous solid. TLC (10% methanol/90% chloroform) R$_f$=0.38. $^1$H NMR (CDCl$_3$, 300 MHz) δ 0.91 (t, 3H), 1.60-1.78 (m, 2H), 3.40-3.51 (m, 2H), 4.58 (s, 2H), 6.98 (dd, 1H), 7.14 (d, 2H), 7.20 (d, 2H), 7.43 (dd, 1H), 7.52-7.65 (m, 2H), 8.03 (dd, 1H), 8.19 (dd, 1H), 8.45 (dd, 1H), 9.86 (s, 1H). MS (DCI/NH$_3$) m/e 399 (M+H)$^+$.

EXAMPLE 132

3-(1-Hydroxy-2,2,2-trifluoroethyl)-2-{N-propyl-N-[(2'-[1H-tetrazol-5-yl]biphenyl-4-yl)methyl]amino}pyridine

EXAMPLE 132A

2-{N-Propyl-N-[(2'-[N-triphenylmethyl-1H-tetrazol-5-yl]biphenyl-4-yl)methyl]amino}-3-(1-trimethylsilyloxy-2,2,2-trifluoroethyl)pyridine To the compound resulting from Example 131A (265.5 mg, 0.414 mmol) was added (trifluoromethyl)-trimethylsilane (92.7 mg, 0.652 mmol), prepared by the method of Krishnamurti et al., J. Am. Chem. Soc. 56, 984 (1991), in tetrahydrofuran (3 mL). The reaction was cooled to 0° C. and treated with 1.0M tetrabutylammonium fluoride in tetrahydrofuran (2.0 μL, 2.0 μmol). After 30 minutes at 0° C. and 30 minutes at ambient temperature, the mixture was evaporated under reduced pressure, and the residue was chromatographed on silica gel eluting with 10% ethyl acetate in hexane to afford 304.8 mg (94%) of the desired product as a foam. TLC (20% ethyl acetate/80% hexane) $R_f$=0.38. $^1$H NMR (CDCl$_3$, 300 MHz) δ 0.02 (s, 9H), 0.70 (t, 3H), 1.30–1.53 (m, 2H), 2.93 (t, 2H), 4.12 (d, 1H), 4.22 (d, 1H), 5.61 (q, 1H), 6.87–7.55 (br envelope, 23H), 7.89 (dd, 1H), 7.97 (d, 1H), 8.41 (dd, 1H). MS (DCI/NH$_3$) m/e 783 (M+H)$^+$.

EXAMPLE 132B 3-(1-Hydroxy-2,2,2-trifluoroethyl)-2-{N-Propyl-N-[(2'-[N-triphenylmethyl-1H-tetrazol-5-yl]biphenyl-4-yl)methyl]amino}-pyridine The compound resulting from Example 132A (341.6 mg, 0.436 mmol) in tetrahydrofuran (5 mL) was treated with 1.0M tetrabutylammonium fluoride in tetrahydrofuran (0.8 mL, 0.8 mmol). After 45 minutes at ambient temperature, the mixture was evaporated under reduced pressure, and the residue was chromatographed on silica gel eluting with 20% ethyl acetate in hexane to afford 309.2 mg (100%) of the desired product as a foam. TLC (20% ethyl acetate/80% hexane) $R_f$=0.23. $^1$H NMR (CDCl$_3$, 300 MHz) δ 0.75 (t, 3H), 1.20–1.38 (m, 2H), 2.80–3.10 (m, 2H), 4.03 (d, 2H), 5.17 (q, 1H), 6.90–7.57 (br envelope, 23H), 7.62 (dd, 1H), 7.86 (dd, 1H), 8.10 (br, 1H), 8.51 (dd, 1H). MS (DCI/NH$_3$) m/e 711 (M+H)$^+$.

EXAMPLE 132C 3-(1-Hydroxy-2,2,2-trifluoroethyl)-2-{N-propyl-N-[(2'-[1H-tetrazol-5-yl]biphenyl-4-yl)methyl]amino}pyridine The compound resulting from Example 132B (62.0 mg, 0.0872 mmol) in 15:15:1 (v/v/v) acetic acid/tetrahydrofuran/water was heated at reflux for 90 minutes. The solvent was evaporated under reduced pressure, and toluene was added and evaporated. Chromatography of the residue on silica gel eluting with 2–4% methanol in chloroform afforded 38.7 mg (95%) of the desired product as a white solid. TLC (10% methanol/90% chloroform) $R_f$=0.30. $^1$H NMR (CDCl$_3$, 300 MHz) δ 0.96 (t, 3H), 1.63–1.79 (m, 2H), 2.84–2.99 (m, 1H), 3.09–3.25 (m, 1H), 4.18 (d, 1H), 4.47 (d, 1H), 5.31 (q, 1H), 7.05–7.15 (m, 4H), 7.25–7.30 (m, 1H), 7.41 (dd, 1H), 7.50–7.62 (m, 2H), 7.70 (d, 1H), 8.21 (dd, 1H), 8.59 (dd, 1H). MS (DCI/NH$_3$) m/e 469 (M+H)$^+$. Anal calcd for C$_{24}$H$_{23}$N$_6$OF$_3$. 0.5 H$_2$O: C, 60.37; H, 5.07; N, 17.60. Found: C, 60.13; H, 4.76; N, 17.31.

EXAMPLE 133

3-(1-Hydroxyethyl)-2-{N-propyl-N-[(2'-[1H-tetrazol-5-yl]biphenyl-4-yl)methyl]amino}pyridine

EXAMPLE 133A 3-(1-Hydroxyethyl)-2-{N-propyl-N-[(2'-[N-triphenylmethyl-1H-tetrazol-5-yl]biphenyl-4-yl)methyl]amino}pyridine To the compound resulting from Example 131A (172.5 mg, 0.269 mmol) in ether (3 mL) was added 1.5M methylmagnesium bromide in tetrahydrofuran/toluene (0.27 mL, 0.41 mmol). After 10 minutes at ambient temperature, tetrahydrofuran (2 mL) was added to effect solution and the reaction was stirred for an additional 15 minutes. The reaction was quenched with saturated aqueous ammonium chloride solution (0.05 mL) and then the mixture was filtered and the filtrate evaporated under reduced pressure. Chromatography on silica gel eluting with 25% ethyl acetate in hexane afforded 164.5 mg (93%) of the desired product as a foam. TLC (20% ethyl acetate/80% hexane) $R_f$=0.08. $^1$H NMR (CDCl$_3$, 300 MHz) δ 0.75 (t, 3H), 1.44 (d, 3H), 1.33–1.48 (m, 2H), 2.85–3.10 (m, 2H), 4.05 (d, 1H), 4.12 (d, 1H), 5.04 (q, 1H), 5.22 (s, 1H), 6.88–7.53 (br envelope, 23H), 7.57 (dd, 1H), 7.88 (dd, 1H), 8.34 (dd, 1H). MS (DCI/NH$_3$) m/e 657 (M+H)$^+$.

EXAMPLE 133B 3-(1-Hydroxyethyl)-2-{N-propyl-N-[(2'-[1H-tetrazol-5-yl]biphenyl-4-yl)methyl]amino}pyridine The compound resulting from Example 133A (52.7 mg, 0.0802 mmol) in 15:15:1 (v/v/v) acetic acid/tetrahydrofuran/water (2 mL) was heated at reflux for 90 minutes. The solvent was evaporated under reduced pressure, and toluene was added and evaporated. Chromatography of the residue on silica gel eluting with 1.8–5% methanol in chloroform afforded 16.4 mg (49%) of the desired product as a white solid. TLC (10% methanol/90% chloroform) $R_f$=0.27. $^1$H NMR (CDCl$_3$, 300 MHz) δ 0.96 (t, 3H), 1.47 (d, 3H), 1.50–1.67 (m, 2H), 2.97–3.20 (m, 2H), 4.20 (d, 1H), 4.32 (d, 1H), 5.07 (q, 1H), 6.98 (d, 4H), 7.05 (d, 2H), 7.17 (dd, 1H), 7.41 (dd, 1H), 7.46–7.62 (m, 2H), 7.74 (dd, 1H), 8.17 (dd, 1H), 8.47 (dd, 1H). MS (DCI/NH$_3$) m/e 415 (M+H)$^+$. Anal calcd for C$_{24}$H$_{26}$N$_6$O. 0.5 H$_2$O: Calcd: C, 68.06; H, 6.42; N, 19.84. Found: C, 68.27; H, 6.20; N, 19.63.

EXAMPLE 134

3-Acetyl-2-{N-propyl-N-[(2'-[1H-tetrazol-5-yl]biphenyl-4-yl)methyl]amino}pyridine

EXAMPLE 134A

3-Acetyl-2-[N-propyl-N-[[2'-(N-triphenylmethyl-1H-tetrazol-5-yl)biphenyl-4-yl]methyl]amino]pyridine The compound resulting from Example 133A (108.6 mg, 0.163 mmol) in dichloromethane (7 mL) was added via cannula to 1,1,1-tris(acetoxy)-1,1-dihydro-1,2-benziodoxol-3(1H)-one (220 mg, 0.519 mmol), prepared by the method of Dess and Martin, J. Org. Chem. 48, 4155 (1983). After stirring at ambient temperature for 30 minutes, the mixture was applied directly to the top of a hexane-packed silica gel column which was eluted with 20% ethyl acetate in hexane to afford 65.7 mg (62%) of the desired product as a foam. TLC (20% ethyl acetate/80% hexane) $R_f$=0.20. $^1$H NMR (CDCl$_3$, 300 MHz) δ 0.73 (t, 3H), 1.40–1.55 (m, 2H), 2.47 (s, 3H), 3.19 (t, 2H), 4.50 (s, 2H), 6.85–7.53 (br envelope, 22H), 7.71 (dd, 1H), 7.88 (dd, 1H), 8.27 (dd, 1H). MS (DCl/NH$_3$) m/e 655 (M+H)$^+$.

EXAMPLE 134B

3-Acetyl-2-{N-propyl-N-[(2'-[1H-tetrazol-5-yl]biphenyl-4-yl)methyl]amino}pyridine The compound resulting from Example 134A (62.8 mg, 0.0959 mmol) in 15:15:1 (v/v/v) acetic acid/tetrahydrofuran/water (2 mL) was heated at reflux for 90 minutes. The solvent was evaporated under reduced pressure, and toluene was added and evaporated. Chromatography of the residue on silica gel eluting with 1.8–6% methanol in chloroform afforded 202.1 mg (93%) of the desired product as a foam. TLC (10% methanol/90% chloroform) R$_f$=0.30. $^1$H NMR (CDCl$_3$, 300 MHz) δ 0.91 (t, 3H), 1.57–1.73 (m, 2H), 2.58 (s, 3H), 3.26–3.37 (m, 2H), 4.40 (s, 2H), 6.95 (dd, 1H), 7.08 (d, 2H), 7.12 (d, 2H), 7.42 (dd, 1H), 7.49–7.63 (m, 2H), 7.78 (dd, 1H), 8.22 (dd, 1H), 8.40 (dd, 1H). MS (DCl/NH$_3$) m/e 413 (M+H)$^+$. Exact Mass (C$_{24}$H$_{24}$N$_6$O) Calcd: 413.2090. Found: 413.2090.

EXAMPLE 135

3-(2,2-Difluoro-2-ethoxycarbonyl-1-hydroxyethyl)-2-{N-propyl-N-[(2'-[1H-tetrazol-5-yl]biphenyl-4-yl)methyl]amino}pyridine

EXAMPLE 135A 3-(2,2-Difluoro-2-ethoxycarbonyl-1-hydroxyethyl)-2-{N-propyl-N-[(2'-[N-triphenylmethyl-1H-tetrazol-5-yl]biphenyl-4-yl)methyl]amino}pyridine The compound resulting from Example 131A (544.4 mg, 0.850 mmol), zinc (90 mg, 1.4 mmol), and ethyl bromodifluoroacetate (189 mg, 0.931 mmol) in tetrahydrofuran (8 mL) were reacted in an ultrasonic cleaning bath at 40° C. for 3 hours. The mixture was poured into saturated sodium bicarbonate solution and extracted with ethyl acetate. The combined organic extracts were dried over sodium sulfate and concentrated in vacuo. Chromatography of the residue on silica gel eluting with 20% ethyl acetate in hexane afforded 394.4 mg (61%) of the desired product as a foam. TLC (20% ethyl acetate/80% hexane) R$_f$=0.23. $^1$H NMR (CDCl$_3$, 300 MHz) δ 0.66 (t, 3H), 1.07–1.38 (m, 2H), 1.38 (t, 3H), 2.78 (dt, 1H), 3.00 (dt, 1H), 3.92 (d, 1H), 4.10 (d, 1H), 4.31–4.51 (m, 2H), 5.32 (br d, 1H), 6.86–7.54 (br envelope, 23H), 7.65 (d, 1H), 7.90 (dd, 1H), 8.52 (dd, 1H), 9.04 (br, 1H). MS (DCl/NH$_3$) m/e 765 (M+H)$^+$.

EXAMPLE 135B 3-(2,2-Difluoro-2-ethoxycarbonyl-1-hydroxyethyl)-2-{N-propyl-N-[(2'-[1H-tetrazol-5-yl]biphenyl-4-yl)methyl]amino}pyridine The compound resulting from Example 134A (148.7 mg, 0.1944 mmol) in 15:15:1 (v/v/v) acetic acid/tetrahydrofuran/water was heated at reflux for 90 minutes. The solvent was evaporated under reduced pressure, and toluene was added and evaporated. Chromatography of the residue on silica gel eluting with 1.5–6% methanol in chloroform afforded 88.6 mg (87%) of the desired product as a white amorphous solid. TLC (10% methanol/90% chloroform) R$_f$=0.38. $^1$H NMR (CDCl$_3$, 300 MHz) δ 0.93 (t, 3H), 1.33 (t, 3H), 1.52–1.78 (m, 2H), 2.93 (dt, 1H), 3.15 (dt, 1H), 4.20 (d, 1H), 4.30 (d, 1H), 4.30–4.45 (m, 2H), 5.33 (dd, 1H), 7.11 (d, 2H), 7.14 (d, 2H), 7.24 (dd, 1H), 7.41 (dd, 1H), 7.50–7.62 (m, 2H), 7.65 (dt, 1H), 8.24 (dd, 1H), 8.58 (dd, 1H). MS (DCl/NH$_3$) m/e 523 (M+H)$^+$. Anal calcd for C$_{27}$H$_{28}$N$_6$O$_3$F$_2$. 0.25 H$_2$O: C, 61.53; H, 5.45; N, 15.95. Found: C, 61.59; H, 5.34; N, 15.83.

EXAMPLE 136

3-(2'-Carboxy-2',2'-difluoro-1'-hydroxyethyl)-2-[N-propyl-N-[[2'-(1H-tetrazol-5-yl)biphenyl-4-yl]methyl]amino]pyridine The compound resulting from Example 135A (69.0 mg, 0.132 mmol) was stirred in 1M aqueous potassium hydroxide solution at ambient temperature for 1 hour. The mixture was made acidic with 2M hydrochloric acid and the resulting solid was collected by filtration, washed with water and dissolved in 10% methanol in chloroform. The solution was dried over sodium sulfate and evaporated under reduced pressure to afford 50.9 mg (78%) of the desired product as a white solid. TLC (25% acetic acid/25% ethyl acetate/25% n-butanol/25% water) R$_f$=0.62. $^1$H NMR (DMSO-d$_6$, 300 MHz) δ 0.73 (t, 3H), 1.27–1.43 (m, 2H), 2.75–2.90 (m, 1H), 3.03–3.23 (m, 1H), 4.20 (d, 1H), 4.27 (d, 1H), 5.70 (dd, 1H), 7.02 (d, 2H), 7.10–7.20 (m, 4H), 7.29 (d, 2H), 7.52–7.73 (m, 4H), 7.89 (d, 1H), 8.30 (dd, 1H). MS (DCl/NH$_3$) m/e 495 (M+H)$^+$.

EXAMPLE 137

3-[2,2-Difluoro-2-(ethoxycarbonyl)acetyl]-2-{N-propyl-N-[(2'-[1H-tetrazol-5-yl]biphenyl-4-yl]methyl]amino}pyridine

EXAMPLE 137A

3-[2,2-Difluoro-2-(ethoxycarbonyl)acetyl]-2-{N-propyl-N-[(2'-[N-triphenylmethyl-1H-tetrazol-5-yl]biphenyl-4-yl]methyl]amino}pyridine The compound resulting from Example 135A (237.0 mg, 0.3099 mmol) in dichloromethane (12 mL) was added via cannula to 1,1,1-tris(acetoxy)-1,1-dihydro-1,2-benziodoxol-3(1H)-one (380 mg, 0.89 mmol), prepared by the method of Dess and Martin, J. Org. Chem. 48, 4155 (1983). After stirring at ambient temperature for 2.5 hours, the mixture was applied directly to the top of a hexane-packed silica gel column which was eluted with 15% ethyl acetate in hexane to afford 199.6 mg (84%) of the desired product as a yellow amorphous solid. TLC (20% ethyl acetate/80% hexane) R$_f$=0.25. $^1$H NMR (CDCl$_3$, 300 MHz) δ 0.73 (t, 3H), 1.31 (t, 3H), 1.43–1.57 (m, 2H), 3.18 (t, 2H), 4.37 (q, 2H), 4.53 (s, 2H), 6.71 (dd, 1H), 6.86–6.93 (m, 6H), 6.96 (d, 2H), 7.05 (d, 2H), 7.17–7.33 (m, 9H), 7.38 (dd, 1H), 7.40–7.53 (m, 2H), 7.90 (dd, 1H), 8.07 (dd, 1H), 8.32 (dd, 1H). MS (DCl/NH$_3$) m/e 763 (M+H)$^+$.

EXAMPLE 137B

3-[2,2-Difluoro-2-(ethoxycarbonyl)acetyl]-2-{N-propyl-N-[(2'-[1H-tetrazol-5-yl]biphenyl-4-yl]methyl]amino}pyridine The compound resulting from Example 137A (85.4 mg, 0.112 mmol) in 15:15:1 (v/v/v) acetic acid/tetrahydrofuran/water was heated at reflux for 90 minutes. The solvent was evaporated under reduced pressure, and toluene was added and evaporated. Chromatography of the residue on silica gel eluting with 1.6–4% methanol in chloroform afforded 48.5 mg (83%) of the desired product as a yellow amorphous solid. TLC (10% methanol/90% chloroform) R$_f$=0.36. $^1$H NMR (CDCl$_3$, 300 MHz) δ 0.87 (t, 3H), 1.36 (t, 3H), 1.56–1.76

(m, 2H), 3.33 (t, 2H), 4.41 (q, 2H), 4.79 (s, 2H), 6.75 (dd, 1H), 7.18 (d, 2H), 7.30 (d, 2H), 7.41 (dd, 1H), 7.51–7.63 (m, 2H), 8.06 (dd, 1H), 8.27 (dd, 1H), 8.35 (dd, 1H). MS (CDl/NH$_3$) m/e 521 (M+H)$^+$. Anal calcd for C$_{27}$H$_{26}$N$_6$O$_3$F$_2$. 0.33 H$_2$O: C, 61.60; H, 5.10; N, 15.96. Found: C, 61.20; H, 4.57; N, 15.62.

EXAMPLE 138

3-Difluoroacetyl-2-{N-propyl-N-[(2'-[1H-tetrazol-5-yl]biphenyl-4-yl)methyl]amino}pyridine The compound resulting from Example 137 (34.4 mg, 0.0661 mmol) was stirred in 1M aqueous potassium hydroxide solution at 0° C. for 45 minutes. The mixture was made acidic with 2M hydrochloric acid, and the resulting solid was collected by filtration, washed with water and dissolved in 10% methanol in chloroform. The solution was dried over sodium sulfate and evaporated to afford 23.3 mg of a yellow solid. A portion (9.7 mg) of this material was heated to reflux in ethanol for 2 hours and evaporated to afford 9.0 mg (72%) of the desired product as a foam. TLC (10% methanol/90% chloroform) R$_f$=0.30. $^1$H NMR (CDCl$_3$, 300 MHz) δ 0.91 (t, 3H), 1.58–1.78 (m, 2H), 3.42 (t, 2H), 4.57 (s, 2H), 6.43 (t, J=54 Hz, 1H), 6.92 (dd, 1H), 7.11 (d, 2H), 7.14 (d, 2H), 7.40 (dd, 1H), 7.50–7.64 (m, 2H), 7.97 (dd, 1H), 8.23 (dd, 1H), 8.46 (dd, 1H). MS (DCl/NH$_3$) m/e 449 (M+H)$^+$. Exact mass. (C$_{24}$H$_{23}$N$_6$OF$_2$, M+H) Calcd: 449.1901. Found: 449.1904. Anal calcd for C$_{24}$H$_{22}$N$_6$OF$_2$. 0.3 H$_2$O: C, 63.51; H, 5.02; N, 18.52. Found: C, 63.90; H, 5.08; N, 17.99.

EXAMPLE 139

3-(2-Ethoxycarbonyl-1-hydroxyethyl)-2-{N-propyl-N-[(2'-[1H-tetrazol-5-yl]biphenyl-4-yl)methyl]amino}pyridine

EXAMPLE 139A 3-(2-Ethoxycarbonyl-1-hydroxyethyl)-2-{N-propyl-N-[(2'-[N-triphenylmethyl-1H-tetrazol-5-yl]biphenyl-4-yl)methyl]amino}pyridine 1.3M n-Butyllithium in hexane (0.70 mL, 0.90 mmol) was added to diisopropyl amine (0.150 mL, 1.07 mmol) in tetrahydrofuran (8 mL) at 0° C. After 15 minutes, the mixture was cooled to −78° C. and treated with ethyl acetate (0.090 mL, 0.92 mmol). After 20 minutes at −78° C., the compound resulting from Example 131A (515.0 mg, 0.804 mmol) was added and the reaction was stirred at −78° C. for 45 minutes. The reaction was quenched with saturated sodium bicarbonate solution and allowed to warm to ambient temperature. The mixture was diluted with ethyl acetate, washed with water and brine, dried over sodium sulfate and evaporated under reduced pressure. Chromatography of the residue on silica gel eluting with 30% ethyl acetate in hexane afforded 556.1 mg (97%) of the desired product as a white amorphous solid. TLC (20% ethyl acetate/80% hexane) R$_f$=0.21. $^1$H NMR (CDCl$_3$, 300 MHz) δ 0.78 (t, 3H), 1.23 (t, 3H), 1.35–1.50 (br, 2H), 2.46–2.68 (m, 2H), 2.83–3.13 (br, 2H), 4.03–4.24 (m, 4H), 4.85 (br, 1H), 5.48 (br, 1H), 6.86–7.54 (br envelope, 23H), 7.67 (br, 1H), 7.88 (dd, 1H), 8.37 (dd, 1H). MS (DCl/NH$_3$) m/e 729 (M+H)$^+$.

EXAMPLE 139B 3-(2-Ethoxycarbonyl-1-hydroxyethyl)-2-{N-propyl-N-[(2'-[1H-tetrazol-5-yl]biphenyl-4-yl)methyl]amino}pyridine The compound resulting from Example 139A (141.6 mg, 0.1943 mmol) in 15:15:1 (v/v/v) acetic acid/tetrahydrofuran/water (3 mL) was heated at reflux for 90 minutes. The solvent was evaporated under reduced pressure, and toluene was added and evaporated. Chromatography of the residue on silica gel eluting with 1.6–5% methanol in chloroform afforded 87.1 mg (92%) of the desired product as a yellow amorphous solid. TLC (10% methanol/90% chloroform) R$_f$=0.30. MS (DCl/NH$_3$) m/e 487 (M+H)$^+$. Anal calcd for C$_{27}$H$_{30}$N$_6$O$_3$: C, 66.65; H, 6.21; N, 17.27. Found: C, 66.62; H, 6.41; N, 16.61.

EXAMPLE 140

3-(2-Carboxy-1-hydroxyethyl)-2-{N-propyl-N-[(2'-[1H-tetrazol-5-yl]biphenyl-4-yl)methyl]amino}pyridine The compound resulting from Example 139 (65.3 mg, 0.134 mmol) was stirred in 1.0M aqueous potassium hydroxide solution (4 mL) with ethanol (0.2 mL) to effect solution. After 45 minutes, the reaction was acidified with 2M hydrochloric acid, diluted with brine, and extracted into 25% isopropanol in chloroform. The solution was dried over sodium sulfate and evaporated under reduced pressure to afford 61.0 mg (99%) of the desired product as an amorphous solid. TLC (25% acetic acid/25% ethyl acetate/25% n-butanol/25% water) R$_f$=0.74. $^1$H NMR (CDCl$_3$, 300 MHz) δ 0.93 (t, 3H), 1.37–1.56 (m, 1H), 156–1.73 (m, 1H), 1.88 (br dd, 1H), 2.57 (dd, 1H), 3.52 (t, 2H), 4.51 (s, 2H), 5.22 (dd, 1H), 7.00 (d, 2H), 7.05 (d, 2H), 7.30–7.60 (m, 4H), 7.71–7.78 (m, 2H), 8.52 (dd, 1H). MS (DCl/NH$_3$) m/e 459 (M+H)$^+$.

EXAMPLE 141

3-(Methylaminocarbonylamino)-2-{N-propyl-N-[(2'-[1H-tetrazol-5-yl]biphenyl-4-yl)methyl]amino}pyridine

EXAMPLE 141A 3-(Methylaminocarbonylamino)-2-{N-propyl-N-[(2'-[N-triphenylmethyl-1H-tetrazol-5-yl]biphenyl-4-yl)methyl]amino}pyridine The compound resulting from Example 93 (630 mg, 1 mmol) was dissolved in 5 mL of methylene chloride and treated with 65 mg (1.14 mmol) of methylisocyanate. After stirring overnight, the solvent was removed in vacuo and the residue obtained chromatographed on silica gel eluting with 50% ethyl acetate in hexane to afford 390 mg of the title compound.

EXAMPLE 141B 3-(Methylaminocarbonylamino)-2-{N-propyl-N-[(2'-[1H-tetrazol-5-yl]biphenyl-4-yl)methyl]amino}pyridine The compound resulting from Example 141A (320 mg) was dissolved in 3 mL of methylene chloride and 4 mL of formic acid and stirred at ambient temperature for 2 hours. The solvents were removed in vacuo and the residue obtained chromatographed on silica gel eluting with ethyl acetate containing 5% formic acid and 5% water to give 110 mg of the title compound. $^1$H NMR (CD$_3$OD, 300 MHz) δ 0.85 (t, J=7 Hz, 3H), 1.45 (m, 2H), 2.72 (s, 3H), 3.05 (t, J=7 Hz, 2H), 4.20 (s, 2H), 6.98 (d, J=8 Hz, 2H), 7.05 (dd, J=8 Hz, 6 Hz, 1H), 7.10 (d, J=8 Hz, 2H), 7.50–7.70 (m, 4H), 7.93 (dd, J=6 Hz, 2 Hz, 1H), 8.17 (dd, J=8 Hz, 2 Hz, 1H).

EXAMPLE 142

2-{N-Butyl-N-[(2'-[1H-tetrazol-5-yl]biphenyl-4-yl)methyl]amino}pyridine-3-carbonitrile

EXAMPLE 142A

2-{Butylamino}pyridine-3-carbonitrile

2-Chloronicotinitrile (1.30 g, 9.60 mmol) was refluxed with 3 mL of n-butylamine and 10 mL of isopropyl alcohol overnight. The solvents were removed in vacuo and the residue obtained chromatographed on silica gel eluting with 2:1 hexane/ethyl acetate to give 1.6 g of the title compound.

EXAMPLE 142B

2-{N-Butyl-N-[(2'-[N-triphenylmethyl-1H-tetrazol-5-yl]biphenyl-4-yl)methyl]amino}pyridine-3-carbonitrile To the compound resulting from Example 142A (1.60 g, 9.14 mmol) dissolved in 3.5 mL of tetrahydrofuran and 2.23 mL of 1,3-dimethyl-3,4,5,6-tetrahydro-2(1H)-pyrimidinone (DMPU) and cooled to 0° C. was added 1M lithium hexamethyldisilazide in tetrahydrofuran (9.1 mL). After 10 minutes at 0° C., a solution of 5.32 g (9.55 mmol) of N-triphenylmethyl-5-[2-(4'-bromomethylbiphenyl)]tetrazole, prepared by the method of Aldrich described in European Patent Application Number 291969, published Nov. 23, 1988, in 20 mL of tetrahydrofuran was added dropwise. The mixture was stirred at ambient temperature for 90 minutes. Toluene (100 mL) was added followed by 4 drops of concentrated hydrochloric acid. The mixture was washed with water, dried over sodium sulfate and concentrated under reduced pressure. The residue was chromatographed on silica gel eluting with 25% ether in hexane to give 3.6 g (60%) of the title compound.

EXAMPLE 142C

2-{N-Butyl-N-[(2'-[1H-tetrazol-5-yl]biphenyl-4-yl)methyl]amino}pyridine-3-carbonitrile The compound resulting from Example 142B (600 mg, 0.922 mmol) was stirred for 4 hours at ambient temperature with 7 mL of methylene chloride and 10 mL of 88% formic acid. The volatiles were removed under reduced pressure and chased with toluene. The residue obtained was crystallized from a mixture of ethanol and ether and then from acetone and ether to give 180 mg of the title compound. m.p. 173°–174° C. $^1$H NMR (CD$_3$OD, 300 MHz) δ 0.92 (t, J=7 Hz, 3H), 1.35 (m, 2H), 1.68 (m, 2H), 3.65 (t, J=7 Hz, 2H), 4.95 (s, 2H), 6.72 (dd, J=8 Hz, 6 Hz, 1H), 7.05 (d, J=8 Hz, 2H), 7.22 (d, J=8 Hz, 2H), 7.50–7.70 (m, 4H), 7.85 (dd, J=8 Hz, 2 Hz, 1H), 8.30 (dd, J=6 Hz, 2 Hz, 1H).

EXAMPLE 143

3-Aminomethyl-2-{N-butyl-N-[(2'-[1H-tetrazol-5-yl]biphenyl-4-yl)methyl]amino}pyridine

EXAMPLE 143A

3-Aminomethyl-2-{N-butyl-N-[(2'-[N-triphenylmethyl-1H-tetrazol-5-yl]biphenyl-4-yl)methyl]amino}pyridine The compound resulting from Example 142B (1.52 g, 2.33 mmol) in 50 mL of ether was added dropwise to a suspension of 0.26 g of lithium aluminide hydride (LAH) in ether. The mixture was refluxed for 1 hour and then cooled in an ice bath. The excess LAH was destroyed by the addition of 0.26 mL of water, 0.26 mL of 4N sodium hydroxide and finally 0.78 mL of water. The inorganic salts were removed by filtration and the filtrate concentrated in vacuo to afford 1.2 g of the title compound.

EXAMPLE 143B

3-Aminomethyl-2-{N-butyl-N-[(2'-[1H-tetrazol-5-yl]biphenyl-4-yl)methyl]amino}pyridine The compound resulting from Example 143A was treated with formic acid in methylene chloride by the procedure described in Example 141B. The crude product was chromatographed on silica gel eluting with 5% formic acid, 5% water, 90% ethyl acetate to give the title compound. $^1$H NMR (CDCl$_3$, 300 MHz) δ 0.90 (t, J=7 Hz, 3H), 1.38 (m, 2H), 1.50 (m, 2H), 3.12 (t, J=7 Hz, 2H), 3.90 (s, 2H), 4.22 (s, 2H), 6.70 (s, 4H), 7.15 (dd, J=8 Hz, 6 Hz, 1H), 7.20–7.70 (m, 5H), 8.05 (dd, J=6 Hz, 2 Hz, 1H).

EXAMPLE 144

3-Acetylaminomethyl-2-{N-butyl-N-[(2'-[1H-tetrazol-5-yl]biphenyl-4-yl)methyl]amino}pyridine

EXAMPLE 144A

3-Acetylaminomethyl-2-{N-butyl-N-[(2'-[N-triphenylmethyl-1H-tetrazol-5-yl]biphenyl-4-yl)methyl]amino}pyridine The compound resulting from Example 143A (300 mg, 0.46 mmol) in 30 mL of methylene chloride and 0.1 mL pyridine was stirred at ambient temperature for 90 minutes with 60 μL of acetic anhydride. The solution was washed with sodium bicarbonate, dried and concentrated in vacuo. The residue obtained was chromatographed on silica gel eluting with 5% water, 5% formic acid, and 90% ethyl acetate to give 240 mg of the title compound.

EXAMPLE 144B

3-Acetylaminomethyl-2-{N-butyl-N-[(2'-[1H-tetrazol-5-yl]biphenyl-4-yl)methyl]amino}pyridine The compound resulting from Example 144A (240 mg, 0.34 mmol) was stirred with 4 mL of methylene chloride and 6 mL of 88% formic acid for 2 hours. The solvent was removed under reduced pressure and the residue obtained chromatographed on silica gel eluting with 5% water, 5% formic acid, and 90% ethyl acetate to give 90 mg of the title compound. m.p. 108°–110° C. $^1$H NMR (CDCl$_3$, 300 MHz) δ 0.92 (t, J=7 Hz, 3H), 1.35 (m, 2H), 1.49 (m, 2H), 2.02 (s, 3H), 3.20 (t, J=7 Hz, 2H), 4.10 (d, J=6 Hz, 2H), 4.18 (s, 2H), 6.02 (broad, 1H), 7.00 (s, 4H), 7.05 (dd, J=8 Hz, 6 Hz, 1H), 7.40–7.60 (m, 4H), 7.95 (dd, J=8 Hz, 2 Hz, 1H), 8.38 (dd, J=6 Hz, 2 Hz, 1H).

EXAMPLE 145

3-Methanesulfonamidomethyl-2-{N-butyl-N-[(2'-[1H-tetrazol-5-yl]biphenyl-4-yl)methyl]amino}pyridine

EXAMPLE 145A

3-Methanesulfonamidomethyl-2-{N-butyl-N-[(2'-[N-triphenylmethyl-1H-tetrazol-5-yl]biphenyl-4-yl)methyl]amino}pyridine To the compound resulting from Example 143A (500 mg, 0.76 mmol) dissolved in 5 mL of methylene chloride and 0.1 mL of triethylamine and cooled to −20° C. was added 80 μL (1.0 mmol) of methanesulfonyl chloride. The solution was stirred for 3 hours at −20° C. then washed with water, dried and concentrated in vacuo. The residue obtained was chromatographed on silica gel eluting with 2:1 hexane/ethyl acetate followed by ethyl acetate to afford 130 mg of the title compound.

EXAMPLE 145B

3-Methanesulfonamidomethyl-2-{N-butyl-N-[(2'-[1H-tetrazol-5-yl]biphenyl-4-yl)methyl]amino}pyridine The compound resulting from Example 145A (280 mg, 0.38 mmol) was stirred for 2 hours with 4 mL of methylene chloride and 6 mL of formic acid. The volatiles were removed under reduced pressure and 50% formic acid was added. The by-product was removed by filtration and the filtrate concentrated under reduced pressure. The residue obtained was crystallized from ether to give 110 mg of the title compound. $^1$H NMR (CDCl$_3$, 300 MHz) δ 0.93 (t, J=7 Hz, 3H), 1.35 (m, 2H), 1.58 (m, 2H), 2.82 (s, 3H), 3.13 (t, J=7 Hz, 2H), 4.18 (s, 2H), 4.38 (s, 2H), 7.07 (d, J=8 Hz, 2H), 7.03 (m, 1H), 7.14 (d, J=8 Hz, 2H), 7.42 (dd, J=8 Hz, 2 Hz, 1H), 7.48–7.62 (m, 3H), 7.65 (broad, 1H), 8.00 (dd, J=8 Hz, 2 Hz, 1H), 8.40 (dd, J=6 Hz, 2 Hz, 1H).

EXAMPLE 146

2-{N-Butyl-N-[(2'-[1H-tetrazol-5-yl]biphenyl-4-yl)methyl]amino}pyridine-3-carboxamide The compound resulting from Example 142 (100 mg) was refluxed in 3 mL of ethanol and 3 mL of 10% potassium hydroxide in water for 16 hours. The solvent was removed under reduced pressure and water was added. The mixture was acidified with formic acid and the resulting oil was chromatographed on silica gel eluting with 2.5% formic acid and 2.5% water in ethyl acetate to afford 55 mg of the title compound. $^1$H NMR (CDCl$_3$, 300 MHz) δ 0.95 (t, J=7 Hz, 3H), 1.40 (m, 2H), 1.54 (m, 2H), 3.40 (t, J=7 Hz, 2H), 4.00 (s, 2H), 5.78 (br, 1H), 6.70 (d, J=8 Hz, 1 Hz, 1H), 6.90 (d, J=8 Hz, 2H), 7.28 (dd, J=8 Hz, 6 Hz, 1H), 7.45–7.60 (m, 2H), 7.96 (dd, J=8 Hz, 1 Hz, 1H), 8.28 (dd, J=8 Hz, 2 Hz, 1H), 8.62 (dd, J=6 Hz, 2 Hz, 1H), 9.10 (br, 1H).

EXAMPLE 147

3-Trifluoromethanesulfonamido-2-{N-propyl-N-[(2'-[1H-tetrazol-5-yl]biphenyl-4-yl)methyl]amino}pyridine

EXAMPLE 147A

3-Trifluoromethanesulfonamido-2-{N-propyl-N-[(2'-[N-triphenylmethyl-1H-tetrazol-5-yl]biphenyl-4-yl)methyl]amino}pyridine To the compound resulting from Example 93A (250 mg, 0.40 mmol) dissolved in 20 mL of methylene chloride was added 110 mg of 2,6-di-tert-butyl-4-methylpyridine. The solution was cooled to −20° C. and 84 μL of trifluoromethanesulfonic anhydride was added. The mixture was stirred for 1 hour and then washed with sodium bicarbonate, dried and concentrated under reduced pressure to give the title compound.

EXAMPLE 147B

3-Trifluoromethanesulfonamide-2-{N-propyl-N-[(2'-[1H-tetrazol-5-yl]biphenyl-4-yl)methyl]amino}pyridine The product resulting from Example 147A was dissolved in 3 mL of methylene chloride and 4 mL of formic acid and stirred at ambient temperature for 2 hours. The solvents were evaporated under reduced pressure and the residue obtained chromatographed on silica gel eluting with 5% formic acid and 5% water in ethyl acetate to give 110 mg of the title compound. $^1$H NMR (CD$_3$OD, 300 MHz) δ 0.88 (t, J=7 Hz, 3H), 1.56 (m, 2H), 3.54 (t, J=7 Hz, 2H), 4.85 (s, 2H), 7.02 (d, J=8 Hz, 2H), 7.06 (dd, J=8 Hz, 6 Hz, 1H), 7.18 (d, J=8 Hz, 2H), 7.45–7.70 (m, 5H), 7.90 (dd, J=8 Hz, 2 Hz, 1H).

EXAMPLE 148

3-Acetylamino-2-{N-propyl-N-[(2'-[1H-tetrazol-5-yl]biphenyl-4-yl)methyl]amino}pyridine

EXAMPLE 148A

3-Acetylamino-2-{N-propyl-N-[(2'-[N-triphenylmethyl-1H-tetrazol-5-yl]biphenyl-4yl)methyl]amino}pyridine To the compound resulting from Example 93A (500 mg, 0.796 mmol) dissolved in 10 mL of pyridine was added 0.30 mL of acetic anhydride. After stirring overnight, water was added and the mixture extracted with ethyl acetate. The combined organic extracts were dried and concentrated under reduced pressure. The residue obtained was chromatographed on silica gel eluting with 20% ethyl acetate in hexane to give 400 mg of the title compound.

EXAMPLE 148B

3-Acetylamino-2-{N-propyl-N-[(2'-[1H-tetrazol-5-yl]biphenyl-4-yl)methyl]amino}pyridine The compound resulting from Example 148A was dissolved in 4 mL of methylene chloride containing 6 mL of formic acid and left at ambient temperature for 2 hours. The solvents were evaporated under reduced pressure and 50% formic acid was added to the residue obtained. The triphenylmethanol by-product was removed by filtration and the filtrate concentrated in vacuo. The residue was crystallized from a mixture of ethyl acetate and hexane to give 300 mg of the title compound. m.p. 170°–171° C. $^1$H NMR (CDCl$_3$, 300 MHz) δ 0.98 (t, J=7 Hz, 3H), 1.42 (m, 2H), 2.12 (s, 3H), 3.18 (t, J=7 Hz, 2H), 4.00 (s, 2H), 6.76 (q, 4H), 7.21 (dd, J=8 Hz, 6 Hz, 1H), 7.41 (dd, J=8 Hz, 2 Hz, 1H), 7.45–7.66 (m, 2H), 7.90 (dd, J=8 Hz, 2 Hz, 1H), 8.19 (dd, J=8 Hz, 2 Hz, 1H), 8.25 (dd, J=6 Hz, 2 Hz, 1H).

EXAMPLE 149

3-Trifluoromethanesufonamidomethyl-2-{N-butyl-N-[(2'-[1H-tetrazol-5-yl]biphenyl-4-yl)methyl]amino}pyridine

EXAMPLE 149A

3-Trifluoromethanesufonamidomethyl-2-{N-butyl-N-[(2'-N-triphenylmethyl-1H-tetrazol-5-yl]biphenyl-4-yl)methyl]amino}pyridine The compound resulting from Example 143A (330 mg, 0.504 mmol) was dissolved in 20 mL of methylene chloride containing 0.13 g of 2,6-di-tert-butyl-4-methylpyridine and cooled to −20° C. Trifluoromethanesulfonic anhydride (0.11 mL, 0.655 mmol) was added and the solution stirred at −20° C. for 2 hours. The mixture was washed with sodium bicarbonate, dried and the solvent removed under reduced pressure. The residue obtained was chromatographed on silica gel eluting with 30% ethyl acetate in hexane to give 140 mg of the title compound.

EXAMPLE 149B

3-Trifluoromethanesufonamidomethyl-2-{N-butyl-N-[(2'-[1H-tetrazol-5-yl]biphenyl-4-yl)methyl]amino}pyridine The compound reuslting from Example 149A was kept at ambient temperature for 2 hours in 2 mL of methylene chloride containing 3 mL of formic acid. The solvents were removed in vacuo and the residue chromatographed on silica gel eluting with 20% ethanol in methylene chloride to give 80 mg of the title compound. m.p. 95° C. $^1$H NMR (CD$_3$OD, 300 MHz) δ 0.85 (t, J=7 Hz, 3H), 1.27 (m, 2H), 1.45 (m, 2H), 3.05 (t, J=7 Hz, 2H), 4.28 (s, 2H), 4.48 (s, 2H), 7.02 (d, J=8 Hz, 2H), 7.12 (dd, J=8 Hz, 6 Hz, 1H), 7.19 (d, J=8 Hz, 2H), 7.50–7.70 (m, 4H), 7.85 (dd, J=8 Hz, 2 Hz, 1H), 8.22 (dd, J=6 Hz, 2 Hz, 1H).

EXAMPLE 150

6-Chloro-3-trifluoromethanesulfonamido-2-{N-propyl-N-[(2'-[1H-tetrazol-5-yl]biphenyl-4-yl)methyl]amino}pyridine

EXAMPLE 150A

6-Chloro-3-nitro-2-{N-propyl-N-[(2'-[N-triphenylmethyl-1H-tetrazol-5-yl]biphenyl-4-yl)methyl]amino}pyridine N-Triphenylmethyl-5-[2-(4'-propylaminomethyl-biphenyl)]tetrazole (3.06 g, 5.72 mmol), the compound resulting from Example 96A, 2,6-dichloro-3-nitropyridine (900 mg, 4.66 mmol) and triethylamine (2.5 mL) were refluxed for 4 hours in 10 mL of tetrahydrofuran. The solvent was removed under reduced pressure, and the residue was dissolved in ethyl acetate, washed with water, dried and concentrated under reduced pressure to give the title compound as a yellow crystalline solid (2.4 g, 74%).

EXAMPLE 150B

3-Amino-6-chloro-2-{N-propyl-N-[(2'-[N-triphenylmethyl-1H-tetrazol-5-yl]biphenyl-4-yl)methyl]amino}pyridine The compound resulting from Example 150A (1.7 g, 2.45 mmol) was hydrogenated in 250 mL of ethyl acetate and 250 mL of isopropyl alcohol over 850 mg of 10% platinum on carbon for 2 hours. The solvent was removed under reduced pressure and the residue chromatographed on silica gel leuting with 20% ethyl acetate in hexane to give 1.17 of the title compound.

EXAMPLE 150C

6-Chloro-3-trifluoromethanesulfonamido-2-{N-propyl-N-[(2'-[N-triphenylmethyl-1H-tetrazol-5-yl]biphenyl-4-yl)methyl]amino}pyridine The compound resulting from Example 150B (330 mg, 0.498 mmol) and 123 mg (0.6 mmol) of 2,6-di-tert-butyl-4-methylpyridine were dissolved in 25 mL of methylene chloride at −20° C. and 0.1 mL of trifluoromethanesulfonic anhydride was added. After stirring at −20° C. for 1 hour, the solution was washed with sodium bicarbonate solution, dried and evaporated under reduced pressure. The residue was chromatographed on silica gel eluting with 25% ethyl acetate in hexane to give 230 mg of the title compound (57%).

EXAMPLE 150D

6-Chloro-3-trifluoromethanesulfonamido-2-{N-propyl-N-[(2'-[(1H-tetrazol-5-yl]biphenyl-4-yl)methyl]amino}pyridine The compound resulting from Example 150C (230 mg, 0.29 mmol) was stirred for 12 hours with 1.5 mL of methylene chloride and 2 mL of formic acid. The solvents were removed under reduced pressure and the residue chromatographed on silica gel eluting with 1:1 ethyl acetate/hexane containing 2% acetic acid to afford 110 mg (68%) of the title compound. $^1$H NMR (CD$_3$OD, 300 MHz) δ 0.85 (t, J=7 Hz, 3H), 1.52 (m, 2H), 3.45 (t, J=7 Hz, 2H), 4.66 (s, 2H), 6.88 (d J=8 Hz, 1H), 7.01 (d, J=8 Hz, 2H), 7.26 (d, J=8 Hz, 2H), 7.49 (d, J=8 Hz, 1H).

EXAMPLE 151

3-Carboxycarbonylamino-2-{N-propyl-N-[(2'-[1H-tetrazol-5-yl]biphenyl-4-yl)methyl]amino}pyridine

EXAMPLE 151A

3-Carbethoxycarbonylamino-2-{N-propyl-N-[(2'-[N-triphenylmethyl-1H-tetrazol-5-yl]biphenyl-4-yl)methyl]amino}pyridine To the compound resulting from Example 93A dissolved in methylene chloride containing triethylamine and cooled to 0° C. is added ethyl oxalyl chloride. Work up and purification by the procedure described in Example 148A affords the title compound.

EXAMPLE 151B

3-Carboxycarbonylamino-2-{N-propyl-N-[(2'-[1H-tetrazol-5-yl]biphenyl-4-yl)methyl]amino}pyridine The compound resulting from Example 151A is dissolved in one part methylene chloride and one and a half parts of formic acid and stirred for 2 hours at ambient temperature to afford 3-carboxycarbonylamino-2-{N-propyl-N-[(2'-[1H-tetrazol-5-yl]biphenyl-4-yl)methyl]amino}pyridine. Hydrolysis in ethanol/aqueous sodium hydroxide solution at ambient temperature affords the title compound.

EXAMPLE 152

2-{N-propyl-N-[(2'-[1H-tetrazol-5-yl]biphenyl-4-yl)methyl]amino}methylpyridine-3-carboxylic acid

EXAMPLE 152A

Ethyl 2-bromomethylpyridine-3-carboxylate

Ethyl 2-methylpyridine-3-carboxylate is refluxed with N-bromosuccinimide in carbon tetrachloride with 1% equivalent dibenzyl peroxide to give the title compound.

EXAMPLE 152B

2-{N-propyl-N-[(2'-[N-triphenylmethyl-1H-tetrazol-5-yl]biphenyl-4-yl)methyl]amino}methylpyridine-3-carboxylic acid The compound resulting from Example 152A is reacted with N-triphenylmethyl-5-[2-(4'-propylaminomethyl-biphenyl)]tetrazole, the compound resulting from Example 96A, in tetrahydrofuran containing triethylamine to give the title compound.

EXAMPLE 152C

2-{N-propyl-N-[(2'-[1H-tetrazol-5-yl]biphenyl-4-yl)methyl]amino}methylpyridine-3-carboxylic acid The compound resulting from Example 152B is dissolved in a solution of one part methylene chloride with 1.5 parts formic acid to remove the triphenylmethyl protecting group. The resulting compound is heated with sodium hydroxide in ethanol/water to give the title compound.

EXAMPLE 153

2-Propyl-3-{N-carboxymethyl-N-[(2'-[1H-tetrazol-5-yl]biphenyl-4-yl)methyl]amino}pyridine

EXAMPLE 153A

3-Nitro-2-[1,1-bis(ethoxycarbonyl)propyl]pyridine

Diethyl ethylmalonate is dissolved in tetrahydrofuran and treated with one equivalent of sodium bis(trimethylsilyl)amide followed by 2-chloro-3-nitropyridine to give the title compound.

EXAMPLE 153B

3-Nitro-2-propylpyridine

The compound resulting from Example 153A is refluxed for 2 hours in 48% hydrobromic acid. The solvent is removed in vacuo and the solution neutralized to give the title compound.

EXAMPLE 153C

3-Amino-2-propylpyridine

The compound resulting from Example 153B is hydrogenated in ethanol using a palladium on carbon catalyst to give the title compound.

EXAMPLE 153D

2-Propyl-3-{N-[(2'-[N-triphenylmethyl-1H-tetrazol-5-yl]biphenyl-4-yl)methyl]amino}pyridine The compound resulting from Example 153C is dissolved in tetrahydrofuran containing 3 equivalents of 1,3-dimethyl-3,4,5,6-tetrahydro-2(1H)-pyrimidinone (DMPU) at −20° C. and treated with 1 equivalent of sodium bis(trimethylsilyl)amide followed by 1 equivalent of N-triphenylmethyl-5-[2-(4'-bromomethylbiphenyl)]tetrazole, prepared as described by P. E. Aldrich, et al. in European Patent Application Number 291969, to give the title compound.

EXAMPLE 153E

2-Propyl-3-{N-ethoxycarbonylmethyl-N-[(2'-[N-triphenylmethyl-1H-tetrazol-5-yl]biphenyl-4-yl)methyl]amino}pyridine The compound resulting from Example 153D is dissolved in tetrahydrofuran containing 3 equivalents of DMPU at −20° C. and treated with one equivalent of sodium bis(trimethylsilyl)amide followed by one equivalent of ethyl bromoacetate to give the title compound.

EXAMPLE 153F

2-Propyl-3-{N-carboxymethyl-N-[(2'-[1H-tetrazol-5-yl]biphenyl-4-yl)methyl]amino}pyridine The compound resulting from Example 153E is dissolved in 1 part methylene chloride and 1.5 parts formic acid and stirred at ambient temperature to give 2-propyl-3-{N-ethoxycarbonylmethyl-N-[(2'-[1H-tetrazol-5-yl]biphenyl-4-yl)methyl]amino}pyridine. This ester is hydrolyzed with potassium hydroxide in ethanol/water to give the title compound.

EXAMPLE 154

3-Trifluoromethanesufonamido-2-{N-propyl-N-[(2'-[1H-tetrazol-5-yl]biphenyl-4-yl)methyl]amino}pyrazine Starting with 3-nitro-2-chloropyrazine, prepared by the method of Hartman et al., J. Med. Chem. 27, 1634 (1984), instead of 3-nitro-2-chloropyridine and following the procedure described in Example 84A gives 3-nitro-2-{N-propyl-N-[(2'-[N-triphenylmethyl-1H-tetrazol-5-yl]biphenyl-4-yl)methyl]amino}pyrazine. Following the procedure described in Example 93A, catalytic hydrogenation affords the 3-amino compound. Treatment of the 3-amino compound by the procedure described in Example 145A gives the N-trifluoromethane-sulfonamido compound. Following the procedure described in Example 145B gives the title compound.

EXAMPLE 155

4-Trifluoromethanesufonamido-3-{N-propyl-N-[(2'-[1H-tetrazol-5-yl]biphenyl-4-yl)methyl]amino}pyridazine

EXAMPLE 155A

4-Nitro-3-{N-propyl-N-[(2'-[N-triphenylmethyl-1H-tetrazol-5-yl]biphenyl-4-yl)methyl]amino}pyridazine-1-oxide N-Triphenylmethyl-5-[2-(4'-propylaminomethylbiphenyl)]tetrazole, the compound resulting from Example 96A, is reacted with 4-nitro-3-methoxypyridazine-1-oxide, prepared using the procedure of Yanai et al., Chem. Pharm. Bull. 20, 166 (1972), by the procedure described in Example 84A to give the title compound.

EXAMPLE 155B

4-Amino-3-{N-propyl-N-[(2'-[N-triphenylmethyl-1H-tetrazol-5-yl]biphenyl-4-yl)methyl]amino}pyridazine The compound resulting from Example 155A is hydrogenated following the procedure described in Example 93A until 4 equivalents of hydrogen have been absorbed to give the desired compound.

EXAMPLE 155C

4-Trifluoromethanesufonamido-3-{N-propyl-N-[(2'-[1H-tetrazol-5-yl]biphenyl-4-yl)methyl]amino}pyridazine The compound resulting from Example 155B is treated by the procedure described in Example 145A to give the N-trifluorosulfonamido compound. This compound is deprotected by the procedure described in Example 145B to give the title compound.

EXAMPLE 156

3-{N-Propyl-N-[(2'-[1H-tetrazol-5-yl]biphenyl-4-yl)methyl]amino}pyridine-4-carboxylic acid

EXAMPLE 156A

Ethyl 3-aminopyridine-4-carboxylate

A suspension of 3-aminopyridine-4-carboxylic acid (2.00 g, 14.5 mmol), prepared by the method of Crum and Fuchsman, J. Het. Chem. 3, 252 (1966), in ethanol (~4 g) was treated with 4.0 g of sulfuric acid and warmed on a steam bath for 4 hours. After cooling to ambient temperature, water (~40 mL) and solid sodium carbonate were added to basify the solution which was then extracted with chloroform (3×). The combined organic extracts were washed with brine, dried over magnesium sulfate and concentrated under reduced pressure. The residue obtained was flash chromatographed on silica gel eluting with 2:1 hexane/ethyl acetate to afford the title compound. $^1$H NMR (CDCl$_3$, 300 MHz) δ 1.41 (t, J=7 Hz, 3H), 4.37 (q, J=7 Hz, 2H), 7.60 (d, J=6 Hz, 1H), 7.93 (d, J=6 Hz, 1H), 8.19 (s, 1H). MS (DCI/NH$_3$) m/e 167 (M+H)$^+$, 184 (M+H+NH$_3$)$^+$.

EXAMPLE 156B

Ethyl 3-allylaminopyridine-4-carboxylate

To a 0° C. solution of the compound resulting from Example 156A (750 mg, 4.52 mmol) and 1,3-dimethyl-3,4,5,6-tetrahydro-2(1H)-pyrimidinone (DMPU) (1.30 mL, 1.38 g, 10.75 mmol) in 35 mL of tetrahydrofuran was added 1M lithium hexamethyldisilazide in tetrahydrofuran (4.7 mL, 4.7 mmol). After stirring at 0° C. for 30 minutes, allyl bromide (0.80 mL, 9.24 mmol) was added. The cooling bath was removed and the reaction mixture stirred at ambient temperature overnight. The solvent was removed under reduced pressure and the residue diluted with water and ethyl acetate. The aqueous phase was further extracted with ethyl acetate. The combined organic extracts were washed with brine, dried over magnesium sulfate and concentrated in vacuo. The residue obtained was flash chromatographed on silica gel eluting with 5:1 hexane/ethyl acetate to afford the title compound (465 mg). $^1$H NMR (CDCl$_3$, 300 MHz) δ 1.41 (t, J=7 Hz, 3H), 3.93-3.98 (m, 2H), 4.36 (q, J=7 Hz, 2H), 5.22 (dq, J=10 Hz, 1H), 5.23 (dq, J=16 Hz, 1H), 5.89-6.02 (m, 1H), 7.65 (d, J=6 Hz, 1H), 7.92 (d, J=6 Hz, 1H), 8.22 (s, 1H). MS (DCl/NH$_3$) m/e 207 (M+H)$^+$, 224 (M+H+NH$_3$)$^+$.

EXAMPLE 156C

Ethyl 3-propylaminopyridine-4-carboxylate

A suspension of the compound resulting from Example 156B (457 mg, 2.22 mmol) and platinum oxide (55 mg) in 25 mL of ethyl acetate was stirred under a balloon of hydrogen gas at ambient temperature overnight. The catalyst was removed by filtration through silica gel and the filtrate was concentrated under reduced pressure to afford the title compound (448 mg). $^1$H NMR (CDCl$_3$, 300 MHz) δ 1.04 (t, J=7 Hz, 3H), 1.39 (t, J=7 Hz, 3H), 1.66-1.80 (m, 2H), 3.26 (q, 2H), 4.35 (q, 2H), 7.62 (d, J=5 Hz, 1H), 7.88 (d, J=5 Hz, 1H), 8.23 (s, 1H). MS (DCl/NH$_3$) m/e 209 (M+H)$^+$.

EXAMPLE 156D

Ethyl 3-{N-propyl-N-[(2'-[N-triphenylmethyl-1H-tetrazol-5-yl]biphenyl-4-yl)methyl]amino}pyridine-4-carboxylate To a 0° C. solution of the compound resulting from Example 156C (405 mg, 1.95 mmol) and 1,3-dimethyl-3,4,5,6-tetrahydro-2(1H)-pyrimidinone (DMPU) (0.5 mL, 0.53 g, 4.13 mmol) in tetrahydrofuran (20 mL) was added 1M lithium hexamethyldisilazide in tetrahydrofuran (LHMDS) (2.1 mL, 2.1 mmol). After stirring at 0° C. for 30 minutes, a solution of N-triphenylmethyl-5-[2-(4'-bromomethyl-biphenyl)]tetrazole (1.19 g, 2.13 mmol), prepared as described by P. E. Aldrich, et al. in European Patent Application Number 291,969, in 10 mL of tetrahydrofuran was added. After stirring at 0° C. for 15 minutes, the ice bath was removed and the reaction was allowed to warm to ambient temperature overnight. The volatiles were removed in vacuo and the residue diluted with ethyl acetate. The solution was washed with water. The aqueous phase was back-extracted with ethyl acetate. The combined organic extracts were washed with brine, dried over magnesium sulfate and concentrated under reduced pressure. Flash chromatography of the residue on silica gel eluting with hexane in ethyl acetate afforded the title compound (190 mg, 14%). $^1$H NMR (CDCl$_3$, 300 MHz) δ 0.77 (t, J=7 Hz, 3H), 1.36 (t, J=7 Hz, 3H), 1.42-1.55 (m, 2H), 3.01 (t, J=7 Hz, 2H), 4.23 (s, 2H), 4.36 (q, J=7 Hz, 2H), 6.87-7.50 (m, 23H), 7.91 (dm, J=8 Hz, 1H), 8.17 (d, J=5 Hz, 1H), 8.38 (s, 1H). MS (DCl/NH$_3$) m/e 685 (M+H)$^+$.

EXAMPLE 156E

3-{N-Propyl-N-[(2'-[1H-tetrazol-5-yl]biphenyl-4-yl)methyl]amino}pyridine-4-carboxylic acid To the compound resulting from Example 156D (188 mg, 0.27 mmol) in 0.75 mL of ethanol and 0.75 mL of tetrahydrofuran was added p-toluenesulfonic acid (55 mg, 0.29 mmol). After stirring at ambient temperature for 5 hours, the solvents were removed under reduced pressure. The residue obtained was dissolved in 6 mL of methanol and treated with 1.5 mL of 2N sodium hydroxide (3 mmol). An additional aliquot of methanol was added (5 mL) and stirring was continued at ambient temperature overnight. The reaction mixture was heated at 70°-80° C. for 2 hours and then concentrated under reduced pressure. The residue obtained was dissolved in water and then acidified with 6N hydrochloric acid and extracted with ethyl acetate. The combined organic extracts were washed with brine, dried over magnesium sulfate and concentrated under reduced pressure. The residue obtained was flash chromatographed on silica gel eluting with mixtures of water, formic acid and ethyl acetate to afford the title compound which was precipitated from ethyl acetate/hexane. $^1$H NMR (DMSO-d$_6$, 300 MHz) δ 0.76 (t, J=8 Hz, 3H), 1.35-1.47 (m, 2H), 3.11 (bt, 2H), 4.41 (s, 2H), 7.03 (d, J=8 Hz, 2H), 7.25 (d, J=8 Hz, 2H), 7.50-7.70 (m, 5H), 8.29 (d, J=5 Hz, 1H), 8.60 (s, 1H). Anal calcd for C$_{23}$H$_{22}$N$_6$O$_2$.0.25 H$_2$O: C, 65.94; H, 5.41; N, 20.06. Found: C, 66.10; H, 5.30; N, 20.24. MS (DCl/NH$_3$) m/e 415 (M+H)$^+$.

EXAMPLE 157

3-{N-Butyl-N-[(2'-[1H-tetrazol-5-yl]biphenyl-4-yl)methyl]amino}pyrazine-2-carboxylic acid

EXAMPLE 157A

Methyl 3-bromopyrazine-2-carboxylate

To a rapidly stirring heterogeneous mixture of 3-aminopyrazine-2-carboxylic acid methyl ester (2.00 g, 13.1 mmol) in 48% hydrobromic acid (7.9 mL) cooled to 0° C. was added bromine (2.00 mL, 6.2 g, 38.8 mmol) dropwise over 5 minutes. Then a solution of sodium nitrite (2.27 g, 32.8 mmol) in 9.5 mL of water was added dropwise over 10 minutes. The reaction mixture was stirred at 0° C. for 15-30 minutes and then basified with 60 mL of saturated sodium bicarbonate solution and extracted with ethyl acetate followed by chloroform. The combined organic extracts were dried over magnesium sulfate and concentrated under reduced pressure. The residue obtained was flash chromatographed on silica gel eluting with mixtures of hexane and ethyl acetate to afford the title compound (1.265 g, 46%). m.p. 43.5°–44° C. $^1$H NMR (CDCl$_3$, 300 MHz) δ 4.04 (s, 3H), 8.50 (bs, 1H), 8.60 (bs, 1H). MS (DCl/NH$_3$) m/e 217/219 (M+H)$^+$, 234/236 (M+H+NH$_3$)$^+$.

EXAMPLE 157B

Methyl 3-{N-Butyl-N-[(2'-[N-triphenylmethyl-1H-tetrazol-5-yl]biphenyl-4-yl)methyl]amino}pyrazine-2carboxylate A solution of the compound resulting from Example 157A (320 mg, 1.47 mmol), N-triphenylmethyl-5-[2-(4'-butylaminomethyl-biphenyl)]tetrazole, prepared by the procedure described in Example 19A, (825 mg, 150 mmol), and triethylamine (0.31 mL, 0.225 g, 2.22 mmol) in 1.5 mL tetrahydrofuran was refluxed for 5 hours. The reaction mixture was allowed to stand at ambient temperature overnight. It was diluted with ethyl acetate, washed with 1 M phosphoric acid (2×), saturated sodium bicarbonate solution (2×) and brine, dried and concentrated in vacuo. The residue obtained was flash chromatographed on silica gel eluting with 3:1 hexane-ethyl acetate to give the title compound (708 mg, 70%). $^1$H NMR (CDCl$_3$, 300 MHz) δ 0.85 (t, J=7 HZ, 3H), 1.18 (m, 2H), 1.52 (m, 2H), 3.29 (t, J=7.5 Hz, 2H), 3.88 (s, 3H), 4.60 (s, 2H), 6.88–7.52 (m, 23H), 7.92 (d, J=3 Hz), 8.12 (m, 1H). MS (FAB) m/e 686 (M+H)$^+$.

EXAMPLE 157C

3-{N-Butyl-N-[(2'-[1H-tetrazol-5-yl]biphenyl-4-yl)methyl]amino}pyrazine-2-carboxylic acid A solution of the compound resulting from Example 157B (500 mg, 0.73 mmol) and p-toluenssulfonic acid monohydrate (165 mg) in 2 mL of ethanol and 2 mL of tetrahydrofuran were stirred at ambient temperature for 3 hours. The volatiles were removed under reduced pressure and the residue dissolved in 15 mL of methanol. A solution of 2N sodium hydroxide (3.6 mL) was added, and the reaction mixture was stirred overnight at ambient temperature and heated at reflux for 4 hours. The volatiles were removed under reduced pressure and the resulting solution diluted with water and washed with ether (3×). The aqueous phase was acidified with 1M phosphoric acid to pH 4 and the resulting precipitate collected by filtration, washed with water and dried to afford the title compound (256 mg). The compound was further purified by dissolving it in 1M sodium hydroxide solution and washing with ethyl acetate (3×). The aqueous solution was acidified with 6M hydrochloric acid and extracted with ethyl acetate (3×). The combined organic extracts were washed with brine, dried over magnesium sulfate and concentrated to ~5 mL. Hexane was added to precipitate out a solid. The solid was triturated with additional hexane, collected by filtration and dried to afford pure title compound (~140 mg). $^1$H NMR (DMSO-d$_6$, 300 MHz) δ 0.82 (t, J=7.5 Hz, 3H), 1.12–1.23 (m, 2H), 1.45–1.55 (m, 2H), 3.35 (bt, J=8 Hz, 2H), 4.75 (s, 2H), 7.03 (d, J=8 Hz, 2H), 7.20 (d, J=8 Hz, 2H), 7.53–7.72 (m, 4H), 7.91 (d, J=3 Hz, 1H), 8.19 (d, J=3 Hz, 1H). MS (DCl/NH$_3$) m/e 430 (M+H)$^+$. Anal calcd for C$_{23}$H$_{23}$N$_7$O$_2$: C, 64.32; H, 5.40, N, 22.83. Found: C, 64.31; H, 5.22; N, 22.46.

EXAMPLE 158

4-{N-Butyl-N-[(2'-[1H-tetrazol-5-yl]biphenyl-4-yl)methyl]amino}-2-chloro-6-methylpyrimidine

EXAMPLE 158A

4-Hydroxy-6-methyl-2-methylthiopyrimidine

To a solution of sodium (1.25 g, 54 mmol, 1.1 equivalents) dissolved in anhydrous methanol (100 mL) was added 4-hydroxy-6-methyl-pyrimidine-2-thiol (7.00 g, 49.2 mmol). The mixture was warmed to ~40° C. and methyl iodide (13.06 mL, 49.2 mmol) was added. The mixture was heated under reflux for 3 hours and then cooled to ambient temperature and allowed to stand overnight. The crystals were filtered, washed with methanol and dried to give 7.10 g (75%) of the title compound. $^1$H NMR (DMSO-d$_6$, 300 MHz) δ 2.17 (s, 3H), 2.48 (s, 3H), 5.60 (bs, 1H). MS (DCl/NH$_3$) m/e 157 (M+H)$^+$, 174 (M+H+NH$_3$)$^+$.

EXAMPLE 158

4-Chloro-6-methyl-2-methylthiopyrimidine

The compound resulting from Example 158A (5.71 g, 36 mmol) was dissolved in phosphorus oxychloride (20 mL) and heated at reflux for 2 hours. The excess phosphorus oxychloride was removed under reduced pressure and the residue poured onto ice. The mixture was extracted with ether (2×) and the combined extracts were dried over sodium sulfate and concentrated in vacuo. The oil was purified by short path distillation to afford 3.71 g (57%) of the title compound. $^1$H NMR (CDCl$_3$, 300 MHz) δ 2.44 (s, 3H), 2.57 (s, 3H), 6.86 (s, 1H). MS (DCl/NH$_3$) m/e 175/177 (M+H)$^+$.

EXAMPLE 158C

4-Butylamino-6-methyl-2-methylthiopyrimidine

The compound resulting from Example 158B (3.71 g, 21.2 mmol) was dissolved in 20% (w/w) butylamine/ethanol (9.2 mL, 23.3 mmol) containing triethylamine (4.5 mL, 31 mmol, 1.5 equivalents) and heated at reflux overnight. The volatiles were removed in vacuo and the residue purified by flash chromatography on silica gel eluting with 30% ethyl acetate in hexane to afford 3.52 g (78%) on the title compound as a clear, colorless oil. $^1$H NMR (CDCl$_3$, 300 MHz) δ 0.95 (t, J=7 Hz, 3H), 1.40 (m, 2H), 1.60 (m, 2H), 2.28 (s, 3H), 2.50 (s, 3H), 3.29 (m, 2H), 4.77 (bs, 1H), 5.84 (s, 1H). MS (DCl/NH$_3$) m/e 212 (M+H)$^+$.

EXAMPLE 158D

4-Butylamino-2-hydroxy-6-methylpyrimidine

The compound resulting from Example 158C (1.00 g, 4.73 mmol) was suspended in 6N hydrochloric acid (3 mL) and heated at reflux overnight. The solution was lyophilized to afford the title compound as a white solid. $^1$H NMR (CD$_3$OD, 300 MHz) δ 0.97 (t, J=7 Hz, 3H), 1.45 (m, 2H), 1.65 (m, 2H), 2.23 (s, 3H), 3.38 (t, J=7 Hz, 2H), 5.80 (s, 1H). MS (DCl/NH$_3$) m/e 182 (M+H)$^+$.

EXAMPLE 158E

4-Butylamino-2-chloro-6-methylpyrimidine

The compound resulting from Example 158D was dissolved in phosphorus oxychloride (5 mL) and the resultant solution was heated at reflux for 2 hours. The excess phosphorus oxychloride was removed by atmospheric distillation to yield a yellow oil. This residue was poured onto ice and extracted with ether. Sodium bicarbonate was added to the ice-water layer and this was also extracted with ether. The combined organic extracts were washed with sodium bicarbonate solution, dried over potassium carbonate and concentrated in vacuo to yield 874 mg (90%) of crude product. This material was purified by flash chromatography on silica gel eluting with ethyl acetate in hexane to give a residue which crystallized under reduced pressure affording the title product (375 mg, 40%). $^1$H NMR (CDCl$_3$, 300 MHz) δ 0.96 (t, J=7 Hz, 3H), 1.42 (m, 2H), 1.60 (m, 2H), 2.33 (s, 3H), 3.27 (m, 2H), 5.00 (bs, 1H), 6.08 (s, 1H). MS (DCl/NH$_3$) m/e 200/202 (M+H)$^+$.

EXAMPLE 158F

4-{N-Butyl-N-[(2'-[N-triphenylmethyl-1H-tetrazol-5-yl]biphenyl-4-yl)methyl]amino}-2-chloro-6-methylpyrimidine To a stirred solution of the compound resulting from Example 158E (369 mg, 1.84 mmol) in anhydrous tetrahydrofuran (4 mL) at 0° C. was added a 1M solution of lithium hexamethyldisilazide in tetrahydrofuran (1.9 mL, 1.03 equivalents). After 20 minutes, a solution of N-triphenylmethyl-5-[2-(4'-bromomethyl-biphenyl)]tetrazole (1.26 g of 83% pure material, 1.84 mmol, 1 equivalent), prepared as described by P. E. Aldrich, et al. in European Patent Application Number 291,969, in tetrahydrofuran (2.5 mL) was added. The cooling bath was removed and the mixture was allowed to warm to ambient temperature and stirred for 2 days. The mixture was poured into ether and washed with saturated aqueous sodium bicarbonate, water, 1N phosphoric acid and saturated aqueous sodium chloride, dried over magnesium sulfate and concentrated in vacuo. The residue obtained was flash chromatographed on silica gel eluting with 20% ethyl acetate in hexanes to afford the title compound.

EXAMPLE 158G

4-{N-Butyl-N-[(2'-[1H-tetrazol-5-yl]biphenyl-4-yl)methyl]amino}-2-chloro-6-methyl]pyrimidine To the compound resulting from Example 158F (50 mg, 74 μmol) dissolved in tetrahydrofuran (1 mL) was added ethanol (1 mL) followed by p-toluenesulfonic acid monohydrate (14 mg, 74 μmol). After 2 hours, the solvent was removed in vacuo. The residue obtained was purified by flash chromatography on silica gel eluting with ethyl acetate in hexanes containing 0.5% acetic acid to give the desired compound (17.6 mg, 54%). $^1$H NMR (CDCl$_3$, 300 MHz) δ 0.95 (t, J=7 Hz, 3H), 1.35 (m, 2H), 1.58 (m, 2H), 2.19 (s, 3H), 3.38 (bm, 2H), 4.79 (bs, 1H), 6.17 (s, 1H), 7.20 (d, J=8 Hz, 2H), 7.25 (d, J=8 Hz, 2H), 7.43 (dd, J=8 Hz, 2 Hz, 1H), 7.54 (bd, J=7 Hz, 2 Hz, 1H), 7.60 (bd, J=7 Hz, 2 Hz, 1H), 8.05 (dd, J=8 Hz, 1 Hz, 1H). MS (DCl/NH$_3$) m/e 434/436 (M+H)$^+$.

EXAMPLE 159

Methyl 2-{N-butyl-N-[(2'-[1H-tetrazol-5-yl]biphenyl-4-yl)methyl]amino}-6-fluoropyridine-3-carboxylate To a solution of the compound resulting from Example 19A, (275 mg, 0.5 mmol, 1 equivalent) in anhydrous tetrahydrofuran (2 mL) was added triethylamine (140 μL, 1 mmol, 2 equivalents) followed by 2,6-difluoronicotinic acid methyl ester (86.5 mg, 0.5 mmol). The resultant solution was heated at reflux overnight and then concentrated under reduced pressure. The residue obtained was purified by flash chromatography on silica gel eluting with 20% ethyl acetate in hexanes to give the title compound (200 mg, 57%) as a colorless oil. $^1$H NMR (CDCl$_3$, 300 MHz) δ 0.83 (t, J=7 Hz, 3H), 1.19 (m, 2H), 1.49 (m, 2H), 3.26 (t, J=7 Hz, 2H), 3.78 (s, 3H), 4.51 (s, 2H), 6.24 (dd, J=8 Hz, 3 Hz, 1H), 7.00 (d, J=8 Hz, 2H), 7.07 (d, J=8 Hz, 2H), 7.25 (m, 15H), 7.44 (bd, J=8 Hz, 2 Hz, 1H), 7.50 (bd, J=8 Hz, 2 Hz, 1H), 7.90 (dd, J=8 Hz, 2 Hz, 1H), 8.03 (t, J=8 Hz, 1H). MS (DCl/NH$_3$) m/e 703 (M+H)$^+$.

EXAMPLE 160

2-{N-Propyl-N-[(2'-[1H-tetrazol-5-yl]biphenyl-4-yl)methyl]amino}-6-fluoropyridine-3-carboxylic acid

EXAMPLE 160A

Methyl 2-{N-propyl-N-[(2'-[N-triphenylmethyl-1H-tetrazol-5-yl]biphenyl-4-yl)methyl]amino}-6-fluoropyridine-3-carboxylate To a suspension of the compound resulting from Example 96A, (272 mg, 0.5 mmol) in anhydrous tetrahydrofuran (3 mL) was added triethylamine (140 μL, 1 mmol) followed by methyl 2,6-difluoronicotinate (6.5 mg, 0.5 mmol). The mixture was heated at reflux overnight and the volatiles were removed in vacuo. The residue obtained was flash chromatographed on silica gel eluting with 20% ethyl acetate in hexane to afford the title compound (200 mg, 58%) as a colorless oil. $^1$H NMR (CDCl$_3$, 300 MHz) δ 0.76 (t, J=7 Hz, 3H), 1.53 (dt, J=7 Hz, 6.5 Hz, 2H), 3.22 (t, J=7 Hz, 2H), 3.78 (s, 3H), 4.52 (s, 2H), 6.23 (dd, J=8 Hz, 3 Hz, 1H), 6.91 (dd, J=7 Hz, 1 Hz, 1H), 7.00 (d, J=8 Hz, 2H), 7.07 (d, J=8 Hz, 2H), 7.24 (m, 15H), 7.39 (bd, J=8 Hz, 1 Hz, 1H), 7.48 (bd, J=8 Hz, 1 Hz, 1H), 7.90 (dd, J=8 Hz, 1 Hz, 1H), 8.02 (t, J=8 Hz, 1H). MS (DCl/NH$_3$) m/e 689 (M+H)$^+$.

EXAMPLE 160B

2-{N-Propyl-N-[(2'-[1H-tetrazol-5-yl]biphenyl-4-yl)methyl]amino}-6-fluoropyridine-3-carboxylic acid and 2-{N-Propyl-N-[(2'-[1H-tetrazol-5-yl]biphenyl-4-yl)methyl]amino}-6-methoxypyridine-3-carboxylic acid To the compound resulting from Example 160A (150 mg, 0.218 mmol) dissolved in tetrahydrofuran (2 mL) was added methanol (1 mL) followed by p-toluenesulfonic acid monohydrate (45 mg, 0.218 mmol). The mixture was heated at reflux for 10 minutes, cooled to ambient temperature and partitioned between ethyl acetate and water. The organic phase was washed with brine, dried over sodium sulfate and concentrated in vacuo.

The residue obtained was dissolved in 1:1 tetrahydrofuran/metanol (3 mL) and 4N sodium hydroxide was added. The mixture was heated at reflux for 2 hours, cooled to ambient temperature and partitioned between ethyl acetate and 1N hydrochloric acid. The organic phase was dried over magnesium sulfate and concentrated under reduced pressure. The residue obtained was flash chromatographed on silica gel to give the title compound as a colorless oil (16 mg, 17%). $^1$H NMR (CDCl$_3$, 300 MHz) δ 1.01 (t, J=7 Hz, 3H), 1.63 (m, 2H), 3.38 (m, 2H), 4.40 (bs, 2H), 6.90 (d, J=8 Hz, 2H), 6.98 (d, J=8 Hz, 2H), 7.12 (bs, 2H), 7.41 (dd, J=8 Hz, 0.5 Hz, 1H), 7.53 (bd, J=7.5 Hz, 1 Hz, 1H), 7.59 (td, J=7.5 Hz, 1 Hz, 1H), 7.90 (dd, J=7.5 Hz, 1 Hz, 1H), 8.70 (t, J=7.5 Hz, 1H). MS (DCl/NH$_3$) m/e 433 (M+H)+. (Also obtained was 2-{N-propyl-N-[(2'-[1H-tetrazol-5-yl]biphenyl-4-yl)methyl]amino}-6-methoxypyridine-3-carboxylic acid (17 mg, 18%).)

EXAMPLE 161

2-{N-Propyl-N-[(2'-[1H-tetrazol-5-yl]biphenyl-4-yl)methyl]amino}-6-methoxypyridine-3-carboxylic acid The title compound was prepared as described in Examples 160A and 160B. $^1$H NMR (CDCl$_3$, 300 MHz) δ 1.00 (t, J=7 Hz, 3H), 1.52 (m, 2H), 3.68 (m, 2H), 4.08 (s, 3H), 6.90 (d, J=8 Hz, 3H), 6.98 (d, J=8 Hz, 2H), 7.39 (dd, J=8 Hz, 1 Hz, 1H), 7.50 (bd, J=8 Hz, 1 Hz, 1H), 7.57 (bd, J=8 Hz, 1 Hz, 1H), 7.83 (dd, J=8 Hz, 1 Hz, 1H), 8.41 (d, J=8 Hz, 1H). MS (DCl/NH$_3$) m/e 445 (M+H)+.

EXAMPLE 162

2-{N-Butyl-N-[(2'-[1H-tetrazol-5-yl]biphenyl-4-yl)methyl]amino}-6-fluoropyridine-3-carboxylic acid

EXAMPLE 162A

Methyl 2-{N-butyl-N-[(2'-[1H-tetrazol-5-yl]biphenyl-4-yl)methyl]amino}-6-fluoropyridine-3-carboxylate To the compound resulting from Example 159 (200 mg, 0.285 mmol) dissolved in tetrahydrofuran (2 mL) was added methanol (2 mL) followed by p-toluenesulfonic acid monohydrate (54 mg, 0.285 mmol). The mixture was heated at reflux for 20 minutes, cooled to ambient temperature and partitioned between ethyl acetate and sodium bicarbonate solution. The organic phase was dried over magnesium sulfate and concentrated in vacuo. The title compound was used without further purification.

EXAMPLE 162B

2-{N-Butyl-N-[(2'-[1H-tetrazol-5-yl]biphenyl-4-yl)methyl]amino}-6-fluoropyridine-3-carboxylic acid and 2-{N-Butyl-N-[2'-[1H-tetrazol-5-yl]biphenyl-4-yl)methyl]amino}-6-methoxypyridine-3-carboxylic acid The compound resulting from Example 162A was dissolved in 1:1 tetrahydrofuran/methanol (2 mL) and 4N sodium hydroxide (0.5 mL) was added. The solution was heated at reflux overnight, cooled to ambient temperature and partitioned between ethyl acetate and 1N hydrochloric acid. The organic phase was dried over magnesium sulfate and concentrated in vacuo. The residue obtained was purified by flash chromatography on silica gel eluting with 95:5:0.5 chloroform/methanol/acetic acid. The resulting four component mixture was separated by preparative HPLC to give 12.5 mg of the title compound. $^1$H NMR (CDCl$_3$, 300 MHz) δ 0.93 (t, J=7 Hz, 3H), 1.42 (m, 2H), 1.55 (m, 2H), 3.55 (t, J=7 Hz, 2H), 4.34 (s, 2H), 6.89 (d, J=8 Hz, 2H), 7.00 (t, J=8 Hz, 2H), 7.09 (dd, J=8 Hz, 3 Hz, 1H), 7.40 (dd, J=8 Hz, 1 Hz, 1H), 7.52 (bd, J=8 Hz, 1 Hz, 1H), 7.58 (bd, J=8 Hz, 1 Hz, 1H), 7.92 (dd, J=8 Hz, 1 Hz, 1H), 8.68 t, J=8 Hz, 1H). MS (DCl/NH$_3$) m/e 447 (M+H)+. (Also obtained was 2-{N-butyl-N-[(2'-[1H-tetrazol-5-yl]biphenyl-4-yl)methyl]amino}-6-methoxypyridine-3-carboxylic acid (12 mg, 10%).)

EXAMPLE 163

2-{N-Butyl-N-[(2'-[1H-tetrazol-5-yl]biphenyl-4-yl)methyl]amino}-6-methoxypyridine-3-carboxylic acid The title compound was prepared by the method described in Examples 162A and 162B. $^1$H NMR (CD$_3$OD, 300 MHz) δ 0.88 (t, J=7 Hz, 3H), 1.32 (m, 2H), 1.50 (m, 2H), 3.55 (dd, J=7.5 Hz, 7.3 Hz, 2H), 4.00 (s, 3H), 4.66 (s, 2H), 6.69 (d, J=8 Hz, 1H), 7.03 (d, J=8 Hz, 2H), 7.22 (d, J=8 Hz, 2H), 7.50 (dd, J=7 Hz, 1 Hz, 1H), 7.57 (dd, J=7 Hz, 1 Hz, 1H), 7.64 (m, 2H), 8.16 (d, J=8 Hz, 1H). MS (DCl/NH$_3$) m/e 459 (M+H)+.

EXAMPLE 164

3-{N-Butyl-N-[(2'-[1H-tetrazol-5-yl)methyl]amino} benzoic acid

EXAMPLE 164A

Ethyl 3-aminobenzoate

To 3-aminobenzoic acid (7.00 g, 0.52 mol) dissolved in 300 mL of absolute ethanol was added ~3.5 mL of concentrated sulfuric acid. The reaction mixture was heated at reflux for 2 days and then cooled to ambient temperature. Potassium carbonate (8.9 g) was added and then most of the ethanol was removed under reduced pressure. The solution was partitioned between chloroform and water. The organic phase was washed with brine, dried over sodium sulfate and concentrated under reduced pressure. The residue obtained was filtered through silica gel eluting with ethyl acetate to afford the title compound. $^1$H NMR (CDCl$_3$, 300 MHz) δ 1.40 (t, 3H), 3.85 (bs, 2H), 4.35 (q, 2H), 6.90 (m, 1H), 7.25 (m, 1H), 7.45 (m, 2H). MS (DCl/NH$_3$) m/e 166 (M+H)+, 183 (M+H+NH$_3$)+.

EXAMPLE 164B

Ethyl 3-butylaminobenzoate

To the compound resulting from Example 164A (3.5 g, 0.02 mol) dissolved in 30 mL (0.26 mol) of n-butyl iodide was added 3.7 g (0.027 mol) of potassium carbonate. The reaction was refluxed for 4 hours, cooled to ambient temperature and stirred overnight. The reaction mixture was partitioned between chloroform and water; and the organic phase was washed with brine, dried over sodium sulfate and concentrated in vacuo to afford a solid. Purification by flash chromatography on silica gel eluting with 8% ethyl acetate in hexane afforded the title compound as a white crystalline solid (2.1 g). $^1$H NMR (CDCl$_3$, 300 MHz) δ 0.95 (t, 3H), 1.40 (t, 3H), 1.45 (m, 2H), 1.60 (m, 2H), 3.15 (t, 2H), 3.70 (bs, 1H), 4.35 (q, 2H), 6.75 (ddd, 1H), 7.20 (dd, 1H), 7.25 (dd, 1H), 7.35 (ddd, 1H). MS (DCl/NH$_3$) m/e 222 (M+H)+, 239 (M+H+NH$_3$)+.

EXAMPLE 164C

Ethyl 3-{N-butyl-N-[(2'-[N-triphenylmethyl-1H-tetrazol-5-yl]biphenyl-4-yl)methyl]amino}benzoate The compound resulting from Example 164B (1.00 g, 4.5 mmol), 1.92 g 83% pure (2.9 mmol) N-triphenylmethyl-5-[2-(4'-bromomethylbiphenyl)]tetrazole, prepared as described by P. E. Aldrich, et al. in European Patent Application Number 291,969, and 700 mg potassium carbonate were heated in 2.5 mL of dimethylformamide at 55°–65° C. for 8 hours and then cooled to ambient temperature and allowed to stand overnight.

The reaction mixture was diluted with ethyl acetate and washed with water and brine, dried over sodium sulfate and concentrated under reduced pressure. The residue obtained was flash chromatographed on silica gel eluting with 12% ethyl acetate in hexane to afford 735 mg (36%) of the title compound as a white amorphous solid. $^1$H NMR (CDCl$_3$, 300 MHz) δ 0.95 (t, 3H), 1.25–1.40 (m, t, 5H), 1.60 (m, 2H), 3.30 (t, 2H), 4.35 (q, 2H), 4.45 (s, 2H), 6.70 (dd, 1H), 6.90–7.50 (m, 25H), 7.90 (dd, 1H). MS (DCl/NH$_3$) m/e 698 (M+H)$^+$.

EXAMPLE 164D

Ethyl 3-{N-butyl-N-[(2'-[1H-tetrazol-5-yl]biphenyl-4-yl)methyl]amino}benzoate

To the compound resulting from Example 164C (715 mg, 1.0 mmol) dissolved in 7 mL of ethanol and 2 mL of tetrahydrofuran was added 195 mg (1.0 mmol) p-toluenesulfonic acid monohydrate. The reaction was stirred at ambient temperature for 2 hours and then concentrated under reduced pressure. The residue obtained was flash chromatographed on silica gel eluting with 97:3:0.5 chloroform/ethanol/acetic acid to afford 350 mg of the title compound (77%). $^1$H NMR (CDCl$_3$, 300 MHz) δ 1.00 (t, 3H), 1.35 (t, 3H), 1.40 (m, 2H), 1.70 (m, 2H), 3.50 (t, 2H), 4.35 (q, 2H), 4.65 (s, 2H), 6.85 (ddd, 1H), 7.15–7.65 (m, 10H), 8.20 (dd, 1H). MS (DCl/NH$_3$) m/e 456 (M+H)$^+$.

EXAMPLE 164E

3-{N-Butyl-N-[(2'-[1H-tetrazol-5-yl]biphenyl-4-yl)methyl]amino}benzoic acid

To the compound resulting from Example 164D (336 mg, 0.74 mmol) dissolved in 0.5 mL of tetrahydrofuran was added ~1 mL of ethanol followed by 0.8 mL of 2N sodium hydroxide. The reaction was stirred for ~2 hours at ambient temperature. An additional aliquot of 2N sodium hydroxide (0.2 mL) was added and the reaction stirred overnight at ambient temperature. An additional aliquot of 2N sodium hydroxide (0.2 mL) was added and stirring continued for an additional 4 hours. 1N Hydrochloric acid (25 mL) was added and the mixture extracted with ethyl acetate. The combined organic extracts were washed with brine, dried over sodium sulfate and concentrated in vacuo to afford 330 mg of an off-white amorphous solid. Chromatography on silica gel eluting with 95:5:0.5 chloroform/ethanol/acetic acid afforded 270 mg of an off-white amorphous solid which was precipitates from methylene chloride in hexane to afford 220 mg of the title compound as a white solid. $^1$H NMR (CD$_3$OD, 300 MHz) δ 1.00 (t, 3H), 1.40 (m, 2H), 1.65 (m, 2H), 3.45 (t, 2H), 4.60 (s, 2H), 6.85 (ddd, 1H), 7.05 (d, 2H), 7.15–7.30 (d, m, 4H), 7.40 (dd, 1H), 7.50–7.70 (m, 4H). MS (DCl/NH$_3$) m/e 428 (M+H)$^+$. Anal calcd for C$_{25}$H$_{25}$N$_5$O$_2$: C, 70.24; H, 5.89; N, 16.38. Found: C, 70.07; H, 6.08; N, 16.17.

EXAMPLE 165

4-{N-Butyl-N-[(2'-[1H-tetrazol-5-yl]biphenyl-4-yl)methyl]amino}benzoic acid

The title compound was prepared in analogy to Example 164 starting from 4-aminobenzoic acid instead of 3-aminobenzoic acid. Tosic acid deprotection of ethyl 4-{N-butyl-N-[(2'-[N-triphenylmethyl-1H-tetrazol-5-yl]biphenyl-4-yl)methyl]amino}benzoate followed by ester hydrolysis afforded, after purification by flash chromatography on silica gel eluting with 95:5:0.25 chloroform/ethanol/acetic acid, the title compound (100 mg, 26%) as a solid. $^1$H NMR (CD$_3$OD, 300 MHz) δ 1.00 (t, 3H), 1.40 (m, 2H), 1.65 (m, 2H), 3.50 (t, 2HO, 4.65 (s, 2H), 6.70 (m, 2H), 7.10 (m, 2H), 7.20 (m, 2H), 7.55 (m, 2H), 7.65 (m, 2H), 7.80 (m, 2H). MS (DCl/NH$_3$) m/e 428 (M+H)$^+$, 445 (M+H+NH$_3$)$^+$.

EXAMPLE 166

2-{N-Butyl-N-[(2'-[1H-tetrazol-5-yl]biphenyl-4-yl)methyl]amino}pyridine-5-carboxylic acid

EXAMPLE 166A

Ethyl 2-chloropyridine-5-carboxylate

To 6.85 g (44 mmol) of 6-chloronicotinic acid dissolved in 50 mL of tetrahydrofuran was added ethanol (6 mL), dimethylaminopyridine (700 mg) and 1-(3-dimethylaminopropyl-3-ethylcarbodiimide hydrochloride (EDCl) (9.4 g, 49 mmol). The reaction was stirred at ambient temperature for 4 hours and then concentrated under reduced pressure. The residue was diluted with ethyl acetate, washed with water (2×), saturated sodium bicarbonate (2×) and brine, dried over sodium sulfate and concentrated in vacuo. The residue obtained was flash chromatographed on silica gel eluting with 10% ethyl acetate in hexane to afford 6.00 g of the title compound as a colorless oil. $^1$H NMR (CDCl$_3$, 300 MHz) δ 1.40 (t, 3H), 4.40 (q, 2H), 7.40 (d, 1H), 8.25 (dd, 1H), 9.00 (d, 1H). MS (DCl/NH$_3$) m/e 186/188 (M+H)$^+$, 203/205 (M+H+NH$_3$)$^+$.

EXAMPLE 166B

Ethyl 2-butylaminopyridine-5-carboxylate

To the compound resulting from Example 166A (3.00 g, 16 mmol) dissolved in 12 mL of ethanol was added 6 mL (60 mmol) of n-butylamine. The reaction was heated at 95° C. for 4 hours. The volatiles were removed under reduced pressure and the residue partitioned between saturated sodium bicarbonate solution and ethyl acetate. The organic phase was washed with brine, dried over sodium sulfate and concentrated to afford 3.5 g. Flash chromatography on silica gel eluting with 30% ethyl acetate in hexane afforded 2.5 g of the title compound as a white solid. $^1$H NMR (CDCl$_3$, 300 MHz) δ 0.95 (t, 3H), 1.35 (t, 3H), 1.45 (m, 2H), 1.65 (m, 2H), 3.30 (m, 2H), 4.30 (q, 2H), 5.00 (bs, 1H), 6.35 (d, 1H), 8.00 (dd, 1H), 8.75 (d, 1H). MS (DCl/NH$_3$) m/e 223 (M+H)$^+$.

EXAMPLE 166C

Ethyl 2-{N-butyl-N-[(2'-[N-triphenylmethyl-1H-tetrazol-5-yl]biphenyl-4-yl)methyl]amino}pyridine-5-carboxylate To the compound resulting from Example 166B (813 mg, 3.7 mmol) dissolved in ~3 mL freshly distilled tetrahydrofuran and cooled to 0° C. was added 3.7 mL of 1.0M lithium hexamethyldisiliazide in tetrahydrofuran. The reaction was stirred at 0° C. for 10 minutes and then 2.46 g 83% pure N-triphenylmethyl-5-[2-(4'-bromomethyl-biphenyl)]tetrazole, prepared as described by P. E. Aldrich, et al. in European Patent Application Number 291,969, in 5 mL of tetrahydrofuran was slowly added. The reaction was stirred at 0° C. for 30 minutes and then allowed to warm to ambient temperature and stirred overnight. The reaction mixture was poured into ~50 mL of saturated ammonium chloride solution and extracted with ethyl acetate (~120 mL). The organic solution was washed with brine, dried over sodium sulfate and concentrated in vacuo to afford 3.4 g. Purification by flash chromatography on silica gel eluting with 15% ethyl acetate in hexane afforded 1.7 g (67%) of the title compound as an amorphous solid. $^1$H NMR (CDCl$_3$, 300 MHz) δ 0.90 (t, 3H), 1.30 (m, 2H), 1.35 (t, 3H), 1.60 (m, 2H), 3.40 (t, 2H), 4.30 (q, 2H), 4.70 (s, 2H), 6.35 (d, 1H), 6.90 (m, 8H), 7.10 (m, 2H), 7.20–7.50 (m, 12H), 7.90 (m, 2H), 8.80 (d, 1H), MS (DCl/NH$_3$) m/e 699 (M+H)$^+$.

EXAMPLE 166D

2-{N-Butyl-N-[(2'-[1H-tetrazol-5-yl]biphenyl-4yl)methyl]amino}pyridine-5-carboxylic acid To the compound resulting from Example 166C (910 mg, 1.3 mmol) dissolved in 2 mL of tetrahydrofuran was added 2 mL of ethanol followed by 251 mg (1.3 mmol) of p-toluenesulfonic acid. The reaction was stirred for 5 hours at ambient temperature and then 3 mL of 4N sodium hydroxide was added. The reaction was then stirred overnight at ambient temperature and acidified with concentrated hydrochloric acid to pH ~0 to give a precipitate which was collected by filtration. Flash chromatography on silica gel eluting with 93.5:7.5:0.25 chloroform/ethanol/acetic acid afforded 370 mg (67%) of the title compound as a white solid. $^1$H NMR (CD$_3$OD, 300 MHz) δ 0.95 (t, 3H), 1.40 (m, 2H), 1.60 (m, 2H), 3.55 (t, 2H), 4.80 (s, 2H), 6.60 (d, 1H), 7.10 (m, 2H), 7.20 (m, 2H), 7.55 (m, 2H), 7.65 (m, 2H), 8.00 (dd, 1H), 8.70 (d, 1H). MS (DCl/NH$_3$) m/e 429 (M+H)$^+$. Anal calcd for C$_{24}$H$_{24}$N$_6$O$_2$: C, 67.27; H, 5.65; N, 19.61. Found: C, 67.15; H, 5.85; N, 19.15.

EXAMPLE 167

2-{N-Butyl-N-[(2'-[1H-tetrazol-5-yl]biphenyl-4-yl)methyl]amino}pyrimidine-5-carboxylic acid

EXAMPLE 167A

Ethyl 2-ethylthiopyrimidine-5-carboxylate

Ethyl 3,3-diethoxypropionate (25 g, 0.13 mol) and 12.7 mL (0.16 mol) of ethyl formate were added dropwise to 6.20 g (0.15 mol) of 60% by weight sodium hydride (in mineral oil) in 130 mL of ether, which had been passed over alumina prior to use. The reaction was stirred overnight at ambient temperature and then concentrated in vacuo. Water (130 mL) at 10° C. was added followed by 28 g (0.15 mol) 2-ethylthiopseudourea hydrobromide. The mixture was stirred at 5°–10° C. for 15 minutes and then placed in the refrigerator overnight. Filtration and washing with cold water afforded 18.5 g of a yellow solid which was dissolved in 270 mL of 80° C. ethanol and allowed to cool to ambient temperature and let stand for 3 days. The resultant crystals were filtered and dried to afford 8.5 g of the intermediate aldehyde. m.p. 143°–144° C.

The solid was suspended in 23 mL of acetic anhydride and heated at 105° C. for 4 hours and then the solution was concentrated under reduced pressure. Water (~60 mL) at 5° C. was added to afford a solid which was filtered, dried and recrystallized from hot ethanol/water to afford the title compound (5.1 g). m.p. 45°–46° C. $^1$H NMR (CDCl$_3$, 300 MHz) δ 1.40 (2t, 6H), 3.20 (q, 2H), 4.40 (q, 2H), 9.05 (s, 2H). MS (DCl/NH$_3$) m/e 213 (M+H)$^+$.

EXAMPLE 167B

Ethyl 2-butylaminopyrimidine-5-carboxylate

The compound resulting from Example 167A (974 mg, 4.6 mmol) was dissolved in 4 mL of ethanol and 2 mL of n-butylamine (20 mmol) and heated to 105°–120° C. in a sealed tube for 3 hours. The solution was cooled to ambient temperature and concentrated in vacuo; and the residue obtained was partitioned between saturated sodium bicarbonate solution and ethyl acetate. The organic phase was washed with brine, dried over sodium sulfate and concentrated in vacuo to afford 986 mg of crude material. Purification by flash chromatography on silica gel eluting with 20% ethyl acetate in hexane afforded 850 mg of the title compound as a white solid. $^1$H NMR (CDCl$_3$, 300 MHz) δ 0.95 (t, 3H), 1.35 (t, 3H), 1.40 (m, 2H), 1.60 (m, 2H), 3.50 (q, 2H), 4.35 (q, 2H), 5.70 (bs, 1H), 8.80–8.90 (2 bs, 2H). MS (DCl/NH$_3$) m/e 224 (M+H)$^+$.

EXAMPLE 167C

Ethyl 2-{N-butyl-N-[(2'-[N-triphenylmethyl-1H-tetrazol-5-yl]biphenyl-4-yl)methyl]amino}pyrimidine-5-carboxylate To the compound resulting from Example 167B (573 mg, 2.57 mmol) dissolved in ~3 mL of tetrahydrofuran and 0.62 mL (5.14 mmol) 1,3-dimethyl-3,4,5,6-tetrahydro-2(1H)-pyrimidinone (DMPU) and cooled to 5° C. under nitrogen was added 2.57 mL of a 1.0M solution of lithium hexamethyldisilazide in tetrahydrofuran. After stirring at 5° C. for ~15 minutes, 1.72 g of 83% pure (1.43 g, 2.57 mmol) N-triphenylmethyl-5-[2-(4'-bromomethyl-biphenyl)]tetrazole, prepared as described by P. E. Aldrich, et al. in European Patent Application Number 291,969, in 5 mL of tetrahydrofuran was added. The solution was allowed to gradually warm to ambient temperature and stirred overnight under nitrogen. The reaction was worked up by the procedure described in Example 166C and purified by flash chromatography on silica gel eluting with 12.5% ethyl acetate in hexane to afford 1.2 g (67%) of the title compound as an amorphous solid. $^1$H NMR (CDCl$_3$, 300 MHz) δ 0.90 (t, 3H), 1.30 (m, 2H), 1.40 (t, 3H), 1.60 (m, 2H), 3.50 (t, 2HO, 4.35 (q, 2H), 4.85 (s, 2H), 6.90 (m, 6H), 7.00 (d, 2H), 7.10 (d, 2H), 7.20–7.50 (m, 12HO), 7.95 (dd, 1H), 8.80–8.90 (2 bs, 2H). MS (FAB) m/e 700 (M+H)$^+$.

EXAMPLE 167D

2-{N-Butyl-N-[(2'-[1H-tetrazol-5-yl]biphenyl-4-yl)methyl]amino}pyrimidine-5-carboxylic acid To the compound resulting from Example 167C (1.1 g, 1.57 mmol) dissolved in 2 mL of tetrahydrofuran and 2.5 mL of ethanol was added ~300 mg of p-toluenesulfonic acid monohydrate. The reaction was stirred at ambient temperature for 5 hours, concentrated to ~½ the original volume and stirred for an additional 2 hours. The solvents were removed under reduced pressure and the residue dissolved in 29 mL methanol. 4N Sodium hydroxide solution (3.4 mL) was added and the reaction stirred at ambient temperature overnight. The reaction mixture was concentrated under reduced pressure and the residue obtained was partitioned between 15 mL of 1N hydrochloric acid and 40 mL of ethyl acetate. The organic phase was washed with brine, dried over sodium sulfate and concentrated under reduced pressure. The residue obtained was flash chromatographed on silica gel eluting with 92.5:7.5:0.25 chloroform/ethanol/acetic acid to give a white solid. The solid was dissolved in isopropanol, filtered through a cotton plug and concentrated to 5-6 mL. Hexane (~100 mL) was added and the solution refrigerated overnight and then placed in a freezer to afford the title compound (550 mg, 81%). $^1$H NMR (CD$_3$OD, 300 MHz) δ 0.90 (t, 3H), 1.35 (m, 2H), 1.60 (m, 2H), 3.65 (t, 2H), 4.90 (s, 2H), 7.10 (m, 2H), 7.20 (m, 2H), 7.55 (m, 2H), 7.65 (m, 2H), 8.80 (bs, 2H). MS (DCl/NH$_3$) m/e 430 (M+H)$^+$.

EXAMPLE 168

6-{N-Butyl-N-[(2'-[1H-tetrazol-5-yl]biphenyl-4-yl)methyl]amino}-3-chloropyridazine-5-carboxylic acid

EXAMPLE 168A 2,6-Dichloropyridazine-4-carboxylic acid 2,6-Dihydroxy-4-methylpyridazine, prepared by the method of Mizzoni and Spoerri, J. Amer. Chem. Soc. 76, 2201 (1954), was chlorinated by the method of Kuraishi, Chem. Pharm. Bull. 5, 587 (1957), to give 2,6-dichloro-4-methylpyridazine. The dichloro-compound (10.00 g, 60 mmol) was dissolved in 60 mL of concentrated sulfuric acid and treated with finely powdered potassium dichromate (21.2 g, 72 mmol) in small portions; a water bath was used intermittently to keep the temperature of the reaction between 35°-40° C. After stirring for 2 hours after the completion of the addition, the reaction mixture was poured onto ~500 g of crushed ice and extracted with ether (~1 L total volume). The combined organic extracts were washed with brine, dried over sodium sulfate and concentrated in vacuo. The solid obtained was recrystallized from ~55 mL boiling water to afford 8.1 g of the title compound. MS (FAB) m/e 193/195 (M+H)$^+$.

EXAMPLE 168B

Ethyl 2,6-dichloropyridazine-4-carboxylate

To the compound resulting from Example 168A (7.1 g, 37 mmol) dissolved in ~40 mL of tetrahydrofuran was added 5 mL of ethanol followed by 500 mg of dimethylaminopyridine and 1-(3-dimethylaminopropyl-3-ethylcarbodiimide hydrochloride (7.8 g, 40 mmol). The reaction was stirred at ambient temperature overnight and then concentrated in vacuo. The residue obtained was partitioned between ethyl acetate and water. The organic phase was washed with water, saturated sodium bicarbonate solution (2×) and brine, dried over sodium sulfate and concentrated in vacuo. The residue obtained was flash chromatographed on silica gel eluting with 3:1 hexane/ethyl acetate to afford 5.00 g (61%) of the title compound. MS (DCl/NH$_3$) m/e 221/223 (M+H)$^+$, 228/240 (M+H+NH$_3$)$^+$. $^1$H NMR (CDCl$_3$, 300 MHz) δ 1.45 (t, 3H), 4.50 (q, 2H), 7.85 (s, 1H).

EXAMPLE 168C

Ethyl 6-{N-butyl-N-[(2'[N-triphenylmethyl-1H-tetrazol-5-yl]biphenyl-4-yl)methyl]amino}-3-chloropyridazine-5-caboxylate The compound resulting from Example 168B (520 mg, 2.35 mmol) and 1.26 g (2.3 mmol) of N-triphenylmethyl-5-[2-(4'-butylaminomethyl-biphenyl)]tetrazole, the compound resulting from Example 19A, were dissolved in ~2.3 mL of tetrahydrofuran and treated with 0.42 mL (3.0 mmol) of anhydrous triethylamine. The reaction was refluxed overnight and the volatiles removed under reduced pressure. The residue obtained was partitioned between ethyl acetate and saturated sodium bicarbonate solution. The organic phase was washed with brine, dried over sodium sulfate and concentrated under reduced pressure. The residue obtained was purified by flash chromatography on silica gel eluting with 1:3 ethyl acetate/hexane to give 1.35 g (78%) of the title compound as an amorphous solid. $^1$H NMR (CDCl$_3$, 300 MHz) δ 0.85 (t, 3H), 1.20 (m, 2H), 1.30 (t, 3H), 1.55 (m, 2H), 3.30 (t, 2H), 4.30 (q, 2H), 4.60 (s, 2H), 6.90 (m, 6H), 7.00 (d, 2H), 7.05 (d, 2H), 7.20-7.50 (m, 13H), 7.90 (dd, 1H). MS (FAB) m/e 734/736 (M+H)$^+$.

EXAMPLE 168D

6-{N-Butyl-N-[(2'-[1H-tetrazol-5-yl]biphenyl-4-yl)methyl]amino}-3-chloropyridazine-5-carboxylic acid To the compound resulting from Example 168C (500 mg, 0.68 mmol) dissolved in 6 mL of tetrahydrofuran was added 0.70 mL of ethanol followed by 150 mg (0.79 mmol) p-toluenesulfonic acid monohydrate. An additional 1 mL of tetrahydrofuran was added and the solution stirred at ambient temperature for 2 hours. The solvents were removed under reduced pressure and the residue placed under high vacuum overnight. The residue was redissolved in ~1 mL tetrahydrofuran and ~1.5 mL of ethanol and treated with 80 mg of p-toluenesulfonic acid monohydrate. After warming at ~50° C. for 45 minutes, the solvents were removed under reduced pressure. The residue obtained was flash chromatographed on silica gel eluting with 97:3:0.5 chloroform/ethanol/acetic acid.

The deprotected compound was dissolved in methanol (10 mL) and treated with 3 mL of 4N sodium hydroxide solution. After stirring at ambient temperature for 3 hours, the volatiles were removed under reduced pressure. The solution was diluted with 10 mL of water and adjusted to pH ~1 with concentrated hydrochloric acid. The mixture was extracted with ethyl acetate and the combined organic extracts washed with brine, dried over sodium sulfate and concentrated in vacuo. The residue obtained was purified by flash chromatography on silica gel eluting with a mixture of water and acetic acid in ethyl acetate to afford 160 mg of solid. The solid was dissolved in isopropanol, filtered through cotton and precipitated with hexane to afford the title compound (143 mg) as a bright yellow powder. $^1$H NMR (CD$_3$OD, 300 MHz) δ 0.90 (t, 3H), 1.25 (m, 2H), 1.60 (m, 2H), 3.45 (t, 2H), 4.80 (s, 2H), 7.05 (m, 2H), 7.30 (m, 2H), 7.55 (m, 2H), 7.60 (s, 1H), 7.65 (m, 2H). MS (FAB) m/e 464/466 (M+H)$^+$. Anal calcd for $C_{23}H_{22}ClN_7O_2 \cdot 0.25 C_3H_8O$: C, 59.56; H, 5.05; N, 20.47. Found: C, 59.36; H, 4.72; N, 20.20.

EXAMPLE 169

3-{N-Butyl-N-[(2'-[1H-tetrazol-5-yl]biphenyl-4-yl)methyl]amino}pyridazine-4-carboxylic acid

EXAMPLE 169A

3-{N-Butyl-N-[(2'-[N-triphenylmethyl-1H-tetrazol-5-yl]biphenyl-4-yl)methyl]amino}pyridazine-4-carboxylic acid The compound resulting from Example 168C (610 mg, 0.83 mmol) was dissolved in 4:1 ethyl acetate/ethanol, treated with 140 mg of 10% palladium on carbon, and placed under a balloon of hydrogen gas. Triethylamine (175 μL, 1.26 mmol) was added and the compound was hydrogenolyzed at atmospheric pressure for 24 hours. The catalyst was removed by filtration through Celite and the filtrate concentrated in vacuo. The residue obtained was partitioned between saturated sodium bicarbonate solution and ethyl acetate and the organic solution was washed with brine, dried over sodium sulfate and concentrated in vacuo. The residue obtained was purified by flash chromatography on silica gel eluting with ethyl acetate in hexane to afford 260 mg of the desired compound. $^1$H NMR (CDCl$_3$, 300 MHz) δ 0.85 (t, 3H), 1.20 (m, 2H), 1.30 (t, 3H), 1.55 (m, 2H), 3.35 (t, 2H), 4.30 (q, 2H), 4.70 (s, 2H), 6.90 (m, 6H), 7.05 (m, 4H), 7.15–7.50 (m, 13H), 7.90 (dd, 1H), 8.70 (d, 1H). MS (FAB) m/e 700 (M+H)$^+$.

EXAMPLE 169B

3-{N-Butyl-N-[(2'-[1H-tetrazol-5-yl]biphenyl-4-yl)methyl]amino}pyridazine-4-carboxylic acid To the compound resulting from Example 169A (235 mg, 0.34 mmol) dissolved in 1 mL of tetrahydrofuran was added 1 mL of ethanol followed by 104 mg (0.55 mmol) of p-toluenesulfonic acid monohydrate. The reaction mixture was warmed to 45°–50° C. for 75 minutes and then concentrated in vacuo. The residue obtained was dissolved in 7–10 mL of methanol and treated with 1 mL of 4N sodium hydroxide solution. After stirring at ambient temperature for 4 hours, the solution was concentrated under reduced pressure. The residue obtained was diluted with water, acidified to pH ~1 with concentrated hydrochloric acid and extracted with ethyl acetate. The aqueous phase was adjusted to pH ~4 with sodium bicarbonate and again extracted with ethyl acetate. The combined organic extracts were washed with brine, dried over sodium sulfate and concentrated under reduced pressure to afford 230 mg of a yellow solid. The solid was purified by flash chromatography on silica gel eluting with 13:1:1 ethyl acetate/water/acetic acid to give 140 mg of an amorphous solid. This solid was dissolved in isopropanol, filtered through cotton and precipitated with hexane to afford the title compound (107 mg, 74%) as a pale yellow solid. $^1$H NMR (CD$_3$OD, 300 MHz) δ 0.90 (t, 3H), 1.30 (m, 2H), 1.65 (m, 2H), 3.50 (t, 3H), 4.85 (s, 2H), 7.05 (m, 2H), 7.30 (m, 2H), 7.55 (m, 2H), 7.65 (m, 3H), 8.65 (d, 1H). MS (FAB) m/e 430 (M+H)$^+$.

EXAMPLE 170

3-{N-Butyl-N-[(2'-[1H-tetrazol-5-yl]biphenyl-4-yl)methyl]amino}pyridazine-6-carboxylic acid

EXAMPLE 170A

6-Methyl-4,5-dihydropyridazine-3-one

To ethyl levulinate (39 mL, 0.278 mol) and 23.5 mL (0.417 mol) of a 55% solution of hydrazine hydrate was added 20 mL of ethanol. The exothermic mixture was heated at reflux for 1 hour, cooled to ambient temperature and allowed to stand for 2 days. The reaction was concentrated in vacuo to afford an oil which solidified under vacuum. The solid was dissolved in hot water (100 mL) and refrigerated for 20 hours. White needles were filtered off and dried to afford 16 g of the title compound. $^1$H NMR (CDCl$_3$, 300 MHz) δ 2.05 (s, 3H), 2.50 (m, 4H), 8.45 (bs, 1H). MS (DCl/NH$_3$) m/e 113 (M+H)$^+$.

EXAMPLE 170B

3-Hydroxy-6-methylpyridazine

The compound resulting from Example 170A (19 g, 0.17 mol) was ground to a powder and added to ~550 mL of anhydrous toluene, which had been stored over 4 Å molecular sieves, and warmed to ~45° C. To this solution was added a solution of 42 g (0.187 mol) of 2,3-dichloro-5,6-dicyano-1,4-benzoquinone (DDQ) in ~700 mL of anhydrous toluene. The reaction was warmed at 95° C. under nitrogen overnight and at reflux for 4 hours. An additional 21 g (0.09 mol) of DDQ was added and the reaction refluxed overnight. The mixture was cooled to ambient temperature and the insoluble solids removed by filtration. From the filtrate was recovered 25 g of solid which was purified by flash chromatography on silica gel to afford 900 mg of the title compound. $^1$H NMR (CDCl$_3$, 300 MHz) δ 2.35 (s, 3H), 6.90 (d, 1H), 7.15 (d, 1H), 11.05 (bs, 1H). MS (DCl/NH$_3$) m/e 111 (M+H)$^+$, 128 (M+H+NH$_3$)$^+$.

EXAMPLE 170C

Ethyl 3-chloropyridazine-6-carboxylate

The compound resulting from Example 170B was chlorinated by the procedure described by Overend and Wiggins, J. Chem. Soc. 239 (1947) to give 4-chloro-6-methylpyridazine. $^1$H NMR (CDCl$_3$, 300 MHz) δ 2.70 (s, 3H), 7.35 (d, 1H), 7.45 (d, 1H). MS (DCl/NH$_3$) m/e 129/131 (M+H)$^+$, 146/148 (M+H+NH$_3$)$^+$. The chloro-compound was oxidized by the procedure of Horner et al., J.Chem. Soc. 2195 (1948) to give 4-chloropyridazine-6-carboxylic acid. $^1$H NMR (CD$_3$OD, 300 MHz) δ 7.95 (d, 1H), 8.30 (d, 1H). MS (FAB) m/e 159/161 (M+H)$^+$. The carboxylic acid (243 mg, 1.53 mmol) was dissolved in ~15 mL of ethanol and treated with 24 mg (0.2 mmol) of dimethylaminopyridine (DMAP) followed by 324 mg (1.69 mmol) 1-(3-dimethylaminopropyl-3-ethylcarbodiimide hydrochloride (EDCl). The reaction was stirred at ambient temperature for 4 hours and then worked up by the procedure described in Example 166A. The crude product was purified by flash chromatography on silica gel to give 150 mg (52%) of the title compound as a white crystalline solid. $^1$H NMR (CDCl$_3$, 300 MHz) δ 1.45 (t, 3H), 4.55 (q, 2H), 7.65 (d, 1H), 8.15 (d, 1H). MS (DCl/NH$_3$) m/e 187/189 (M+H)$^+$, 204/206 (M+H+NH$_3$)$^+$.

EXAMPLE 170D

Ethyl 3-{N-butyl-N-[(2'-[N-triphenylmethyl-1H-tetrazol-5-yl]biphenyl-4-yl)methyl]amino}pyridazine-6-carboxylate The compound resulting from Example 170C (127 mg, 0.68 mmol) and 390 mg (0.71 mmol) of N-triphenylmethyl-5-[2-(4'-butylaminomethyl-biphenyl)]tetrazole, prepared by the procedure described in Example 19A, were slurried in 0.7 mL of Aldrich Gold Label tetrahydrofuran and 123 μL (0.88 mmol) triethylamine and heated to reflux for 20 hours. The tetrahydrofuran evaporated leaving a solid which was partitioned between ethyl acetate and saturated sodium bicarbonate solution. The organic phase was concentrated in vacuo and the solid suspended in 0.7 mL of toluene. Diisopropylethylamine (90–100 μL) was added and the reaction heated at 110° C. overnight. The reaction mixture was partitioned between ethyl acetate and saturated sodium bicarbonate solution. The organic phase was washed with brine, dried over sodium sulfate and concentrated under reduced pressure to give 453 mg of a brown residue. Purification by flash chromatography on silica gel eluting with 40% ethyl acetate in hexane afforded 180 mg of the title compound as a solid. $^1$H NMR (CDCl$_3$, 300 MHz) δ 0.90 (t, 3H), 1.35 (m, 2H), 1.45 (q, 3H), 1.60 (m, 2H), 3.60 (t, 2H), 4.45 (q, 2H), 4.70 (s, 2H), 6.50 (d, 1H), 6.90 (m, 6H), 7.00 (d, 2H), 7.10 (d, 2H), 7.20–7.50 (m, 12H), 7.70 (d, 1H), 7.95 (dd, 1H). MS (FAB) m/e 700 (M+H)$^+$.

EXAMPLE 170E

3-{N-Butyl-N-[(2'-[1H-tetrazol-5-yl]biphenyl-4-yl)methyl]amino}pyridazine-6-carboxylic acid To the compound resulting from Example 170D (125 mg, 0.18 mmol) dissolved in 0.7 mL of tetrahydrofuran and 0.7 mL of absolute ethanol was added 57 mg (0.30 mmol) of p-toluenesulfonic acid monohydrate. The reaction was stirred at 45°–50° C. for 75 minutes. The volatiles were removed under reduced pressure and the residue was diluted with 5 mL of methanol. A solution of 4N sodium hydroxide (0.5 mL) was added and the reaction stirred at ambient temperature for 5 hours. The methanol was removed under reduced pressure and the residue partitioned between ethyl acetate and 1N hydrochloric acid. The organic phase was washed with brine, dried over sodium sulfate and concentrated under reduced pressure. The residue obtained was purified by flash chromatography on silica gel eluting with a mixture of ethyl acetate, water and acetic acid to afford 67 mg of a white powder. This solid was precipitated first from methylene chloride/hexane and then from methanol/ether to give a white solid (55 mg), which upon preparative HPLC eluting with trifluoroacetic acid in acetonitrile afforded 23 mg of the title compound. $^1$H NMR (CD$_3$OD, 300 MHz) δ 1.00 (t, 3H), 1.40 (m, 2H), 1.65 (m, 2H), 3.70 (t, 2H), 4.95 (s, 2H), 7.10 (d, 2H), 7.25 (m, 3H), 7.55 (m, 2H), 7.70 (m, 2H), 8.00 (d, 1H). MS (FAB) m/e 430 (M+H)$^+$.

EXAMPLE 171

3-Chloro-6-{N-propyl-N-[(2'-[1H-tetrazol-5-yl]biphenyl-4-yl)methyl]amino}pyridazine-5-carboxylic acid

EXAMPLE 171A

Ethyl 3-chloro-6-{N-propyl-N-[(2'-[N-triphenylmethyl-1H-tetrazol-5-yl]biphenyl-4-yl)methyl]amino}pyridazine-5-carboxylate To the compound resulting from Example 168B (1.86 g, 8.5 mmol) and N-triphenylmethyl-5-[2-(4'-propylaminomethyl-biphenyl)]tetrazole, the compound resulting from Example 96A, (5.1 g, 9.5 mmol) dissolved in 9 mL of Aldrich gold label tetrahydrofuran was added triethylamine (1.65 mL, 12 mmol) and the solution was refluxed for 24 hours. The reaction mixture was concentrated under reduced pressure and the residue obtained partitioned between ethyl acetate and saturated sodium bicarbonate solution. The organic phase was washed with brine, dried over sodium sulfate and concentrated under reduced pressure. The residue obtained was purified by flash chromatography on silica gel eluting with 3:1 hexane/ethyl acetate to give the title compound as an amorphous solid (4.1 g, 67%). $^1$H NMR (CDCl$_3$, 300 MHz) δ 0.80 (t, 3H), 1.30 (t, 3H), 1.60 (m, 2H), 3.30 (t, 2H), 4.35 (q, 2H), 4.65 (s, 2H), 6.90 (m, 6H), 7.00 (d, 2H), 7.05 (d, 2H), 7.20–7.50 (m, 13H), 7.90 (dd, 1H). MS (FAB) m/e 720 (M+H)$^+$.

EXAMPLE 171B

3-Chloro-6-{N-propyl-N-[(2'-[1H-tetrazol-5-yl]biphenyl-4-yl)methyl]amino}pyridazine-5-carboxylic acid To the compound resulting from Example 171A (800 mg, 1.1 mmol) dissolved in 3 mL tetrahydrofuran was added 2 mL of ethanol followed by 265 mg (1.4 mmol) of p-toluenesulfonic acid monohydrate. The reaction was warmed at 40°–45° C. for 2.5 hours and then the volatiles were removed under reduced pressure. The residue obtained was diluted with 20 mL of methanol and 3 mL of 4N sodium hydroxide solution was added. The solution was stirred at ambient temperature for 2 hours and then concentrated in vacuo. The residue obtained was partitioned between ether and water. The aqueous phase was washed with ether (2×), acidified to pH 3 with 1M phosphoric acid and extracted with ethyl acetate (4×). The combined organic extracts were washed with brine, dried over sodium sulfate and concentrated in vacuo to afford 495 mg of a yellow solid. The solid was dissolved in isopropanol, filtered through cotton and precipitated with hexane to afford the title compound (360 mg) as a yellow solid. $^1$H NMR (CD$_3$OD, 300 MHz) δ 0.85 (t, 3H), 1.65 (m, 2H), 3.40 (t, 2H), 4.80 (s, 2H), 7.05 (m, 2H), 7.25 (m, 1H), 7.55 (m, 2H), 7.65 (m, 3H), MS (FAB) m/e 450/452 (M+H)$^+$.

EXAMPLE 172

3-{N-Propyl-N-[(2'-[1H-tetrazol-5-yl]biphenyl-4-yl)methyl]amino}pyridazine-4-carboxylic acid

EXAMPLE 172A

Ethyl 3-{N-propyl-N-[(2'-[N-triphenylmethyl-1H-tetrazol-5-yl]biphenyl-4-yl)methyl]amino}pyridazine-4-carboxylate The compound resulting from Example 171A (1.71 g, 2.4 mmol) was dissolved in ~120 mL of 3:1 ethyl acetate/ethanol and hydrogenolyzed under a hydrogen balloon over a 10% palladium on carbon catalyst (470 mg) overnight. The catalyst was removed by filtration through Celite and the filtrate concentrated in vacuo. The residue obtained was purified by flash chromatography on silica gel eluting with 4:6 ethyl acetate/hexane to give 790 mg of the title compound as a solid. $^1$H NMR (CDCl$_3$, 300 MHz) δ 0.80 (t, 3H), 1.30 (t, 3H), 1.60 (m, 2H), 3.30 (t, 2H), 4.30 (q, 2H), 4.70 (s, 2H), 6.90 (m, 6H), 7.05 (m, 4H), 7.20–7.50 (m, 13H), 7.90 (dd, 1H), 8.70 (d, 1H). MS (FAB) m/e 686 (M+H)$^+$.

EXAMPLE 172B

3-{N-Propyl-N-[(2'-[1H-tetrazol-5-yl]biphenyl-4-yl)methyl]amino}pyridazine-4-carboxylic acid The compound resulting from Example 172A (780 mg, 1.1 mmol) was deprotected with p-toluenesulfonic acid monohydrate and hydrolyzed with sodium hydroxide by the procedures described in Example 171B. The crude material was purified by flash chromatography on silica gel eluting with 13:1:1 ethyl acetate/water/acetic acid to give a residue which was crystallized from isopropanol/hexane to give 150 mg of the title compound. $^1$H NMR (CD$_3$OD, 300 MHz) δ 0.85 (t, 3H), 1.65 (m, 2H), 3.50 (t, 2H), 4.80 (s, 2H), 7.05 (m, 2H), 7.30 (m, 2H), 7.55 (m, 2H), 7.65 (m, 3H), 8.65 (d, 1H). MS (DCl/NH₃) m/e 416 (M+H)⁺.

EXAMPLE 173

2-{N-Butyl-N-[(2'-[1H-tetrazol-5-yl]biphenyl-4-yl)methyl]amino}-4-[2-(N-methylpyrrolidin-2-yl)ethyl]amino-6-methylpyrimidine

EXAMPLE 173A

2-Butylamino-4-chloro-6-methylpyrimidine

To 2-amino-4-chloro-6-methylpyrimidine (10.0 g, 69.7 mmol) dissolved in 70 mL of anhydrous tetrahydrofuran was added 21 mL (2.5 equilvalents) of 1,3-dimethyl-3,4,5,6-tetrahydro-2(1H)-pyrimidinone (DMPU) at ambient temperature. The solution was cooled to −10° C. and 69.6 mL (1.0 equivalent) of 1M lithium hexamethyldisilazide in tetrahydrofuran was added. The solution was stirred at 0° C. for 30 minutes and then 7.92 mL (1.0 equivalent) of 1-iodobutane was added at 0° C., and the reaction was allowed to warm to ambient temperature. The reaction mixture was poured into ethyl acetate and washed with water (2×); the aqueous washes were back-extracted with ethyl acetate (2×). The combined organic extracts were dried over potassium carbonate and concentrated in vacuo. The residue was purified by flash chromatography on silica gel eluting with 13% ethyl acetate in hexane to afford 4.6 g (33%) of the title compound. ¹H NMR (CDCl₃, 300 MHz) δ 0.93 (t, 3H), 1.40 (m, 2H), 1.57 (m, 2H), 2.30 (s, 3H), 3.41 (m, 2H), 5.12 (bs, 1H), 6.43 (s, 1H). MS (DCl/NH₃) m/e 200 (M+H)⁺.

EXAMPLE 173B

2-{N-Butyl-N-[(2'-[N-triphenylmethyl-1H-tetrazol-5-yl]biphenyl-4-yl)methyl]amino}-4-chloro-6-methylpyrimidine To the compound resulting from Example 173A (1.5 g, 7.538 mmol) dissolved in 5 mL of tetrahydrofuran under nitrogen at 0° C. was added 8.29 mL (1.1 equivalents) of a 1M solution of lithium hexamethyldisilazide in tetrahydrofuran. The solution was stirred at 0° C. for 30 minutes and then a solution of 4.92 g (1.0 equivalent) of 83% pure N-triphenylmethyl-5-[2-(4'-bromomethylbiphenyl)]tetrazole, prepared as described by P. E. Aldrich, et al. in European Patent Application Number 291969, in 8 mL of tetrahydrofuran was added at 0° C. The solution was allowed to warm to ambient temperature and stirred for 2.5 days at ambient temperature. The mixture was poured into ethyl acetate and washed with water (2×). The aqueous washes were back-extracted with ethyl acetate. The combined organic extracts were dried over magnesium sulfate and concentrated under reduced pressure. The residue obtained was flash chromatographed on silica gel eluting with 7% ethyl acetate in hexane to give partially purified material. This material was re-chromatographed eluting with 4-6% ethyl acetate in hexane to give the title compound. ¹H NMR (CDCl₃, 300 MHz) δ 0.93 (t, 3H), 1.25 (m, 2H), 1.49 (m, 2H), 2.19 (s, 3H), 3.42 (m, 2H), 4.78 (s, 2H), 6.49 (s, 1H), 6.90 (d, J=8 Hz, 1H), 6.99 (d, J=8 Hz, 2H), 7.05 (d, J=8 Hz, 2H), 7.25 (m, 15H), 7.38 (td, J=8 Hz, 2 Hz, 1H), 7.47 (td, J=8 Hz, 2 Hz, 1H), 7.91 (dd, J=8 Hz, 1H). MS (DCl/NH₃) m/e 676 (M+H)⁺.

EXAMPLE 173C

2-{N-Butyl-N-[(2'-[N-triphenylmethyl-1H-tetrazol-5-yl]biphenyl-4-yl)methyl]amino}-4-[2(N-methylpyrrolidin-2-yl)ethyl]amino-6-methylpyrimidine The compound resulting from Example 173B (185.6 mg, 0.2812 mmol) was combined with ~2 mL of 2-(2-aminoethyl)-1-methylpyrrolidine and heated at ~80° C. in a sealed tube for 2.5 days. The volatiles were removed under reduced pressure and the residue obtained was flash chromatographed on silica gel eluting with 10% methanol in chloroform; the partially purified material was re-chromatographed eluting with 5% methanol in chloroform to afford 100 mg of the title compound. ¹H NMR (CDCl₃, 300 MHz) δ 0.88 (t, 3H), 1.25 (m, 2H), 1.60 (m, 8H), 2.17 (s, 3H), 2.31 (s, 3H), 3.11 (m, 2H), 3.32 (m, 2H), 3.43 (m, 3H), 4.81 (d, 2H), 5.55 (s, 1H), 6.90 (d, J=8 Hz, 2H), 6.94 (d, J=8 Hz, 2H), 7.28 (m, 15H), 7.38 (d, J=8 Hz, 1H), 7.44 (td, J=8 Hz, 1 Hz, 1H), 7.49 (td, J=8 Hz, 1 Hz, 1H), 7.88 (dd, J=8 Hz, 1 Hz, 1H). MS (DCl/NH₃) m/e 768 (M+H)⁺.

EXAMPLE 173D

2-{N-Butyl-N-[(2'-[1H-tetrazol-5-yl]biphenyl-4-yl)methyl]amino}-4-[2-(N-methylpyrrolidin-2-yl)ethyl]amino-6-methylpyrimidine To the compound resulting from Example 173C (100 mg, 0.1304 mmol) dissolved in 0.2 mL of tetrahydrofuran and 0.2 mL of ethanol was added 74.2 mg (3 equivalents) of p-toluenesulfonic acid monohydrate. The solution was stirred at ambient temperature for 4 days. The solution was concentrated under reduced pressure and the residue obtained purified by preparative HPLC. The peak was collected and lyophilized to afford 64 mg of the title compound. ¹H NMR (DMSO-d₆, 300 MHz) δ 0.88 (t, 3H), 1.39 (m, 2H), 1.55 (m, 2H), 1.75 (m, 6H), 2.25 (s, 3H), 2.50 (s, 3H), 2.75 (m, 2H), 3.05 (m, 2H), 3.40 (m, 3H), 4.87 (bs, 2H), 5.95 (s, 1H), 7.10 (d, 2H), 7.21 (d, 2H), 7.63 (m, 4H), 8.80 (bs, 1H), 9.60 (bs, 1H). MS (DCl/NH₃) m/e 526 (M+H)⁺.

EXAMPLE 174

2-{N-Butyl-N-[(2'-[1H-tetrazol-5-yl]biphenyl-4-yl)methyl]amino}-4-[2-(pyridin-2-yl)ethyl]amino-6-methylpyrimidine

EXAMPLE 174A

2-{N-Butyl-N-[(2'-[N-triphenylmethyl-1H-tetrazol-5-yl]biphenyl-4-yl)methyl]amino}-4-[2-(pyridin-2-yl)ethyl]amino-6-methylpyrimidine The compound resulting from Example 173B (197.3 mg, 0.292 mmol) was mixed with 2 mL of 2-(2-aminoethyl)pyridine at 80°-85° C. in a sealed tube. After the reaction was allowed to heat overnight at 80° C., the mixture was cooled to ambient temperature and concentrated under reduced pressure. The residue obtained was flash chromatographed on silica gel eluting with 50% ethyl acetate in hexane to afford the title compound (145 mg, 65%). MS (DCl/NH₃) m/e 762 (M+H)⁺.

EXAMPLE 174B

2-{N-Butyl-N-[(2'-[1H-tetrazol-5-yl[biphenyl-4-yl)methyl]amino}-4-[2-(pyridin-2-yl)ethyl]amino-6-methylpyrimidine To the compound resulting from Example 174A (145 mg, 0.1905 mmol) dissolved in 0.25 mL of tetrahydrofuran and 0.2 mL of ethanol was added 109 mg (3 equivalents) of p-toluenesulfonic acid monohydrate. The reaction was stirred at ambient temperature for 4 hours and then concentrated in vacuo. The residue obtained was again taken up in tetrahydrofuran/ethanol, 109 mg (3 equivalents) of p-toluenesulfonic acid monohydrate was added and the reaction mixture was allowed to stir overnight at ambient temperature. The solvents were removed under reduced pressure, and the residue obtained was purified by preparative HPLC. The peak was collected and lyophilized to afford 81 mg of the title compound. $^1$H NMR (CDCl$_3$, 300 MHz) δ 0.95 (t, 3H), 1.35 (m, 2H), 1.65 (m, 2H), 2.22 (s, 3H), 3.43 (m, 2H), 3.98 (m, 2H), 4.84 (bs, 2H), 5.88 (s, 1H), 6.90 (m, 2H), 7.07 (d, J=8 Hz, 2H), 7.51 (td, J=8 Hz, 1 Hz, 1H), 7.59 (td, J=8 Hz, 1 Hz, 1H), 7.73 (m, 2H), 7.86 (dd, J=8 Hz, 1 Hz, 1H), 8.25 (m, 1H), 8.68 (m, 1H), 8.74 (m, 1H). MS (DCl/NH$_3$) m/e 520 (M+H)$^+$.

EXAMPLE 175

4-{N-Butyl-N-[(2'-[1H-tetrazol-5-yl]biphenyl-4-yl)methyl]amino}-6-methyl-2-methylthiopyrimidine

EXAMPLE 175A

4-{N-Butyl-N-[(2'-[N-triphenylmethyl-1H-tetrazol-5-yl]biphenyl-4-yl)methyl]amino}-6-methyl-2-methylthiopyrimidine 4-Hydroxy-6-methyl-2-methylthiopyrimidine (10.0 g, 64.13 mmol), prepared by the procedure described in Example 158A, was dissolved in ~45 mL (483 mmol, 7 equivalents) of phosphorus oxychloride under nitrogen and heated at reflux for 6.5 hours. The phosphorus oxychloride was distilled off and the remaining residue was dissolved in ether and poured onto ice. The aqueous phase was extracted several times with ether. The combined ether extracts were dried over magnesium sulfate and the 4-chloro-6-methyl-2-methylthiopyrimidine crystallized from the ether to afford 6.91 g (62%) as pale orange needles. $^1$H NMR (CDCl$_3$, 300 MHz) δ 2.45 (s, 3H), 2.58 (s, 3H), 6.77 (s, 1H). MS (DCl/NH$_3$) m/e 175 (M+H)$^+$. The chloro-compound was reacted with n-butylamine by the procedure described in Example 158C to give 4-butylamino-6-methyl-2-methylthiopyrimidine.

To 500 mg (2.37 mmol) of the above pyrimidine in 2 mL of anhydrous tetrahydrofuran at 0° C. under nitrogen was added 2.61 mL (1.1 equivalents) of a solution of 1M lithium hexamethyldisilazide in tetrahydrofuran dropwise. The solution was stirred at 0° C. for ~30 minutes and then a solution of 1.55 g (1.0 equivalents) of 83% pure N-triphenylmethyl-5-[2-(4'-bromomethylbiphenyl)]tetrazole, prepared as described by P. E. Aldrich, et al. in European Patent Application No. 291969, in tetrahydrofuran (~3 mL) was added. After 10 minutes at 0° C., the reaction was allowed to warm to ambient temperature and stirred for 2 days. The mixture was poured into ethyl acetate and washed 2× with water. The combined aqueous washings were back-extracted with ethyl acetate. The combined organic extracts were dried over magnesium sulfate and concentrated in vacuo. The residue obtained was purified by flash chromatography on silica gel eluting with 15% ethyl acetate in hexane. The partially purified product was rechromatographed eluting with 20% ethyl acetate in hexane to afford 963.6 mg of ~80% pure product. $^1$H NMR (CDCl$_3$, 300 MHz) δ 0.94 (t, 3H), 1.27 (m, 2H), 1.42 (m, 2H), 2.29 (s, 3H), 2.50 (s, 3H), 3.29 (m, 2H), 4.64 (bs, 2H), 5.74 (s, 1H), 6.93 (m, 4H), 7.10 (d, J=8 Hz, 1H), 7.25 (m, 15H), 7.48 (m, 2H), 7.92 (dd, J=8 Hz, 1 Hz, 1H). MS (DCl/NH$_3$) m/e 688 (M+H)$^+$.

EXAMPLE 175B

4-{N-Butyl-N-[(2'-[1H-tetrazol-5-yl]biphenyl-4-yl)methyl]amino}-6-methyl-2-methylthiopyrimidine To the compound resulting from Example 175A (963.6 mg, 1.403 mmol) dissolved in 1 mL of tetrahydrofuran and 1 mL of ethanol was added 800.4 mg (3 equivalents) of p-toluenesulfonic acid monohydrate. The reaction was stirred at ambient temperature for two days and then concentrated in vacuo. The residue obtained was purified by preparative HPLC and lyophilized. The partially purified material was washed with water and again purified by preparative HPLC to afford one major peak, the title compound. $^1$H NMR (CD$_3$OD, 300 MHz) δ 0.99 (t, 3H), 1.40 (m, 2H), 1.66 (m, 2H), 2.41 (s, 3H), 3.59 (m, 2H), 5.07 (bs, 2H), 6.65 (s, 1H), 7.13 (m, 2H), 7.21 (d, J=8 Hz, 2H), 7.56 (td, 2H), 7.68 (m, 2H). MS (DCl/NH$_3$) m/e 446 (M+H)$^+$.

EXAMPLE 176

2-{N-Butyl-N-[(2'-[1H-tetrazol-5-yl]biphenyl-4-yl)methyl]amino}-4-[2-(N,N-dimethylamino)ethyl]amino-6-methylpyrimidine

EXAMPLE 176A

2-{N-Butyl-N-[(2'-[N-triphenylmethyl-1H-tetrazol-5-yl]biphenyl-4-yl)methyl]amino}-4-[2-(N,N-dimethylamino)ethyl]amino-6-methylpyrimidine The compound resulting from Example 173B, 2-{N-butyl-N-[(2'-[N-triphenylmethyl-1H-tetrazol-5-yl]biphenyl-4-yl)methyl]amino}-4-chloro-6-methylpyrimidine, (205 mg, 0.3037 mmol) was combined with 2 mL of N,N-dimethylethylenediamine at 80° C. in a sealed tube overnight. The solvents were removed under reduced pressure and the residue obtained flash chromatographed on silica gel eluting with 5% methanol in chloroform to afford 101.4 mg (46%) of the title compound. MS (DCl/NH$_3$) m/e 728 (M+H)$^+$.

EXAMPLE 176B

2-{N-Butyl-N-[(2'-[1H-tetrazol-5-yl]biphenyl-4-yl)methyl]amino}-4-[2-(N,N-dimethylamino)ethyl]amino-6-methylpyrimidine To the compound resulting from Example 176A (101.4 mg, 0.1395 mmol) dissolved in 0.2 mL of tetrahydrofuran and 0.2 mL of ethanol was added 79.6 mg (3 equivalents) of p-toluenesulfonic acid monohydrate. After stirring 3 days at ambient temperature, the solvents were removed under reduced pressure and the residue subjected to preparative HPLC to afford 60 mg of the title compound. $^1$H NMR (CD$_3$OD, 300 MHz) δ 0.98 (t, 3H), 1.40 (m, 2H), 1.67 (m, 2H), 2.37 (s, 3H), 2.81 (s, 6H), 3.23 (m, 2H), 3.61 (m, 2H), 3.72 (m, 2H), 4.95 (s, 2H), 6.02 (s, 1H), 7.14 (d, J=8 Hz, 2H), 7.21 (d, J=8 Hz, 2H), 7.57 (td, 2H), 7.68 (m, 2H). MS (DCl/NH$_3$) m/e 486 (M+H)$^+$.

EXAMPLE 177

2-{N-Butyl-N-[(2'-[1H-tetrazol-5-yl]biphenyl-4-yl)methyl]amino}-4-(N,N-diethyl)amino-6-methylpyrimidine

EXAMPLE 177A

2-{N-Butyl-N-[(2'-[N-triphenylmethyl-1H-tetrazol-5-yl]biphenyl-4-yl)methyl]amino}-4-(N,N-diethyl)amino-6-methylpyrimidine The compound resulting from Example 173B (209 mg, 0.3096 mmol) was combined with 2 mL of diethylamine in a sealed tube at 80° C. for 2 days and at 100° C. for 3 days. The solvents were removed under reduced pressure and the residue obtained was flash chromatographed on silica gel eluting with 8% ethyl acetate in hexane to afford 131.6 mg (60%) of the title compound. MS (DCl/NH$_3$) m/e 713 (M+H)$^+$.

EXAMPLE 177B

2-{N-Butyl-N-[(2'-[1H-tetrazol-5-yl]biphenyl-4-yl)methyl]amino}-4-(N,N-diethyl)amino-6-methylpyrimidine To the compound resulting from Example 177A (131.6 mg, 0.1848 mmol) dissolved in 0.2 mL of tetrahydrofuran and 0.2 mL of ethanol was added 105.5 mg (3 equivalents) of p-toluenesulfonic acid monohydrate. After stirring for 3.5 days at ambient temperature, the solvents were removed under reduced pressure. The residue obtained was flash chromatographed on silica gel eluting with mixtures of acetic acid and ethanol in chloroform; the product was re-chromatographed by preparative HPLC to afford the title compound. $^1$H NMR (CD$_3$OD, 300 MHz) δ 0.97 (t, 3H), 1.10 (t, 3H), 1.23 (t, 3H), 1.38 (m, 2H), 1.64 (m, 2H), 2.36 (s, 3H), 3.58 (m, 6H), 4.90 (s, 2H), 6.25 (s, 1H), 7.13 (d, J=8 Hz, 2H), 7.21 (d, J=8 Hz, 2H), 7.55 (m, 2H), 7.66 (m, 2H). MS (DCl/NH$_3$) m/e 471 (M+H)$^+$.

EXAMPLE 178

2-{N-Butyl-N-[(2'-[1H-tetrazol-5-yl]biphenyl-4-yl)methyl]amino}-4-[3-N,N-dimethylamino)propyl]amino-6-methylpyrimidine

EXAMPLE 178A

2-{N-Butyl-N-[(2'-[N-triphenylmethyl-1H-tetrazol-5-yl]biphenyl-4-yl)methyl]amino}-4-[3-(N,N-dimethylamino)propyl]amino-6-methylpyrimidine The compound resulting from Example 173B (213.5 mg, 0.3163 mmol) was combined with 2 mL of 3-dimethylaminopropylamine in a sealed tube at 80° C. for 3.5 days. The solvents were removed under reduced pressure and the residue was flash chromatgraphed on silica gel eluting with 7% methanol in chloroform to afford 47 mg (20%) of the title compound. $^1$H NMR (CDCl$_3$, 300 MHz) δ 0.91 (t, 3H), 1.30 (m, 2H), 1.60 (m, 4H), 2.18 (s, 3H), 2.49 (bs, 6H), 3.38 (m, 2H), 3.56 (m, 4H), 4.81 (s, 2H), 5.66 (s, 1H), 7.00 (m, 4H), 7.27 (m, 15H), 7.45 (m, 4H). MS (DCl/NH$_3$) m/e 742 (M+H)$^+$.

EXAMPLE 178B

2-{N-Butyl-N-[(2'-[1H-tetrazol-5-yl]biphenyl-4-yl)methyl]amino}-4-[3-(N,N-dimethylamino)propyl]amino-6-methylpyrimidine To the compound resulting from Example 178A (47 mg, 0.06343 mmol) dissolved in 0.1 mL of tetrahydrofuran and 0.1 mL of ethanol was added 36.2 mg (3 equivalents) of p-toluenesulfonic acid monohydrate. The solution was stirred overnight at ambient temperature and concentrated under reduced pressure. The residue obtained was chromatographed on preparative HPLC to afford 23 mg of the title compound. $^1$H NMR (CD$_3$OD, 300 MHz) δ 0.97 (t, 3H), 1.40 (m, 2H), 1.65 (m, 2H), 1.90 (m, 2H), 2.33 (s, 3H), 2.82 (s, 6H), 3.07 (m, 2H), 3.43 (m, 2H), 3.60 (m, 2H), 4.93 (s, 2H), 5.96 (s, 1H), 7.13 (d, J=8 Hz, 2H), 7.21 (d, J=8 Hz, 2H), 7.58 (m, 2H), 7.66 (m, 2H). MS (DCl/NH$_3$) m/e 500 (M+H)$^+$. Anal Calcd for C$_{28}$H$_{37}$N$_9$.2CF$_3$CO$_2$H: C, 52.82; H, 5.40; N, 17.32. Found: C, 52.93; H, 5.64; N, 16.65.

EXAMPLE 179

2-{N-Propyl-N-[(2'-[1H-tetrazol-5-yl]biphenyl-4-yl)methyl]amino}-5-phenylpyridine-3-carboxylic acid

EXAMPLE 179A

Ethyl 2-hydroxy-5-phenylpyridine-3-carboxylate

Dimethylformamide (DMF) (8.1 g, 8.6 mL, 110 mmol) was added dropwise to 13.8 g (8.4 mL, 90 mmol) of phosphorus oxychloride, while the internal temperature was maintained at 25°-30° C. using an ice bath. After stirring for 5 minutes at ambient temperature, phenylacetic acid (4.1 g, 30 mmol) was added dropwise as a solution in 15 mL of DMF. The mixture was heated at 70° C. overnight. The resultant brown solution was poured onto 125 g of ice and neutralized by the careful addition of potassium carbonate. The solution was heated to 50° C., and 36 mL of 50% aqueous sodium hydroxide was added at a rate to maintain the internal temperature in the 50°-60° C. range. The reaction mixture was heated at 50° C. for 2 hours and then cooled to ambient temperature. Water was added, and the aqueous mixture was extracted twice with ethyl acetate. The combined organic extracts were dried over sodium sulfate, filtered through Celite and concentrated in vacuo. The crude product was combined with 3.4 g of ethyl cyanoacetate (3.2 mL, 30 mmol) and 0.3 mL piperidine in 7 mL of ethanol. The solution was stirred for 72 hours at ambient temperature. Diisopropylethylamine (1 mL) was added, and the mixture was heated at reflux for 24 hours. The solvents were removed in vacuo, and the residue was chromatographed on silica gel using 5% methanol/0.5% acetic acid in chloroform to isolate the desired product (blue spot under 254 nM UV light). Final purification by ether precipitation gave the product as a white solid. $^1$H NMR (CDCl$_3$, 300 MHz) δ 1.43 (t, J=7 Hz, 3H), 4.44 (q, J=7 Hz, 2H), 7.35–7.53 (m, 6H); 8.20 (bs, 1H), 8.50 (d, J=3 Hz, 2H). MS (DCl/NH$_3$) m/e 244 (M+H)$^+$.

EXAMPLE 179B

Ethyl 2-propylamino-5-phenylpyridine-3-carboxylate

The compound resulting from Example 179A (165 mg, 0.68 mmol) was suspended in 2 mL of phosphorus oxychloride and heated at 80° C. for 2.5 hours. The solvents were removed in vacuo; the residue was neutralized with saturated aqueous bicarbonate and extracted with ethyl acetate. The combined organic extracts were dried over sodium sulfate, filtered through Celite and concentrated in vacuo. The crude product was combined with 1 mL of ethanol and 1 mL of n-propylamine, then heated at 80° C. overnight. The solvents were removed in vacuo, and the residue was purified by flash chromatography on silica gel, using an elution gradient of 10% →25% ethyl acetate in hexanes, to give 52 mg (27%) of the desired product as well as 32 mg (16%) of the corresponding n-propyl amide. MS (DCI/NH$_3$) m/e 285 (M+H)$^+$.

EXAMPLE 179C

2-{N-Propyl-N-[(2'-[N-triphenylmethyl-1H-tetrazol-5-yl]biphenyl-4-yl)methyl]amino}-5-phenylpyridine-3-carboxylic acid The compound resulting from Example 179B (50 mg, 0.18 mmol was dissolved in a mixture of 0.18 mL of tetrahydrofuran (THF) and 0.18 mL of 1,3-dimethyl-3,4,5,6-tetrahydro-2(1H)-pyrimidinone (DMPU). The resultant solution was cooled to 0° C., and then 0.18 mL of a 1.0M solution of lithium hexamethyldisilazide in THF (1.0 equivalent) was added dropwise over 5 minutes. The solution was stirred at 0° C. for 30 minutes, and then a solution of N-triphenylmethyl-5-[2-(4'-bromomethyl-biphenyl)]tetrazole (0.225 mmol, 1.25 equivalents), prepared as described by P. E. Aldrich, et al. in European Patent Application Number 291969, in 2 mL of THF was added dropwise. The solution was allowed to warm to ambient temperature while stirring overnight. The reaction mixture was poured into 1N aqueous phosphoric acid and extracted with ethyl acetate. The combined organic extracts were washed with saturated aqueous bicarbonate and brine, dried over sodium sulfate and concentrated in vacuo. The residue was purified by flash chromatography on silica gel eluting with a gradient of 10%→20% ethyl acetate in hexanes to afford 50 mg (37%) of the title compound. $^1$H NMR (CDCl$_3$, 300 MHz) δ 0.77 (t, J=8 Hz,3H), 1.35 (t, J=7 Hz, 3H), 1.55 (sextet, J=8 Hz, 2H), 3.35 (bd t, 2H), 4.34 (q, J=7 Hz, 2H), 4.64 (s, 2H), 6.89 (m, 6H), 7.07 (s, 4H), 7.20–7.60 (m, 17H); 7.90 (dd, J=2 Hz,8 Hz, 1H), 8.15 (d, J=3 Hz, 1H), 8.50 (d, J=3 Hz,1H). MS (FAB) m/e 761 (M+H)$^+$.

EXAMPLE 179D

2-{N-Propyl-N-[(2'-[1H-tetrazol-5-yl]biphenyl-4-yl)methyl]amino}-5-phenylpyridine-3--carboxylic acid The compound resulting from Example 179C (48 mg, 0.06 mmol) was dissolved in a mixture of 0.54 mL of ethanol and 0.54 mL of tetrahydrofuran. p-Toluenesulfonic acid monohydrate (30 mg) was added, and the resultant solution was stirred until no starting material remained (~8 hrs). The solvents were removed in vacuo, and the residue was taken up in 0.34 mL of methanol. Aqueous 5N sodium hydroxide solution (6 mL) was added. The mixture was stirred overnight. The solvents were removed in vacuo; the residue was taken up in water and washed with ethyl acetate. The aqueous phase was acidified with 1N phosphoric acid and extracted twice with ethyl acetate. The combined organic extracts were washed with brine, dried over sodium sulfate and concentrated in vacuo. The residue obtained was triturated with ether to precipitate the title compound as a white solid (20 mg, 65%). $^1$H NMR (CDCl$_3$, 300 MHz) δ 0.99 (t, J=7 Hz, 3H), 1.25 (s, 1H), 1.60 (bd, 2H), 3.60 (bd, 2H), 4.45 (s, 2H), 6.94 (d, J=8 Hz, 2H), 7.01 (d, J=8 Hz, 2H), 7.40 (dd, J=2 Hz, 7 Hz, 1H), 7.45–7.60 (m, 4H), 7.80 (d, J=8 Hz, 2H), 7.96 (dd, J=2 Hz, 8 Hz, 1H), 8.71 (d, J=3 Hz, 2H), 8.92 (d, J=3 Hz, 2H). MS (FAB) m/e 491 (M+H)$^+$.

EXAMPLE 180

5-Fluoro-2-{N-propyl-N-[(2'-[1H-tetrazol-5-yl]biphenyl-4-yl)methyl]amino}pyridine-3-carboxylic acid

EXAMPLE 180A

Ethyl 2,6-dichloro-5-fluoropyridine-3-carboxylate 2,6-Dichloro-5-fluoropyridine-3-carboxylic acid (5.00 g, 23.81 mmol) was mixed with ~13 mL of thionyl chloride under nitrogen. The reaction was heated and the excess thionyl chloride was distilled off. The resulting liquid was diluted with ~5 mL methylene chloride, cooled to 0° C. and treated with 4.98 mL (1.5 equivalents) of triethylamine followed by 2.79 mL (2.0 equivalents) of ethanol dropwise. The reaction was allowed to warm to ambient temperature and stirred for 1 hour. A 1:1 mixture of sodium bicarbonate solution and ether (~80 mL) was added and the organic layer was washed with saturated sodium bicarbonate solution, 1N phosphoric acid and brine, dried over magnesium sulfate and concentrated in vacuo. The residue obtained was flash chromatographed on silica gel eluting with 5% ethyl acetate in hexane to give the title compound (5.32 g, 94%) as a yellow liquid. $^1$H NMR (CDCl$_3$, 300 MHz) δ 1.42 (t, 3H), 4.43 (q, 2H), 8.00 (d, 1H). MS (DCl/NH$_3$) m/e 239 (M+H)$^+$.

EXAMPLE 180B

Ethyl 2-chloro-5-fluoro-6-methylthiopyridine-3-carboxylate

To 589 mg (8.402 mmol) of sodium thiomethoxide dissolved in ~8 mL of a 1:1 mixture of water and tetrahydrofuran under nitrogen at ambient temperature was added 2.00 g (1.0 equivalent) of the compound resulting from Example 180A in tetrahydrofuran. The reaction was stirred at ambient temperature for ~3 hours and then diluted with ether. The ether solution was washed twice with 0.5N sodium hydroxide solution and brine, dried over magnesium sulfate and concentrated in vacuo to afford the title compound as a white solid. $^1$H NMR (CDCl$_3$, 300 MHz) δ 1.40 (t, 3H), 2.62 (s, 3H), 4.38 (q, 2H), 7.76 (d, 1H). MS (DCl/NH$_3$) m/e 250 (M+H)$^+$.

EXAMPLE 180C

Ethyl 2-chloro-5-fluoropyridine-3-carboxylate

The compound resulting from Example 180B (960 mg, 3.855 mmol) was dissolved in ethanol and treated under nitrogen with Raney nickel, which had been washed with water and ethanol. The reaction was allowed to reflux 24 hours and then the Raney nickel was removed by filtration through Celite. The filtrate and ethanol washings were concentrated in vacuo. The solid obtained was flash chromatographed on silica gel eluting with 5% ethyl acetate in hexane to afford the title compound (233.4 mg, 30%). $^1$H NMR (CDCl$_3$, 300 MHz) δ 1.43 (t, 3H), 4.44 (q, 2H), 7.92 (dd, J=8 Hz, 3 Hz, 1H), 8.40 (d, 1H). MS (DCl/NH$_3$) m/e 204 (M+H)$^+$.

EXAMPLE 180D

Ethyl 5-fluoro-2-{N-propyl-N-[(2'-[N-triphenylmethyl-1H-tetrazol-5-yl]biphenyl-4-yl)methyl]amino}pyridine-3-carboxylate To the compound resulting from Example 180C (157.4 mg, 0.7754 mmol) dissolved in ~0.6 mL of tetrahydrofuran was added 415 mg (1.0 equivalent) of N-triphenylmethyl-5-[2-(4'-propylaminomethyl-biphenyl)-]tetrazole, the compound resulting from Example 96A, followed by 270 μL of triethylamine. The solution was refluxed under nitrogen overnight and then concentrated in vacuo. The residue obtained was flash chromatographed on silica gel eluting with 6% ethyl acetate in hexane to afford the title compound (58.6 mg, 11%). $^1$H NMR (CDCl$_3$, 300 MHz) δ 0.75 (t, 3H), 1.37 (t, 3H), (m, 2H), 3.15 (m, 2H), 4.32 (q, 2H), 4.51 (s, 2H), 6.90 (m, 4H), 7.27 (m, 15H), 7.39 (td, J=8 Hz, 1 Hz, 1H), 7.46 (td, J=8 Hz, 1 Hz, 1H), 7.05 (m, 1H), 7.28 (dd, J=8 Hz, 3 Hz, 1H), 7.90 (dd, J=8 Hz, 1 Hz, 1H), 8.12 (d, 1H). MS (FAB) m/e 703 (M+H)+.

EXAMPLE 180E

5-Fluoro-2-{N-propyl-N-[(2'-[1H-tetrazol-5yl]biphenyl-4-yl)methyl]amino}pyridine-3-carboxylic acid To 58.6 mg (83.5 μmol) of the compound resulting from Example 180D in 1 mL of methanol and 1 mL of tetrahydrofuran was added 16 mg (1.0 equivalent) of p-toluenesulfonic acid monohydrate. The reaction was heated to ~60° C. under nitrogen for 60 minutes. The deprotected compound in solution was treated with 1 mL of 1:1 methanol/tetrahydrofuran and 0.21 mL (10 equivalents) of 4N sodium hydroxide solution. The reaction was heated at reflux overnight and then concentrated in vacuo. The product was purified by flash chromatography eluting with 95:5:0.5 chloroform/methanol/acetic acid to afford 24 mg (65%) of partially purified compound. Preparative HPLC and lyophilization afforded 10.4 mg of pure title compound. $^1$H NMR (CDCl$_3$, 300 MHz) δ 0.99 (t, 3H), 1.59 (m, 2H), 3.50 (m, 2H), 4.34 (s, 2H), 6.84 (d, J=8 Hz, 2H), 7.00 (d, J=8 Hz, 2H), 7.39 (m, 1H), 7.54 (td, J=8 Hz, 1 Hz, 2H), 8.01 (dd, J=8 Hz, 1 Hz, 1H), 8.25 (dd, J =8 Hz, 3 Hz, 1H), 8.54 (d, 1H). MS (FAB) m/e 432 (M+H)+.

EXAMPLE 181

3-Benzyloxy-2-{N-butyl-N-[(2'-[1H-tetrazol-5-yl]biphenyl-4-yl)methyl]amino}pyridine

EXAMPLE 181A

3-Benzyloxy-2-butylaminopyridine

To 2-amino-3-benzyloxypyridine (2.50 g, 12.5 mmol) dissolved in tetrahydrofuran (10 mL) and cooled to 0° C. was slowly added a solution of 1N lithium hexamethyldisilazide in tetrahydrofuran (12.5 mL, 12.5 mmol). The ice bath was removed and the solution stirred for 30 minutes. The bath was replaced and n-butyl iodide (2.30 g, 1.4 mL, 12.5 mmol) was added to the solution. After the addition was complete, the bath was removed and the solution stirred at ambient temperature overnight. The reaction mixture was evaporated in vacuo and the residue dissolved in ethyl acetate (25 mL). The solution was washed with water (25 mL) and brine (25 mL), dried and concentrated in vacuo. Purification by flash chromatography on silica gel eluting with 10% ethyl acetate in hexane afforded the desired product as an offwhite solid (2.75 g, 86% yield). $^1$H NMR (CDCl$_3$, 300 MHz) δ 0.95 (t, J=7 Hz, 3H), 1.42 (sextet, J=7 Hz, 2H), 1.60 (m, 2H), 3.44 (dt, J=7 Hz, 1 Hz, 2H), 4.92 (bt, 1H), 5.06 (s, 2H), 6.45 (dd, J=8 Hz, 6 Hz 1H), 6.86 (dd, J=8 Hz, 1 Hz, 1H), 7.37 (m, 5H), 7.73 (dd, J=6 Hz, 1 Hz, 1H). MS (DCl/NH$_3$) m/e 257 (M+H)+.

EXAMPLE 181B

3-Benzyloxy-2-{N-butyl-N-[(2'-[N-triphenylmethyl-N-triphenylmethyl-1H-tetrazol-5-yl]biphenyl-4-yl)methyl]amino}pyridine To the compound resulting from Example 181A (1.35 g, 5.3 mmol) dissolved in tetrahydrofuran (5 mL) and cooled in an ice bath was slowly added a 1N solution of lithium hexamethyldisilazide in tetrahydrofuran (5.3 mL, 5.3 mmol). The solution was stirred at 0° C. for 30 minutes and then N-triphenylmethyl-5-[2-(4'-bromomethyl-biphenyl)]tetrazole (3.54 g, 5.3 mmol), prepared as described by P. E. Aldrich, et al., in European Patent Application Number 291969, was added portionwise to the cooled solution. After the addition was complete, the reaction was stirred overnight at ambient temperature. The solvent was evaporated under reduced pressure and the residue taken up in ethyl acetate (20 mL). The solution was washed with water (25 mL) and brine (25 mL), dried and evaporated in vacuo to give a dark brown oil. Purification by flash chromatography on silica gel eluting with 10% ethyl acetate in hexane afforded the desired product as a white solid (2.40 g, 62% yield). $^1$H NMR (CDCl$_3$, 300 MHz) δ 0.75 (t, J=7 Hz, 3H), 1.07 (sextet, J=7 Hz, 2H), 1.46 (m, 2H), 3.32 (t, J=8 Hz, 2H), 4.64 (s, 2H), 5.03 (s, 2H), 6.67 (dd, J=8 Hz, 6 Hz, 1H), 6.90 (m, 5H), 7.03 (m, 5H), 7.18-7.51 (m, 18H), 7.85 (m, 2H). MS (DCl/NH$_3$) m/e 733 (M+H)+.

EXAMPLE 181C

3-Benzyloxy-2-{N-butyl-N-[(2'-[1H-tetrazol-5-yl]biphenyl-4-yl)methyl]amino}pyridine To the compound resulting from Example 181B (2.40 g, 3.27 mmol) dissolved in tetrahydrofuran (5 mL) and ethanol (5 mL) was added p-toluenesulfonic acid monohydrate (0.62 g, 3.3 mmol). The mixture was stirred overnight at ambient temperature and the solvents evaporated under reduced pressure. The residue was triturated with hexanes and purified by flash chromatography on silica gel eluting with a 0.5:5:95 mixture of acetic acid, ethanol and methylene chloride to give a yellow oil which was repeatedly dissolved in toluene or diethyl ether and evaporated until a solid resulted. The yellow solid was triturated with hexanes and dried overnight in vacuo at 50° C. (1.23 g, 76% yield). $^1$H NMR (CDCl$_3$, 300 MHz) δ 0.76 (t, J=8 Hz, 3H), 1.10 (m, J=8 Hz, 2H), 1.48 (bm, 2H), 3.32 (t, J=8 Hz, 2H), 4.45 (s, 2H), 5.05 (s, 2H), 6.68 (br dd, 1H), 7.02 (d, J=8 Hz, 2H), 7.09 (d, J=8 Hz, 1H), 7.17 (d, J=8 Hz, 2H), 7.38 (m, 6H), 7.54 (m, 4H), 8.10 (d, J=8 Hz, 1H). MS (DCl/NH$_3$) m/e 491 (M+H)+.

EXAMPLE 182

2-{N-Butyl-N-[(2'-[1H-tetrazol-5-yl]biphenyl-4-yl)methyl]amino}-3-hydroxypyridine The compound resulting from Example 181 (200 mg, 0.41 mmol) was stirred under nitrogen in 100 mL of ethyl acetate containing 3 mL of triethylamine until it dissolved. 10% Palladium on carbon catalyst (100 mg)

was added, and the nitrogen inlet was replaced with a balloon of hydrogen. The mixture was stirred at ambient temperature for 7 hrs. The hydrogen was purged with nitrogen; the mixture was filtered through a pad of Celite, and the solvents were removed in vacuo. The residue was purified by flash chromatography using 5% methanol and 0.5% acetic acid in chloroform to elute the product as a white solid (158 mg, 96% yield). $^1$H NMR (CDCl$_3$+CD$_3$OD, VT 40° C., 300 MHz) δ 0.85 (t, J=7 Hz, 3H), 1.37 (sextet, J=7 Hz, 2H), 1.49 (pentet, J=7 Hz, 2H), 2.01 (s, 1H), 3.32 (t, J=7 Hz, 2H), 4.54 (s, 2H), 6.79 (dd, J=6 Hz, 8 Hz, 1H), 7.04 (d, J=8 Hz, 2H), 7.13 (m, 2H), 7.26 (d, J=8 Hz, 2H), 7.45–7.70 (m, 5H). MS (DCl/NH$_3$) m/e 401 (M+H)$^+$.

EXAMPLE 183

3-Acetoxy-2-{N-butyl-N-[(2'-[1H-tetrazol-5-yl]biphenyl-4-yl)methyl]amino}pyridine To the compound resulting from Example 182 (75 mg, 0.19 mmol) dissolved in 2 mL of dimethylformamide and 2 mL of pyridine was added two drops of acetic anhydride. The reaction was stirred at ambient temperature for 1 hour and the solvents were removed in vacuo. The residue was dissolved in ether, washed with saturated aqueous bicarbonate, dried over sodium sulfate, and concentrated in vacuo to give 41 mg (53% yield) of the title compound as a white solid, which was washed with ether. $^1$H NMR (CDCl$_3$, 300 MHz) δ 0.94 (t, J=7 Hz, 3H), 1.35 (sextet, J=7 Hz, 2H), 1.64 (m, 2H), 2.21 (s, 3H), 3.46 (dd, J=7 Hz, 8 Hz, 2H), 4.70 (s, 2H), 6.81 (dd, J=5 Hz, 8 Hz, 1H), 7.16 (d, J=8 Hz, 2H), 7.19 (dt, 1H); 7.28 (d, J=8 Hz, 2H), 7.42 (dd, J=2 Hz, 8 Hz, 1H), 7.55 (dt, J=2 Hz, 8 Hz, 1H), 7.59 (dt, J=2 Hz, 8 Hz, 1H), 8.09 (dd, J=1 Hz, 5 Hz, 1H), 8.24 (dd, J=1 Hz, 8 Hz, 1H). MS (DCI/NH$_3$) m/e 443 (M+H)$^+$.

EXAMPLE 184

2-{N-Butyl-N-[(2'-[1H-tetrazol-5-yl]biphenyl-4-yl)methyl]amino}-3-(N-methylaminocarboxy)pyridine To the compound resulting from Example 182 (32 mg, 0.08 mmol) dissolved in 1 mL of dimethylformamide and 0.2 mL of triethylamine was added two drops of methyl isocyanate. The reaction was stirred at ambient temperature for 2 hours and the solvents were removed in vacuo. The residue was purified by flash chromatography on silica gel eluting with 5% methanol and 0.5% acetic acid in chloroform. After solvent removal in vacuo, toluene was used to remove the last traces of acetic acid. The residue was triturated with ether to give 16 mg (49%) of the title compound as a white solid, which was washed with ether. The 300 MHz $^1$H NMR spectrum was found to be consistent with the proposed structure. MS (DCI/NH$_3$) m/e 458 (M+H)$^+$.

EXAMPLE 185

2-{N-Butyl-N-[(2'-[1H-tetrazol-5-yl]biphenyl-4-yl)methyl]amino}pyridine-3-phosphate To the compound resulting from Example 182 (25 mg, 0.06 mmol) dissolved in 0.5 mL of pyridine was added three drops of phosphorus oxychloride. The reaction was stirred at ambient temperature for 2.5 hours. The mixture was cooled to 0° C.; ten drops of water were added followed by 3 drops of 1N sodium hydroxide. The solution was allowed to warm to ambient temperature over 1 hour. The product was purified by reverse-phase HPLC using a Vydac C-18 column, eluting with a gradient of 0→70% acetonitrile in 0.1% aqueous trifluoracetic acid to afford 4 mg of the title compound (15% yield). $^1$H NMR (CDCl$_3$, 300 MHz) δ 0.92 (t, J=7 Hz, 3H), 1.36 (sextet, J=7 Hz, 2H), 1.68 (m, 2H), 3.68 (dd, J=7 Hz, 8 Hz, 2H), 4.96 (s, 2H), 7.10 (d, J=8 Hz, 2H), 7.12 (t, J=8 Hz, 1h), 7.29 (d, J=8 Hz, 2H), 7.55 (m, 2H), 7.66 (d, J=8 Hz, 1H), 7.68 (dt, J=1 Hz, 7 Hz, 1H), 7.74 (dd, J=1 Hz, 6 Hz, 1H), 8.12 (d, J=8 Hz, 1H). MS (DCl/NH$_3$) m/e 481 (M+H)$^+$.

EXAMPLE 186

Methyl 4-{N-butyl-N-[(2'-[1H-tetrazol-5-yl]biphenyl-4-yl)methyl]amino}pyrimidine-6-carboxylate Methyl 2,6-dichloro-4-pyrimidine carboxylate, prepared according to the procedure described in J. Org. Chem. 26, 2755, (1961), and the compound resulting from Example 19A are reacted by the procedure described in Example 97A to give methyl 2-chloro-4-{N-butyl-N-[(2'-[N-triphenylmethyl-1H-tetrazol-5-yl]biphenyl-4-yl)methyl]amino}pyrimidine-6-carboxylate.

A solution of the above compound in ethyl acetate is treated with triethylamine and 10% palladium on carbon and stirred under a hydrogen atmosphere (1 atmosphere) until the starting material is consumed. The catalyst is removed by filtration and the filtrate concentrated under reduced pressure. Silica gel chromatography affords the title compound.

EXAMPLE 187

4-{N-Butyl-N-[(2'-[1H-tetrazol-5-yl]biphenyl-4-yl)methyl]amino}pyrimidine-6-carboxylic acid The compound resulting from Example 186 is hydrolyzed according to the procedure described in Example 119A to afford the title compound.

EXAMPLE 188

Methyl 4-{N-propyl-N-[(2'-[1H-tetrazol-5-yl]biphenyl-4-yl)methyl]amino}pyrimidine-6-carboxylate Methyl 2,6-dichloro-4-pyrimidine carboxylate, prepared according to the procedure described in J. Org. Chem. 26, 2755, (1961), and the compound resulting from Example 96A are reacted by the procedure described in Example 97A to give methyl 2-chloro-4-{N-propyl-N-[(2'-[N-triphenylmethyl-1H-tetrazol-5-yl]biphenyl-4-yl)methyl]amino}pyrimidine-6-carboxylate.

A solution of the above compound is dechlorinated according to the procedure described in Example 186 to give methyl 4-{N-propyl-N-[(2'-[N-triphenylmethyl-1H-tetrazol-5-yl]biphenyl-4-yl)methyl]amino}pyrimidine-6-carboxylate.

The above compound is deprotected using the procedure described in Example 95B to give the title compound.

EXAMPLE 189

4-{N-Propyl-N-[(2'-[1H-tetrazol-5-yl]biphenyl-4-yl)methyl]amino}pyrimidine-6-carboxylic acid The compound resulting from Example 188 is hydrolyzed according to the procedure described in Example 119A to give the title compound.

EXAMPLE 190

2-{N-Butyl-N-[(2'-[1H-tetrazol-5-yl]biphenyl-4-yl)methyl]amino}pyridine-4-carboxylic acid A solution of the compound resulting from Example 19A in xylene is treated with triethylamine and 2-chloropyridine-4-carboxylic acid, prepared according to J. Med. Chem. 19, 483 (1976). The solution is refluxed until starting material are consumed. Normal work up and purification on silica gel affords 2-{N-butyl-N-[(2'-[N-triphenylmethyl-1H-tetrazol-5-yl]biphenyl-4-yl)methyl]amino}pyridine-4-carboxylic acid.

The above compound is deprotected according to the procedure described in Example 96C to give the title compound.

EXAMPLE 191

Methyl 2-{N-butyl-N-[(2'-[1H-tetrazol-5-yl]biphenyl-4-yl)methyl]amino}pyridine-4-carboxylate A solution of the compound resulting from the first step in Example 190, 2-{N-butyl-N-[(2'-[N-triphenylmethyl-1H-tetrazol-5-yl]biphenyl-4-yl)methyl]amino}pyridine-4-carboxylic acid, in diethyl ether is cooled to 0° C. and treated with excess ethereal diazomethane until the reaction mixture stays light yellow. After 1 hour at 0° C., the excess diazomethane is destroyed with acetic acid. The solution is concentrated under reduced pressure and the trityl group is removed following the procedure described in Example 95B to afford the title compound.

EXAMPLE 192

2-{N-Propyl-N-[(2'-[1H-tetrazol-5-yl]biphenyl-4-yl)methyl]amino}pyridine-4-carboxylic acid A solution of the compound resulting from Example 96A in xylene is treated with triethylamine and 2-chloropyridine-4-carboxylic acid and warmed at relux until the starting material is consumed. Work up and purification affords 2-{N-propyl-N-[(2'-[N-triphenylmethyl-1H-tetrazol-5-yl]biphenyl-4-yl)methyl]amino}pyridine-4-carboxylic acid.

The above compound is deprotected according to the procedure described in Example 96C to afford the title compound.

EXAMPLE 193

Methyl 2-{N-propyl-N-[(2'-[1H-tetrazol-5-yl]biphenyl-4-yl)methyl]amino}pyridine-4-carboxylate The compound resulting from the first step of Example 192 is treated with excess diazomethane according to the procedure described in Example 191. The resulting ester is deblocked according to the procedure described in Example 95B to afford the title compound.

EXAMPLE 194

4-Methyl-2-{N-propyl-N-[(2'-[1H-tetrazol-5-yl]biphenyl-4-yl)methyl]amino}pyridine-3-carboxylic acid

EXAMPLE 194A

Ethyl 4-methyl-2-propylaminopyridine-3-carboxylate

Following the procedure of Baldwin, et al., J. Org. Chem., 43(12), 2529 (1978), 5.70 g of 2-propylidenecyanoacetate (37 mmol) was reacted with 4.43 g of dimethylformamide dimethylacetal (37 mmol). The resulting adduct was reacted with hydrogen bromide in acetic acid to give ethyl 2-bromo-5-methylnicotinate. The crude bromide was dissolved in 30 mL of ethanol, 15 mL of n-propylamine was added, and the resultant solution was heated in a sealed tube at 100° C. for 5 hours. After cooling to ambient temperature, the volatiles were removed in vacuo and the residue was chromatographed on silica gel eluting with 20% ethyl acetate in hexanes to afford 3.3 g (40% overall) of the title product. $^1$H NMR (CDCl$_3$, 300 MHz) δ 1.00 (t, J=7 Hz, 3H), 1.40 (t, J=7 Hz, 3H), 1.65 (sextet, J=7 Hz, 2H), 2.44 (s, 3H), 3.43 (dt, J=5 Hz, 7 Hz, 2H), 4.36 (q, J=7 Hz, 2H), 6.34 (d, J=5 Hz, 1H), 7.68 (bs, 1H), 8.06 (d, J=5 Hz, 1H). MS (DCl/NH$_3$) m/e 223 (M+H)$^+$.

EXAMPLE 194B

Ethyl 4-methyl-2-{N-propyl-N-[(2'-[N-triphenylmethyl-1H-tetrazol-5yl]biphenyl-4-yl)methyl]amino}pyridine-3-carboxylate Using the procedure described in Example 156D but without the 1,3-dimethyl-3,4,5,6-tetrahydro-2(1H)-pyrimidinone (DMPU) co-solvent, 0.55 g (2.5 mmol) of the compound resulting from Example 194A was deprotonated with 2.5 mL of 1M lithium hexamethyldisilazide in tetrahydrofuran and alkylated with 2.5 mmol of N-triphenylmethyl-5-[2-(4'-bromomethylbiphenyl)]tetrazole, prepared as described by P. E. Aldrich, et al., in European Patent Application Number 291969. After workup, the crude product was purified by flash chromatography on silica gel eluting with a gradient of 10%–15% ethyl acetate in hexanes to give 0.86 g (49% yield) of the title compound. $^1$H NMR (CDCl$_3$, 300 MHz) δ 0.72 (t, J=7 Hz, 3H), 1.30 (t, J=7 Hz, 3H), 1.48 (sextet, J=7 Hz, 2H), 2.30 (s, 3H), 3.11 (t, J=7 Hz, 2H), 4.37 (q, J=7 Hz, 2H), 4.55 (s, 2H), 6.59 (d, J=5 Hz, 1H), 6.90 (dt, J=8 Hz, 2 Hz, 6H), 7.07 (s, 4H), 7.25 (m, 9H), 7.38 (dt, J=2 Hz, 8 Hz, 1H), 7.44 (dd, J=2 Hz, 7 Hz, 1H), 7.48 (dt, J=2 Hz, 7 Hz, 1H), 7.89 (dd, J=2 Hz, 8 Hz, 1H), 8.08 (d, J=5 Hz, 1H).

EXAMPLE 194C

4-Methyl-2-{N-propyl-N-[(2'-[1H-tetrazol-5-yl]biphenyl-4-yl)methyl]amino}pyridine-3-carboxylic acid Using the procedure described in Example 156E for detritylation and saponification, 400 mg of the compound resulting from Example 194B was treated with 150 mg of p-toluenesulfonic acid monohydrate in 20 mL of ethanol and 5 mL of tetrahydrofuran, followed by 2 mL of 4N sodium hydroxide in 5 mL of methanol. After standard extractive workup, the crude product was purified by flash chromatography on silica gel eluting with 5% methanol and 0.5% acetic acid in chloroform. The purified product was chased twice with toluene to remove traces of acetic acid, then washed with ether to give 150 mg (61% yield) of the title compound as a white solid. $^1$H NMR (CDCl$_3$, 300 MHz) δ 0.95 (t, J=7 Hz, 3H), 1.53 (sextet, J=7 Hz, 2H), 2.36 (s, 1H), 2.69 (s, 3H), 3.46 (t, J=7 Hz, 2H), 4.37 (s, 2H), 6.88 (d, J=8 Hz, 2H), 7.01 (d, J=8 Hz, 2H), 7.24 (d, J=5 Hz, 1H), 7.41 (dd, J=2 Hz, 8 Hz, 1H), 7.51 (dt, J=2 Hz, 8 Hz, 1H), 7.56 (dt, J=2 Hz, 7 Hz, 1H), 8.00 (dd, J=2 Hz, 8 Hz, 1H), 8.47 (d, J=5 Hz, 1H). MS (DCl/NH$_3$) m/e 429 (M+H)$^+$.

EXAMPLE 195

5-Nitro-2-{N-propyl-N-[(2'-[1H-tetrazol-5-yl]biphenyl-4-yl)methyl]amino}pyridine-3-carboxylic acid

EXAMPLE 195A

2-Hydroxy-5-nitronicotinic acid

2-Hydroxynicotinic acid was added portionwise to sulfuric acid (50 mL) at 0° C. After complete dissolution, nitric acid (3 mL) was added dropwise to the cooled solution. After the addition was complete, the bath was removed and the solution stirred overnight at ambient temperature. The solution was then heated at 50°-70° C. for one and a half hours. The solution was cooled to ambient temperature and poured onto ice (100 g). The pale yellow solid which resulted was collected by filtration and dried in vacuo at 50° C. to give 7.3 g (87% yield) of the title compound which was used without further purification. $^1$H NMR (DMSO-$d_6$, 300 MHz) δ 8.51 (d, 1H,J=3), 9.01 (d,2H,J=3).

EXAMPLE 195B

Ethyl 2-chloro-5-nitronicotinate

Thionyl chloride (32 mL) added slowly to the compound resulting from Example 195A (5.00 g). Dimethylformamide (2 mL) was added dropwise and the mixture heated at reflux for two hours. The reaction was cooled to ambient temperature and the excess thionyl chloride removed in vacuo. The residue was cooled in an ice-bath and treated with ethanol (20 mL). The solution was stirred overnight at ambient temperature. The solvent was evaporated under reduced pressure and the residue treated with saturated sodium bicarbonate solution. The aqueous phase was extracted with ethyl acetate (3×30 mL). The combined organic extracts were dried and evaporated under reduced pressure to give the title compound as a yellow oil (5.04 g, 81% yield) which was used without further purification. $^1$H NMR (CDCl$_3$, 300 MHz) δ 1.45 (t,J=8 Hz, 3H), 4.48 (q, J=8 Hz, 2H), 8.92 (d, J=2 Hz, 1H), 9.32 (d, J=2 Hz, 2H).

EXAMPLE 195C

Ethyl 5-nitro-2-{N-propyl-N-[(2'-[1H-tetrazol-5-yl]biphenyl-4-yl)methyl]amino}pyridine-3-carboxylate The compound resulting from Example 195B (200 mg, 0.87 mmol) was dissolved in ethanol (3 mL). Hünig's base (225 mg, 0.3 mL, 1.75 mmol) and the 5-[2-(4'-propylaminomethyl-biphenyl)]tetrazole hydrochloride (286 mg, 0.87 mmol), the compound resulting from Example 96A, were added to the reaction mixture. The solution was stirred for three hours at ambient temperature. The solvent was then evaporated under reduced pressure and the residue partitioned between ethyl acetate and 1 N sodium hydroxide. The basic solution was acidified with 1 N phosphoric acid and extracted with ethyl acetate (3×25 mL). The combined organic extracts were washed with water (3×20 mL) and brine (25 mL), dried over sodium sulfate and evaporated in vacuo to give a yellow oil. Purification by flash chromatography eluting with 5% ethanol in chloroform gave the product as a pale yellow oil (225 mg, 53% yield). $^1$H NMR (CDCl$_3$, 300 MHz) d 0.90 (t, J=7 Hz, 3H), 1.38 (t, J=7 Hz, 3H), 1.72 (sextet, J=7 Hz, 2H), 3.53 (t, J=7 Hz, 2H), 4.34 (q, J=7 Hz, 2H), 4.96 (s, 2H), 7.24 (m, 4H), 7.41 (dd, J=7 Hz, 1 Hz, 1H), 7.59 (dt, J=7 Hz, 1 Hz, 2H), 8.25 (dd, J=7 Hz, 1 Hz, 1H), 8.55 (d, J=1 Hz, 1H), 9.07 (d, J=1 Hz, 1H). MS (DCl/NH$_3$) m/e 488 (M+H)$^+$, 516 (M+H+NH$_3$)$^+$.

EXAMPLE 195D

5-Nitro-2-{N-propyl-N-[(2'-[1H-tetrazol-5-yl]biphenyl-4-yl)methyl]amino}pyridine-3-carboxylic acid The compound resulting from Example 195C (215 mg, 0.44 mmol) was dissolved in methanol (2 mL). 5 N Sodium hydroxide (2 mL) was added and the reaction stirred overnight at ambient temperature. The solvents were evaporated in vacuo and the residue taken up in water (10 mL). The water was washed with ethyl acetate and then acidified with 1 N phosphoric acid and extracted with ethyl acetate (3×25 mL). The combined organic extracts were dried and evaporated in vacuo to give a yellow oil. Purification by flash chromatography afforded the product as a pale yellow solid (173 mg, 85% yield). $^1$H NMR (CDCl$_3$, 300 MHz) d 0.91 (t, J=7 Hz, 3H), 1.72 (sextet, J=7 Hz, 2H), 3.57 (t, J=7 Hz, 2H), 4.82 (s, 2H), 7.12 (d, J=8 Hz, 2H), 7.21 (d, J=8 Hz, 2H), 7.55 (m, 3H), 7.92 (dd, J=7 Hz, 1 Hz, 1H), 8.78 (d, J=1 Hz, 1H), 9.18 (d, J=1 Hz, 1H). MS (DCl/NH$_3$) m/e 460 (M+H)$^+$.

EXAMPLE 196

5-Methyl-2-{N-propyl-N-[(2'-[1H-tetrazol-5-yl]biphenyl-4-yl)methyl]amino}pyridine-3-carboxylic acid

EXAMPLE 196A

Ethyl 2-bromo-5-methylnicotinate

Propionaldehyde (5.8 g, 7.2 mL, 0.10 mol) and ethyl cyanoacetate (11.3 g, 10.6 mL, 0.10 mol) were dissolved in acetic acid (20 mL). Piperidine (0.5 mL) in acetic acid (20 mL) was added dropwise and the solution stirred overnight at ambient temperature. The reaction mixture was treated with water (100 mL) and extracted with toluene (3×100 mL). The combined organic extracts were dried over magnesium sulfate and evaporated under reduced pressure to give a yellow oil (10.6 g, 70% yield). The yellow oil (10.6 g, 69 mmol) was dissolved in ethanol (50 mL) and dimethylformamide dimethylacetal (9 mL, 68 mmol) was added dropwise over two minutes. The solution was then heated at reflux overnight during which time the reaction mixture turned dark red. The solvent was evaporated in vacuo and the residue (15.7 g, 0.068 mol) was taken up in acetic acid (50 mL). 30% Hydrobromic acid in acetic acid solution (100 mL) was added dropwise to the solution at 40° C. After the addition was complete, the reaction was heated at 60° C. for five hours. The solvents were evaporated in vacuo and the residue made basic with saturated sodium bicarbonate solution. The aqueous solution was extracted with ethyl acetate (2×100 mL). The combined organic extracts were washed with brine, dried over sodium sulfate and evaporated to give a yellow oil. Purification by flash chromatography eluting with 25% EtOAc in hexane gave the desired product as a yellow oil (2.50 g, 15% yield). $^1$H NMR (CDCl$_3$, 300 MHz) δ 1.42 (t, J=8 Hz, 3H), 2.35 (s, 3H), 4.42 (q, J=8 Hz, 2H), 7.87 (d, J=2 Hz, 1H), 8.30 (d, J=2 Hz, 1H). MS (DCl/NH$_3$) m/e 244, 246 (M+H)$^+$.

EXAMPLE 196B

Ethyl 5-methyl-2-propylaminonicotinate

The compound resulting from Example 196A (2.30 g, 9.42 mmol) was dissolved in ethanol (10 mL). n-

Propylamine (1.67 g, 2.3 mL, 28.3 mmol) was added and the solution heated in a high-pressure tube at 100° C. for 24 hours. The solvent was evaporated in vacuo and the residue taken up in ethyl acetate (50 mL) and washed with water (2×50 mL). The organic layer was evaporated in vacuo to give an orange oil which was purified by flash chromatography eluting with 10% ethyl acetate in hexane to give the product was a yellow oil (1.53 g, 73% yield). $^1$H NMR (CDCl$_3$, 300 MHz) δ 1.00 (t, J=7 Hz, 3H), 1.37 (t, J=7 Hz, 3H), 1.67 (sextet, J=7 Hz, 2H), 2.18 (s, 3H), 3.45 (q, J=7 Hz, 2H), 4.31 (q, J=7 Hz, 2H), 7.80 (bt, 1H), 7.94 (d, J=2 Hz, 1H), 8.12 (d, J=2 Hz, 1H). MS (DCl/NH$_3$) m/e 223 (M+H)$^+$.

EXAMPLE 196C

Ethyl 5-methyl-2-{N-propyl-N-[(2'-[N-triphenylmethyl-1H-tetrazol-5-yl]biphenyl-4-yl)methyl]amino}pyridine-3-carboxylate The compound resulting from Example 196B (0.66 g, 2.97 mmol) was alkylated with N-triphenylmethyl-5-[2-(4'-bromomethyl-biphenyl)]tetrazole, prepared as described by P. E. Aldrich, et al., in European Patent Application Number 291969, using the conditions described in Example 194B to give after flash chromatography the product as a yellow glass (1.50 g, 72% yield). $^1$H NMR (CDCl$_3$, 300 MHz) δ 0.73 (t, J=7 Hz, 3H), 1.33 (t, J=7 Hz, 3H), 1.48 (sextet, J=7 Hz, 2H), 2.24 (s, 3H), 3.15 (t, J=7 Hz, 2H), 4.31 (q, J=7 Hz, 2H), 4.54 (s, 2H), 6.89 (m, 6H), 7.05 (s, 4H), 7.24 (m, 9H), 7.44 (m, 3H), 7.73 (d, J=2 Hz, 1H), 7.90 (dd, J=7 Hz, 2 Hz, 1H), 8.08 (d, J=2 Hz, 1H). MS (DCl/NH$_3$) m/e 699 (M+H)$^+$.

EXAMPLE 196D

5-Methyl-2-{N-propyl-N-[(2'-[1H-tetrazol-5yl]biphenyl-4-yl)methyl]amino}pyridine-3-carboxylic acid To the compound resulting from Example 196C (1.45 g, 2.07 mmol) dissolved in tetrahydrofuran (3 mL) and ethanol (3 mL) wad added p-toluenesulfonic acid monohydrate (0.40 g, 2.07 mmol). The reaction was stirred at ambient temperature for 6 hours and the solvents evaporated under reduced pressure. To the residue taken up in methanol (15 mL) was added 4N sodium hydroxide (5 mL). The mixture was stirred overnight at ambient temperature and then heated at 70°-75° C. for 3 hours. The reaction mixture was cooled to ambient temperature, concentrated in vacuo and the residue taken up in water (25 mL). The aqueous solution was acidified with 1N phosphoric acid and extracted with ethyl acetate (3×30 mL). The combined organic extracts were washed with brine, dried over sodium sulfate and evaporated under reduced pressure to give a white solid which was triturated with diethyl ether. Purification by flash chromatography eluting with 95:5:0.5 chloroform/ethanol/acetic acid gave the title compound as a white solid (709 mg, 80% yield) which was dried in vacuo overnight at 50° C. $^1$H NMR (CDCl$_3$, 300 MHz) δ 0.98 (t, J=7Hz, 3H), 1.36 (bs, 2H), 2.47 (s, 3H), 3.50 (bs, 2H), 4.32 (s, 2H), 6.84 (d, J=8 Hz, 2H), 6.69 (d, J=8 Hz), 2H), 7.41 (dd, J=8 Hz, 2 Hz, 1H), 7.52 (m, 2H), 7.93 (d, J32 8 Hz, 2H, 1H), 8.37 (d, J=2 Hz, 1H), 8.47 (d, J=2 Hz, 1H), MS (DCl/NH$_3$) m/e 429 (M+H)$^+$. Anal calcd for C$_{24}$H$_{24}$N$_6$O$_2$: C, 67.27; H, 5.65,N, 19.61. Found: C, 66.92, H, 5.73, N, 18.96.

EXAMPLE 197

5-Chloro-2-{N-propyl-N-[(2'-[1H-tetrazol-5-yl]biphenyl-4-yl)methyl]amino}pyridine-3-carboxylic acid

EXAMPLE 197A

Methyl 2.5-dichloronicotainate

Sodium hypochlorite slution (5.25% by weight, 155 mL, 170 g, 0.12 mol) was added slowly to a 50% aqueous sodium hydroxide solution (21 mL, 32 g, 0.4 mol) cooled in an ice bath at 0° C. During the addition the temperature rose to about 25° C. The mixture was again cooled to 0° C. and then 2-hydroxynicotinic acid (13.9 g, 0.10 mol) was added portionwise, during which time the temperature rose to 15° C. After complete dissolution of the acid, the ice bath was removed, and the solution was allowed to stir overnight at ambient temperature. Sodium sulfite (1.4 g) in water (5 mL) was added and the solution was stirred for one hour. The reaction was made strongly acidic with concentrated hydrochloric acid (50 mL) and the resulting slurry was cooled in an ice bath for 15 minutes. The resulting solid was collected by filtration, washed with water and acetone, and dried in vacuo at 65° C. overnight. The product (14.2 g, 82% yield) was used without further purification.

The above 5-chloro-2-hydroxynicotinic acid (5.00 g, 0.029 mol) was carefully treated with thionyl chloride (32 mL). Dimethylformamide (2 mL) was slowly added to the solution, and the mixture was heated at reflux for two hours. After cooling to ambient temperature, the excess thionyl chloride was removed under reduced pressure and the residue carefully treated with methanol (25 mL). The solution was stirred for 30 minutes, and then the solvent was evaporated and the residue neutralized with saturated sodium bicarbonate solution. The aqueous solution was extracted with ethyl acetate (3×25 mL) and the combined organic extracts were dried and evaporated in vacuo to give a yellow oil. Purification by flash chromatography eluting with 10% ethyl acetate in hexane afforded the product as a colorless oil that solidified on standing (4.15 g, 70% yield). $^1$H NMR (CDCl$_3$, 300 MHz) δ 3.98 (s, 3H), 8.16 (d, J=3 Hz, 1H), 8.48 (d, J=3 Hz, 1H). MS (DCl/NH$_3$) m/e 206, 208 (M+H)$^+$.

EXAMPLE 197B

Methyl-5-chloro-2-propylaminonicotinate

To the compound resulting from Example 197A (2.09 g, 10.14 mmol) dissolved in methanol (3 mL) was added n-propylamine (2.1 g, 3 mL, 35.5 mmol). The solution was stirred at ambient temperature for 7.5 hours. and then the solvent evaporated in vacuo. The resulting white solid was taken up in ethyl acetate, washed with water and brine, dried and evaporated in vacuo. The resulting white solid was purified by flash chromatography eluting with 25% ethyl acetate in hexane to afford three products: methyl 5-chloro-2-propylaminonicotinate (0.38 g, 16% yield), N-propyl-5-chloro-2-propylaminonicotinamide (0.105 g, 4% yield), and N-propyl-2,5-dichloronicotinamide (1.65 g, 70% yield). For the title compound: $^1$H NMR (CDCl$_3$, 300 MHz) δ 1.00 (t, J=7 Hz, 3H), 1.66 (sextet, J=7 Hz, 2H), 3.45 (dt, J=7 Hz, 1 Hz, 2H), 3.87 (s, 3H), 7.96 (bs, 1H), 8.06 (d, J=2 Hz, 1H), 8.21 (d, J=2 Hz, 1H). MS (DCl/NH$_3$) m/e 229/231 (M+H)$^+$.

EXAMPLE 197C

Methyl 5-chloro-2-{N-propyl-N-[(2'-[N-triphenylmethyl-1H-tetrazol-5-yl]biphenyl-4-yl)methyl]amino}pyridine-3-carboxylate The compound resulting from Example 197B (180 mg, 0.79 mmol) was alkylated with N-triphenylmethyl-5-[2-(4'-bromomethyl-biphenyl)]tetrazole (550 mg), prepared as described by P. E. Aldrich, et al., in European Patent Application Number 291969, and 1M lithium hexamethyldisilazide in tetrahydrofuran (0.8 mL) using the conditions described in Example 194B. Flash chromatography of the crude product gave the title compound as a pale yellow solid (250 mg, 45% yield). $^1$H NMR (CDCl$_3$, 300 MHz) δ 0.75 (t, J=7 Hz, 3H), 1.51 (sextet, J=7 Hz, 2H), 3.18 (t, J=7 Hz, 2H), 3.81 (s, 3H), 4.53 (s, 2H), 6.90 (m, 6H), 7.03 (dd, J=8 Hz, 7 Hz, 4H), 7.26 (m, 8H), 7.43 (m, 4H), 7.87 (d, J=2 Hz, 1H), 7.90 (dd, J=7 Hz, 1 Hz, 1H), 8.14 (d, J=2 Hz, 1H).

EXAMPLE 197D

5-Chloro-2-{N-propyl-N-[(2'-[1H-tetrazol-5-yl]biphenyl-4-yl)methyl]amino}pyridine-3-carboxylic acid To the compound resulting from Example 197C (240 mg, 0.34 mmol) dissolved in tetrahydrofuran (1 mL) and ethanol (1 mL) was added p-toluenesulfonic acid monohydrate (75 mg, 0.40 mmol). The reaction was stirred at ambient temperature overnight and the solvents were evaporated under reduced pressure. To the residue taken up in methanol (2 mL) was added 5N sodium hydroxide (2 mL), and the mixture was stirred for four hours at ambient temperature and concentrated in vacuo. The residue was taken up in water (10 mL), acidified with 1N phosphoric acid and extracted with ethyl acetate (3×20 mL). The combined organic extracts were washed with brine, dried over sodium sulfate and evaporated in vacuo to give a white solid which was triturated with diethyl ether. Purification by flash chromatography 95:5:0.5 chloroform/ethanol/acetic acid gave the title compound as a white solid (109 mg, 69% yield) which was dried in vacuo overnight at 50° C. $^1$H NMR (CDCl$_3$, 300 MHz) δ 0.94 (t, J=7 Hz, 3H), 1.53 (sextet, J=7 Hz, 2H), 3.52 (t, J=7 Hz, 2H), 4.48 (s, 2H), 7.02 (s, 4H), 7.55 (m, 3H), 7.80 (dd, J=7 Hz, 1 Hz, 1H), 8.45 (d, J= 2 Hz, 1H), 8.61 (d, J=2 Hz, 1H). MS (DCl/NH$_3$) m/e 449,451 (M+H)$^+$. Anal calcd for C$_{23}$H$_{21}$N$_6$O$_3$Cl: C, 59.42; H, 4.55; N, 18.08. Found: C, 59.13, H, 4.62, N, 17.15.

EXAMPLE 198

5-Amino-2-{N-propyl-N-[(2'-[1H-tetrazol-5-yl]biphenyl-4-yl)methyl]amino}pyridine-3-carboxylic acid

EXAMPLE 198A

Ethyl 5-amino-2-{N-propyl-N-[(2'-[N-triphenylmethyl-1H-tetrazol-5-yl]biphenyl-4-yl)methyl]amino}pyridine-3-carboxylate To the compound resulting from 195C (500 mg, 0.69 mmol) dissolved in ethyl acetate (5 mL) was added 10% palladium on carbon (75 mg). The mixture was stirred under hydrogen for 10 hours and then the catalyst was removed by filtration and washed with ethyl acetate (50 mL) and ethanol (25 mL). The solvents were evaporated under reduced pressure to give the title compound as a yellow solid (395 mg, 82% yield). The yellow solid contained a small amount (<5%) of the starting material but was used without further purification.

EXAMPLE 198B

5-Amino-2-{N-propyl-N-[(2'-[1H-tetrazol-5-yl]biphenyl-4-yl)methyl]amino}pyridine-3-carboxylic acid The compound resulting from Example 198A was deprotected and saponified in the manner described for Example 195D to give a light yellow solid. $^1$H NMR (CD$_3$OD, 300 MHz) d 0.90 (t, J=7 Hz, 3H), 1.48 (q, J=7 Hz, 2H), 3.51 (t, J=7 Hz, 2H), 4.54 (s, 2H), 7.00 (d, J=12 Hz, 2H), 7.13 (d, J=12 Hz, 2H), 7.55 (m, 6H), 8.12 (d, J=2 Hz, 1H). MS (DCl/NH$_3$) m/e 429 (M+H)$^+$.

EXAMPLE 199

5-Acetylamino-2-{N-propyl-N-[(2'-[1H-tetrazol-5-yl]biphenyl-4-yl)methyl]amino}pyridine-3-carboxylic acid The compound resulting from Example 198A (50 mg) was dissolved in chloroform (1 mL) and treated with acetic anhydride (0.2 mL). Triethylamine (0.1 mL) was added and the reaction mixture stirred overnight at ambient temperature. The solvents were evaporated in vacuo and the residue treated with saturated sodium bicarbonate solution and extracted with ethyl acetate. The combined organic extracts were dried and concentrated in vacuo to give a yellow solid. Purification by flash chromatography eluting with 25% ethyl acetate in hexane afforded a yellow solid which was deprotected and saponified by the procedure described in Example 195D to give the product as an off-white solid which was further purified by flash chromatography eluting with 0.5:5:95 acetic acid/ethanol/chloroform. $^1$H NMR (CD$_3$OD, 300 MHz) d 0.90 (t, J=7 Hz, 3H), 1.48 (m, J=7 Hz, 2H), 2.20 (s, 3H), 3.50 (q, J=7 Hz, 2H), 4.58 (s, 2H), 7.02 (d, J=10 Hz, 2H), 7.14 (d, J=10 Hz, 2H), 7.55 (m, 4H), 8.43 (bs, 1H), 8.93 (b, 1H). MS (DCl/NH$_3$) m/e 472 (M+H)$^+$.

EXAMPLE 200

2-{N-Propyl-N-[(2'-[1H-tetrazol-5-yl]biphenyl-4-yl)methyl]amino}-3-trifluoroacetylaminopyridine

EXAMPLE 200A

2-{N-Propyl-N-[(2'-[N-triphenylmethyl-1H-tetrazol-5-yl]biphenyl-4-yl)methyl]amino}-3-trifluoroacetylpyridine To the compound resulting from Example 93A (100 mg, 0.16 mmol) dissolved in 5 mL of methylene chloride and cooled in an ice bath was added 25.7 μL (2 equivalents) of pyridine followed by 34 μL (1.5 equivalents) of trifluoroacetic anhydride. The resulting mixture was stirred for 1 hour and then concentrated in vacuo. The residue obtained was purified by flash chromatography on silica gel eluting with 15–20% ethyl acetate in hexane to afford 100 mg (86%) of the title compound.

EXAMPLE 200B

2-{N-Propyl-N-[(2'-[1H-tetrazol-5-yl]biphenyl-4-yl)methyl]amino}-3-trifluoroacetylaminopyridine To the compound resulting from Example 200A (100 mg, 0.14 mmol) dissolved in 1 mL of methylene chloride was added 1.5 mL of 88% formic acid. The reaction was stirred for 3 hours at ambient temperature and then concentrated in vacuo and chased with toluene. The residue obtained was chromatographed on silica gel eluting with 4% methanol in methylene chloride to afford the title compound 67 mg (100%). $^1$H NMR (CDCl$_3$, 300 MHz) δ 0.98 (t, J=7.5 Hz, 3H), 1.96 (q, J=7.5 Hz, 2H), 3.19 (t, J=7.5 Hz, 2H), 4.09 (s, 2H), 6.94 (s, 4H), 7.23 (d, J=5.1 Hz, 1H), 7.39 (dd, J=1.2 Hz, 7.5 Hz, 1H), 7.55 (m, 2H), 8.00 (dd, J=1.2 Hz, 7.5 Hz, 1H), 8.30 (dd, J=1.2 Hz, 7.5 Hz, 1H), 8.37 (dd, J=1.5 Hz, 6 Hz, 2H), 9.33 (bs, 1H).

EXAMPLE 201

3-Ethoxy[(bis)carbonyl]amino-2-{N-propyl-N-[(2'-[1H-tetrazol-5-yl]biphenyl-4-yl)methyl]amino}pyridine To the compound resulting from Example 93A (150 mg, 0.24 mmol) dissolved in 6 mL of methylene chloride cooled in an ice bath was added 0.1 mL of triethylamine followed by 54 mg (2 equivalents) of ethyl oxalyl chloride. The resulting mixture was stirred for 2 hours and then concentrated in vacuo. The residue obtained was chromatographed on silica gel eluting with 15% ethyl acetate in hexane to afford 3-ethoxy[(bis)carbonyl]amino-2-{N-propyl-N-[(2'-[N-triphenylmethyl-1H-tetrazol-5-yl]biphenyl-4-yl)methyl]amino}pyridine (149 mg, 85%).

The above compound was deprotected by the procedure described in Example 200B. The crude material was chromatographed on silica gel eluting with 5% methanol in methylene chloride to give 100 mg (100%) of the title compound. $^1$H NMR (CDCl$_3$, 300 MHz) δ 1.27 (t, J=5.4 Hz, 3H), 1.42 (t, J=6.9 Hz, 3H), 1.52 (q, J=5.4 Hz, 2H), 3.24 (t, J=5.4 Hz, 2H), 4.10 (s, 2H), 4.45 (q, J=6.9 Hz, 2H), 6.90 (d, 2H), 7.40 (dd, J=1.2 Hz, 7.5 Hz, 1H), 7.55 (m, 2H), 8.00 (dd, J=1.2 Hz, 7.5 Hz, 1H), 8.32 (dd, J=1.5 Hz, 4.5 Hz, 1H), 8.40 (dd, J=7.5 Hz, 1H), 9.90 (bs, 1H).

EXAMPLE 202

3-Carboxycarboxamido-2-{N-propyl-N-[(2'-[1H-tetrazol-5-yl]biphenyl-4-yl)methyl]amino}pyridine To the compound resulting from Example 201 (100 mg, 0.206 mmol) dissolved in 5 mL of ethanol was added 25 mL of aqueous sodium hydroxide solution (2 mmol). The reaction was stirred at ambient temperature overnight and then concentrated in vacuo. The aqueous solution was washed with ethyl acetate and then acidified with formic acid and extracted with ethyl acetate (2×150 mL). The combined organic extracts were washed with water and brine, dried over sodium sulfate and concentrated in vacuo to afford 56 mg (60%) of the title compound. $^1$H NMR (CDCl$_3$, 300 MHz) δ 0.77 (t, J=7.5 Hz, 3H), 1.42 (q, J=7.5 Hz, 2H), 3.30 (t, J=7.5 Hz, 2H), 4.32 (s, 2H), 6.98 (d, J=8.7 Hz, 2H), 7.04 (dd, J=5.1 Hz, 6 Hz, 1H), 7.23 (d, J=8.7 Hz, 2H), 7.54 (t, J=9 Hz, 2H), 7.65 (m, 2H), 8.12 (d, J=6 Hz, 1H), 8.16 (d, J=9 Hz, 2H), 10.10 (bs, 1H).

EXAMPLE 203

2-{N-Propyl-N-[(2'-[1H-tetrazol-5-yl]biphenyl-4-yl)methyl]amino}pyridine-3-(N-benzenesulfonyl)carboxamide

EXAMPLE 203A

2-{N-Propyl-N-[(2'-[N-triphenylmethyl-1H-tetrazol-5-yl]biphenyl-4-yl)methyl]amino}pyridine-3-(N-benzenesulfonyl)carboxamide The compound resulting from Example 87C was hydrolyzed by the method described in Example 86 to afford 2-{N-propyl-N-[(2'-[N-triphenylmethyl-1H-tetrazol-5-yl]biphenyl-4-yl)methyl]amino}pyridine-3-carboxylic acid. To this acid (930 mg, 1.42 mmol) dissolved in 2 mL of methylene chloride at ambient temperature was added thionyl chloride (420 µL, 5.7 mmol). After stirring for 1 hour at ambient temperature under a nitrogen atmosphere, benzene sulfonamide (1.3 g, 8.5 mmol) was added. The reaction was cooled to −78° C. and triethylamine (2 mL) was added dropwise. The reaction was allowed to warm to ambient temperature and then stirred overnight. The reaction mixture was diluted with methylene chloride, suspended on ~5 g of silica gel and placed on a silica gel column. Eluting with 1:1 hexane/ethyl acetate afforded 390 mg (35%) of the title compound. $^1$H NMR (CDCl$_3$, 300 MHz) δ 0.82 (t, J=7 Hz, 3H), 1.47–1.59 (m, 2H), 3.08 (bt, J=7 Hz, 3H), 4.23 (s, 2H), 6.87–7.63 (m, 25H), 7.87–7.96 (m, 2H), 8.10 (d, J=8 Hz, 2H), 8.31 (dd, J=8 Hz, 2 Hz, 1H), 8.53 (dd, J=5 Hz, 2 Hz, 1H), 14.49 (bs, 1H). MS (FAB) m/e 818 (M+Na)$^+$.

EXAMPLE 203B

2-{N-Propyl-N-[(2'-[1H-tetrazol-5-yl]biphenyl-4-yl)methyl]amino}pyridine-3-(N-benzenesulfonyl)carboxamide To the compound resulting from Example 203A (360 mg, 0.45 mmol) dissolved in 3 mL of methylene chloride was added 20 mL of 88% formic acid. The reaction was stirred for 2 days at ambient temperature and then concentrated in vacuo and chased with toluene. The crude product was chromatographed on silica gel eluting with ethanol in methylene chloride to afford 225 mg (90%) of the title compound. $^1$H NMR (CD$_3$OD, 300 MHz) δ 0.68 (t, J=7 Hz, 3H), 1.31–1.44 (m, 2H), 3.06–3.15 (m, 3H), 4.42 (s, 2H), 6.89–7.22 (m, 6H), 7.41–7.64 (m, 6H), 7.90 (dd, J=8 Hz, 2 Hz, 1H), 7.98–8.04 (m, 2H), 8.30 (dd, J=5 Hz, 2 Hz, 1H). MS (DCl/NH$_3$) m/e 554 (M+H)$^+$.

EXAMPLE 204

2-{N-Allyl-N-[(2'-[1H-tetrazol-5-yl]biphenyl-4-yl)methyl]amino}pyridine-3-carboxylic acid

EXAMPLE 204A

Methyl 2-allylaminopyridine-3-carboxylate

Methyl 2-chloropyridine-3-carboxylate (5 g) was reacted neat with allylamine (3.1 g) with heating at 140° C. for 4 hours. The volatiles were removed under reduced pressure and the residue chromatographed on silica gel eluting with ethyl acetate in hexane to afford 4.12 g of the title compound. MS (DCl/NH$_3$) m/e 207 (M+H)$^+$.

EXAMPLE 204B

Methyl 2-{N-ally-N-[(2'-[N-triphenylmethyl-1H-tetrazol-5-yl]biphenyl-4-yl)methyl]amino}pyridine-3-carboxylate The compound resulting from Example 204A (1.47 g, 1 equivalent) was reacted with N-triphenylmethyl-5-[2-(4'-butylaminomethyl-biphenyl)]tetrazole (4.00 g, 7.18 mmol), prepared as described by P. E. Aldrich, et al., in European Patent Application Number 291969, by the procedure described in Example 153D to give 2.81 g of the title compound. MS (DCl/NH$_3$) m/e 683 (M+H)$^+$.

EXAMPLE 204C

2-{N-Cyclopropylmethyl-N-[(2'-[1H-tetrazol-5-yl]biphenyl-4-yl)methyl]amino}pyridine-3-carboxylic acid The compound resulting from Example 204B (1.81 g, 2.65 mmol) was deprotected by dissolving in 20 mL of dioxane and 20 mL of ethanol and treated with 2 g of sodium hydroxide dissolved in 20 mL of water. The reaction was stirred at ambient temperature for two days during which time an additional 20 mL of dioxane was added. The reaction was quenched with 4.5 mL of 12N hydrochloric acid and concentrated in vacuo. The unreacted starting material was extracted with ether. The crude carboxylic acid was dissolved in 20 mL of dioxane and 20 mL of ethanol and treated with 2 mL of 12N hydrochloric acid at ambient temperature for 4 hours and 70° C. for 15 minutes. The solvent was removed under reduced pressure and the residue chromatographed on silica gel eluting with 16:1:1 ethyl acetate/formic acid/water to afford 631 mg (57%) of the title compound which could be recrystallized from ethanol/ether to afford 463 mg. $^1$H NMR (DMSO-d$_6$, 300 MHz) δ 3.90 (d, J=6 Hz, 2H), 4.67 (s, 2H), 5.10 (m, 1H), 5.15 (d, J=1 Hz, 1H), 5.84 (m, 1H), 6.82 (dd, J=4 Hz, 7 Hz, 1H), 7.02 (d, J=7 Hz, 2H), 7.22 (d, J=7 Hz, 2H), 7.56 (t, J=7 Hz, 2H), 7.65 (m, 2H), 7.92 (dd, J=1 Hz, 7 Hz, 1H), 8.24 (dd, J=3 Hz, 6 Hz, 1H). MS (DCl/NH$_3$) m/e 413 (M+H)$^+$.

EXAMPLE 205

2-{N-(2-Pyridyl)methyl-N-[(2'-[1H-tetrazol-5-yl]biphenyl-4-yl)methyl]amino}pyridine-3-carboxylic acid The title compound was prepared in analogy to Example 204 using 2-pyridylmethylamine instead of allylamine. $^1$H NMR (DMSO-d$_6$, 300 MHz) δ 4.63 (s, 2H), 4.68 (s, 2H), 6.84 (dd, J=5 Hz, 7 Hz, 1H), 7.02 (d, J=7 Hz, 2H), 7.12 (d, J=7 Hz, 2H), 7.21 (t, J=6 Hz, 1H), 7.33 (d, J=7 Hz, 1H), 7.35–7.50 (m, 3H), 7.57 (d, J=6 Hz, 1H), 7.70 (t, J=7 Hz, 1H), 7.91 (d, J=7 Hz, 1H), 8.21 (d, J=3 Hz, 1H), 8.46 (d, J=3 Hz, 1H). MS (DCl/NH$_3$) m/e 464 (M+H)$^+$.

EXAMPLE 206

2-{N-Cyclopropylmethyl-N-[(2'-[1H-tetrazol-5-yl]biphenyl-4-yl)methyl]amino}pyridine-3-carboxylic acid The title compound was prepared in analogy to Example 204 using cyclopropylmethylamine instead of allylamine. $^1$H NMR (DMSO-d$_6$, 300 MHz) δ 0.00 (m, 2H), 0.38 (m, 2H), 0.98 (m, 1H), 3.15 (d, J=7 Hz, 2H), 4.80 (s, 2H), 6.88 (dd, J=6 Hz, 8 Hz, 1H), 7.02 (d, J=7 Hz, 2H), 7.25 (d, J=7 Hz, 2H), 7.57 (t, J=7 Hz, 2H), 7.65 (td, J=1 Hz, 7 Hz, 2H), 7.95 (dd, J=1 Hz, 7 Hz, 1H), 8.30 (dd, J=5 Hz, 1 Hz, 1H). MS (DCl/NH$_3$) m/e 207 (M+H)$^+$.

EXAMPLE 207

4-{N-Propyl-N-[(2'-[1H-tetrazol-5-yl]biphenyl-4-yl)methyl]amino}pyridine-3-carboxylic acid

EXAMPLE 207A

Methyl 4-chloropyridine-3-carboxylate

4-Chloronicotinic acid, prepared as described by W. C. J. Ross in J. Chem. Soc. (C), 1816 (1966), (2.54 g, 16.1 mmol) in methanol (30 mL) at 0° C. was treated with diazomethane in ether until gas evolution ceased; the ice bath was removed halfway through the esterification. The excess diazomethane was removed with a nitrogen stream and the solvent was removed under reduced pressure. The residue was taken up in saturated sodium bicarbonate solution and extracted with ethyl acetate (2×). The combined organic extracts were washed with 1M aqueous sodium hydroxide solution (2×) and brine, dried over sodium sulfate, filtered and concentrated in vacuo to afford 2.35 g (85%) of the title compound as a yellow oil. A portion (1.47 g) was distilled at b.p. 75°–85° C. at ~1 mm mercury to afford 1.15 g as a pale yellow crystalline solid.

EXAMPLE 207B

Methyl 4-{N-propyl-N-[(2'-[N-triphenylmethyl-1H-tetrazol-5-yl]biphenyl-4-yl)methyl]amino}pyridine-3-carboxylate The compound resulting from Example 207A (700 mg, 4.08 mmol), N-triphenylmethyl-5-[2-(4'-propylaminomethyl-biphenyl)]tetrazole (1.45 g, 2.71 mmol), prepared as described in Example 72B, isopropanol (10 mL) and triethylamine (1.1 mL, 7.89 mmol, 2.9 equivalents) were stirred in a sealed tube at 110°–120° C. for 6 hours and cooled to ambient temperature. The volatiles were removed under reduced pressure and the residue taken up in 1M aqueous sodium hydroxide solution and extracted with ethyl acetate (2×). The combined organic extracts were washed with brine, dried over sodium sulfate, filtered, and concentrated under reduced pressure. The residue obtained was chromatographed on silica gel eluting with ethyl acetate in hexane to afford 454 mg (25%) of the title compound as a foam. Anal calcd for C$_{43}$H$_{38}$N$_6$O$_2$: C, 76.99; H, 5.71; N, 12.53. Found: C, 77.42; H, 6.09; N, 12.40.

EXAMPLE 207C

Methyl 4-{N-propyl-N-[(2'-[1H-tetrazol-5-yl)]biphenyl-4-yl)methyl]amino}pyridine-3-carboxylate The compound resulting from Example 207B (430 mg, 0.64 mmol) was taken up in 15:15:1 acetic acid/tetrahydrofuran/water (21 mL) and heated at reflux for 2 hours. The reaction was cooled to ambient temperature, concentrated under reduced pressure, diluted with water and extracted with methylene chloride (5×). The combined organic extracts were dried over sodium sulfate, filtered and concentrated under reduced pressure to afford 400 mg of crude title compound as a glass. Chromatography on silica gel eluting with methanol in chloroform afforded a residue which was dissolved in chloroform and filtered through Celite. The filtrate was concentrated in vacuo and chased with toluene to afford 294 mg of the title compound as a yellow foam. m.p. 115°-120° C.

EXAMPLE 207D

4-{N-Propyl-N-[(2'-[1H-tetrazol-5-yl]biphenyl-4-yl)methyl]amino}pyridine-3-carboxylic acid The compound resulting from Example 207C (237 mg, 0.55 mmol) was stirred in 1M aqueous potassium hydroxide solution for 24 hours at ambient temperature. The solution was acidified to pH 4 with 2M hydrochloric acid. The non-homogeneous mixture was extracted with 15% isopropanol in chloroform. The combined extracts were dried over sodium sulfate, filtered and concentrated under reduced pressure. The residue obtained was dissolved in 5% methanol in chloroform, filtered through Celite and concentrated in vacuo to afford 223 mg (98%) of the title compound as a yellow solid. m.p. 195°-200° C. $^1$H NMR (DMSO-$d_6$, 300 MHz) δ 0.80 (t, 3H), 1.51–1.70 (m, 2H), 3.35 (t, 2H), 4.68 (s, 2H), 6.96 (d, 1H), 7.07 (d, 2H), 7.20 (d, 2H), 7.49–7.73 (m, 4H), 8.18 (d, 1H), 8.45 (s, 1H).

EXAMPLE 208

5-Iodo-2-{N-butyl-N-[(2'-[1H-tetrazol-5-yl]biphenyl-4-yl)methyl]amino}pyridine-3-carboxylic acid

EXAMPLE 208A

Methyl 2-hydroxynicotinate

2-Hydroxynicotinic acid (6.95 g, 50 mmol) was dissolved in 125 mL of methanol, 75 mL of benzene, and 0.75 mL of concentrated sulfuric acid under nitrogen and heated at reflux for 2.5 hours. A Dean-Stark trap was added to the apparatus and heating was continued overnight. The volatiles were removed under reduced pressure and the resulting solid was suspended in cold water (150 mL) and filtered to remove unreacted starting material. The filtrate was extracted with methylene chloride and chloroform. The combined organic extracts were concentrated in vacuo to afford 2.5 g. Recrystallization from hot benzene afforded 1.7 g (22%) of the title compound. $^1$H NMR (CD$_3$OD, 300 MHz) δ 3.83 (s, 3H), 6.45 (t, 1H), 7.68 (dd, 1H), 8.29 (dd, 1H). MS (DCl/NH$_3$) m/e 154 (M+H)$^+$.

EXAMPLE 208B

Methyl 2-hydroxy-5-iodo-nicotinate

To the compound resulting from Example 208A (1.7 g, 11.1 mmol) dissolved in 40 mL of anhydrous methylene chloride was added 3.25 g (1.3 equivalents) of N-iodosuccinimide. The reaction was heated at reflux under nitrogen in the dark for 48 hours. The red solution was concentrated under reduced pressure to afford a red-yellow solid. The solid was taken up in chloroform and washed with 10% aqueous sodium thiosulfate (2×) and brine, dried over sodium sulfate and concentrated under reduced pressure to afford the title compound as a pale yellow solid. $^1$H NMR (CDCl$_3$, 300 MHz) δ 3.99 (s, 3H), 8.44 (m, 2H). MS (DCl/NH$_3$) m/e 280 (M+H)$^+$.

EXAMPLE 208C

Methyl 2-chloro-5-iodo-nicotinate

The compound resulting from Example 208B (500 mg, 1.79 mmol) was refluxed under nitrogen in 5 mL of phosphorus oxychloride for ~7 hours. The phosphorus oxychloride was removed under reduced pressure and the residue was taken up in ether and saturated sodium bicarbonate solution. The organic layer was washed with saturated sodium bicarbonate solution, water and brine, dried over magnesium sulfate and concentrated under reduced pressure. The residue obtained was chromatographed on silica gel eluting with 10% ethyl acetate in hexane to afford 3.68 g (69%) of the title compound as a white solid. $^1$H NMR (CDCl$_3$, 300 MHz) δ 3.98 (s, 3H), 8.44 (d, 1H), 8.71 (d, 1H). MS (DCl/NH$_3$) m/e 298 (M+H)$^+$.

EXAMPLE 208D

Methyl 5-Iodo-2-{N-butyl-N-[(2'-[N-triphenylmethyl-1H-tetrazol-5-yl]biphenyl-4-yl)methyl]amino}pyridine-3-carboxylate The compound resulting from Example 208C (368 mg, 1.24 mmol) was mixed with ~2 mL of anhydrous tetrahydrofuran, 816 mg (1.2 equivalents) of N-triphenylmethyl-5-[2-(4'-butylaminomethyl-biphenyl)]tetrazole, prepared as described in Example 19A, and 0.69 mL (4 equivalents) of triethylamine. The solution was refluxed under nitrogen overnight and then concentrated under reduced pressure. The residue was flash chromatographed on silica gel eluting with ethyl acetate in hexane to afford 402 mg (40%) of the title compound as a white foam. $^1$H NMR (CDCl$_3$, 300 MHz) δ 0.82 (t, 3H), 1.18 (m, 2H), 1.49 (m, 2H), 3.22 (m, 2H), 3.80 (s, 3H), 4.53 (bs, 2H), 6.90 (d, 4H), 6.99 (d, 2H), 7.08 (d, 2H), 7.27 (m, 10H), 7.42 (m, 4H), 7.90 (m, 1H), 8.10 (dd, 1H), 8.33 (dd, 1H). MS (DCl/NH$_3$) m/e 811 (M+H)$^+$.

EXAMPLE 208E

5-Iodo-2-{N-butyl-N-[(2'-[1H-tetrazol-5-yl]biphenyl-4-yl)methyl]amino}pyridine-3-carboxylic acid To the compound resulting from Example 208D (160 mg, 0.1975 mmol) dissolved in 2 mL of methanol and 2 mL of tetrahydrofuran under nitrogen was added 38 mg (1 equivalent) of p-toluenesulfonic acid monohydrate. The solution was heated at 60° C. for ~1 hour to remove the trityl group.

To the above solution was added 0.5 mL (10 equivalents) of 4N aqueous sodium hydroxide solution. The reaction mixture was heated at reflux overnight and then concentrated under reduced pressure. The residue obtained was flash chromatographed on silica gel eluting with 95:5:0.5 chloroform/methanol/acetic acid to give partially purified material. This material was further purified by preparated HPLC to afford the title compound. $^1$H NMR (CDCl$_3$, 300 MHz) δ 0.93 (t, 3H), 1.39 (m, 2H), 1.54 (m, 2H), 3.59 (m, 2H), 4.40 (bs, 2H), 6.87 (d, 2H), 7.01 (d, 2H), 7.54 (m, 2H), 7.96 (dd, 1H), 8.88 (d, 1H), 8.91 (d, 1H). MS (DCl/NH$_3$) m/e 555 (M+H)$^+$. Anal calcd for $C_{24}H_{23}IN_6O_2 \cdot 0.6$ CF$_3$COOH: C, 48.60; H, 3.82; N, 13.49. Found: C, 48.49; H, 3.96; N, 13.43.

EXAMPLE 209

2-{N-Propyl-N-[(2'-[1H-tetrazol-5-yl]biphenyl-4-yl)methyl]amino}pyridine-3,4-dicarboxylic acid

EXAMPLE 209A

5-Chloro-1-methyl-3-{N-propyl-N-[(2'-[N-triphenylmethyl-1H-tetrazol-5-yl]biphenyl-4-yl)methyl]amino}-2-[1H]-pyridazinone 3,5-Dichloro-1-methyl-2-(1H)-pyrazinone, prepared according to the method of Vekemans, Pollers-Wieers and Hoornaert, J. Het. Chem. 20, 919 (1983), is combined in ethanol with 1.0 equivalent of N-triphenylmethyl-5-[2-(4'-propylaminomethyl-biphenyl)]tetrazole, prepared by the procedure described in Example 72B, and 2.0 equivalents of ethyldiisopropylamine. The reaction is heated at 80° C. for 6 hours. The product is isolated by flash chromatography.

EXAMPLE 209B

2-{N-Propyl-N-[(2'-[N-triphenylmethyl-1H-tetrazol-5-yl]biphenyl-4-yl)methyl]amino}pyridine-3,4-dicarboxylic acid dimethyl ester The compound resulting from Example 209A is dehalogenated using 10% palladium on carbon in 1:1 ethanol/ethylacetate. The reaction is stirred overnight under a hydrogen atmosphere to afford 1-methyl-3-{N-propyl-N-[(2'-[N-triphenylmethyl-1H-tetrazol-5-yl]biphenyl-4-yl)methyl]amino}-2-(1H)-pyridazinone. Diels-Alder cycloaddition with dimethyl acetylenedicarboxylate (3 equivalents, neat) at 140° C. according to the method of Tutonda et al., Tet. Letters 27, 2509 (1986) provides the title compound.

EXAMPLE 209C

2-{N-Propyl-N-[(2'-[1H-tetrazol-5-yl]biphenyl-4-yl)methyl]amino}pyridine-3,4-dicarboxylic acid The compound resulting from Example 209B is deprotected and hydrolyzed by the procedure described in Example 179D to afford the title compound.

EXAMPLE 210

2-{N-Propyl-N-[(2'-[1H-tetrazol-5-yl]biphenyl-4-yl)methyl]amino}pyridine-3-carboxylic acid mono-potassium salt To the compound resulting from Example 88 (8.93 g, 21.57 mmol) suspended in 60 mL of methanol was added a solution of 1.42 g (21.56 mmol) of 85.5% potassium hydroxide pellets dissolved in 10 mL of methanol. The mixture was warmed until a clear solution resulted and then concentrated under reduced pressure. Toluene (50 mL) was added and again removed in vacuo. A solution of 5 mL of isopropanol in 150 mL of ether was added to the residue and the mixture stirred first with a spatula and then with a magnetic stirrer for 3 hours to give the title compound as a white solid which was dried in a vacuum oven for 3 hours at 40° C. to afford 8.92 g. m.p. 155° C. $^1$H NMR (DMSO-d$_6$, 300 MHz) d 0.71 (t, J=7 Hz, 3H), 1.48 (m, 2H), 3.20 (t, J=7 Hz, 2H), 4.60 (s, 2H), 6.72 (dd, J=8 Hz, 4 Hz, 1H), 6.98 (d, J=8 Hz, 2H), 7.05 (dd, J=7 Hz, 2 Hz, 1H), 7.77 (dd, J=8 Hz, 2 Hz, 1H), 8.18 (dd, J=4 Hz, 2 Hz, 1H).

EXAMPLE 211

2-{N-Propyl-N-[(2'-[1H-tetrazol-5-yl]biphenyl-4-yl)methyl]amino}pyridine-3-carboxylic acid mono-sodium salt The title compound was prepared in analogy to Example 210 using one equivalent of sodium hydroxide instead of potassium hydroxide. m.p. 185° C. $^1$H NMR (DMSO-d$_6$, 300 MHz) d 0.73 (t, J=7 Hz, 3H), 1.50 (m, 2H), 3.22 (t, J=7 Hz, 2H), 4.62 (s, 2H), 6.75 (dd, J=8 Hz, 4 Hz, 1H), 7.02 (d, J=8 Hz, 2H), 7.09 (d, J=8 Hz, 2H), 7.25–7.45 (m, 4H), 7.51 (dd, J=7 Hz, 2 Hz, 1H), 7.80 (dd, J=8 Hz, 2 Hz, 1H), 8.21 (dd, J=4 Hz, 2 Hz, 1H).

EXAMPLE 212

2-{N-Propyl-N-[(2'-[1H-tetrazol-5-yl]biphenyl-4-yl)methyl]amino}pyridine-3-carboxylic acid di-sodium salt The title compound was prepared in analogy to Example 211 using two equivalents of sodium hydroxide. m.p. 230° C. $^1$H NMR (DMSO-d$_6$, 300 MHz) d 0.72 (t, J=7 Hz, 3H), 1.48 (m, 2H), 3.30 (t, J=7 Hz, 2H), 4.70 (s, 2H), 6.55 (dd, J=8 Hz, 4 Hz, 1H), 7.00 (d, J=8 Hz, 2H), 7.13 (d, J=8 Hz, 2H), 7.25–7.45 (m, 4H), 7.45 (dd, J=8 Hz, 2 Hz, 1H), 7.50 (dd, J=7 Hz, 2 Hz, 1H), 7.95 (dd, J=4 Hz, 2 Hz, 1H).

EXAMPLE 213

2-{N-Propyl-N-[(4'-[fluoro]-2-[1H-tetrazol-5-yl]biphenyl-5-yl)methyl]amino}pyridine-3-carboxylic acid 4-Methyl-salicylic acid is converted to methyl 2-methoxy-4-methylbenzoate by the method of Cannon, J. Med. Chem. 23, 750 (1980). The methyl ester is then hydrolyzed with sodium hydroxide to the benzoic acid.

Using the method of Carini et al., J. Med. Chem. 34, 2525 (1991), the above benzoic acid is converted into N-triphenylmethyl-5-[2-(3-bromomethyl-4'-fluorobiphenyl-5-yl)]tetrazole in seven steps.

The above tetrazole is reacted with ethyl 2-propylaminopyridine-3-carboxylate using the procedure described in Example 142B except that the reaction is run at −30° C. to give ethyl 2-{N-propyl-N-](4'-[fluoro]-2-[1H-tetrazol-5-yl]biphenyl-5-yl)methyl]amino}pyridine-3-carboxylate.

The above ethyl ester is dissolved in a 3:2 mixture of formic acid and methylene chloride for 2 hours to remove the triphenylmethyl protecting group. The resulting compound is hydrolyzed with sodium hydroxide in ethanol to afford the title compound.

EXAMPLE 214

2{N-Propyl-N-[(4'-[fluoro]-2-[1H-tetrazol-5-yl]biphenyl-4-yl)methyl]amino}pyridine-3-carboxylic acid Following the procedure described in Example 213 and starting with 5-methyl-salicylic acid instead of 4-methyl-salicylic acid gives the title compound.

EXAMPLE 215

2-{N-Propyl-N-[(2-carboxy-3'-hydroxy-biphenyl-4-yl)methyl]amino}pyridine-3-carboxylic acid

EXAMPLE 215A

Methyl 2-methoxy-4'-methyl-biphenyl-2-carboxylate

4-Bromotoluene is reacted with n-butyllithium in ether to give a solution of 4-tolyllithium. This is reacted with 3-fluoroanisole and then with carbon dioxide by the method described by Huisgen and Riss, Annalen der Chemie 594, 137 (1955) to give 2-methoxy-4'-methyl-biphenyl-2-carboxylic acid. This acid is converted to the title compound using diazomethane in ether.

EXAMPLE 215B

Methyl 4'-bromomethyl-2-methoxy-biphenyl-2-carboxylate

The compound resulting from Example 215A is reacted with N-bromosuccinimide in carbon tetrachloride using a catalytic amount of dibenzoyl peroxide to give the title compound.

EXAMPLE 215C

Ethyl 2-{N-propyl-N-[(2'-methoxycarbonyl-3'-methoxy-biphenyl-4-yl)methyl]amino}pyridine-3-carboxylate To the compound resulting from Example 87B, ethyl 2-propylaminopyridine-3-carboxylate, dissolved in tetrahydrofuran containing 4 equivalents of 1,3-dimethyl-3,4,5,6-tetrahydro-2(1H)-pyrimidinone (DMPU) and cooled to −30° C. is added dropwise a 1M solution of lithium hexamethyldisiliazide in tetrahydrofuran (1 equivalent). The solution is stirred for 10 minutes at −30° C. and then the compound resulting from Example 215B in tetrahydrofuran is added dropwise. The solution is allowed to warm to ambient temperature and toluene is added. The mixture is washed with water, dried and concentrated in vacuo to give the title compound.

EXAMPLE 215D

2-{N-Propyl-N-[(2-carboxy-3'-hydroxy-biphenyl-4-yl)methyl]amino}pyridine-3-carboxylic acid The compound resulting from Example 215C is hydrolyzed with sodium hydroxide in ethanol to give the diacid and then treated with boron tribromide in methylene chloride to give the title compound.

EXAMPLE 216

5,5-Dibenzylamino-2-{N-propyl-N-[(2'-[1H-tetrazol-5-yl]biphenyl-4-yl)methyl]amino}pyridine-3-carboxylic acid To the compound resulting from Example 198A (50 mg, 0.07 mmol) dissolved in tetrahydrofuran (1 mL) and 1,3-dimethyl-3,4,5,6-tetrahydro-2(1H)-pyrimidinone (DMPU) (1 mL) and cooled to 0° C. in an ice bath was treated with 1N lithium hexamethyldisilazide in tetrahydrofuran (0.15 mL). The solution was allowed to warm to ambient temperature and stirring was continued for 30 minutes. Benzyl bromide (0.18 mL) was added and the reaction stirred overnight at ambient temperature. The solvents were evaporated under reduced pressure and the residue treated with saturated sodium bicarbonate solution and extracted with ethyl acetate. The combined organic extracts were dried and concentrated in vacuo to give a yellow solid which was purified by flash chromatography 0.5:5:95 acetic acid/ethanol/methylene chloride to give a yellow solid which was deprotected and saponified by the procedure described in Example 195D to give the product as a pale yellow solid (15 mg, 35% yield), which was purified by flash chromatography 0.5:5:95 acetic acid/ethanol/chloroform.

EXAMPLE 217

6-Benzyloxy-2-{N-propyl-N-[(2'-[1H-tetrazol-5-yl]biphenyl-4-yl)methyl]amino}pyridine-3-carboxylic acid

EXAMPLE 217A

Methyl 6-phenylmethoxy-2-{N-propyl-N-[(2'-[1H-tetrazol-5-yl]biphenyl-4-yl)methyl]amino}pyridine-3-carboxylate and Benzyl 6-phenylmethoxy-2-{N-propyl-N-[(2'-[1H-tetrazol-5-yl]biphenyl-4-yl)methyl]amino}pyridine-3-carboxylate Benzyl alcohol (35 μL, 37 mg, 0.34 μmol) was added to a suspension of 60% oil dispersion sodium hydride (8.7 mg, 5.2 mg NaH, 0.22 μmol) in 0.15 mL of dimethylformamide under an argon atmosphere. The mixture was stirred at ambient temperature for 20 minutes, and then a solution of the resultant compound from Example 159 (47.6 mg, approx. 68 μmol) in 0.2 mL dimethylformamide was added rapidly dropwise. The resulting yellow solution was stirred at ambient temperature for 6 hours, then at 80° C. for a further 16 hours. The solution was concentrated under high vacuum, and the residue was partitioned between 10 mL 0.1M aqueous sodium hydrogen sulfate and 20 mL of methylene chloride. The aqueous phase was extracted with 2×10 mL of methylene chloride, and the combined organic phases were washed with 10 mL brine, dried over sodium sulfate, filtered, the filtrate concentrated under reduced pressure to a yellow oil, 70.5 mg. Preparative TLC (EtOAc-hexane 1:2 plus 0.5% HOAc) provided 18.2 mg (29.8 μmol, 44%) of the less polar product (benzyl ester) as a glass. TLC (1% HOAc in 1:1 EtOAc-hexane) $R_f$=0.29. $^1$H NMR (CDCl$_3$, 300 MHz) d 0.83 (t, J=7.5 Hz, 3H), 1.56–1.71 (m, 2H), 3.36–3.45 (m, 2H), 4.73 (s, 2H), 5.22 (s, 2H), 5.33 (s, 2H), 6.19 (d, J=9 Hz, 1H), 7.07 (m, 2H), 7.20 (br d, J=8 Hz, 2H), 7.23–7.45 (m, 14H), 7.50–7.61 (m, 2H), 7.98 (d, J=9 Hz, 1H), 8.25 (m, 1H). MS (DCl/NH$_3$) m/e 611 (M+H)$^+$. Also isolated was 11.1 mg (20.8 μmol, 31%) of the corresponding methyl ester as a glass. TLC (1% HOAc in 1:1 EtOAc-hexane) $R_f$=0.24. $^1$H NMR (CDCl$_3$, 300 MHz) d 0.87 (t, J=7.5 Hz, 3H), 1.60–1.75 (m, 2H), 3.40–3.49 (m, 2H), 3.77 (s, 3H), 4.75 (s, 2H), 5.33 (s, 2H), 6.19 (d, J=8 Hz, 1H), 7.15 (m, 2H), 7.23–7.43 (m, 16H), 7.50–7.62 (m, 2H), 7.94 (d, J=8 Hz, 1H), 8.29 (m, 1H). MS (DCl/NH$_3$) m/e 535 (M+H)$^+$.

EXAMPLE 217B

6-Benzyloxy-2-{N-propyl-N-[(2'-[1H-tetrazol-5-yl]biphenyl-4-yl)methyl]amino}pyridine-3-carboxylic acid The resultant more polar methyl ester from Example 217A (10.4 mg, 19.5 μmol) was dissolved in 0.1 mL of methanol and 0.09 mL 1.0M aqueous sodium hydroxide. The solution was heated (in a sealed vial) at 80° C. for 28 hours, then cooled and concentrated to an aqueous residue by means of a stream of nitrogen. The residue was partitioned between 5 mL of methylene chloride and 2 mL 1.0M aqueous sodium hydrogen sulfate, then the aqueous phase was extracted with 2×2 mL methylene chloride. The combined organic phases were washed with 2 mL brine, dried through a plug of sodium sulfate, and evaporated under high vacuum to provide a colorless glass. Purification by preparative TLC (1% HOAc in 1:1 CH$_2$Cl$_2$-EtOAc) produced 9.0 mg (17.3 μmol, 89%) of the title compound as a colorless glass. m.p. 68°-82° C. $^1$H NMR (CDCl$_3$, 300 MHz) d 0.88 (t, J=7.5 Hz, 3H), 1.37-1.52 (br m, 2H), 3.21-3.31 (br m, 2H), 4.12 (s, 2H), 5.49 (s, 2H), 6.65 (d, J=7.5 Hz, 2H), 6.77 (d, J=9 Hz, 1H), 6.86 (d, J=7.5 Hz, 2H), 7.20-7.55 (m, 10H), 7.84 (dd, J=1.5, 7 Hz, 1H), 8.25 (d, J=7.5 Hz, 1H). MS (DCl/NH$_3$) m/e 521 (M+H)$^+$.

EXAMPLE 218

6-(2-Pyridinyl)methoxy-2-{N-propyl-N-[(2'-[1H-tetrazol-5-yl]biphenyl-4-yl)methyl]amino}pyridine-3-carboxylic acid

EXAMPLE 218A

Methyl 6-(2-pyridinyl)methoxy-2-{N-propyl-N-[(2'-[1H-tetrazol-5-yl]biphenyl-4-yl)methyl]amino}pyridine-3-carboxylate and 2-Pyridinylmethyl 6-(2-pyridinyl)methoxy-2-{N-propyl-N-[(2'-[1H-tetrazol-5-yl]biphenyl-4-yl)methyl]amino}pyridine-3-carboxylate The title compound was prepared by the procedure described in Example 217A, with the substitution of 2-hydroxymethylpyridine for benzyl alcohol. Thus, the less polar product (methyl ester) was obtained in 20% yield. TLC (0.5% HOAc-2.5% MeOH-CH$_2$Cl$_2$) R$_f$=0.30. $^1$H NMR (CDCl$_3$, 300 MHz) δ 0.81 (t, J=8.5 Hz, 3H), 1.55-1.70 (br m, 2H), 3.20-3.27 (m, 2H), 3.86 (s, 3H), 4.44 (s, 2H), 5.19 (s, 2H), 6.27 (d, J=8.5 Hz, 1H), 6.93-7.03 (m, 4H), 7.14-7.19 (m, 1H), 7.37 (br d, J=8.5, 7 Hz, 1H), 7.43-7.46 (m, 1H), 7.49-7.60 (m, 3H), 7.93 (d, J=8.5 Hz, 1H), 8.04-8.09 (m, 1H), 8.14 (m, 1H). MS (DCl/NH$_3$) m/e 536 (M+H)$^+$. In addition, the 2-pyridinylmethyl ester was obtained in 13% yield. TLC (0.5% HOAc-2.5% MeOH-CH$_2$Cl$_2$) R$_f$=0.24. $^1$H NMR (CDCl$_3$) δ 0.78 (t, J=8 Hz, 3H), 1.51-1.70 (br m, 2H), 3.32-3.40 (br m, 2H), 4.55 (s, 2H), 5.15 (s, 2H), 5.39 (s, 2H), 6.29 (d, J=8 Hz, 1H), 6.77 (d, J=7.5 Hz, 2H), 6.92 (d, J=7.5 Hz, 2H), 7.15-7.23 (m, 2H), 7.34-7.46 (m, 3H), 7.50-7.62 (m, 2H), 7.67-7.77 (m, 2H), 7.95-8.00 (m, 2H), 8.12-8.17 (m, 1H), 8.39-8.44 (m, 1H). MS (DCl/NH$_3$) m/e 613 (M+H)$^+$.

EXAMPLE 218B 6-(2-Pyridinyl)methoxy-2-{N-propyl-N-[(2'-[1H-tetrazol-5-yl]biphenyl-4-yl)methyl]amino}pyridine-3-carboxylic acid The title compound was prepared by the procedure described in Example 217B using the mixture of both resultant products from Example 218A as the substrate. Thus 10.5 mg (19.6 μmol) of the mixture of esters was treated with 0.18 mL of 1.0M aqueous sodium hydroxide in 0.36 mL methanol as described to produce the title compound in 80% yield. m.p. 77°-83° C. TLC (1% HOAc-EtOAc) R$_f$=0.15. $^1$H NMR (CDCl$_3$, 300 MHz) δ 0.83 (t, J=7.5 Hz, 3H), 1.25-1.45 (bm, 2H), 3.15-3.30 (m, 2H), 4.12 (s, 3H), 5.51 (s, 2H), 6.72 (bd, J=7.5 Hz, 2H), 6.80-6.95 (m, 3H), 7.20-7.29 (m, 1H), 7.35 (bd, J=6.5 Hz, 1H), 7.42-7.58 (m, 3H), 7.74 (td, J=1.5, 7.5 Hz, 1H), 7.88 (bd, J=8 Hz, 1H), 8.35 (bd, J=9 Hz, 1H), 8.49-8.52 (m, 1H); MS (DCl/NH$_3$) m/e 522 (M+H)$^+$.

EXAMPLE 219

6-{N-Propyl-N-[(2'-[1H-tetrazol-5-yl]biphenyl-4-yl)methyl]amino}-2-pyridone-5-carboxylic acid The resultant less polar benzyl ester from Example 217A is hydrogenolyzed using 1 atmosphere hydrogen over 10% palladium on carbon in methanol with added triethylamine to provide the title compound.

EXAMPLE 220

6-(2-Hydroxyphenyl)methoxy-2-{N-propyl-N-[(2'-[1H-tetrazol-5-yl]biphenyl-4-yl)methyl]amino}pyridine-3-carboxylic acid The title compound is prepared by the procedures described in Example 217 substituting 2-hydroxymethylpyridine for benzyl alcohol.

EXAMPLE 221

3-(N-Cyanoguanidinyl)-2-{N-propyl-N-[(2'-[1H-tetrazol-5-yl]biphenyl-4-ylmethyl]amino}pyridine

EXAMPLE 221A 3-(S-Methyl-N'-cyanoisothioureido)-2-}N-propyl-N-[(2'-[N-triphenylmethyl-1H-tetrazol-5-yl]biphenyl-4-ylmethyl]amino}pyridine The procedure of Arrowsmith, J. E.; Campbell, S. F.; Cross, P. E. ; Burges, R. A.; Gardiner, D. G. J. Med. Chem. 1989, 32, 562–568, is adapted. The resultant compound from Example 93A can be reacted with dimethyl N-cyanodithioiminocarbonate to provide the title compound.

EXAMPLE 221B 3-(N-Cyanoguanidinyl)-2-{N-propyl-N-[(2'-[1H-tetrazol-5-yl]biphenyl-4-ylmethyl]amino}pyridine The resultant compound from Example 221A is dissolved in a mixture of ethanol and concentrated ammonium hydroxide according to the procedure of Arrowsmith, J. E.; Campbell, S. F.; Cross, P. E.; Burges, R. A.; Gardiner, D. G. J. Med. Chem. 1989, 32, 562–568 to provide the desired compound.

EXAMPLE 222

3-[(5-Amino-1,2,4-triazol-3-yl)amino]-2-{N-propyl-N-[(2'-[1H-tetrazol-5-yl]biphenyl-4-ylmethyl]amino}pyridine The title compound is prepared by the procedure described in Example 221B substituting hydrazine monohydrate for 30% aqueous ammonium hydroxide.

EXAMPLE 223

3-[(5-Amino-1,2,4-oxadiazol-3-yl)amino]-2-{N-propyl-N-[(2'-[1H-tetrazol-5-yl]biphenyl-4-ylmethyl]amino}pyridine The title compound is prepared by the procedure described in Example 221B substituting hydroxylamine hydrochloride and one equivalent of diisopropylethylamine for 30% aqueous ammonium hydroxide.

EXAMPLE 224

3-Thioureido-2-{N-propyl-N-[(2'-[1H-tetrazol-5-yl]biphenyl-4-ylmethyl]amino}pyridine The procedure of Example 221A with the substitution of N,N'-thiocarbonyldiimidazole for dimethyl N-cyanodithioiminocarbonate gives an intermediate thionoimidazolide. This intermediate is then treated with concentrated aqueous ammonium hydroxide with heating, followed by hydrolysis of the trityl protecting group according to the procedure of Example 221B, to give the title compound.

EXAMPLE 225

3-Ureido-2-{N-propyl-N-[(2'-[1H-tetrazol-5-yl]biphenyl-4-ylmethyl]amino}pyridine The procedure of Example 221A with the substitution of trimethylisocyanate for dimethyl N-cyanodithioiminocarbonate gives an intermediate N-trimethylsilyl urea. This intermediate is then hydrolyzed according to the procedure of Example 221B to provide the title compound.

EXAMPLE 226

2-{N-[(2'-[1H-Tetrazol-5-yl]biphenyl-4-ylmethyl]amino}pyridine-3-carboxylic acid To the compound resulting from Example 206 (25 mg, 0.06 mmol) dissolved in dimethylformamide (3 mL) was added 10% palladium on carbon (8 mg). The suspension was stirred for 4 hours under 1 atmosphere of hydrogen gas and then diluted with ethyl acetate (200 mL) and filtered. The filtrate was washed with saturated aqueous brine, dried over sodium sulfate and concentrated in vacuo to afford the title compound as a colorless powder (17 mg). $^1$H NMR (DMSO-$d_6$, 300 MHz) d 4.70 (s, 2H), 6.63 (m, 1H), 7.04 (d, J=9 Hz, 2H), 7.23 (d, J=9 Hz, 2H), 7.50-7.70 (m, 5H), 8.10 (m, 1H), 8.25 (m, 1H), 8.50 (bs, 1H).

EXAMPLE 227

2-{N-Propyl-N-[1-carboxy-2-(biphenyl-4-yl)ethyl]amino}pyridine-3-carboxylic acid Biphenylalanine methyl ester, prepared as described in *Chem. Pharm. Bull.* 24, 3149 (1976), is protected using Cbz-N-hydroxysuccinimide to give the N-Cbz compound. This compound is reacted with sodium hydride and n-propyltriflate to give the N-Cbz-N-propylbiphenylalanine methyl ester. Catalytic hydrogenation using palladium on carbon under hydrogen removes the Cbz-group and gives the N-propyl compound. This compound is coupled with methyl 2-chloronicotinate in dimethylformamide containing triethylamine with heating and then the diester is hydrolyzed under basic conditions to afford the dicarboxylic title compound.

EXAMPLE 228

2-{N-Propyl-N-[(2'-[trifluoromethanesulfonamido]-biphenyl-4-yl)methyl]amino}pyridine-3-carboxylic acid

EXAMPLE 228A 2-(p-Tolyl)aniline

A solution of 1.00 g (4.7 mmol) of 2-(p-tolyl)benzoic acid, 1.2 mL (5.6 mmol) of diphenylphosporyl azide and 0.8 mL (5.8 mmol) of triethylamine in 20 mL of anhydrous toluene was heated at 65°-70° C. for 75 minutes and then at 90°-100° C. for 1 hour. The toluene was removed under reduced pressure and the residue applied to ~100 g of silica gel and eluted with 5:95 ethyl acetate in hexanes to afford 700 mg of a colorless oil. To that oil was added ~5 mL of 8N hydrochloric acid and the solution was stirred and heated at 100°-110° C. for 15 minutes and at ambient temperature overnight. The solution was reluxed for an additional 90 minutes, then basified to pH ~10 and extracted with ethyl acetate. The combined organic extracts were washed with brine, dried over sodium sulfate and concentrated in vacuo to provide 670 mg of an oily residue. Trituration with hexane afforded 130 mg which was further purified by flash chromatography on silica gel eluting with 1:2 ethyl acetate in hexane to afford 84 mg of the title compound as a white solid. MS (DCl/NH$_3$) m/e 184 (M+H)$^+$, 201 (M+H+NH$_3$)$^+$.

EXAMPLE 228B 2-(p-Tolyl)aniline trifluorosulfonamide

To the compound resulting from Example 228A (34 mg, 0.19 mmol) in 2 mL of methylene chloride was added 47 mg (0.23 mmol) of 2,6-di-t-butyl-4-methylpyridine. To the solution cooled to 0° C. under nitrogen was added 30 μL (0.18 mmol) of trifluoroacetic anhydride. The reaction was stirred at ~5° C. for 1 hour and then allowed to warm to ambient temperature over 3 hours. The solution was diluted with ethyl acetate and washed 2× with water and 2× with brine, dried over sodium sulfate and concentrated under reduced pressure to afford 60 mg of soft yellow solid. The solid was dissolved in methylene chloride and treated with hexane to afford 26 mg of the title compound.

EXAMPLE 228C 2-(p-Bromomethylphenyl)aniline trifluorosulfonamide

The compound resulting from Example 228B (21 mg, 0.067 mmol) was slurried in ~3.5 mL of carbon tetrachloride, 12 mg (0.067 mmol) N-bromosuccinimide, and 1 mg (4.0 μmol) 2-(4-biphenylyl)-5-phenyloxazole (BPO). The slurry was refluxed for 5 hours and then cooled to ambient temperature overnight. The reaction mixture is worked up to afford the title compound.

EXAMPLE 228D

2-{N-Propyl-N-[(2'-[trifluoromethanesulfonamido]-biphenyl-4-yl)methyl]amino}pyridine-3-carboxylic acid The compound resulting from Example 228C is reacted with n-propylamine in tetrahydrofuran by the procedure described in Example 72B to afford the N-propylaminomethyl compound. Treatment of this compound with ethyl 2-chloronicotinate by the procedure described in Example 72B gives ethyl 2-{N-propyl-N-[(2'-[trifluoromethanesulfonamido]biphenyl-4-yl)methyl]amino}pyridine-3-carboxylate. Ester hydrolysis using sodium hydroxide in methanol/water affords the title compound.

EXAMPLE 229

2-{N-Butyl-N-[(2'-[1H-tetrazol-5-yl]biphenyl-4-yl)methyl]amino}pyridine-3-carboxylic acid

EXAMPLE 229A

Ethyl 2-{N-butyl-N-[(2'-[1H-tetrazol-5-yl]biphenyl-4-yl)methyl]amino}pyridine-3-carboxylate Ethyl 2-chloropyridine-3-carboxylate (8.00 g) was heated at 100° C. for 5 hours with 16 mL of n-butylamine and 34 mL of ethanol in an autoclave. The product was chromatographed on silica gel to give 7.69 g of ethyl 2-butylaminopyridine-3-carboxylate. This compound was reacted with N-triphenylmethyl-5-[2-(4'-bromomethyl-biphenyl)]tetrazole, prepared as described by P. E. Aldrich, et al., in European Patent Application Number 291969, using the procedure described in Example 87 to give ethyl 2-{N-butyl-N-[(2'-[N-triphenylmethyl-1H-tetrazol-5-yl]biphenyl-4-yl)methyl]amino}pyridine-3-carboxylate in 61% yield. m.p. 90°-94° C. Treatment of 1.50 g of this compound with 14 mL of methylene chloride and 21 mL of 88% formic acid for 1 hour at ambient temperature gave 690 mg of the title compound. m.p. 120°-121° C. $^1$H NMR (CDCl$_3$, 300 MHz) d 0.85 (t, J=7 Hz, 3H), 1.22 (m, 2H), 1.36 (t, J=7 Hz, 3H), 1.55 (m, 2H), 3.29 (t, J=7 Hz, 2H), 4.31 (q, J=7 Hz, 2H), 4.60 (s, 2H), 6.69 (dd, J=4 Hz, 8 Hz, 1H), 7.11 (d, J=8 Hz, 2H), 7.25 (d, J=8 Hz, 2H), 7.45 (dd, J=8 Hz, 2 Hz, 1H), 7.50-7.70 (m, 4H), 7.92 (dd, J=8 Hz, 1 Hz, 1H), 8.05 (dd, J=4 Hz, 2 Hz, 1H), 8.17 (dd, J=8 Hz, 1 Hz, 1H).

EXAMPLE 229B

2-{N-Butyl-N-[(2'-[1H-tetrazol-5-yl]biphenyl-4-yl)methyl]amino}pyridine-3-carboxylic acid The compound resulting from Example 229A (565 mg) was refluxed for 90 minutes with 0.4 g of sodium hydroxide in 4 mL of water and 24 mL of ethanol to give 467 mg of the title compound. m.p. 203°-205° C. $^1$H NMR (DMSO-d$_6$, 300 MHz) d 0.79 (t, J=7 Hz, 3H), 1.15 (m, 2H), 3.25 (t, J=7 Hz, 2H), 4.67 (s, 2H), 6.80 (dd, J=8 Hz, 4 Hz, 1H), 7.02 (d, J=8 Hz, 2H), 7.23 (d, J=8 Hz, 2H), 7.50-7.70 (m, 4H), 7.88 (dd, J=8 Hz, 2 Hz, 1H), 8.22 (dd, J=4 Hz, 2 Hz, 1H).

EXAMPLE 230

2-{N-Propyl-N-[(2'-[1H-tetrazol-5-yl]biphenyl-4-yl)methyl]amino}-4-trifluoromethyl-pyridine-3-carboxylic acid Claisen condensation of ethyl trifluoroacetoacetic ester is reacted with malonamic acid ethyl ester in the presence of sodium ethoxide in ethanol according to the procedure of Portnoy, J. Org. Chem., 3377 (1965) gives ethyl 6-hydroxy-4-trifluoromethylpyridin-2-one-3-carboxylate. Chlorination with phosphorus oxychloride gives ethyl 2,6-dichloro-4-trifluoromethylnicotinate. Treatment of the dichloro compound with N-triphenylmethyl-5-[2-(4'-propylaminomethyl-biphenyl)]tetrazole, prepared as described in Example 72B, in tetrahydrofuran containing triethylamine affords ethyl 6-chloro-2-{N-propyl-N-[(2'-[N-triphenylmethyl-1H-tetrazol-5-yl]biphenyl-4-yl)methyl]amino}-4-trifluoromethyl-pyridine-3-carboxylate. Treatment with Raney nickel removes the chlorine to give ethyl 2-{N-propyl-N-[(2'-[N-triphenylmethyl-1H-tetrazol-5-yl]biphenyl-4-yl)methyl]amino}-4-trifluoromethyl-pyridine-3-carboxylate. This compound is treated with p-toluenesulfonic acid monohydrate in methanol to detritylate and then treated with sodium hydroxide in methanol to hydrolyze the ester and give the title compound.

EXAMPLE 231

2-{N-Propyl-N-[(2'-[1H-tetrazol-5-yl]biphenyl-4-yl)methyl]amino}-5-trifluoromethyl-pyridine-3-carboxylic acid Ethyl 5-iodopyridin-2-one-3-carboxylate, prepared by the method of Taylor, J. Org. Chem. 54, 36 (1989), is treated with tert-butyldimethylsilyl chloride (TBSCl) in methylene chloride containing triethylamine to give the O-silylated pyridine. Treatment of ethyl 2-tert-butyldimethylsilyloxy-5-iodopyridine-3-carboxylate with bis(trifluoromethyl)cadmium in the presence of copper (I) bromide in dimethylformamide gives the ethyl 2-tert-butyldimethylsilyloxy-5-trifluoromethylpyridine-3-carboxylate compound. Treatment of the silyloxy compound with aqueous hydrochloric acid in tetrahydrofuran removes the silyl protecting group. Treatment of ethyl 2-hydroxy-5-trifluoromethylpyridine-3-carboxylate with phosphorus oxychloride affords the 2-chloro compound. Treatment of ethyl 2-chloro-5-trifluoromethylpyridine-3-carboxylate with N-triphenylmethyl-5-[2-(4'-propylaminomethyl-biphenyl)]tetrazole, prepared as described in Example 72B, in tetrahydrofuran containing triethylamine affords the tertiary amine. Treatment of ethyl 2-{N-propyl-N-[(2'-[N-triphenylmethyl-1H-tetrazol-5-yl]biphenyl-4-yl)methyl]amino}-5-trifluoromethyl-pyridine-3-carboxylate with p-toluenesulfonic acid monohydrate in methanol to detritylate followed by sodium hydroxide in methanol hydrolysis gives the title compound.

EXAMPLE 232

2-{N-Propyl-N-[(2'-[1H-tetrazol-5-yl]biphenyl-4-yl)methyl]amino}-6-trifluoromethyl-pyridine-3-carboxylic acid Ethyl 6-trifluoromethylpyridin-2-one-3-carboxylate, prepared by the method described in Helv. Chim. Acta. 71, 596 (1988), is chlorinated with phosphorus oxychloride to give the 2-chloro compound. Treatment of ethyl 2-chloro-6-trifluoromethylpyridine-3-carboxylate with N-triphenylmethyl-5-[2-(4'-propylaminomethyl-biphenyl)]tetrazole, prepared as described in Example 72B, in tetrahydrofuran containing triethylamine affords the tertiary amine. Treatment of ethyl 2-{N-propyl-N-[(2'-[N-triphenylmethyl-1H-tetrazol-5-yl]biphenyl-4-yl)methyl]amino}-6-trifluoromethyl-pyridine-3-carboxylate with p-toluenesulfonic acid monohydrate in methanol to detritylate followed by sodium hydroxide in methanol hydrolysis gives the title compound.

EXAMPLE 233

5-[2-(4'-N-Propylaminomethyl-biphenyl)]tetrazole hydrochloride

EXAMPLE 233A

N-Benzyloxymethyl-5-(2-bromophenyl)tetrazole 5-(2-Bromophenyl)-[1H]-tetrazole was nitrogen-protected as the benzyloxymethyl (BOM) ether by reaction of a solution of the tetrazole in anhydrous dimethylformamide with technical grade BOM-chloride and anhydrous potassium carbonate. The reaction was complete in less than 60 minutes and the work up involved filtration through Celite and evaporation of the solvent under reduced pressure. The residue obtained was purified by chromatography to afford the title product in 70% yield as an oil which crystallized on standing.

EXAMPLE 233B

N-(4-Bromobenzyl-N-propylamine

To 4-bromobenzaldehyde (100 g, 0.54 mol) and n-propylamine (36.3 g, 0.60 mol) in methanol (100 mL) was added 5% platinum on carbon (1.00 g). This mixture was shaken in a Parr hydrogenation reactor overnight to complete formation of the Schiff base. The reaction was then hydrogenated under 4 atmospheres of hydrogen until the theoretical uptake of hydrogen had been consumed. The catalyst was removed by filtration through a 0.45 m nylon frit and washed with methanol. The filtrate was concentrated under reduced pressure and the residue obtained dissolved in ether (500 mL).

The ether solution was washed with water (2×100 mL), 10% sodium bicarbonate solution (2×100 mL), and water (2×100 mL), dried over magnesium sulfate, filtered, and concentrated under reduced pressure to afford the crude title compound (121.34 g). GC-MS showed this material to be 98.5% pure product containing 1.5% of the desbromo compound; the yield is 96.93% based on the GC purity of the product obtained. A sample of this material was purified by bulb-to-bulb distillation (bath temperature 130°-150° C., 0.18 torr). $^1$H NMR (CDCl$_3$, 300 MHz) d 0.92 (t, J=7.4 Hz, 3H), 1.36 (bs, 1H) 1.53 (tq, J$_1$=J$_2$=7.4 Hz, 2H) 2.57 (t, J=7.4 Hz, 2H),3.74 (s, 2H), 7.20 (d, J=9 Hz, 2H), 7.44 (d, J=9 Hz, 2H). IR (film) 1430, 1060 cm$^{-1}$. MS (DCl/NH$_3$) m/e 228, 230 (M+H)$^+$.

EXAMPLE 233C

4-[(N-tert-Butyloxycarbonyl-N-propylamino)methyl]-phenyl boronic acid

To the compound resulting from Example 233B in methylene chloride at 0° C. was added triethylamine (2 equivalents) and di-tert-butyldicarbonate (1.05 equivalents). The cooling bath was removed and the mixture allowed to warm to ambient temperature. The solution was diluted with a suitable solvent (ether or hexane), washed with 2N hydrochloric acid, dried over sodium sulfate and concentrated in vacuo. The Boc-protected compound was obtained as a colorless oil in quantitative yield and was used without further purification.

Grignard formation was effected by treatment of magnesium (1.2 equivalents) in tetrahydrofuran with dibromoethane (0.05 equivlants) followed by heating to reflux and then adding a solution of the protected compound from above in tetrahydrofuran. The reaction mixture turned brown and after 4 hours, most of the metal had been consumed. The Grignard reagent was cooled in a dry ice/acetone bath and then transferred via cannula into a −70° C. solution of trimethyl borate (2.5 equivalents) (∼2 M in tetrahydrofuran). Upon completion of the addition, the cooling bath was removed and the mixture allowed to warm to ambient temperature. The solution was diluted with ether (4 volumes), washed with 3N hydrochloric acid, ensuring that the aqueous layer was pH 2 or lower. The pH was then adjust to 10 by the addition of 1N sodium hydroxide and the ether layer was discarded. The aqueous solution was cooled to 0° C., carefully acidified to pH 2 with 3N hydrochloric acid and extracted with ether. The combined organic extracts were dried over sodium sulfate and concentrated in vacuo to about 20% of volume whereupon the boronic acid crystallizes in 36% yield.

EXAMPLE 233D

N-Benzyloxymethyl-5-{2-[4'-(N-propyl-N-tert-butyloxycarbonylamino)methyl-biphenyl]}tetrazole To palladium tetrakis(triphenylphosphine) (0.05 equivalents) dissolved in toluene was added a solution of the compound resulting from Example 233A (1 equivalent). After 10 minutes, a 2M aqueous solution of sodium carbonate was added followed by the compound resulting from Example 233C dissolved in the minimum amount of ethanol. The two-phase mixture was rapidly stirred under reflux for 2.5 hours and then cooled to ambient temperature. The solution was diluted with ether and the organic phase was dried over sodium sulfate and concentrated in vacuo to afford a brown oil. Filtration through silica gel eluting with 35% ether in hexanes afforded the title compound as a colorless oil (87%).

EXAMPLE 233E

5-[2-(4'-N-Propylaminomethyl-biphenyl)]tetrazole hydrochloride

To the compound resulting from Example 233D (1.00 g, 1.94 mmol) dissolved in 1 mL of absolute ethanol at ambient temperature was added a solution of anhydrous hydrogen chloride (g) dissolved in ethanol (5 mL, 11.2 M). There was observed an immediate evolution of carbon dioxide which lasted about 90 minutes; also during this time a heavy white precipitate appeared. After 3 hours, the solvent was removed in vacuo and the residue triturated with 8 mL of ethyl acetate. The white solid was then dried in vacuo at 60° C. to afford the title compound (553 mg, 86%).

In addition, the following compounds can be prepared according to the methods outlined above:

2-{N-Butyl-N-[(2'-[1H-tetrazol-5-yl]biphenyl-4-yl)methyl]amino}pyridine-3-carboxylic acid;

2-{N-Ethyl-N-[(2'-[1H-tetrazol-5-yl]biphenyl-4-yl)methyl]amino}pyridine-3-carboxylic acid;

2-{N-Allyl-N-[(2'-[1H-tetrazol-5-yl]biphenyl-4-yl)methyl]amino}pyridine-3-carboxylic acid;

2-{N-(2-Propynyl)-N-[(2'-[1H-tetrazol-5-yl]biphenyl-4-yl)methyl]amino}pyridine-3-carboxylic acid;

2-{N-Cyclopropylmethyl-N-[(2'-[1H-tetrazol-5-yl]biphenyl-4-yl)methyl]amino}pyridine-3-carboxylic acid;

2-{N-(2-Butyl)-N-[(2'-[1H-tetrazol-5-yl]biphenyl-4-yl)methyl]amino}pyridine-3-carboxylic acid;

2-{N-(3,3,3-Trifluoropropyl)-N-[(2'-[1H-tetrazol-5-yl]biphenyl-4-yl)methyl]amino}pyridine-3-carboxylic acid;

2-{N-(3-Methylbutyl)-N-[(2'-[1H-tetrazol-5-yl]biphenyl-4-yl)methyl]amino}pyridine-3-carboxylic acid;

2-{N-(3,3-Dimethylbutyl)-N-[(2'-[1H-tetrazol-5-yl]biphenyl-4-yl)methyl]amino}pyridine-3-carboxylic acid;

4-Trifluoromethyl-2-{N-propyl-N-[(2'-[1H-tetrazol-5-yl]biphenyl-4-yl)methyl]amino}pyridine-3-carboxylic acid;

6-Methyl-4-trifluoromethyl-2-{N-propyl-N-[(2'-[1H-tetrazol-5-yl]biphenyl-4-yl)methyl]amino}pyridine-3-carboxylic acid;

4,6-Dimethyl-2-{N-propyl-N-[(2'-[1H-tetrazol-5-yl]biphenyl-4-yl)methyl]amino}pyridine-3-carboxylic acid;

6-Dimethylamino-2-{N-propyl-N-[(2'-[(2'-[1H-tetrazol-5-yl]biphenyl-4-yl)methyl]amino}pyridine-3-carboxylic acid;

6-Hydroxy-2-{N-propyl-N-[(2'-tetrazol-5-yl]biphenyl-4-yl)methyl]amino}pyridine-3-carboxylic acid;

4-{N-propyl-N-[(2'-[1H-tetrazol-5-yl]biphenyl-4-yl)methyl]amino}pyridine-3-carboxylic acid;

3-{N-propyl-N-[(2'-[1H-tetrazol-5-yl]biphenyl-4-yl)methyl]amino}pyridine-2-carboxylic acid;

2-{N-propyl-N-[(2'-[1H-tetrazol-5-yl]biphenyl-4-yl)methyl]amino}pyridine-6-carboxylic acid;

3-Trifluoromethanesulfonamido-2-{N-propyl-N-[(2'-[1H-tetrazol-5-yl]biphenyl-4-yl)methyl]amino}pyridine;

3-Acetylamino-2-{N-propyl-N-[(2'-[1H-tetrazol-5-yl]biphenyl-4-yl)methyl]amino}pyridine;

2-{N-propyl-N-[(2'-[1H-tetrazol-5-yl]biphenyl-4-yl)methyl]amino}pyridine-3-carbonitrile;

2-{N-propyl-N-[(2'-[1H-tetrazol-5-yl]biphenyl-4-yl)methyl]amino}pyridine-3-carboxamide;

3-Aminomethyl-2-{N-propyl-N-[(2'-[1H-tetrazol-5-yl]biphenyl-4-yl)methyl]amino}pyridine;

3-Methanesulfonamidomethyl-2-{N-propyl-N-[(2'-[1H-tetrazol-5-yl]biphenyl-4-yl)methyl]amino}pyridine;

3-Trifluoromethanesulfonamidomethyl-2-{N-propyl-N-[(2'-[1H-tetrazol-5-yl]biphenyl-4-yl)methyl]amino}pyridine;

3-Acetylaminomethyl-2-{N-propyl-N-[(2'-[1H-tetrazol-5-yl]biphenyl-4-yl)methyl]amino}pyridine;

3-Methylaminocarbonylaminomethyl-2-{N-propyl-N-[(2'-[1H-tetrazol-5-yl]biphenyl-4-yl)methyl]amino}pyridine;

3-Trifluoromethyl-2-{N-propyl-N-[(2'-[1H-tetrazol-5-yl]biphenyl-4-yl)methyl]amino}pyridine;

3-Trifluoromethyl-2-{N-propyl-N-[(2'-[1H-tetrazol-5-yl]biphenyl-4-yl)methyl]amino}pyridine;

2-Chloro-3-{N-propyl-N-[(2'-[1H-tetrazol-5-yl]biphenyl-4-yl)methyl]amino}pyridine;

2-Methoxy-5-{N-propyl-N-[(2'-[1H-tetrazol-5-yl]biphenyl-4-yl)methyl]amino}pyridine;

2-Phenoxy-5-{N-propyl-N-[(2'-[1H-tetrazol-5-yl]biphenyl-4-yl)methyl]amino}pyridine;

3,6-Dimethyl-2-{N-propyl-N-[(2'-[1H-tetrazol-5-yl]biphenyl-4-yl)methyl]amino}pyridine;

Trimethylacetoxymethyl 2-{N-propyl-N-[(2'-[1H-tetrazol-5-yl]biphenyl-4-yl)methyl]amino}pyridine-3-carboxylate, Cyclohexyloxycarbonyloxymethyl 2-{N-propyl-N-[(2'-[1H-tetrazol-5-yl]biphenyl-4-yl)methyl]amino}pyridine-3-carboxylate;

Methoxycarbonylmethyl 2-{N-propyl-N-[(2'-[1H-tetrazol-5-yl]biphenyl-4-yl)methyl]amino}pyridine-3-carboxylate, Methoxycarbonylaminomethyl 2-{N-propyl-N-[(2'-[1H-tetrazol-5-yl]biphenyl-4-yl)methyl]amino}pyridine-3-carboxylate;

Acetamidomethyl 2-{N-propyl-N-[(2'-[1H-tetrazol-5-yl]biphenyl-4-yl)methyl]amino}pyridine-3-carboxylate;

Methylaminocarbonylaminomethyl 2-{N-propyl-N-[(2'-[1H-tetrazol-5-yl]biphenyl-4-yl)methyl]amino}pyridine-3-carboxylate;

2-{N-Propyl-N-[(2'-[trifluoromethanesulfonamido]-biphenyl-4-yl)methyl]amino}pyridine-3-carboxylic acid;

2-{N-Propyl-N-[(2'-[trifluoromethanesulfonamidomethyl]biphenyl-4-yl)methyl]amino}pyridine-3-carboxylic acid;

2-{N-Propyl-N-[(2'-[1H-tetrazol-5-yl]biphenyl-4-yl)methyl]amino}pyridine-3-sulfonic acid;

2-{N-Butyl-N-[(2'-[1H-tetrazol-5-yl]biphenyl-4-yl)methyl]amino}pyridine-3-sulfonic acid;

2-{N-Propyl-N-[(2'-[1H-tetrazol-5-yl]biphenyl-4-yl)methyl]amino}pyridine-3-sulfonamide;

2-{N-Propyl-N-[(2'-[1H-tetrazol-5-yl]biphenyl-4-yl)methyl]amino}pyridine-6-sulfonic acid;

6-Methyl-2-{N-propyl-N-[(2'-[1H-tetrazol-5-yl]biphenyl-4-yl)methyl]amino}pyrimidine-4-carboxylic acid;

4-{N-Propyl-N-[(2'-[1H-tetrazol-5-yl]biphenyl-4-yl)methyl]amino}-2-(2'-pyridylmethylamino)-5-methylpyrimidine;

6-{N-Propyl-N-[(2'-[1H-tetrazol-5-yl]biphenyl-4-yl)methyl]amino}pyrimidine-4-carboxylic acid;

Methoxycarbonylaminomethyl 4-{N-propyl-N-[(2'-[1H-tetrazol-5-yl]biphenyl-4-yl)methyl]amino}pyrimidine-5-carboxylate;

Acetamidomethyl 4-{N-propyl-N-[(2'-[1H-tetrazol-5-yl]biphenyl-4-yl)methyl]amino}pyrimidine-5-carboxylate;

Methylaminocarbonylaminomethyl 4-{N-propyl-N-[(2'-[1H-tetrazol-5-yl]biphenyl-4-yl)methyl]amino}pyrimidine-5-carboxylate;

3-{N-Propyl-N-[(2'-[1H-tetrazol-5-yl]biphenyl-4-yl)methyl]amino}pyrazine-2-carboxylic acid;

4-{N-Propyl-N-[(2'-[1H-tetrazol-5-yl]biphenyl-4-yl)methyl]amino}pyridazine-5-carboxylic acid; and 4-{N-Propyl-N-[(2'-[1H-tetrazol-5-yl]biphenyl-4-yl)methyl]amino}pyridazine-3-carboxylic acid.

The compounds of the present invention can be used in the form of salts derived from inorganic or organic acids. Pharmaceutically acceptable salts are described in Berge, et al., J. Pharmaceutical Sciences 66 1–19 (1977). These salts include but are not limited to the following: acetate, adipate, alginate, citrate, ascorbate, aspartate, benzoate, benzenesulfonate, bisulfate, borate, butyrate, camphorate, camphorsulfonate, citrate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxyethanesulfonate, lactobionate, lactate, laurate, lauryl sulfate, maleate, methanesulfonate, nicotinate, 2-naphthalenesulfonate, oleate, oxalate, palmitate, pamoate, pectinate, persulfate, phosphate, 3-phenylpropionate, picrate, pivalate, propionate, stearate, succinate, tartrate, thiocyanate, toluenesulfonate (tosylate), undecanoate and valerate.

Examples of acids which can be employed to form pharmaceutically acceptable acid addition salts include such inorganic acids as hydrochloric acid, sulphuric acid and phosphoric acid and such organic acids as oxalic acid, maleic acid, succinic acid, methanesulfonic acid and citric acid. Other salts include salts with alkali metals or alkaline earth metals, such as sodium, potassium, calcium or magnesium or with organic bases. The salts can be prepared in situ during the final isolation and purification of the compounds of formula (I), or separately by reacting the free base function with a suitable acid or by reacting the acidic function with a suitable base.

The compounds of the present invention are useful for blocking the interaction of angiotensin II with angiotensin II receptors and for treating hypertension, edema, renal failure, congestive heart failure, glaucoma, psoriasis, benign prostatic hypertrophy, diabetic nephropathy, diabetic retinopathy, or to prevent atherosclerosis or for treating gastrointestinal disorders associated with enhanced contractility and/or motility of intestinal smooth muscle or for treating contractile disorders of the uterus (including premature contractions, dysmenorrhea and the like) or for treating or preventing stroke, cerebral vasospasm or cerebral infarction or for treating CNS disorders (depression, schizophrenia, anxiety or cognitive disorders (Alzheimer's disease, amnesia and senile dementia)) in a human or other mammal. The compounds of the invention are also useful for enhancing intimal wound closure and for reducing luminal thrombogenicity in a human or other mammal.

ANGIOTENSIN II FUNCTIONAL ASSAY

Antagonism of Contraction of Rabbit Aorta

The protocol reported by A. T Chiu and P. Timmermans (P. C. Wong, et al. *Hypertension*, 13, 489–497 (1989)) was followed with a few modifications. Female New Zealand White rabbits weighing 2–5 kg were sedated with carbon dioxide and then sacrificed. Main abdominal aortas were removed and placed in Krebs-Henseleit buffer at room temperature.

| Krebs-Henseleit buffer | |
|---|---|
| Buffer Component | mM concentration |
| sodium chloride | 119.00 |
| potassium chloride | 4.70 |
| potassium dihydrogen phosphate | 1.20 |
| calcium chloride | 2.50 |
| sodium bicarbonate | 20.00 |
| magnesium sulfate | 1.50 |
| dextrose | 11.00 |
| EDTA* disodium calcium salt | 0.01 |

*EDTA = ethylenediamine tetraacetic acid
The buffer contained no cocaine, propanolol or steroid.
The pH of the buffer was 7.40 at 37° C. when saturated with 5% carbon dioxide/95% oxygen.

The tissues were cleaned of extraneous connective tissue, cut into 3 mm rings, and suspended within a 10 mL tissue bath. All dilutions of peptide preparations were made with 0.3% aqueous BSA. The tissues were primed with 55 mM potassium chloride. Tissues were pre-loaded with 1 g of tension. Tension was recorded on a model 7 Grass polygraph using FT03 transducers. At the end of the equilibrium period, a control cumulative concentration-contractile response curve for angiotensin II (A II: $1 \times 10^{-10} - 10^{-8}$M) was obtained. The tissue was washed several times until the baseline was reached. Forty five minutes later, test compound (antagonist) was added and the tissue was incubated for 30 minutes. The concentration-response curve for A II was then repeated in the presence of the test compound. One dose of antagonist was tested per tissue only. For single dose shift experiments a dose of 1 mM of test compound was used, for a full $pA_2$ experiment multiple doses were used depending upon the potency of the antagonist.

All responses to the control agonist were calculated as a percentage of the maximum response. These points in duplicate were plotted and analyzed according to standard Schild analysis (H. O. Schild, *British J Pharmacology and Chemotherapy*, 2, 189–206 (1947). The $pA_2$ values calculated for the compounds of the invention are shown in Table 6. The $pA_2$ value is the negative logarithm of the $[A]_2$ value. $[A]_2$ is the concentration of antagonist which necessitates doubling the agonist concentration in order to achieve the agonist effect which was measured in the absence of antagonist.

The $pA_2$ value, therefore, is a measure of the effectiveness of the compound as an antagonist. The data in Table 5 show that the compounds of the invention are potent antagonists at the angiotensin II receptor.

TABLE 5

| $pA_2$ Values from Isolated Rabbit Aorta Assay | |
|---|---|
| Example | $pA_2$ |
| 53 | 9.90 |
| 71 | 9.68 |
| 76 | 8.81 |
| 82 | 9.48 |
| 88 | 10.1 |
| 99 | 9.60 |
| 114 | 8.79 |
| 121 | 9.59 |
| 135 | 8.47 |
| 137 | 8.34 |
| 140 | 8.84 |
| 147 | 9.20 |
| 157 | 9.87 |
| 160 | 9.63 |
| 162 | 9.51 |
| 163 | 9.51 |
| 167 | 8.48 |
| 168 | 9.07 |
| 169 | 10.05 |
| 172 | 9.67 |
| 180 | 9.04 |
| 194 | 9.64 |
| 203 | 8.65 |
| 206 | 8.93 |
| 226 | 8.89 |
| 229 | 9.47 |
| Sar, −1, Thr-8 All (SARILE) | 9.02 |

The ability of the compounds of the invention to lower blood pressure in vivo can be demonstrated according to the method outlined below.

IN VIVO BLOOD PRESSURE LOWERING

When administered at a dose of 30 mg/kg to renal artery ligated rats (see Cangiano, et al., J. Pharmacol. Exp. Ther. 208 310 (1979)), the compound of Example 88 caused a reduction in mean arterial blood pressure (MAP) as shown in Table 6.

TABLE 6

| | Blood Presure Lowering Effect of Angiotensin II Antagonist In Renal Artery Ligated Hypertensive Rats | | | | | | | |
|---|---|---|---|---|---|---|---|---|
| | Dose | Baseline MAP | Change in Baseline MAP After Test Compound Administration (mm Hg) | | | | | |
| Ex. No. | (mg/kg. iv) | (mm Hg) | 30 min. | 60 min. | 90 min. | 120 min. | 150 min. | 180 min. |
| 88 | 0.3 (n = 5) | 165 | −17 | −22 | −30 | −31 | −32 | −33 |

The total daily dose of the compounds of this invention administered to a human or other mammal in single or in divided doses can be in amounts, for example, from 0.01 to 25 mg/kg body weight or more usually from 0.1 to 15 mg/kg body weight. Single dose compositions can contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches. The term parenteral as used herein includes subcutaneous injections, intravenous, intramuscular, intrasternal injection, or infusion techniques.

Liquid dosage forms for oral administration can include pharmaceutically acceptable emulsions, microemulsions, solutions, suspensions, syrups and elixirs containing inert diluents commonly used in the art such as water. Such compositions can also comprise adjuvants, such as wetting agents; emulsifying and suspending agents; sweetening, flavoring and perfuming agents.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration can include capsules, tablets, pills, powders, prills and granules. In such solid dosage forms the active compound can be admixed with at least one inert diluent such as sucrose, lactose or starch. Such dosage forms can also comprise, as is normal practice, additional substances other than inert diluents, e.g., tableting lubricants and other tableting aids such as magnesium stearate and microcrystalline cellulose. In the case of capsules, tablets and pills, the dosage forms can also comprise buffering agents. Tablets and pills can additionally be prepared with enteric coatings and other release-controlling coatings.

Solid compositions of a similar type can also be employed as fillers in soft and hard-filled gelatin capsules using such exipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulations, ear drops, eye ointments, powders and solutions are also contemplated as being within the scope of this invention.

The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

The compounds of the present invention can be administered alone or in combination or in concurrent therapy with other cardiovascular agents independently selected from diuretics, adrenergic blocking agents, vasodilators, calcium channel blockers, angiotensin converting enzyme (ACE) inhibitors, potassium channel activators, antiserotoninergic agents, thromboxane synthetase inhibitors, renin inhibitors and other agents useful for treating (in a human or other mammal) hypertension, edema or congestive heart failure.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside, flosequinan and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Representative antiserotoninergic agents include ketanserin and the like or a pharmaceutically acceptable salt thereof.

Representative renin inhibitiors include enalkiren, A-72517, PD-134672 or Ro 42-5892 and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compound of formula 1 and the other cardiovascular agent can be administered at the recommended maximum clinical dosage or at lower doses. Dosage levels of the active compounds in the compositions of the invention can be varied so as to obtain a desired therapeutic response depending on the route of administration, severity of the disease and the response of the patient. The combination can be administered as separate compositions or as a single dosage form containing both agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

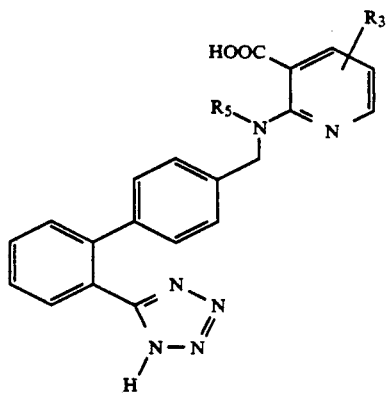

wherein $R_3$ is hydrogen, halo or loweralkyl and $R_5$ is loweralkyl; or a pharmaceutically acceptable salt thereof.

2. The compound of claim 1 wherein $R_3$ is hydrogen, methyl or halo and $R_5$ is n-propyl or n-butyl.

3. A compound of the formula:

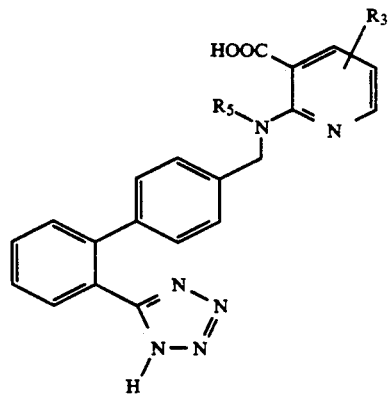

wherein $R_3$ is hydrogen, halo or loweralkyl and $R_5$ is n-propyl or n-butyl; or a pharmaceutically acceptable salt thereof.

4. A compound of the formula:

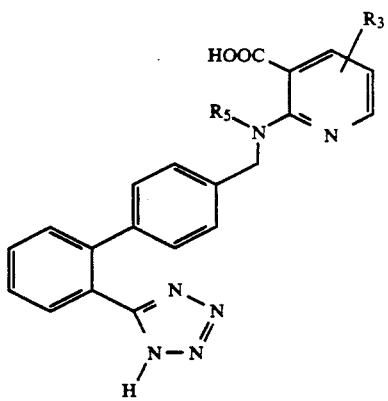

wherein R₃ is hydrogen and R₅ is n-propyl or n-butyl; or a pharmaceutically acceptable salt thereof.

5. 2-{N-Propyl-N-((2'-(1H-tetrazol-5-yl)biphenyl-4-yl)methyl)amino}-pyridine-3-carboxylic acid; or a pharmaceutically acceptable salt thereof.

6. A compound selected from the group consisting of:
2-{N-Propyl-N-((2'-(1H-tetrazol-5-yl)biphenyl-4-yl)methyl)amino}-6-fluoropyridine-3-carboxylic acid;
5-Fluoro-2-{N-propyl-N-((2'-(1H-tetrazol-5-yl)biphenyl-4-yl)methyl)amino}pyridine-3-carboxylic acid;
6-Methyl-2-{N-butyl-N-((2'-(1H-tetrazol-5-yl)biphenyl-4-yl)methyl)amino}pyridine-3-carboxylic acid;
2-{N-Propyl-N-((2'-(1H-tetrazol-5-yl)biphenyl-4-yl)methyl)amino}-6-fluoropyridine-3-carboxylic acid;
2-{N-Butyl-N-((2'-(1H-tetrazol-5-yl)biphenyl-4-yl)methyl)amino}-6-fluoropyridine-3-carboxylic acid;
5-Methyl-2-{N-propyl-N-((2'-(1H-tetrazol-5-yl)biphenyl-4-yl)methyl)amino}pyridine-3-carboxylic acid;
5-Chloro-2-{N-propyl-N-((2'-(1H-tetrazol-5-yl)biphenyl-4-yl)methyl)amino}pyridine-3-carboxylic acid;
5-Iodo-2-{N-butyl-N-((2'-(1H-tetrazol-5-yl)biphenyl-4-yl)methyl)amino}pyridine-3-carboxylic acid;
2-{N-Butyl-N-((2'-(1H-tetrazol-5-yl)biphenyl-4-yl)methyl)amino}pyridine-3-carboxylic acid;
2-{N-Ethyl-N-((2'-(1H-tetrazol-5-yl)biphenyl-4-yl)methyl)amino}pyridine-3-carboxylic acid;
2-{N-(2-Butyl)-N-((2'-(1H-tetrazol-5-yl)biphenyl-4-yl)methyl)amino}pyridine-3-carboxylic acid;
2-{N-(3-Methylbutyl)-N-((2'-(1H-tetrazol-5-yl)biphenyl-4-yl)methyl)amino}pyridine-3-carboxylic acid;
2-{N-(3,3-Dimethylbutyl)-N-((2'-(1H-tetrazol-5-yl)biphenyl-4-yl)methyl)amino}pyridine-3-carboxylic acid; and
4-Methyl-2-{N-propyl-N-((2'-(1H-tetrazol-5-yl)biphenyl-4-yl)methyl)amino}pyridine-3-carboxylic acid;
or a pharmaceutically acceptable salt thereof.

7. 2-{N-Propyl-N-((2'-(1H-tetrazol-5-yl)biphenyl-4-yl)methyl)amino}-pyridine-3-carboxylic acid monopotassium salt.

8. A pharmaceutical composition for blocking the interaction of angiotensin II with angiotensin II receptors comprising a pharmaceutically acceptable carrier and a therapeutically effective amount of a compound of claim 1.

9. A pharmaceutical composition for blocking the interaction of angiotensin II with angiotensin II receptors comprising a pharmaceutically acceptable carrier and a therapeutically effective amount of a compound of claim 5.

10. A pharmaceutical composition for blocking the interaction of angiotensin II with angiotensin II receptors comprising a pharmaceutically acceptable carrier and a therapeutically effective amount of a compound of claim 7.

11. A method of blocking the interaction of angiotensin II with angiotensin II receptors comprising administering to a human or other mammal in need a therapeutically effective amount of a compound of claim 1.

12. A method of treating hypertension or heart failure comprising administering to a human or other mammal in need a therapeutically effective amount of a compound of claim 1.

13. A method of blocking the interaction of angiotensin II with angiotensin II receptors comprising administering to a human or other mammal in need a therapeutically effective amount of a compound of claim 5.

14. A method of treating hypertension or heart failure comprising a administering to a human or other mammal in need a therapeutically effective amount of a compound of claim 5.

15. A method of blocking the interaction of angiotensin II with angiotensin II receptors comprising administering to a human or other mammal in need a therapeutically effective amount of a compound of claim 7.

16. A method of treating hypertension or heart failure comprising administering to a human or other mammal in need a therapeutically effective amount of a compound of claim 7.

* * * * *

UNITED STATES PATENT AND TRADEMARK OFFICE
CERTIFICATE OF CORRECTION

PATENT NO. : 5,250,548  
DATED : October 5, 1993  
INVENTOR(S) : Martin Winn; Biswanath De; Thomas M. Zydowsky, Daniel J. Kerkman;

Page 1 of 7

It is certified that error appears in the above-indentified patent and that said Letters Patent is hereby corrected as shown below:

On the title page item

" [75] Inventors: Martin Winn, Deerfield; Biswanath De, Buffalo Grove; Thomas M. Zydowsky, Waukegan; Daniel J. Kerkman, Lake Villa; John F. DeBernardis, Lindenhurst; Saul H. Rosenberg; Kazumi Shiosaki, both of Libertyville; Fatima Z. Basha, Lake Forest; Andrew S. Tasker, Lindenhurst; Thomas W. von Geldern, Richmond; Jeffrey A. Kester, Deerfield; Steven Boyd, Mundelein; Diane M. Yamamoto; Anthony K. L. Fung, Gurnee, all of Ill. "

Insert

[75] Inventors:  
-- Martin Winn, Deerfield; Biswanath De, Buffalo Grove; Thomas M. Zydowsky, Waukegan; Daniel J. Kerkman, Lake Villa; all of Ill.

COLUMN 4, LINE 42: Delete "--C(O)$R_5$--" and Insert -- --C(O)$R_{53}$--

COLUMN 10, LINE 49: Delete "alkenyl" and Insert --alkynyl--.

UNITED STATES PATENT AND TRADEMARK OFFICE
CERTIFICATE OF CORRECTION

PATENT NO. : 5,250,548
DATED : October 5, 1993
INVENTOR(S) : Martin Winn; Biswanath De; Thomas M. Zydowsky, Daniel J. Kerkman;

It is certified that error appears in the above-indentified patent and that said Letters Patent is hereby corrected as shown below:

COLUMN 48, LINES 55 THRU 70:

Delete  ``

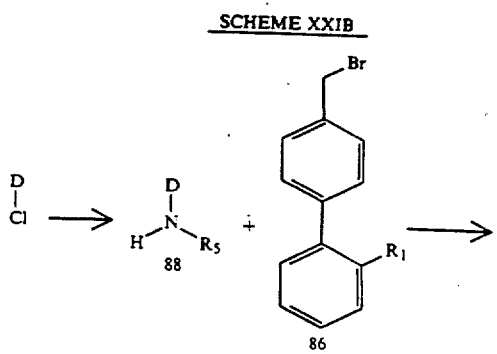

Insert

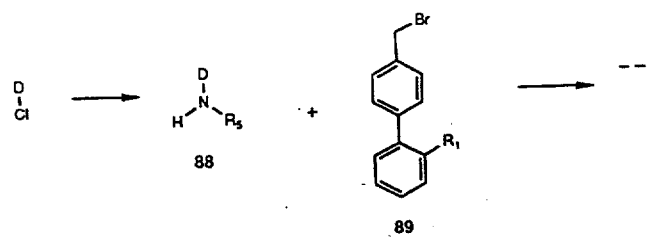

UNITED STATES PATENT AND TRADEMARK OFFICE
CERTIFICATE OF CORRECTION

PATENT NO. : 5,250,548
DATED : October 5, 1993
INVENTOR(S) : Martin Winn; Biswanath De; Thomas M. Zydowsky, Daniel J. Kerkman;

It is certified that error appears in the above-indentified patent and that said Letters Patent is hereby corrected as shown below:

COLUMN 53, LINES 20 THRU 35:

Delete

" 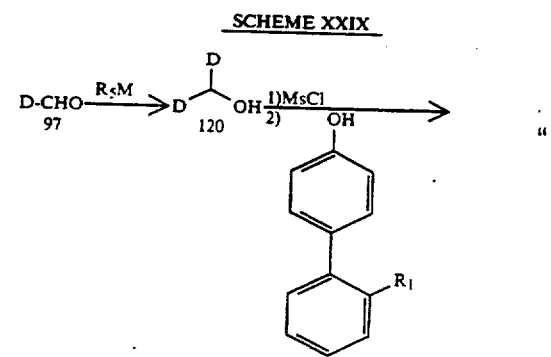 "

Insert

-- 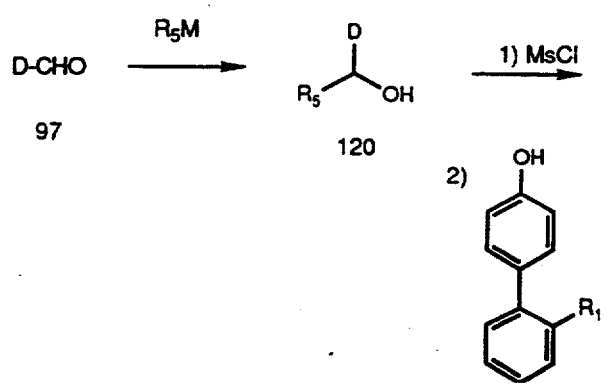 --

UNITED STATES PATENT AND TRADEMARK OFFICE
CERTIFICATE OF CORRECTION

PATENT NO. : 5,250,548
DATED : October 5, 1993
INVENTOR(S) : Martin Winn; Biswanath De; Thomas M. Zydowsky, Daniel J. Kerkman;

It is certified that error appears in the above-indentified patent and that said Letters Patent is hereby corrected as shown below:

COLUMN 68, LINE 36:    Delete "triethyl]amino" and Insert --triethyl]amine--

COLUMN 69, LINE 7:    Delete 2-butyl-5-[methanesulfonamidomethyl]-4-{N-[N-tri-

Insert 2-butyl-5- [methanesulfonamidomethyl]-4-{N-[(2'-[N-tri-

COLUMN 73, LINE 57:    Delete "(1991)" and Insert --(1961)--

COLUMN 79, LINE 9:    Delete "pyrimidine5" and Insert --pyrimidine-5--

COLUMN 83, LINE 5:    Delete "-1.2.4- and Insert -- -1,2,4- --

COLUMN 83, LINE 8:    Delete "-1.2.4- and Insert -- -1,2,4- --

COLUMN 83, LINE 29:    Delete "-1.2.4- and Insert -- -1,2,4- --

UNITED STATES PATENT AND TRADEMARK OFFICE
CERTIFICATE OF CORRECTION

PATENT NO. : 5,250,548
DATED : October 5, 1993
INVENTOR(S) : Martin Winn; Biswanath De; Thomas M. Zydowsky, Daniel J. Kerkman;

It is certified that error appears in the above-indentified patent and that said Letters Patent is hereby corrected as shown below:

COLUMN 102, LINE 68: After "J=9 Hz, 2H), " Insert --7.21(d,J=9Hz,2H),--

COLUMN 107, LINE 48: Replace "for90" with --for 90--

COLUMN 109, LINES 55 AND 56:

Delete
"4-{N-butyl-N-[2'-8 1-tetrazol-5-yl]biphenyl-4-yl)methyl]amino}pyrimi-"

Insert
-- 4-{N-butyl-N-[2'-[1H-tetrazol-5-yl]biphenyl-4-yl)methyl]amino}pyrimi- --

COLUMN 117, LINE 53: Delete "2.2" and Insert --2,2--

COLUMN 119, LINE 4: Delete "(CD1/NH$_3$) and Insert --(DC1/NH$_3$)--

COLUMN 126, LINE 4: Delete

"N-[(2'-[(2'-[1H-tetrazol-5-yl]biphenyl-4-yl)methyl"

Insert

-- N-[(2'-[1H-tetrazol-5-yl]biphenyl-4-yl)methyl --

UNITED STATES PATENT AND TRADEMARK OFFICE
CERTIFICATE OF CORRECTION

PATENT NO. : 5,250,548

DATED : October 5, 1993

INVENTOR(S) : Martin Winn; Biswanath De; Thomas M. Zydowsky, Daniel J. Kerkman;

It is certified that error appears in the above-indentified patent and that said Letters Patent is hereby corrected as shown below:

COLUMN 131, LINES 28 AND 29:
Delete "7.92 (d, J=3 Hz) and

Insert -- 7.92 (d,J=3Hz,1H)

COLUMN 132, LINE 21:   Delete "EXAMPLE 158" and Insert -- EXAMPLE 158B --

COLUMN 136, LINE 16:
Delete
"3-{N-Butyl-N-[(2'-[1H-tetrazol-5-yl)methyl]amino}"

Insert
-- 3-{N-Butyl-N-[(2'-[1H-tetrazol-5-yl]biphenyl-4-yl)methyl]amino} --

COLUMN 146, LINE 28:   Delete "7.25 (m, 1H)" and Insert --7.25 (m, 2H) --

COLUMN 155, LINE 18:   Delete "(m, 2H)" and Insert -- 1.49 (m, 2H)--

COLUMN 163, LINES 64 AND 65:
Delete "(d, J32 8 Hz, 2H, 1H)" and

Insert -- (dd, J=8 Hz, 2H, 1H) --

UNITED STATES PATENT AND TRADEMARK OFFICE
CERTIFICATE OF CORRECTION

PATENT NO. : 5,250,548
DATED : October 5, 1993
INVENTOR(S) : Martin Winn; Biswanath De; Thomas M. Zydowsky, Daniel J. Kerkman;

It is certified that error appears in the above-indentified patent and that said Letters Patent is hereby corrected as shown below:

COLUMN 184, LINE 53: Delete "[(2'-[(2'-[1H-tetrazol-" and

Insert --[(2'-[1H-tetrazol- --

Signed and Sealed this

Eighteenth Day of October, 1994

BRUCE LEHMAN

Attest:

Attesting Officer  Commissioner of Patents and Trademarks

UNITED STATES PATENT AND TRADEMARK OFFICE
CERTIFICATE OF CORRECTION

PATENT NO. : 5,250,548
DATED : October 5, 1993
INVENTOR(S) : Martin Winn; Biswanath De; Thomas M. Zydowsky, Daniel J. Kerkman;

It is certified that error appears in the above-indentified patent and that said Letters Patent is hereby corrected as shown below:

COLUMN 4, LINE 12: Delete "susbstituted" and insert --substituted--

COLUMN 68, LINE 57: Delete "concntrated" and Insert --concentrated--

COLUMN 77, LINE 57: Delete "give." and Insert --give--

COLUMN 97, LINE 17: Delete "compund" and Insert --compound--

COLUMN 98, LINE 17: Delete "compund" and Insert --compound--

Column 103, Line 16: Delete "compund" and Insert --compound--

COLUMN 125, LINE 7: Delete "reuslting" and Insert --resulting--

Signed and Sealed this

Fifteenth Day of November, 1994

Attest:

BRUCE LEHMAN

*Attesting Officer*   *Commissioner of Patents and Trademarks*